US010227619B2

(12) United States Patent
Ajjawi et al.

(10) Patent No.: US 10,227,619 B2
(45) Date of Patent: Mar. 12, 2019

(54) MICROORGANISMS HAVING INCREASED LIPID PRODUCTIVITY

(71) Applicant: Synthetic Genomics, Inc., La Jolla, CA (US)

(72) Inventors: Imad Ajjawi, Santa Brigida (ES); Eric R. Moellering, San Diego, CA (US); Leah Soriaga, San Diego, CA (US); Moena Aqui, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 15/210,845

(22) Filed: Jul. 14, 2016

(65) Prior Publication Data

US 2017/0058303 A1    Mar. 2, 2017

Related U.S. Application Data

(60) Provisional application No. 62/192,510, filed on Jul. 14, 2015, provisional application No. 62/318,161, filed on Apr. 4, 2016.

(51) Int. Cl.
*C12N 1/12* (2006.01)
*C12P 7/64* (2006.01)

(52) U.S. Cl.
CPC .................. *C12P 7/64* (2013.01); *C12N 1/12* (2013.01); *C12P 7/6463* (2013.01)

(58) Field of Classification Search
None
See application file for complete search history.

(56) References Cited

U.S. PATENT DOCUMENTS

2015/0183838 A1    7/2015  Ajjawi et al.
2017/0058303 A1*   3/2017  Ajjawi ................. C12N 1/12
2017/0121742 A1*   5/2017  Ajjawi ................. C12P 7/649

FOREIGN PATENT DOCUMENTS

WO    WO-2013016267 A2 *  1/2013   ................ C12P 7/64
WO    WO 2013/016267 A3    4/2013
WO    WO-2013016267 A3 *  4/2013   ................ C12P 7/64

OTHER PUBLICATIONS

International Search Report dated Dec. 28, 2016, regarding PCT/US2016/042364.
Morin et al.: "*Transcriptomic Analyses during the Transition from Biomass Production to Lipid Accumulation in the Oleaginous Yeast Yarrowia lipolytica*";. PLoS One. 2011, vol. 6, No. 11, p. e27966 (pp. 1-10).
Beacham, et al.: "*Altered Lipid Accumulation in Nannochloropsis salina CCAP849/3 Following EMS and UV Induced Mutagenesis;*" Biotechnology Reports, 2015, vol. 7, pp. 87-94.

(Continued)

*Primary Examiner* — Richard C Ekstrom
(74) *Attorney, Agent, or Firm* — DLA Piper LLP (US)

(57) ABSTRACT

The present invention provides mutant microorganism that have higher lipid productivity than the wild type microorganisms from which they are derived while biomass at levels that are within approximately 50% of wild type biomass productivities under nitrogen replete conditions. Particular mutants produce at least twice as much FAME lipid as wild type while producing at least 75% of the biomass produced by wild type cells under nitrogen replete conditions. Also provided are methods of producing lipid using the mutant strains.

18 Claims, 42 Drawing Sheets

Specification includes a Sequence Listing.

(56) References Cited

OTHER PUBLICATIONS

Boyle, et al.: "Three Acyltransferases and Nitrogen-Responsive Regulator are Implicated in Nitrogen Starvation-Induced Triacylglycerol Accumulation in Chlamydomonas;"J. Biol. Chem., May 4, 2012, vol. 287, No. 19, pp. 15811-15825.
Camacho, et al.: "Continuous Culture of the Marine Microalga Tetraselmis sp.—Productivity Analysis;" Aquaculture, 1990, vol. 90, pp. 75-84.
Carpinelli, et al.: "Chromosome Scale Genome Assembly and Transcriptome Profiling of Nannochloropsis gaditana in Nitrogen Depletion;" Molecular Plant, 2014, vol. 7, No. 2, pp. 323-335.
Del Rio, et al.: "Continuous Culture Methodology for the Screening of Microalgae for Oil;" J. Biotechnol., 2015, vol. 195, pp. 103-107.
D'Ippolito, et al.: "Potential of Lipid Metabolism in Marine Diatoms for Biofuel Production;" Biotechnol. For Biofuels, BioMed Central, 2015, pp. 1-10.
Davey, et al.: "Triacylglyceride Production and Autophagous Responses in Chlamydomonas reinhardtii Depend on Resource Allocation and Carbon Source;" Eukaryotic Cell, Mar. 2014, vol. 13, No. 3, pp. 392-400.
Fan, et al.: "Genomic Foundation of Starch-to-Lipid Switch in Oleaginous Chlorella spp.;" Plant Physiology, 2015, vol. 169, pp. 2444-2461.
Gargouri, et al.: "Identification of Regulatory Network Hubs that Control Lipid Metabolism in Chlamydomonas reinhardtii;" J. Exp. Botany, 2015, pp. 1-16.
Goncalves, et al.: "Metabolic Regulation of Triacylglycerol Accumulation in the Green Algae: Identification of Potential Targets for Engineering to Improve Oil Yield;" Plant Biotechnol. J., 2016, pp. 1-12.
Gonzalez and Gonzalez: "Signal Transduction by Heme-Containing PAS-Domain Proteins;" J. Appl. Physiol., 2004, vol. 96, pp. 774-783.
Hassan, et al.: "Selective Recognition of Acetylated Histones by Bromodomains in Transcriptional Co-Activators;" Biochem. J., 2007, vol. 402, pp. 125-133.
Haynes, et al.: "The Bromodomain: A Conserved Sequence Found in Human, Drosophila and Yeast Proteins;" Nucl. Acids Res., vol. 20, No. 10, pp. 2603.
Hefti, et al.: "The PAS Fold, A Redefinition of the PAS Domain Based Upon Structural Prediction;" Eur. J. Biochem., 2004, vol. 271, pp. 1198-1208.
Heisel, et al.: "Mutations in Histone ACETYLTRANSFERASE1 Affect Sugar Response and Gene Expression in Arabidopsis;" Frontiers in Plant Science, 2013, vol. 4, Art. 245, pp. 1-13.
Henry and Crosson: "Ligand Binding PAS Domains in a Genomic, Cellular, and Structural Context;" Annu. Rev. Microbiol., 2011, vol. 65, pp. 261-286.
Hu, et al.: "Genome-Wide Identification of Transcription Factors and Transcription-Factor Binding Sites in Oleaginous Microalgae Nannochloropsis;" Nature Scientific Reports, 2014, vol. 4, Art. 5454, pp. 1-11.
Jin, et al.: PlantTFDB 3.0: A Portal for the Functional and Evolutionary Study of Plant Transcription Factors; Nucl. Acids Res., 2014, vol. 42, pp. D1182-D1187.
Leverentz and Reece: "Phosphorylation of $Zn(II)_2Cys_6$ Proteins: A Cause or Effect of Transcriptional Activation?" Biochem. Soc. Transactions, 2006, vol. 34, No. 5, 794-797.
Levitan, et al.: An RNA Interference Knock-Down of Nitrate Reductase Enhances Lipid Biosynthesis in the Diatom Phaeodactylum tricomutum; Plant J., 2015, vol. 84, pp. 963-973.
Li, et al.: "Choreography of Transcriptomes and Lipidomes of Nannochloropsis Reveals the Mechanisms of Oil Synthesis in Microalgae;" Plant Cell, 2014, vol. 26, pp. 1645-1665.
Macpherson, et al.: "A Fungal Family of Transcriptional Regulators: the Zinc Cluster Proteins;" Microbiol. Molecular Biol. Reviews, 2006, vol. 70, No. 3, pp. 583-604.

Mandadi, et al.: "BT2, a BTB Protein, Mediates Multiple Responses to Nutrients, Stresses, and Hormones in Arabidopsis;" Plant Physiol., 2009, vol. 150, pp. 1930-1939.
Marchetti, et al.: "Optimizing Conditions for the Continuous Culture of Isochrysis affinis galbana Relevant to Commercial Hatcheries;" Aquaculture, 2012, vol. 326-329, pp. 106-115.
Misra, A.: "The Bromodomain Proteins GTE9 and GTE11 Associate with BT2-Based E3 Ligase Complex and Mediate Responses to Multiple Signals in Arabidopsis Thaliana;" Dissertation for Molecular and Environmental Plant Sciences, Texas A&M University, 2011, pp. 1-104.
Näär and Thakur: "Nuclear Receptor-Like Transcription Factors in Fungi;" Genes Dev., 2009, vol. 23, pp. 419-432.
Ngan, et al.: "Lineage-Specific Chromatin Signatures Reveal a Regulator of Lipid Mtabolism in Microalgae;" Nature Plants, 2015, Art. 15107, pp. 1-11.
Perez-Rodriguez, et al.: "PlnTFDB: Updated Content and New Features of the Plant Transcription Factor Database;" Nucl. Acids Res., 2010, vol. 38, pp. D822-D827.
Pistorius, et al.: "Monitoring of Biomass Composition from Microbiological Sources by Means of FT-IR Spectroscopy;" Biotechnol. Bioeng., 2009, vol. 103, No. 1, pp. 123-129.
Ponting and Aravind: "PAS: A Multifunctional Domain Family Comes to Light;" Cum Biol., 1997, vol. 7, No. 11, pp. R674-R677.
Radakovits, et al.: "Draft Genome Sequence and Genetic Transformation of the Oleaginous Alga Nannochloropsis gaditana;" Nature Commun., 2013, vol. 3, Art. 686, pp. 1-10.
Supplementary Information for: Radakovits, et al.: "Draft Genome Sequence and Genetic Transformation of the Oleaginous Alga Nannochloropsis gaditana;" Nature Commun., 2013, vol. 3, Art. 686, pp. 1-10.
Sananurak, et al.: "Development of a Closed-Recirculating, Continuous Culture System for Microalga (Tetraselmis suecica) and Rotifer (Brachionus plicatilis) Production;" ScienceAsia, 2009, vol. 35, pp. 118-124.
Siaut, et al.: "Oil Accumulation in the Model Green Alga Chlamydomonas reinhardtii: Characterization, Variability Between Common Laboratory Strains and Relationship with Starch Reserves;" BMC Biotechnol., 2011, vol. 7, No. 7, pp. 1-15.
Slocombe, et al.: "Comparison of Screening Methods for High-Throughput Determination of Oil Yields in Micro-Algal Biofuel Strains;" J. Appl. Phycol., 2013, vol. 25, pp. 961-972.
Taylor and Zhulin: "PAS Domains: Internal Sensors of Oxygen, Redox Potential, and Light;" Microbiol. Molecular Biol. Rev., 1999, vol. 63, No. 2, pp. 479-506.
Thakur, et al.: "Mediator Subunit Gal11p/MED15 is Required for Fatty Acid-Dependent Gene Activation by Yeast Transcription Factor Oaf1p;" J. Biol. Chem., 2009, vol. 284, No. 7, pp. 4422-4428.
Trentacoste, et al.: "Metabolic Engineering of Lipid Catabolism Increases Microalgal Lipid Accumulation Without Compromising Growth;"PNAS, 2013, vol. 110, No. 49, pp. 19748-19753.
Supporting Information for: Trentacoste, et al.: "Metabolic Engineering of Lipid Catabolism Increases Microalgal Lipid Accumulation Without Compromising Growth;" PNAS, 2013, vol. 110, No. 49, pp. 19748-19753.
Wang, et al.: "Algal Lipid Bodies: Stress Induction, Purification and Biochemical Characterization in Wild-Type and Starchless Chlamydomonas reinhardtii;" Eukaryotic Cell, 2009, vol. 8, No. 12, pp. 1856-1868.
Weyman, et al.: "Inactivation of Phaeodactylum tricornutum Urease Gene using Transcription Activator-Like Effector Nuclease-Based Targeted Mutagenesis;" Plant Biotechnol. J., 2014, pp. 1-11.
Yuan, et al.: "Nit-4, a Pathway-Specific Regulatory Gene of Neurospora crassa, Encodes a Protein with a Putative Binuclear Zinc DNA-Binding Domain;" Molecular Cellular Biol., 1991, vol. 11, No. 11, pp. 5735-5745.
Yuan and Marmorstein: "Histone Acetyltransferases: Rising Ancient Counterparts to Protein Kinases;" Biopolymers, 2013, vol. 99, No. 2, pp. 98-111.
Zetsche, et al.: "Cpf1 is a Single RNA-Guided Endonuclease of a Class 2 CRISPR-Cas System;" Cell, 2015, vol. 163, pp. 1-13.

\* cited by examiner

FIGS. 1A-B

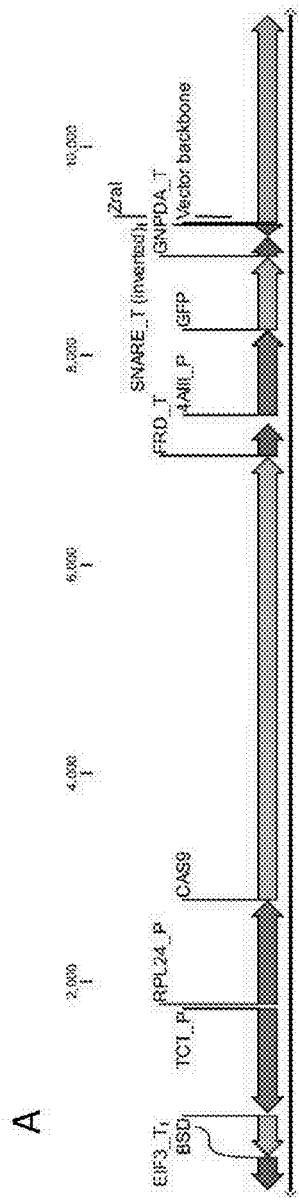
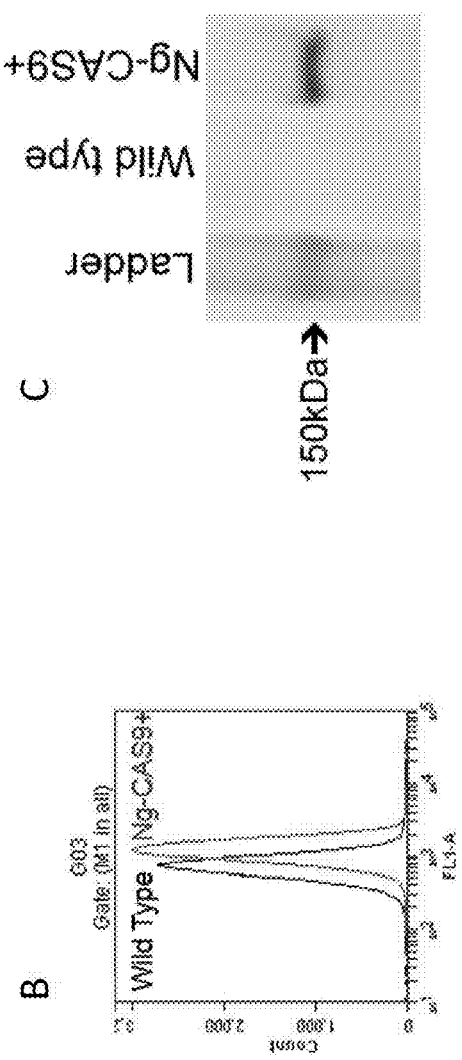
FIGS. 3A-C

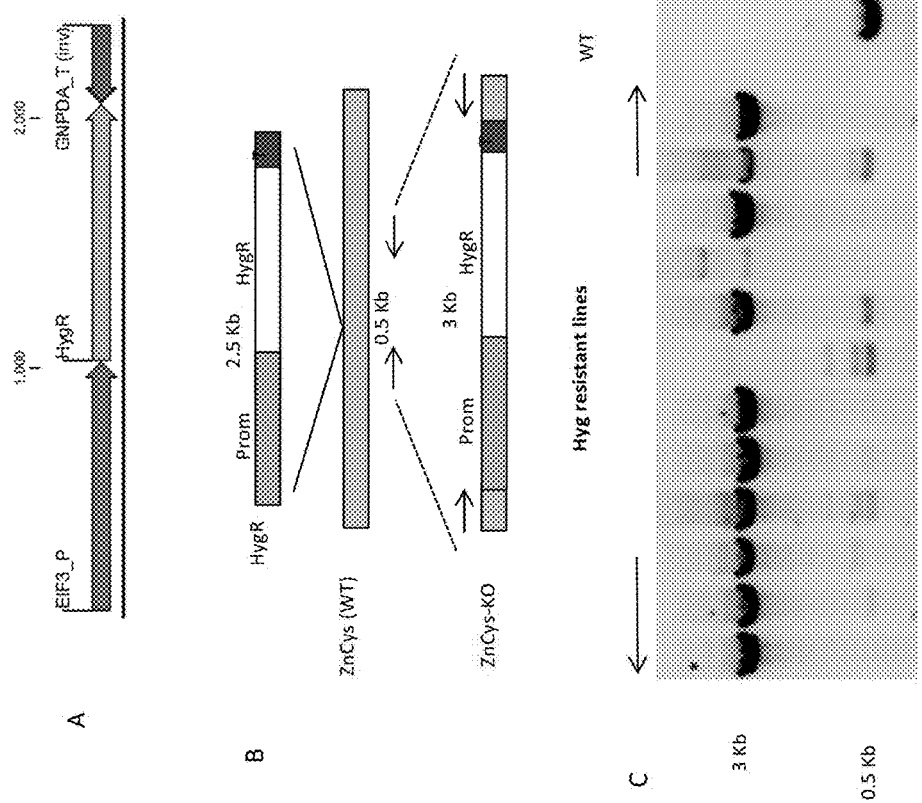
FIGS. 4A-C

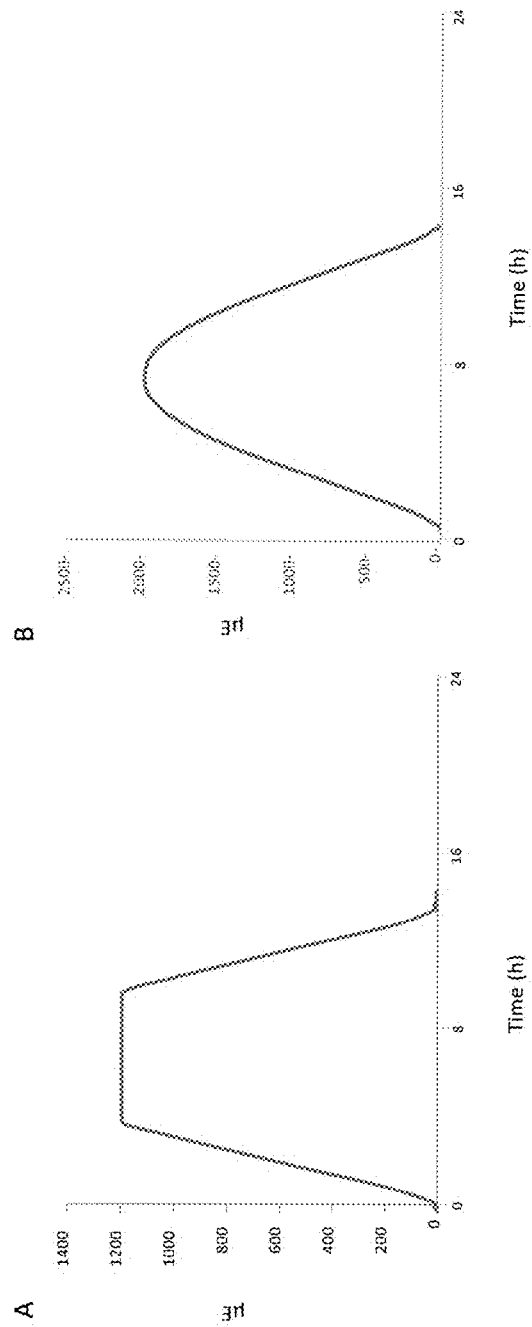
FIGS. 6A-B

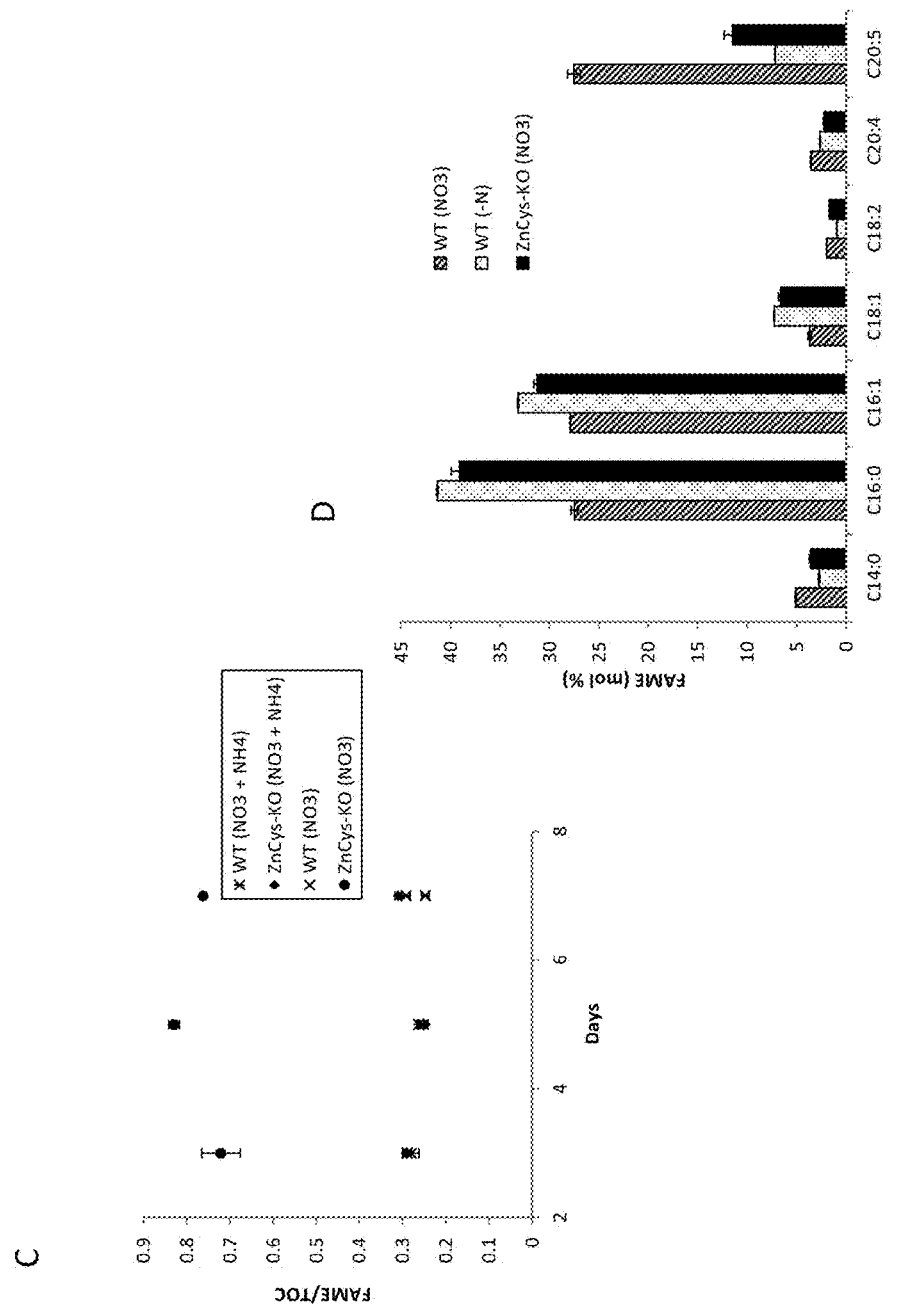
FIGS. 7C-D

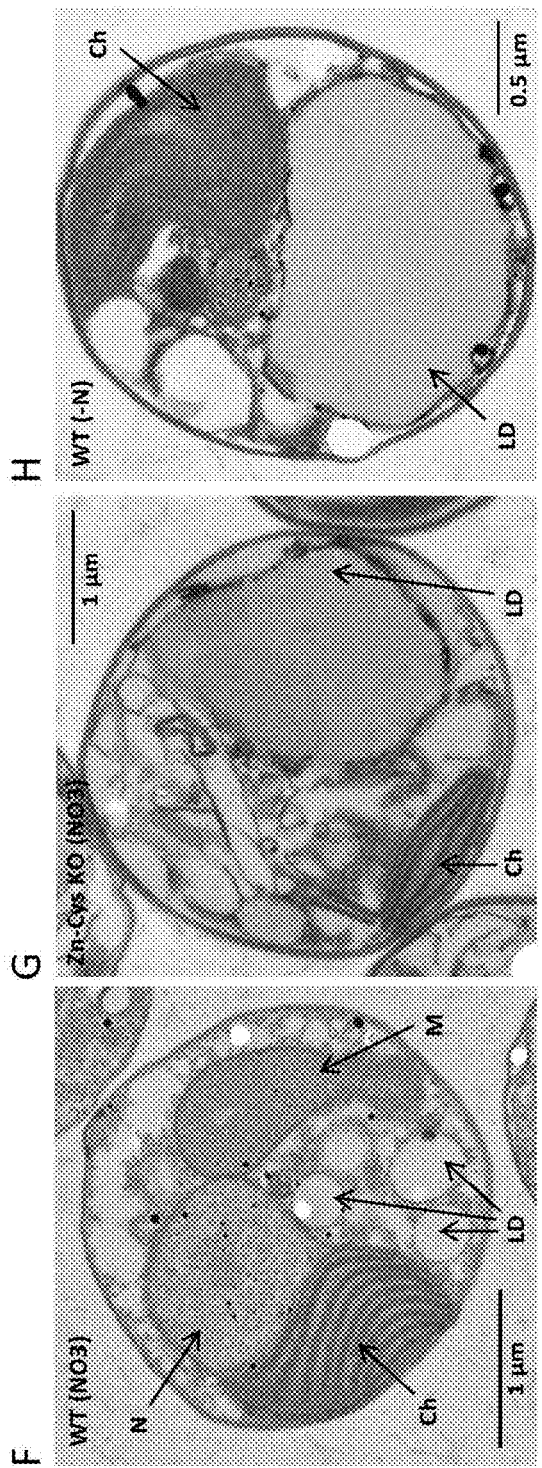
FIGS. 7F-H

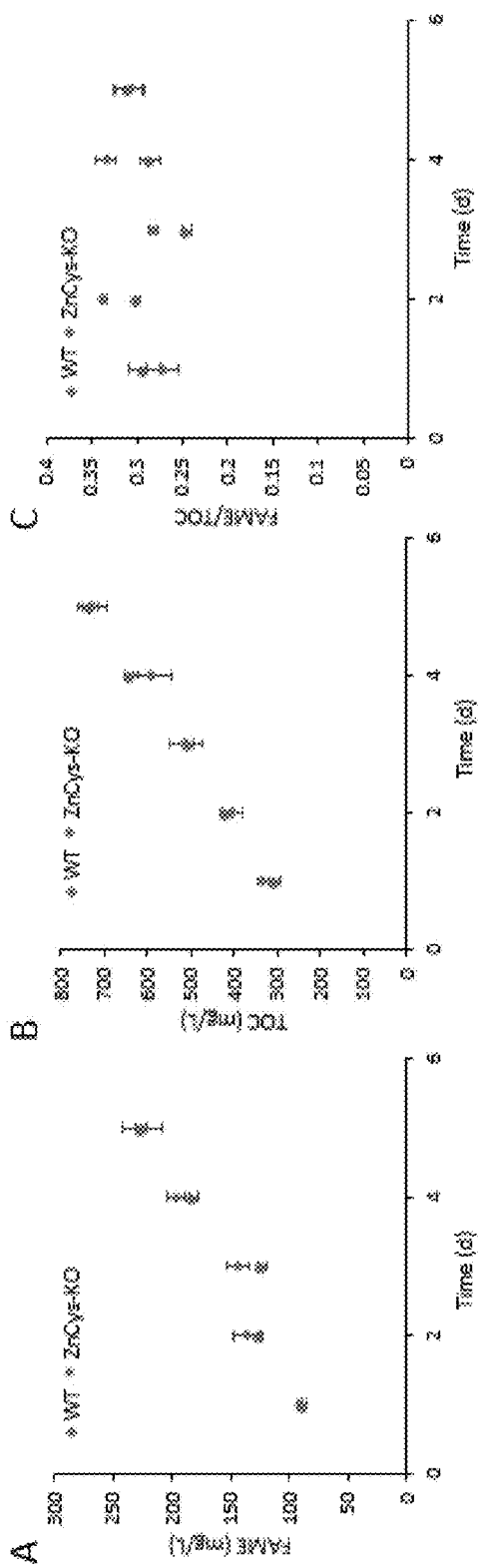
FIGS. 8A-C

| | | |
|---|---|---|
| CCMP529 | 1 | NLWTKTSSVLASGVDMTFGICDQLQEVVGPAFTGSGPIACSPATRSKSQAAQQAQLIHHP |
| CCMP526 | 1 | NLWTKVSSQLASGIDMTFGICDQLQEVVGPAFTGSGPIASSPATRSKSHAAQQAQLLTHP |
| CCMP525 | 1 | NLWTKTSSVLASGVDMTFGICQLQEVVGPAPTCSGPIACSPATRSKSQAVQQAQLLTHP |
| CCMP531 | 1 | NLWTKTSSHLASGVDMTFGICDQLQEVVGPAPTGSGPIACSPATRSFSQABQQAQLIHHP |
| CCMP537 | 1 | NLWTKVSSQLASGIDMTFGICDQLQEVVGPAFTGSGPIASSPATRSKSHAAQQAQLLTHP |
| IMET1 | 1 | NLWTFTSSHLASGVDMTFGICDQLQEVVGPAPTGSGPIACSPATRSKSQAQQQAQLLIHP |
| EMRE2EUKT2845 | 1 | NLWTKVSSQLASGIDMTFGICDQLQEVVGPAPTGSGPIASSPATRSEHAAQQAQLLTHP |
| consensus | 1 | **..**.********.***..*.********.*.*****. |

| | | |
|---|---|---|
| CCMP529 | 61 | GSKECMGPKHLPRELRKMDGVSMLCGPMFIQDELFVYTDERFAATFMTREEVEGKVESS |
| CCMP526 | 61 | SSKESMGPHGLPLDLRNMDGVSMLCGPMFHQDELFVYTDERFAATFMTREEVESKVGSL |
| CCMP525 | 61 | SSKESMGPWNLPDDLPKMDGSMPIQDELFVYTDERFAATFMTREEVSKVGSL |
| CCMP531 | 61 | GSKECMGPKNLPDDLRKMDDGVSMLCGPMFIQDELFYYTDERFAATFMTREEVEGKVESS |
| CCMP537 | 61 | GSKECMGPHGLPLDLRNMDGVSMLCGPMFHQDELFVYTDERFAATFMTREEVESKVGSL |
| IMET1 | 61 | SSKESMGPWNLPDDLPKMDGVSMLCSPMPIQDELFVYTDERFAATFMTREEVEGKVESF |
| EMRE2EUKT2845 | 61 | GSKESMGPHGLPLDLRNMDGVSMLCGPMFHQDELFVYTDERFAATFMTREEVESKVGSL |
| consensus | 61 | **.*..**.*.*.**********.*.*****.********************.*.. |

| | | | |
|---|---|---|---|
| CCMP529 | 121 | AVLPILLLAEIFHPDGLPDVYAAIGAHWFRRRFSSSVGVGGSNGSISSMNSSS | SEQ ID NO:25 |
| CCMP526 | 121 | AVLPILLLAEIFHPDDLPDVYAAIGANWFRRPRSSGSTSESGSSSGSNSSVSS | SEQ ID NO:21 |
| CCMP525 | 101 | AVLPILLLAEIFHPDDLPDVYAAIGANWFRRRPRSSGSGVGGSNGSISEHFSNG | SEQ ID NO:24 |
| CCMP531 | 121 | AVLPILLLAEIFHPDDLPDVYAATGAHWFRRPSSVGVGGSNGSISSMNSSS | SEQ ID NO:22 |
| CCMP537 | 121 | AVLPILLLAEIFHPDGLPDVYAAIGANWFSRPFGMSDSSSSSSTGSSVSSA | SEQ ID NO:23 |
| IMET1 | 121 | AVLPILLLAEIFHPDDLPDVYAAIGAHWFRRRFSSSGVGGSNGSISSMNSSS | SEQ ID NO:22 |
| EMRE2EUKT2845 | 121 | AVLPILLLAEIFHPDDLPIRYAAIGANWFSRESTSESGSSSSSNSSVSS | SEQ ID NO:21 |
| consensus | 121 | ******************.*..**.*.....*.*..*...... | |

| N.gaditana | 507 | SSSSSNSSVSSSGRESAASATSTP-----SASWICRGIEKANTESTASVRERSEVAEAE |
| N.salina | | ------------------------------------------------------------ |
| N.granulata | | ------------------------------------------------------------ |
| N.oceanica | 530 | NGSISSMNSSSSSSSRDSASPSPVSREVPESAWICKGIEKNTESAISVRFRSEAAETS |
| N.oculata | | ------------------------------------------------------------ |

| N.gaditana | 562 | GYSGAAMLSILPIKPSKYSADPETKGSSRSGVSSRLSSRDTFGALPTALPESDDEDLGS |
| N.salina | | ------------------------------------------------------------ |
| N.granulata | | ------------------------------------------------------------ |
| N.oceanica | 590 | GYAGAAMLSILPITRSKYSADPESVQTNSPSGVSSREHSRDTFGALPTALPESDDEIDES |
| N.oculata | | ------------------------------------------------------------ |

| N.gaditana | 622 | LVGRRPSVDRMEGLSPGASEGQDSESSEALFRPLRSGMTVSSDETSGPQASPVSKQVSDP |
| N.salina | | ------------------------------------------------------------ |
| N.granulata | | ------------------------------------------------------------ |
| N.oceanica | 650 | HHHLVLERRGERVGSDSHSQDLLNSPSSDEIPLDASSDDASFRPLRRGMTVLSSETSGPQ |
| N.oculata | | ------------------------------------------------------------ |

| N.gaditana | 682 | GSQHQDSACYSQETIHTSQLSSALRSSVGLSWGGEGTDESGESFPSSQFSSHAQTQGCSS |
| N.salina | | ------------------------------------------------------------ |
| N.granulata | | ------------------------------------------------------------ |
| N.oceanica | 710 | ESPLSKSASOPLSHENERHPHSQPQHSSSHLSSLSSMASHQTGVSWGGSRISECLGNQSR |
| N.oculata | | ------------------------------------------------------------ |

| N.gaditana | 742 | SSGLPQDGKSCGGYSASSDGRGGDMTDGVLPIACSTKASIFLLQEEGSVSGRDLPAAGDN |
| N.salina | | ------------------------------------------------------------ |
| N.granulata | | ------------------------------------------------------------ |
| N.oceanica | 770 | SASQFYNTVQHQERSKRSGEEPHQQHREEQQQHRSPGNSSLDGSSSHSGAMDQDLPTVQL |
| N.oculata | | ------------------------------------------------------------ |

| N.gaditana | 802 | SSYGDLASGRESQGSGKPHQSKESESRKSPGPROGRTLPASSLTMDSEDTGSSVTDPEIYG |
| N.salina | | ------------------------------------------------------------ |
| N.granulata | | ------------------------------------------------------------ |
| N.oceanica | 830 | QAQLFLLQGGTGSSIGLSSDISQEQQSMCNQISPDGVTASEESASRVATESYGSSPSPE |
| N.oculata | | ------------------------------------------------------------ |

| N.gaditana | 862 | SSPSPEPGQSLNTSSRGSARLSMQASSQGGHQTYFGRHEHMEKSSREEVQRSPMASPSVS |
| N.salina | | ------------------------------------------------------------ |
| N.granulata | | ------------------------------------------------------------ |
| N.oceanica | 890 | PHLLGHSRESPTQPAQQQQQSKRQQERQQEDQQQEQGHQQQSQSSQQQQGMSLPISHLPS |
| N.oculata | | ------------------------------------------------------------ |

| N.gaditana | 922 | FAQAGELSSDRRASCSSLSILGGFSGKVESRSGSSESHSKSNNSDLSSCHGPADPNGYGGL |
| N.salina | | ------------------------------------------------------------ |
| N.granulata | | ------------------------------------------------------------ |
| N.oceanica | 950 | MVFSLVPSSVSSSAMLSSRPTTISQSKDEGSRGSASHESMSSTSDLSSCHGPADPNGYGGL |
| N.oculata | | ------------------------------------------------------------ |

| N.gaditana | 982 | QSYPAPLASSLSGAKGLLEAGNGVGSHAISSSVHANQSPAHQKRSTSRAGSRTVPAHNGGDS |
| N.salina | | ------------------------------------------------------------ |
| N.granulata | | ------------------------------------------------------------ |
| N.oceanica | 1010 | HSYTPAPLASFLGGVSSWGSRRGSRKSERSKD-------------------------- |
| N.oculata | | ------------------------------------------------------------ |

| N.gaditana | 1042 | TAGSAASAGARDEEAEPGFLARSL | SEQ ID NO:2 |
| N.salina | | ------------------------ | SEQ ID NO:20 |
| N.granulata | | ------------------------ | SEQ ID NO:18 |
| N.oceanica | | ------------------------ | SEQ ID NO:17 |
| N.oculata | | ------------------------ | SEQ ID NO:19 |

FIG. 10 (cont.)

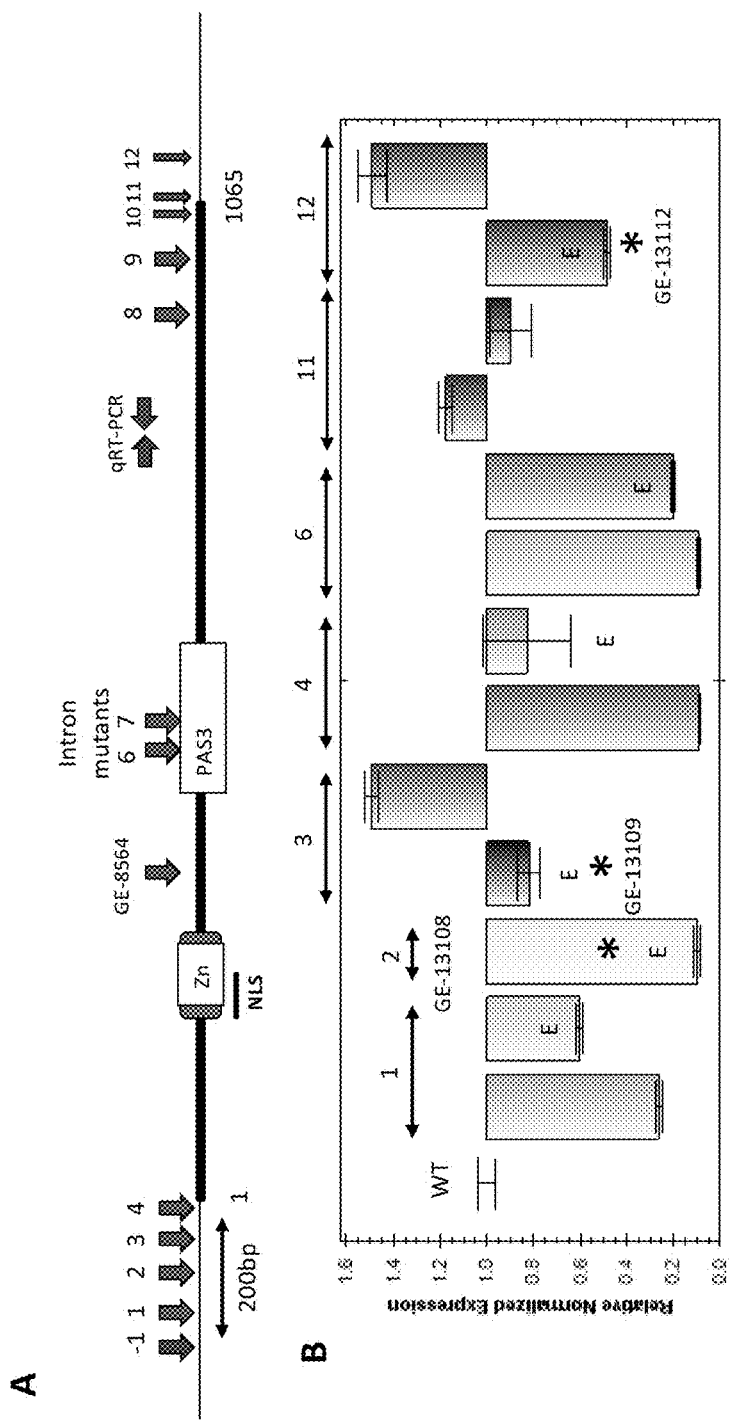
FIGS. 12A-B

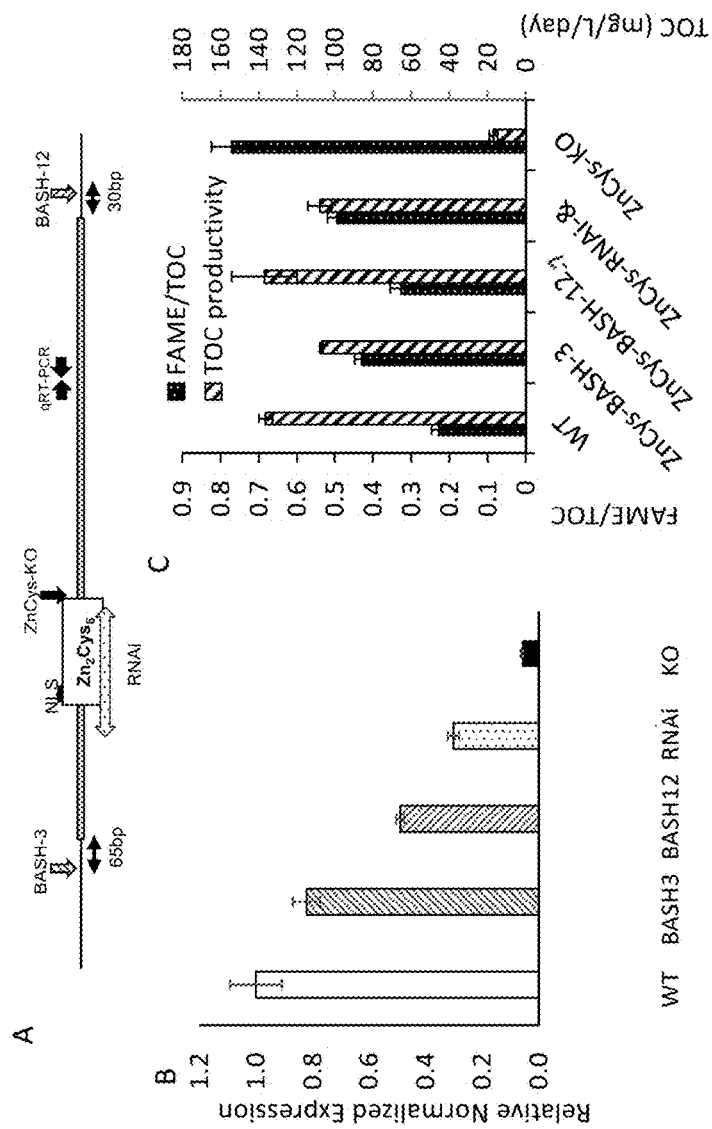
FIGS. 14A-C

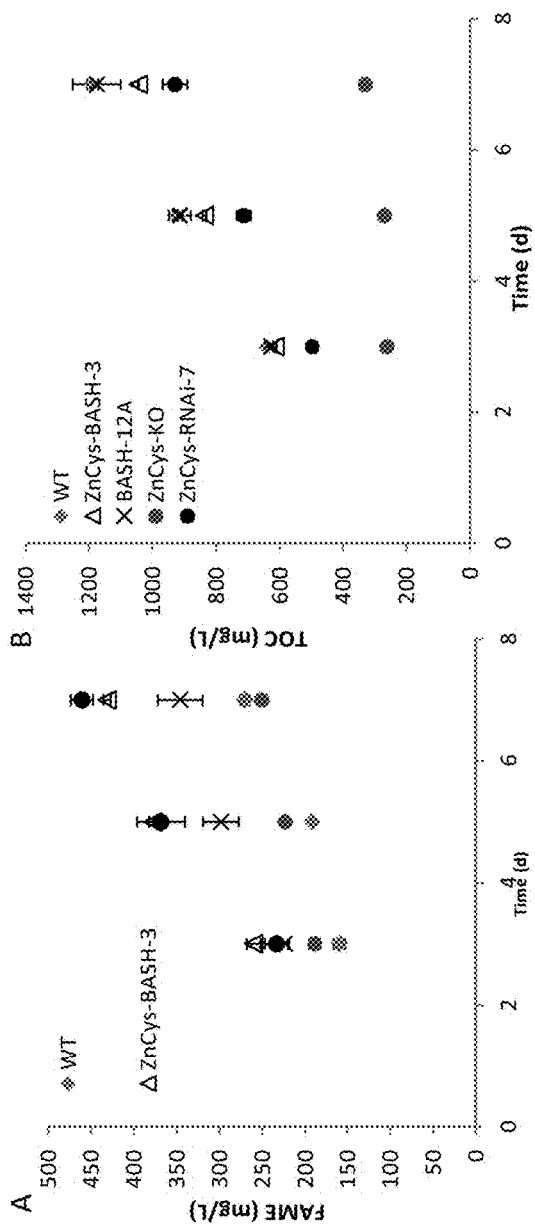
FIGS. 15A-B

| strain | 1 | 2 | 3 | 4 | 5 | 6 | 7 | 8 | 9 | 10 | 11 | 12 | 13 | Avg |
|---|---|---|---|---|---|---|---|---|---|---|---|---|---|---|
| WT (NO3) | 2.41 (0.10) | 2.51 (0.17) | 2.46 (0.09) | 2.28 (0.11) | 2.30 (0.08) | 2.43 (0.06) | 2.41 (0.14) | 2.60 (0.08) | 2.57 (0.08) | 2.43 (0.13) | 2.44 (0.14) | 2.40 (0.09) | 2.38 (0.09) | 2.43 (0.13) |
| GE-13112 (NH4+NO3) | 4.00 (0.30) | 4.42 (0.46) | 4.74 (0.25) | 4.76 (0.38) | 4.78 (0.11) | 4.70 (0.03) | 4.42 (0.10) | 4.44 (0.09) | 4.45 (0.11) | 4.11 (0.12) | 4.07 (0.11) | 4.19 (0.08) | 4.18 (0.09) | 4.44 (0.32) |
| GE-13109 (NH4+NO3) | 3.98 (0.25) | 4.49 (0.31) | 4.91 (0.26) | 4.91 (0.13) | 4.92 (0.13) | 4.84 (0.21) | 4.58 (0.13) | 4.44 (0.29) | 4.15 (0.15) | 3.91 (0.11) | 3.89 (0.14) | 3.93 (0.11) | 3.86 (0.20) | 4.39 (0.45) |
| GE-13108 (NH4+NO3) | 4.30 (0.49) | 5.31 (0.59) | 6.19 (0.60) | 6.07 (0.50) | 6.29 (0.45) | 6.05 (0.34) | 5.20 (0.33) | 4.79 (0.35) | 4.24 (0.18) | 3.32 (0.24) | 3.01 (0.26) | 2.58 (0.33) | 2.34 (0.19) | 4.48 (1.40) |
| RNAi-7 (NO3) | 5.48 (0.15) | 5.52 (0.16) | 5.67 (0.13) | 5.46 (0.10) | 5.33 (0.11) | 5.36 (0.11) | 5.18 (0.04) | 5.03 (0.01) | 4.84 (0.05) | 4.52 (0.08) | 4.52 (0.08) | 4.32 (0.25) | 4.19 (0.11) | 4.82 (0.43) |
| RNAi-7 (NH4+NO3) | 3.26 (0.30) | 4.82 (0.35) | 5.51 (0.24) | 6.14 (0.41) | 5.74 (0.15) | 5.93 (0.11) | 5.75 (0.14) | 5.64 (0.08) | 5.39 (0.15) | 5.08 (0.11) | 5.01 (0.07) | 4.68 (0.16) | 4.51 (0.12) | 5.40 (0.77) |
| GE-8564 (Urea) | 2.64 (0.08) | 2.70 (0.05) | 3.08 (0.07) | 2.80 (0.29) | 3.05 (0.02) | 3.57 (0.07) | 3.55 (0.10) | 3.46 (0.05) | 3.39 (0.09) | 3.16 (0.08) | 3.25 (0.10) | 3.09 (0.08) | 3.05 (0.11) | 3.22 (0.31) |
| GE-8564 (NO3) | 5.46 (0.19) | 5.86 (0.40) | 6.68 (0.26) | 6.40 (0.24) | 5.41 (0.22) | 4.72 (0.22) | 3.85 (0.16) | 3.18 (0.16) | 2.43 (0.06) | 1.77 (0.16) | 1.27 (0.01) | 0.90 (0.05) | 0.69 (0.02) | 3.39 (2.11) |

FIG. 16B

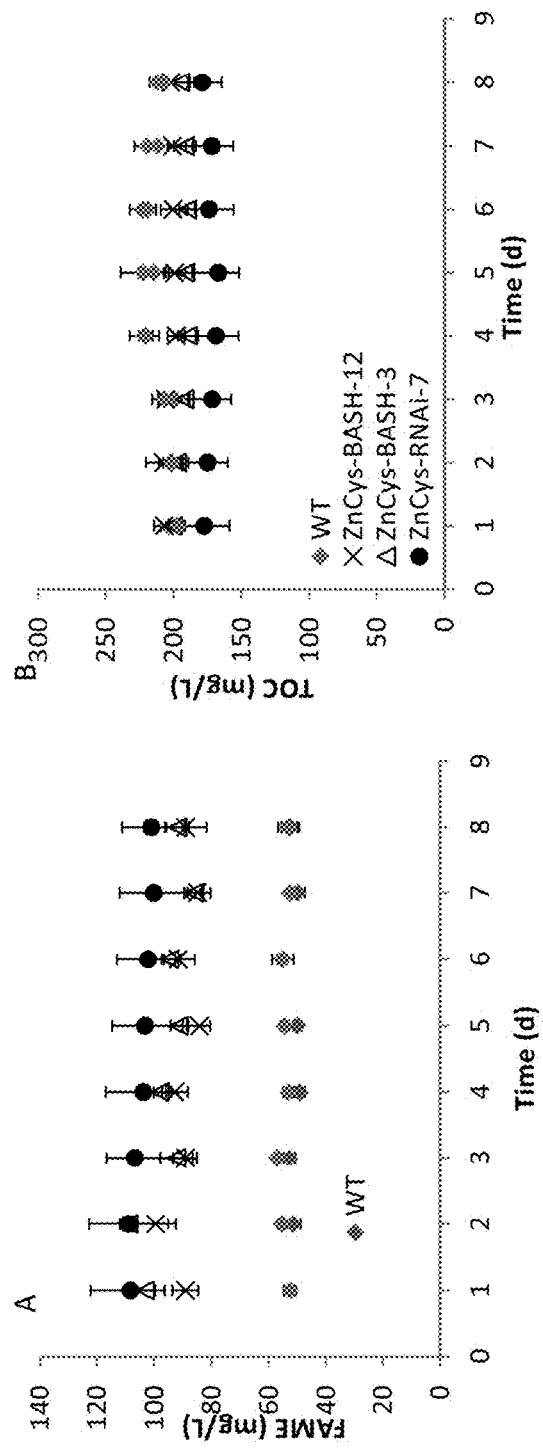
FIGS. 17A-B

| Strain | Day1 | Day2 | Day3 | Day4 | Day5 | Day6 | Day7 | Day8 | Day9 | Day10 | Avg |
|---|---|---|---|---|---|---|---|---|---|---|---|
| WT-3730 | 2.33 (0.02) | 2.43 (0.08) | 2.55 (0.10) | 2.53 (0.04) | 2.41 (0.09) | 2.33 (0.08) | 2.40 (0.01) | 2.44 (0.04) | 2.37 (0.05) | 2.16 (0.31) | 2.40 (0.14) |
| GE-13103 2.5mM NH4Cl | 1.88 (0.15) | 1.86 (0.17) | 2.05 (0.01) | 1.85 (0.02) | 1.70 (0.18) | 1.56 (0.22) | 1.85 (0.11) | 2.22 (0.27) | 3.03 (0.04) | 2.16 (0.17) | 2.02 (0.43) |
| GE-13103 1.0mM NH4Cl | 3.15 (0.10) | 3.06 (0.06) | 3.09 (0.23) | 2.91 (0.04) | 2.71 (0.31) | 2.53 (0.30) | 2.76 (0.37) | 3.03 (0.10) | 3.20 (0.06) | 2.86 (0.07) | 2.93 (0.27) |
| GE-13103 0.5mM NH4Cl | 4.38 (0.05) | 4.51 (0.02) | 4.59 (0.05) | 4.43 (0.03) | 4.26 (0.27) | 3.96 (0.18) | 3.88 (0.20) | 4.12 (0.18) | 4.39 (0.24) | 4.04 (0.16) | 4.25 (0.27) |

FIG. 21B

| Strain | Day1 | Day2 | Day3 | Day4 | Day5 | Day6 | Day7 | Day8 | Day9 | Day10 | Day11 | Avg |
|---|---|---|---|---|---|---|---|---|---|---|---|---|
| WT-3730 | 6.29 (4.21) | 5.53 (4.79) | 5.67 (4.91) | 6.37 (4.26) | 6.05 (4.04) | 6.10 (4.07) | 6.04 (4.03) | 6.03 (4.02) | 6.11 (4.08) | 6.49 (4.33) | 6.65 (4.44) | 6.12 |
| GE-13103 2.5mM NH4Cl | 5.73 (0.26) | 4.67 (0.32) | 2.85 (3.58) | 5.61 (0.50) | 5.27 (0.62) | 5.36 (0.63) | 5.49 (0.52) | 5.56 (0.26) | 5.77 (0.21) | 6.19 (0.36) | 6.44 (0.59) | 5.36 |
| GE-13103 1.0mM NH4Cl | 4.20 (0.49) | 3.99 (0.66) | 2.05 (0.60) | 3.74 (0.71) | 3.59 (0.78) | 3.69 (4.42) | 3.79 (0.93) | 4.12 (0.73) | 4.42 (0.61) | 4.70 (0.54) | 5.11 (0.50) | 3.95 |
| GE-13103 0.5mM NH4Cl | 6.45 (0.23) | 6.14 (0.22) | 4.13 (0.32) | 5.76 (0.24) | 5.55 (0.33) | 5.86 (0.30) | 5.98 (0.36) | 6.31 (0.26) | 6.70 (0.29) | 7.16 (0.09) | 7.84 (0.34) | 6.17 |

FIG. 21D

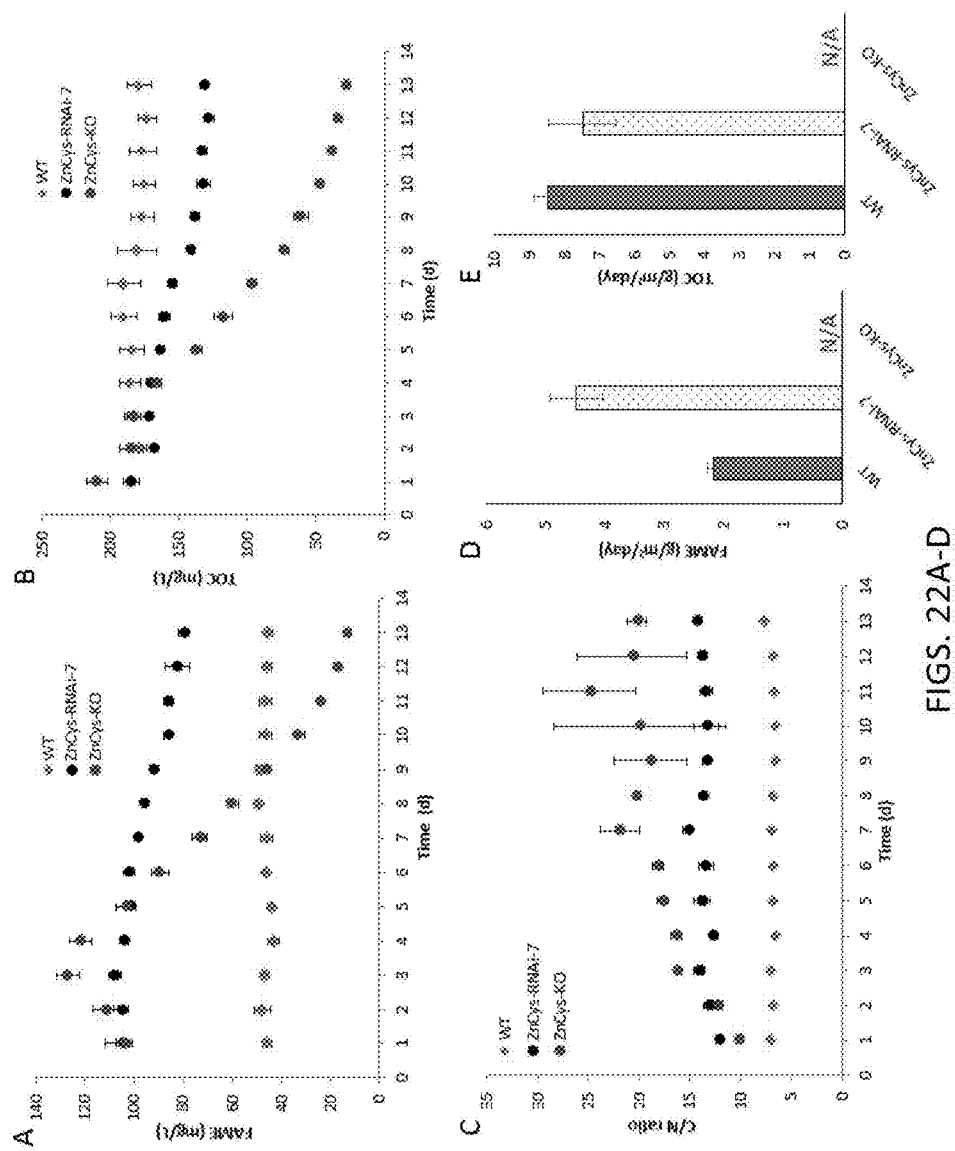
FIGS. 22A-D

MICROORGANISMS HAVING INCREASED LIPID PRODUCTIVITY

CROSS-REFERENCE TO RELATED APPLICATIONS

This application claims benefit of priority under 35 U.S.C. § 119(e) of U.S. Ser. No. 62/192,510, filed Jul. 14, 2015 and U.S. Ser. No. 62/318,161, filed Apr. 4, 2016, the entire contents of which are incorporated herein by reference in their entireties.

INCORPORATION BY REFERENCE OF SEQUENCE LISTING

The material in the accompanying sequence listing is hereby incorporated by reference into the application. The accompanying sequence listing text file, name SGI1920_2WO_Sequence_Listing.txt, was created on Jul. 14, 2016, and is 229 kb. The file can be accessed using Microsoft Word on a computer that uses Window OS.

BACKGROUND OF THE INVENTION

The invention relates to mutant microorganisms, such as algae and heterokonts, having increased lipid productivity and their use in producing lipids.

Many microorganisms such as algae, labyrinthulomycetes ("chytrids"), and oleaginous yeast induce lipid biosynthesis in response to nutrient stress, for example nitrogen starvation. Under conditions of nitrogen depletion, such microorganisms redirect compound biosynthesis from protein to storage lipids, typically triacylglyceride lipids ("TAG"). Because nitrogen depletion simultaneously decreases cell growth, optimal lipid biosynthesis is limited to a relatively short window before the cells become too metabolically impaired to maintain high levels of production.

Microalgal-derived biodiesel has long been considered a viable alternative to conventional petroleum-based fuels. However, despite decades of biological research, depriving strains of essential macronutrients such as nitrogen, phosphorous, or silicon, to obtain high lipid yields—conditions under which growth of the host microorganism is compromised—remains the modus operandi. Little progress has been made in engineering algal strains to accumulate lipid while maintaining growth as there is only nascent understanding of the regulation of metabolism underlying lipid accumulation (Courchesne et al. (2009) *J. Biotechnol.* 141: 31-41; Goncalves et al. (2016) *Plant Biotechnol. J.* doi:1111/12523).

Various attempts to improve lipid productivity by increasing lipid biosynthesis during nutrient replete growth have focused on manipulating genes encoding enzymes for nitrogen assimilation or lipid metabolism as well as genes encoding polypeptides involved in lipid storage. For example, US2014/0162330 discloses a *Phaeodactylum tricornutum* strain in which the nitrate reductase (NR) gene has been attenuated by RNAi-based knockdown; Trentacoste et al. ((2013) *Proc. Natl. Acad. Sci. USA* 110: 19748-19753) disclose diatoms transformed with an RNAi construct targeting the Thaps3_264297 gene predicted to be involved in lipid catabolism; and WO2011127118 discloses transformation of *Chlamydomonas* with genes encoding oleosins (lipid storage protein) as well as with genes encoding diacylglycerol transferase (DGAT) genes. Although in each case increased lipid production was asserted based on microscopy or staining with lipophilic dyes, no quantitation of lipid by the manipulated cells was provided, nor was the relationship between biomass and lipid productivities over time determined.

WO 2011/097261 and US 2012/0322157 report that a gene denoted "SNO3" encoding an arrestin protein has a role in increasing lipid production under nutrient replete conditions when overexpressed in *Chlamydomonas*. However, overexpression of the SNO3 gene was observed to result in the appearance of unidentified polar lipids, which were not quantified, and did not result in an increase in triglycerides (TAG). Another polypeptide identified as potentially regulating stress-induced lipid biosynthesis has been described by Boyle et al. ((2012) *J. Biol. Chem.* 287:15811-15825). Knockout of the NRR1 gene in *Chlamydomonas* encoding a "SQUAMOUSA" domain polypeptide resulted in a reduction of lipid biosynthesis with respect to wild type cells under nitrogen depletion; however, no mutants were obtained demonstrating increased lipid production. US 2010/0255550 recommends the overexpression of putative transcription factors ("TF1, TF2, TF3, TF4, and TF5") in algal cells to increase lipid production, but no mutants having enhanced lipid production are disclosed.

Daboussi et al. 2014 (*Nature Comm.* 5:3881) report that disruption of the UGPase gene in *Phaeodactylum triconornutum*, which is believed to provide precursors to laminarin (storage carbohydrate) synthesis, results in increased lipid accumulation. However, no biochemical data was shown to indicate that laminarin content was affected and lipid and biomass productivities were not reported. Similarly, several groups have reported increases in lipid accumulation in *Chlamydomonas* starchless mutants (Wang et al. 2009 *Eukaryotic Cell* 8:1856-1868; Li et al. 2010 *Metab Eng.* 12:387-391) but successive reports that actually measured lipid productivity concluded that these strains were impaired in growth when grown in phototrophic conditions (Siaut et al. 2011 *BMC Biotechnol.* 11: 7; Davey et al. 2014 *Eukaryot Cell* 13:392-400). These reports concluded that the highest lipid productivities (measured as TAG per liter per day) were actually achieved by the wild-type parental strain.

SUMMARY OF THE INVENTION

Algal mutants having elevated levels of constitutive lipid production are provided herein. As demonstrated in the examples, analysis of early transcriptional profiles of *Nannochloropsis gaditana* to N-deprivation revealed a novel negative regulator of lipid biosynthesis ZnCys-2845, a transcription factor of the fungal Zn(II)2Cys6 gene family. Using Cas9-mediated mutagenesis and RNAi technology, attenuated ZnCys strains were produced that were capable of partitioning approximately 45% of their total carbon content to lipids and of sustaining growth in a continuous growth system, resulting in a doubling of lipid productivity.

A first aspect of the invention is a mutant microorganism that produces at least 25% more lipid than is produced by a control microorganism while producing not less than 45% of the biomass produced by the control microorganism cultured under the same conditions, in which the culture conditions support production of biomass by the control microorganism. For example, a mutant microorganism as provided herein can produce at least 30%, at least 40%, at least 50%, at least 60%, at least 70%, at least 80%, at least 90%, or at least 100% more lipid than is produced by a control microorganism cultured under the same conditions as the mutant microorganism, which can be batch, semi-continuous, or continuous culture conditions, and in various embodiments are culture conditions in which the control microorganism accumulates biomass. The control microorganism can be, in some examples, a wild type microorganism, i.e., a wild type microorganism from which the mutant microorganism is directly or indirectly derived. The mutant microorganism can produce, in various embodiments, at least about 50% of the biomass and at least about 50%, at least 55%, at least 60%, at least 70%, at least 75%, at least 80%, at least 85%, at least 90%, at least 95%, at least 100%, at least 110%, or at least 120% more lipid than is produced by a control microorganism cultured under the same conditions, where the control microorganism produces biomass, for example, produces biomass over the course of the culture or on a daily basis, under the culture conditions in which the mutant produces more lipid. In various examples a mutant microorganism as provided herein produces at least 50% of the biomass and at least 130%, at least 150%, at least 140%, at least 155%, at least 160%, at least 170%, at least 175%, at least 180%, at least 185%, at least 190%, at least 195%, at least 200%, at least 210%, or at least 215% of the amount of lipid produced by a wild type microorganism cultured under the same conditions, under which the wild type microorganism accumulates biomass. For example, the culture conditions can be nitrogen-replete with respect to the control or wild type microorganism.

A mutant microorganism as provided herein can produce at least 25% more FAME lipids than a control or wild type microorganism while producing at least 45% or at least about 50% as much biomass as the control or wild type microorganism over a culture period of at least three days, at least five days, at least seven days, at least eight days, at least ten days, at least twelve days, at least fifteen days, at least twenty days, at least thirty days, or at least sixty days. For example, the average daily FAME productivity can be at least 50% greater than that of a control or wild type microorganism while the average daily biomass (e.g., TOC) productivity can be at least 45% or at least about 50% that of the control or wild type microorganism over a culture period of at least three days, at least five days, at least seven days, at least ten days, at least twelve days, at least fifteen days, at least twenty days, at least thirty days, or at least sixty days. In particular examples, a mutant microorganism as provided herein can produce at least 50% more FAME lipids than a control or wild type microorganism while producing at least 60% as much biomass as the control microorganism over a culture period of at least seven days, at least eight days, or at least ten days where the daily amount of FAME produced by the mutant is not lower than the daily amount of FAME produced by the control or wild type microorganism on any day during the at least seven, at least eight, or at least ten day culture period. In further examples, the average daily FAME productivity of a mutant microorganism as provided herein can be at least 50% higher that the average daily FAME productivity of a control or wild type microorganism the average daily biomass productivity can be at least 50% of the average daily biomass productivity of the control microorganism over a culture period of at least seven days, at least eight days, or at least ten days where the daily amount of FAME produced by the mutant is not lower than the daily amount of FAME produced by the control or wild type microorganism on any day during the at least seven, at least eight, or at least ten day culture period.

For example, a mutant microorganism as provided herein can produce more FAME-derivatizable lipids ("FAME lipids" or "FAME") than a control microorganism while producing not less than 45% of the biomass produced by the control microorganism, when the mutant microorganism and control microorganism are cultured under the same culture conditions under which the control microorganism produces biomass. A mutant microorganism as provided herein can have greater average daily FAME productivity than a control microorganism while exhibiting at least 45% of the average daily biomass productivity of the control microorganism, when the mutant microorganism and control microorganism are cultured under the same culture conditions under which the control microorganism produces biomass. In various examples, a mutant microorganism as provided herein produces at least 50% more FAME lipids while producing not less than about 50%, not less than about 60%, or not less than about 70% of the biomass produced by the control microorganism, when the mutant microorganism and control microorganism are cultured under the same culture conditions under which the culture of the control microorganism produces biomass, which can be nitrogen-replete culture conditions with respect to the control microorganism. The control microorganism in various embodiments can be a wild type microorganism, e.g., a wild type microorganism from which the mutant microorganism is directly or indirectly derived.

In some examples, the culture conditions under which the mutant produces more lipid than a control or wild type microorganism can be culture conditions in which the concentration of ammonium in the culture medium is less than about 2.5 mM, for example, less than about 2 mM, less than about 1.5 mM, less than about 1 mM, or less than or equal to about 0.5 mM. In some examples the culture medium can include no added ammonium or substantially no ammonium. In some examples, the culture medium can include no added source of reduced nitrogen for the microorganism, e.g., no added ammonium, urea, or amino acids that can be metabolized by the microorganism. The culture medium can in some examples include a nitrogen source such as, but not limited to, nitrate. Alternatively or in addition, the culture medium can include urea. In some examples, the culture medium is nutrient replete with respect to a wild type microorganism of the species from which the mutant microorganism is derived.

In various embodiments, the mutant microorganism can be a photosynthetic microorganism and the mutant microorganism can produce at least 25% more FAME lipids than a control microorganism while producing at least 45%, at least 50%, at least 60%, at least 70%, at least 80%, at least 90% or at least 95% the amount of biomass as a control or wild type microorganism under photoautotrophic culture conditions. For example a mutant microorganism as provided herein can be an alga, such as a eukaryotic microalga, and can produce at least 25% more FAME lipids than a control or wild type microorganism while producing at least 45%, at least 50%, at least 60%, at least 70%, at least 80%, at least 90% or at least 95% the amount of biomass as a control microorganism when both the control microorganism are cultured using inorganic carbon as substantially the sole source of carbon in the cultures. The control microorganism can be, for example, a wild type microorganism.

Culture conditions in which a mutant microorganism as provided herein can produce more FAME lipids than a control or wild type microorganism while producing at least 45%, at least 50%, at least 60%, at least 70%, at least 80%, at least 90% or at least 95% the amount of biomass as a control or wild type microorganism include any of batch, continuous, or semi-continuous culture conditions in which the control or wild type microorganism produces biomass. In various embodiments, a mutant microorganism as provided herein can produce at least 50% more FAME lipids than a control or wild type microorganism while producing at least 45%, at least about 50%, at least 55%, at least 60%, at least 65%, at least 70%, at least 75%, at least 80%, at least 85%, at least 90%, or at least 95% as much biomass as the control or wild type microorganism over a culture period of at least three days, at least four days, at least five days, at least seven days, at least eight days, at least ten days, or at least twelve days. In some embodiments the average daily FAME productivity of a mutant microorganism is at least 50% more than that of a control or wild type microorganism while the average daily biomass productivity (e.g., TOC productivity) is at least 45%, at least about 50%, at least 55%, at least 60%, at least 65%, at least 70%, at least 75%, at least 80%, at least 85%, at least 90%, or at least 95% as great as that of the control or wild type microorganism over the culture period, for example, over a culture period of at least three days, at least four days, at least five days, at least seven days, at least ten days, or at least twelve days.

In some examples, a mutant microorganism as provided herein can produce at least 50% more FAME lipids while producing at least about 75% of the amount of biomass produced by a wild type or control microorganism during a culture period of at least three, at least four, at least five, at least six, at least seven, at least eight, at least nine, at least ten, at least eleven, at least twelve, or at least thirteen days, for example, over a culture period of at least five, at least ten, at least fifteen, at least twenty, or at least thirty days where the mutant and control microorganism are cultured under the same conditions, under which both the mutant and control microorganisms produce biomass. For example, a mutant microorganism can demonstrate at least 60%, at least 70%, at least 80%, at least 90%, at least 100%, or at least 110%, or at least 120% higher FAME productivity and exhibit no more than a 35%, 30%, 25%, 20%, 15%, 10%, 5%, 2%, or 1% decline in biomass (e.g., TOC) productivity with respect to a wild type or control microorganism cultured for at least five, at least six, at least seven, or at least eight days under conditions in which both the control and mutant microorganism cultures produce biomass. For example, the average daily FAME productivity of a mutant as provided herein can be at least 60%, at least 70%, at least 80%, at least 90%, at least 100%, or at least 110% more than that of a wild type or control microorganism and the average daily biomass (e.g., TOC) productivity can be at least about 50%, at least about 60%, at least about 70%, or at least about 80% of the average daily biomass productivity of the control microorganism under conditions in which both the control and mutant microorganism cultures are producing biomass. In various embodiments, the average daily FAME productivity of a mutant as provided herein can be at least 60%, at least 70%, at least 80%, at least 90%, at least 100%, or at least 110% more than that of a wild type or control microorganism and the average daily biomass (e.g., TOC) productivity can be at least about 50%, at least about 60%, at least about 70%, or at least about 80% of the average daily biomass productivity of the control microorganism under conditions in which both the control and mutant microorganism cultures are producing biomass on a daily basis. In some examples, a mutant microorganism can produce at least 100% more or at least 120% more FAME lipids than a wild type or control microorganism while producing at least about 75% or at least about 80% of the biomass produced by a control type microorganism cultured under identical conditions which are nitrogen replete with respect to the control microorganism. In other examples a mutant microorganism can produce at least 75%, at least 80%, at least 85% more FAME lipids than a wild type or control microorganism while producing approximately as much biomass as is produced by a wild type microorganism cultured under identical conditions under which the wild type or control microorganism produces biomass, e.g., within 10% or within 5% of the amount of biomass produced by the control microorganism. In various examples, the average daily FAME productivity for at least three, at least four, at least five, at least six, at least seven, at least eight, at least nine, at least ten, at least eleven, at least twelve, or at least thirteen days of culturing, for example, at least five, at least ten, at least fifteen, at least twenty, or at least thirty days of culturing can be at least 80% greater than the average daily FAME productivity of a wild type or control microorganism and the average daily biomass productivity can be substantially the same as that of a control or wild type microorganism cultured under identical conditions under which the wild type or control microorganism produces biomass, e.g., within 10%, within 5%, or within 2% of the biomass productivity of the control microorganism. The conditions in which a mutant microorganism produces at least 80% more FAME lipids than a wild type or control microorganism while producing at least as much biomass as produced by a wild type microorganism can be nutrient replete with respect to the wild type or control microorganism, and can be nitrogen replete with respect to the wild type or control microorganism. In various embodiments the mutant microorganism can be a photosynthetic microorganism, e.g., an alga, and the culture conditions under which the mutant alga has greater FAME productivity while producing at least 50% of the TOC as a control microorganism are photoautotrophic conditions.

A mutant microorganism as provided herein can have a FAME lipids (FAME) to total organic carbon (TOC) ratio at least 30% higher than the FAME/TOC ratio of the control microorganism under culture conditions in which the mutant microorganism produces at least 45% more FAME lipids and at least 50% as much biomass as the control microorganism. The FAME/TOC ratio of a mutant microorganism as provided herein can be, for example, at least 30% higher, at least 40% higher, at least 50% higher, at least 60% higher, at least 70% higher, at least 80% higher, at least 90% higher, at least 100% higher, at least 110% higher, at least 120% higher, at least 130% higher, at least 140% higher, at least 150% higher, or at least 200% higher than the FAME/TOC ratio of a control or wild type microorganism cultured under identical conditions under which the control or wild type organism produces biomass, which may be nitrogen replete with respect to the wild type microorganism. In various embodiments, the FAME/TOC ratio of the mutant is at least 0.3, at least 0.4, at least 0.5, at least 0.6, at least 0.7, or at least 0.8 while the mutant microorganism culture is accumulating TOC. For example, a mutant microorganism as provided herein can have at least 25% higher lipid productivity than a control microorganism while exhibiting not less than 45% or not less than about 50% of the average daily biomass productivity of the control microorganism, and can further have FAME lipids (FAME)/total organic carbon (TOC) ratios at least 30%, at least 50%, at least 70%, or at least 90% higher than the FAME/TOC ratio of a wild type microorganism, for at least three, at least four, at least five, at least six, at least seven, at least eight, at least nine, at least ten, at least eleven, at least twelve, at least thirteen, at least fifteen, at least twenty, at least twenty-five, at least thirty, or at least sixty days of culturing, when the mutant microorganism and control microorganism are cultured under the same culture conditions in which both the mutant microorganism and control microorganism accumulate biomass, e.g., accumulate biomass on a daily basis. In various embodiments, the FAME/TOC ratio of the mutant is at least 0.3, at least 0.4, at least 0.5, at least 0.6, at least 0.7, at least 0.8, or between about 0.35 and 0.85, or between about 0.4 and about 0.8 while the mutant microorganism produces at least 50% of the TOC produced by the control microorganism over a period of at least three, at least four, at least five, at least six, at least seven, at least eight, at least nine, at least ten, at least eleven, at least twelve, at least thirteen, at least fifteen, at least twenty, at least twenty-five, at least thirty, or at least sixty days of culturing, where the mutant and control microorganism are cultured under the same conditions and the mutant produces more lipid than the control microorganism, and both the mutant microorganism and the control microorganism produce biomass.

Thus, a further aspect of the invention is a mutant microorganism that exhibits a higher FAME/TOC ratio than is exhibited by a control microorganism when both the mutant microorganism and control microorganism are cultured under substantially identical conditions under which both the mutant microorganism and the control microorganism culture are accumulating TOC. In various examples, a mutant microorganism has a higher FAME/TOC ratio than is exhibited by a control microorganism when the mutant microorganism and control microorganism are cultured under identical conditions under which both the control microorganism and the mutant microorganism produce biomass and the mutant microorganism culture produces at least about 50%, at least 60%, at least 70%, at least 80%, at least 90%, at least 95%, or about or substantially the same amount of TOC as the wild type microorganism culture. The FAME/TOC ratio of a mutant microorganism as provided herein can be, for example, at least 30% higher, at least 40% higher, at least 50% higher, at least 60% higher, at least 70% higher, at least 80% higher, at least 90% higher, at least 100% higher, at least 110% higher, at least 120% higher, at least 130% higher, at least 140% higher, or at least 150% higher than the FAME/TOC ratio of a control or wild type microorganism during a culture period in which the mutant microorganism produces at least about 50%, at least 60%, at least 70%, at least 80%, at least 90%, at least 95%, or substantially the same amount of TOC as the wild type microorganism culture. For example, the average daily biomass productivity of a mutant microorganism can be at least about 50%, at least 60%, at least 70%, at least 80%, at least 90%, at least 95%, that of a control or wild type microorganism culture, while having a FAME/TOC ratio at least 30% higher, at least 40% higher, at least 50% higher, at least 60% higher, at least 70% higher, at least 80% higher, at least 90% higher, at least 100% higher, at least 110% higher, at least 120% higher, at least 130% higher, at least 140% higher, or at least 150% higher than the FAME/TOC ratio of a control or wild type microorganism averaged over the same time period.

A mutant microorganism as provided herein, e.g., a mutant microorganism such as any described herein that produces at least about 50% of the biomass and at least about 50%, at least 55%, at least 60%, at least 70%, at least 75%, at least 80%, at least 85%, at least 90%, at least 95%, at least 100%, at least 110%, or at least 120% more lipid than is produced by a control microorganism cultured under the same conditions, where the conditions support biomass accumulation by the control microorganism, can have a higher carbon to nitrogen (C:N) ratio than a control microorganism. For example, the C:N ratio can be from about 1.5 to about 2.5 times the C:N ratio of a control microorganism when the mutant microorganism and the control microorganism are cultured under conditions in which both the mutant and the control microorganisms accumulate biomass, and the mutant produces at least 50%, at least 60%, at least 70%, at least 80%, at least 90% or at least 100% more lipid that the control microorganism and at least 50%, at least 60%, at least 70%, at least 80%, or at least 85% of the TOC of the control microorganism. A mutant microorganism as provided herein, e.g., a mutant microorganism such as any described herein that produces at least about 50% of the biomass and at least about 50%, at least 55%, at least 60%, at least 70%, at least 75%, at least 80%, at least 85%, at least 90%, at least 95%, at least 100%, at least 110%, or at least 120% more lipid than is produced by a control microorganism cultured under the same conditions, where the conditions support daily biomass accumulation by the control microorganism, can have a higher carbon to nitrogen (C:N) ratio than a control microorganism. For example, the C:N ratio can be from about 1.5 to about 2.5 times the C:N ratio of a control microorganism when the mutant microorganism and the control microorganism are cultured under conditions in which both the mutant and the control microorganisms accumulate biomass on a daily basis, and the mutant produces at least 50%, at least 60%, at least 70%, at least 80%, at least 90% or at least 100% more lipid that the control microorganism and at least 50%, at least 60%, at least 70%, at least 80%, or at least 85% of the TOC of the control microorganism. In some embodiments the C:N ratio of a mutant as provided herein is between about 7 and between about 20, or between about 8 and about 17, or between about 10 and about 15, during the culture period in which mutant produces at least 50% more lipid that a control microorganism while producing at least 50% as much biomass as the control microorganism. A control microorganism in any of the embodiments or examples herein can be a wild type microorganism.

Alternatively or in addition, mutant microorganism as provided herein, e.g., a mutant microorganism such as any described herein that produces at least about 50% of the biomass and at least about 50%, at least 55%, at least 60%, at least 70%, at least 75%, at least 80%, at least 85%, at least 90%, at least 95%, at least 100%, at least 110%, or at least 120% more lipid than is produced by a control microorganism cultured under the same conditions, where the conditions support biomass accumulation by the control microorganism (e.g. where the conditions support daily biomass accumulation by the control microorganism), can have reduced protein content when compared with a control microorganism. For example, a mutant microorganism as provided herein can have a decrease in protein content of at least 10%, at least 20%, at least 30%, at least 40%, at least 45%, or at least 50% with respect to a control microorganism. The mutant microorganism can partition at least 35%, at least 40%, or at least about 45% of its total carbon to lipid while producing at least 50% more lipid than a control microorganism under the same culture conditions in which the mutant microorganism produces at least 65%, at least 70%, at least 75%, at least 80% as much biomass as the control microorganism.

Further, a mutant microorganism such as any provided herein can in some embodiments have attenuated expression of a gene encoding a protein whose expression affects the expression of other genes, e.g., at least ten, at least twenty, at least thirty, at least forty, at least fifty, at least sixty, at least seventy, at least eighty, at least ninety, or at least 100 additional genes. For example, a mutant as provided herein can have at least ten genes that are upregulated with respect to a wild type microorganism and at least ten genes that are downregulated with respect to a wild type microorganism under conditions in which the mutant phenotype (as disclosed herein) is displayed. A mutant as provided herein can have at least twenty, at least thirty, at least forty, at least fifty, at least sixty, at least seventy, at least eighty, at least ninety, or at least 100 genes that are upregulated with respect to a wild type microorganism and at least twenty, at least thirty, at least forty, at least fifty, at least sixty, at least seventy, at least eighty, at least ninety, or at least 100 genes that are downregulated with respect to a wild type microorganism under conditions in which the mutant phenotype (e.g., greater lipid production with respect to the wild type microorganism) is expressed. In some embodiments, genes encoding polypeptides involved in protein synthesis can be upregulated in a mutant as provided herein, for example, genes encoding ribosomal polypeptides or other polypeptides that function in protein translation, including, without limitation, those belonging to gene ontology (GO) groups such as "translation", "ribosome", and/or "regulation of translation initiation". Alternatively to or in combination with the upregulation of genes encoding polypeptides relating to protein synthesis, one or more genes encoding polypeptides involved in nitrogen assimilation such as one or more of a nitrite reductase, glutamine synthetase, ammonium transporter and/or an enzyme involved in molybdenum cofactor biosynthesis can be downregulated in a mutant as provided herein. Alternatively or in combination with any of the above, a mutant as provided herein can exhibit upregulation of one or more genes related to lipid biosynthesis including but not limited to desaturases, elongases, lipid droplet surface protein, and/or particular lipases, acyltransferases, and glyceraldehyde-3-phosphate dehydrogenases.

A mutant as described herein can be a mutant obtained by classical mutagenesis or can be a genetically engineered mutant. In various embodiments, a mutant microorganism as disclosed herein has been generated by introducing one or more genetic constructs (one or more nucleic acid molecules) into the microorganism. In some examples, one or more genetic constructs introduced into a microorganism are designed to attenuate expression of a native gene.

In various examples, mutants as disclosed herein can have attenuated expression of a fungal type Zn(2)Cys(6) transcription factor, i.e., a gene encoding a polypeptide that has a Zn(2)Cys(6) domain, e.g., has an amino acid sequence encoding a cd00067 "GAL4" domain or a "Zn_clus" domain belonging to pfam PF00172. For example, a mutant microorganism such as any disclosed herein having FAME production that is increased by at least 25% and biomass production that is reduced by no more than 50% with respect to a control microorganism for at least 3, at least 5, at least 7, at least 10, at least 12, at least 13, at least 15, at least 20, at least 25, or at least 30 days of culturing can have attenuated expression of a gene encoding a polypeptide that recruits to pfam PF00172. Alternatively or in addition, a mutant microorganism such as any disclosed herein having a FAME/TOC ratio that is at least 30% higher than the FAME/TOC ratio of a control microorganism under conditions in which the control microorganism is producing biomass can be a mutant microorganism that has attenuated expression of a gene encoding a polypeptide having a Zn(2)Cys(6) domain, e.g., having an amino acid sequence encoding a domain belonging to pfam PF00172 or characterized as a cd00067 "GLA4" domain. In some examples, the Zn(2)Cys(6) domain can have at least 60%, at least 65%, at least 70%, at least 75%, at least 80%, at least 85%, at least 90%, or at least 95% identity to SEQ ID NO:3.

Thus, another aspect of the invention is mutant microorganism having attenuated expression of a gene encoding a polypeptide having a Zn(2)Cys(6) domain, wherein the mutant microorganism has increased partitioning of carbon to lipid with respect to a control microorganism that does not have attenuated expression of the gene encoding a polypeptide having a ZnCys domain. For example, a mutant microorganism as provided herein having attenuated expression of a polypeptide having a Zn(2)Cys(6) domain can have an increased FAME/TOC ratio with respect to a control cell when the mutant microorganism and control microorganism are cultured under identical conditions under which the control microorganism culture experiences an increase in TOC. In some examples, a mutant microorganism as provided herein can have a FAME/TOC ratio that is increased by at least 30%, at least 40%, at least 50%, at least 60%, at least 70%, at least 80%, at least 90%, at least 100%, at least 110%, at least 120%, at least 130%, at least 140%, or at least 150% as compared to the FAME/TOC ratio of a control microorganism when the mutant microorganism and control microorganism are cultured under identical conditions under which the control microorganism culture experiences an increase in TOC. Alternatively or in addition, a mutant microorganism as provided herein having attenuated expression of a gene encoding a polypeptide having a Zn(2)Cys(6) domain can have increased production of FAME lipids with respect to a control microorganism while demonstrating no more than a 45% reduction in TOC production with respect to the control microorganism when the mutant microorganism and control microorganism are cultured under identical conditions under which the control microorganism experiences an increase in TOC. For example, a mutant microorganism as provided herein having attenuated expression of a gene encoding a polypeptide having a Zn(2)Cys(6) domain can produce at least 25% or at least 50% more FAME lipids or at least 75% more FAME lipids with respect to a control microorganism while demonstrating no more than a 50% reduction in TOC production with respect to the control microorganism when the mutant microorganism and control microorganism are cultured under identical conditions under which the control microorganism experiences an increase in TOC. In various embodiments the mutant microorganism can display higher lipid productivity and/or carbon partitioning to lipid over a culture period of at least 3, at least 5, at least 7, at least 10, at least 12 days, at least 13, at least 15, at least 20, or at least 30 days. For example, mutant microorganism can have higher lipid productivity each day of the at least 5, at least 7, at least 10, at least 12 days, at least 15, at least 20, or at least 30 day culture period.

In some exemplary embodiments the amino acid sequence of the polypeptide having a Zn(2)Cys(6) domain is at least 50%, at least 55%, at least 60%, at least 65%, at least 70%, at least 75%, at least 80%, at least 85%, at least 90%, or at least 95% identical to any of SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. In some examples, a mutant microorganism as provided herein can have attenuated expression of a gene encoding a polypeptide having at least 60%, at least 65%, at least 70%, at least 75%, at least 80%, at least 85%, at least 90%, or at least 95% identity to SEQ ID NO:2, SEQ ID NO:5, SEQ ID NO:8, SEQ ID NO:11, or SEQ ID NO:17. For example, a mutant microorganism as provided herein can have attenuated expression of a gene encoding a polypeptide having at least 60%, at least 65%, at least 70%, at least 75%, at least 80%, at least 85%, at least 90%, or at least 95% identity to SEQ ID NO:2 or SEQ ID NO:17, or at least the N-terminal 517 amino acids of SEQ ID NO:2 or the N-terminal 540 amino acids of SEQ ID NO:17. In further examples a mutant microorganism as provided herein has attenuated expression of a gene encoding a polypeptide that includes an amino acid sequence having at least 55%, at least 60%, at least 65%, at least 70%, at least 75%, at least 80%, at least 85%, at least 90%, or at least 95% identity to any of SEQ ID NO:2, SEQ ID NO:17, SEQ ID NO:18, or SEQ ID NO:19, or to amino acids 1-200 of SEQ ID NO:20. In some examples, a mutant microorganism as provided herein can have attenuated expression of a gene encoding a polypeptide having at least 60%, at least 65%, at least 70%, at least 75%, at least 80%, at least 85%, at least 90%, or at least 95% identity to SEQ ID NO:2 or SEQ ID NO:17. Alternatively or in addition, a mutant microorganism as provided herein can have attenuated expression of a gene having a coding sequence with at least 50%, at least 55%, at least 60%, at least 65%, at least 70%, at least 75%, at least 80%, at least 85%, at least 90%, or at least 95% identity to SEQ ID NO:1 or any of SEQ ID NOs:72-84. In various embodiments the microorganism is a diatom or eustigmatophyte alga, and in some examples may be a species of *Nannochloropsis*.

Alternatively or in addition to any of the above, a mutant microorganism as provided herein can have attenuated expression of a gene encoding a polypeptide that has a Zn(2)Cys(6) domain and further includes a PAS3 domain. In some examples the PAS3 domain comprises an amino acid sequence having at least 50%, at least 55%, at least 60%, at least 65%, at least 70%, at least 75%, at least 80%, at least 85%, at least 90%, or at least 95% identity to any of SEQ ID NOs:21-25. The gene whose expression is attenuated can additionally encoding a polypeptide that further includes an amino acid sequence having at least 50%, at least 55%, at least 60%, at least 65%, at least 70%, at least 75%, at least 80%, at least 85%, at least 90%, or at least 95% identity to at least 200 amino acids of any of SEQ ID NOs:18-20.

An attenuated gene encoding a polypeptide having a Zn(2)Cys(6) domain can be a gene that has an insertion, deletion, and/or one or more base changes with respect to the wild type gene. The insertion, deletion, or one or more base changes can be in a coding region, intron, 3' untranslated region, or 5' untranslated region of the gene, or can be upstream of the 5' untranslated region of the gene, e.g., in the promoter region of a gene, where the mutant produces less of an RNA corresponding to the gene and/or produces less of the encoded polypeptide. Alternatively or in addition, a mutant microorganism as provided herein can include an antisense construct, an RNAi construct, a guide RNA (gRNA) as part of a CRISPR system, or a ribozyme that targets the gene encoding the polypeptide having a Zn(2)Cys(6) domain, resulting in reduced expression of the gene.

A mutant microorganism as provided herein can be any eukaryotic microorganism, and in some examples is a heterokont or alga. For example, the mutant microorganism can be a *Labyrinthulomycte* species, such as, for example, a species of *Labryinthula, Labryinthuloides, Thraustochytrium, Schizochytrium, Aplanochytrium, Aurantiochytrium, Oblongichytrium, Japonochytrium, Diplophrys,* or *Ulkenia*. Alternatively a mutant microorganism can be an algal species such as for example, a species belonging to any of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Ehpsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phæodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox*. In some embodiments a mutant microorganism is a diatom or eustigmatophyte alga. In some embodiments the mutant microorganism is a species of *Nannochloropsis*.

A further aspect of the invention is a method of producing lipid, comprising culturing a mutant microorganism as provided herein and isolating lipid from the microorganism, the culture medium, or both. The mutant microorganism can be cultured in a medium that comprises less than about 5 mM ammonium, less than about 2.5 mM ammonium, less than or equal to about 1 mM ammonium, or less than or equal to about 0.5 mM. The culture medium can include, for example, from about 0 to about 2.5 mM ammonium, from about 0.1 to about 2.5 mM ammonium, from about 0.5 to about 2.5 mM ammonium, from about 0 to about 1 mM ammonium, from about 0.1 to about 1 mM ammonium, or from about 0.2 to about 1 mM ammonium. The microorganism can be cultured in a medium that includes nitrate, which in some examples may be substantially the sole nitrogen source in the culture medium or may be present in addition to ammonium that may be present at a concentration of less than 5 mM, less than 2.5 mM, less than 2 mM, or less than 1 mM. Alternatively or in addition, the culture medium can comprise urea, which in some examples can be substantially the sole source of nitrogen in the culture medium. The mutant microorganism can be cultured under batch, continuous, or semi-continuous mode. The mutant microorganism can in some embodiments be a photosynthetic microorganism, e.g. and alga, and can be cultured photoautotrophically.

Yet another aspect of the invention is a method of producing lipid that includes culturing a microorganism under conditions in which the FAME to TOC ratio of the microorganism is maintained between about 0.3 and about 0.8, and isolating lipid from the microorganism, the culture medium, or both. For example, the microorganisms can be cultured such that the FAME to TOC ratio is maintained at between about 0.3 and about 0.8, between about 0.4 and about 0.7, between about 0.4 and about 0.6, or between about 0.45 and about 0.55. The ratio can be maintained at between about 0.3 and about 0.8, for example between about 0.4 and about 0.8, between about 0.4 and about 0.7, between about 0.4 and about 0.6, or between about 0.45 and about 0.55 for at least 3, at least 4, at least 5, at least 6, at least 7, at least 8, at least 9, at least 10, at least 11, at least 12, at least 13, at least 15, at least 20, at least 30 days, or at least 60 days. The microorganism can be cultured under batch, continuous, or semi-continuous mode. The method of producing lipid can include culturing a mutant microorganism such as any provided herein under conditions in which the FAME to TOC ratio of the microorganism is maintained between about 0.3 and about 0.8, between about 0.3 and about 0.8, between about 0.4 and about 0.7, between about 0.4 and about 0.6, or between about 0.45 and about 0.55. For example, the microorganism can be a mutant microorganism having attenuated expression of a Zn(2)Cys(6) regulator gene, such as but not limited to a gene encoding a polypeptide having at least 55%, at least 65%, at least 75%, or at least 85% identity to a polypeptide comprising an amino acid sequence selected from the group consisting of SEQ ID NO:2 and SEQ ID NOs:5-17. Alternatively or in addition, the microorganism can be a mutant microorganism having attenuated expression of a gene that has a coding sequence having at least 50%, at least 55%, at least 60%, least 65%, at least 70%, at least 75%, at least 80%, at least 85% at least 90%, or at least 95% identity to SEQ ID NO:1 or any of SEQ ID NOs:71-84. In any of the above methods for producing lipid, the mutant microorganism can be an alga, and the culturing can be under photoautotrophic conditions, i.e., conditions in which inorganic carbon is substantially the sole carbon source in the culture medium.

Yet another aspect of the invention is a nucleic acid molecule comprising a nucleic acid sequence encoding a polypeptide including an amino acid sequence having at least 50%, at least 55%, at least 60%, at least 65%, at least 70%, or at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. The polypeptide having at least 60% identity to a nucleic acid sequence selected from the group consisting of SEQ ID NO:2 and SEQ ID NOs:5-17 can include an amino acid sequence encoding a Zn(2)Cys(6) domain. The nucleic acid molecule in various examples can be or comprise a cDNA that lacks one or more introns present in the naturally-occurring gene, or, alternatively, can include one or more introns not present in the naturally-occurring gene. The nucleic acid molecule in various examples can have a sequence that is not 100% identical to a naturally-occurring gene. The nucleic acid molecule in various examples can comprise a heterologous promoter operably linked to the sequence encoding a polypeptide that includes an amino acid sequence having at least 50%, at least 55%, at least 60%, at least 65%, at least 70%, or at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17 and/or can comprise a vector that includes a sequence encoding a polypeptide that includes an amino acid sequence having at least 50%, at least 55%, at least 60%, at least 65%, at least 70%, or at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

A further aspect of the invention is a construct designed for attenuating expression of a gene encoding a polypeptide containing a Zn(2)Cys(6) domain. The construct can be or comprise, in various examples, a sequence encoding a guide RNA of a CRISPR system, an RNAi construct, an antisense construct, a ribozyme construct, or a construct for homologous recombination, e.g., a construct having one or more nucleotide sequences having homology to a naturally-occurring Zn(2)Cys(6) domain-encoding gene as disclosed herein and/or sequences adjacent thereto in the native genome from which the gene is derived. For example, the construct can include at least a portion of a gene encoding a polypeptide having a Zn(2)Cys(6) domain, e.g., a sequence homologous to at least a portion of an gene that encodes a polypeptide that includes an amino acid sequence having at least 50%, at least 55%, at least 60%, at least 65%, at least 70%, or at least 75%, at least 80%, at least 85%, at least 90%, or at least 95% identity to SEQ ID NO:2, SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. Alternatively or in addition, the construct can include a sequence having at least 50%, at least 55%, at least 60%, least 65%, at least 70%, at least 75%, at least 80%, at least 85% at least 90%, or at least 95% identity to SEQ ID NO:1 or any of SEQ ID NOs:71-84.

The construct can include, for example, at least a portion of the coding region of a gene encoding a polypeptide having a Zn(2)Cys(6) domain, at least a portion of an intron of a gene encoding a polypeptide having a Zn(2)Cys(6) domain, at least a portion of a 5'UTR of a gene encoding a polypeptide having a Zn(2)Cys(6) domain, at least a portion of the promoter region of a gene encoding a polypeptide having a Zn(2)Cys(6) domain, and/or at least a portion of a 3' UTR of a gene encoding a polypeptide having a Zn(2)Cys(6) domain. In some examples, the construct can be an RNAi, ribozyme, or antisense construct and can include a sequence from the transcribed region of the gene encoding a polypeptide having a Zn(2)Cys(6) domain in either sense or antisense orientation. In further examples a construct can be designed for the in vitro or in vivo expression of a guide RNA (e.g., of a CRISPR system) designed to target a gene encoding a polypeptide having a Zn(2)Cys(6) domain, and can include a sequence homologous to a portion of a gene encoding a polypeptide having a Zn(2)Cys(6) domain, including, for example, an intron, a 5'UTR, a promoter region, and/or a 3' UTR of a gene encoding a polypeptide having a Zn(2)Cys(6) domain. In yet further examples, a construct for attenuating expression a gene encoding a Zn(2)Cys(6) domain-containing polypeptide can be a guide RNA of a CRISPR system or a CRISPRi system or can be an anti sense oligonucleotide, where the sequence having homology to a transcribed region of a gene encoding a polypeptide having a Zn(2)Cys(6) domain is in antisense orientation.

These and other objects and features of the invention will become more fully apparent when the following detailed description of the invention is read in conjunction with the accompanying drawings.

BRIEF DESCRIPTION OF THE DRAWINGS

FIG. 3A-3C, A) provides a map of the vector used in to generate the Cas9 expression strain Ng-CAS9+ in *Nanno-*

*chloropsis*; B) is an overlayed histogram from the Accuri C6 flow cytometer showing GFP fluorescence in the Ng-Cas9 editor strain (right peak, in red) compared to the wild type strain (left peak, in black); C) is an image of a western blot with an anti-FLAG antibody demonstrating Cas9 expression in the Ng-CAS9+ line, with no background in the wild type control.

FIG. 4A-4C, A) provides a diagram of the donor fragment used for gene disruption at Cas9 target sites. The donor fragment construct includes the HygR (hygromycin resistance) gene driven by the EIF3 promoter and followed by the GNPDA terminator in inverted orientation. B) Schematic representation of a Cas9-mediated insertion of the hygromycin resistance (HygR) cassette into the ZnCys locus. The HygR cassette consisted of a promoter (Prom) driving the HygR gene followed by a terminator (T). The resulting mutant genotype (ZnCys-KO) was identified by PCR using primers that flank the insertion (arrows). The diagram is not to scale. C) PCR genotyping of several Hyg resistant colonies transformed with a guide RNA designed to target the ZnCys locus. Presence of a 3 Kb band indicates insertion into the intended locus, while a 0.5 Kb band indicates an intact wild-type locus.

Figure 5:
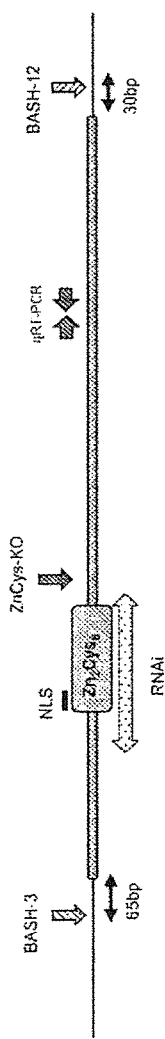

FIG. 5 is a schematic depiction of the *N. gaditana* ZnCys-2845 gene. A box denotes the position of the Zn(2)Cys(6) domain, which was the region targeted by the RNAi construct. Positions of insertions of the donor fragment in the BASH-3, knockout, and BASH-12 mutants are shown by arrows. The general location of the putative monopartite nuclear localization signal is also shown (NLS). The figure is not to scale.

FIG. 6A-6B, A) provides incident irradiance profiles for batch growth assessment B), and the Semi-continuous Productivity Assay.

FIG. 7A-7H, A) is a graph depicting FAME productivity of wild-type and ZnCys-2845 knockout *N. gaditana* cells cultured in batch mode in nitrate-only medium as determined from samples taken on odd days of the culture; B) is a graph depicting TOC productivities for days 3-7 of the batch productivity assay. C) is a graph depicting FAME/TOC ratios calculated from samples taken on odd days of the culture; D) is a bar graph depicting the amount of fatty acids of various chain lengths present in the lipid isolated on day 7 of the batch assay from wild type WT-3730 and ZnCys 2845 knockout strain GE-8564; E) is a bar graph depicting the level of TAG isolated from wild type and ZnCys 2845 knockout strain GE-8564 on day 7 of the batch assay; F) is an electron micrograph of a wild type *Nannochloropsis gaditana* cell cultured in nitrate-only (nitrogen-replete) culture medium, G) is an electron micrograph of a *Nannochloropsis gaditana* ZnCys knockout mutant GE-8564 cell cultured in nitrate-only culture medium, H) is an electron micrograph of a wild type *Nannochloropsis gaditana* cell cultured in nitrogen-deplete culture medium. Error bars in graphs represent the standard deviation for the average value of three cultures (biological replicates). Symbols used in graphs: asterisks represent wild type WT-3730 cultured in nitrate plus ammonium medium PM124, black diamonds represent knockout mutant GE-8564 cultured in nitrate plus ammonium medium PM124, X's represent wild type WT-3730 cultured in nitrate-only medium PM074, and black circles represent knockout mutant GE-8564 cultured in nitrate-only medium PM074. N: nucleus; Ch: chloroplast; LD: lipid droplet; M: mitochondrion.

FIG. 8A-8C, Provides graphs demonstrating repression of the lipid accumulation phenotype of ZnCys-KO by $NH_4^+$ supplementation in a five day batch mode assay. A) FAME (mg/L) per day, B) TOC (mg/L) per day, and C) FAME/TOC values per day of ZnCys-KO (circles) and WT (diamonds) grown in batch mode on medium supplemented with $NH_4^+$ ($SM-NH_4^+/NO_3^-$). Error bars are standard deviations of 2 biological replicates (n=2).

FIG. 9 is an alignment of the PAS3 domain sequences of *N. gaditana* ZnCys-2845 and the PAS3 domain sequences of the ZnCys-2845 orthologs of *N. oceanica, N. oculata, N. salina*, and *N. granulata*.

FIG. 10 is an alignment of the *N. gaditana* polypeptide sequence encoded by the ZnCys-2845 gene and the *N. oceanica* polypeptide sequence encoded by the ortholog of the ZnCys-2845 gene, as well as partial N-terminal sequences of polypeptides encoded by orthologous genes in *N. granulata, N. oculata*, and *N. salina*.

Figure 11A:
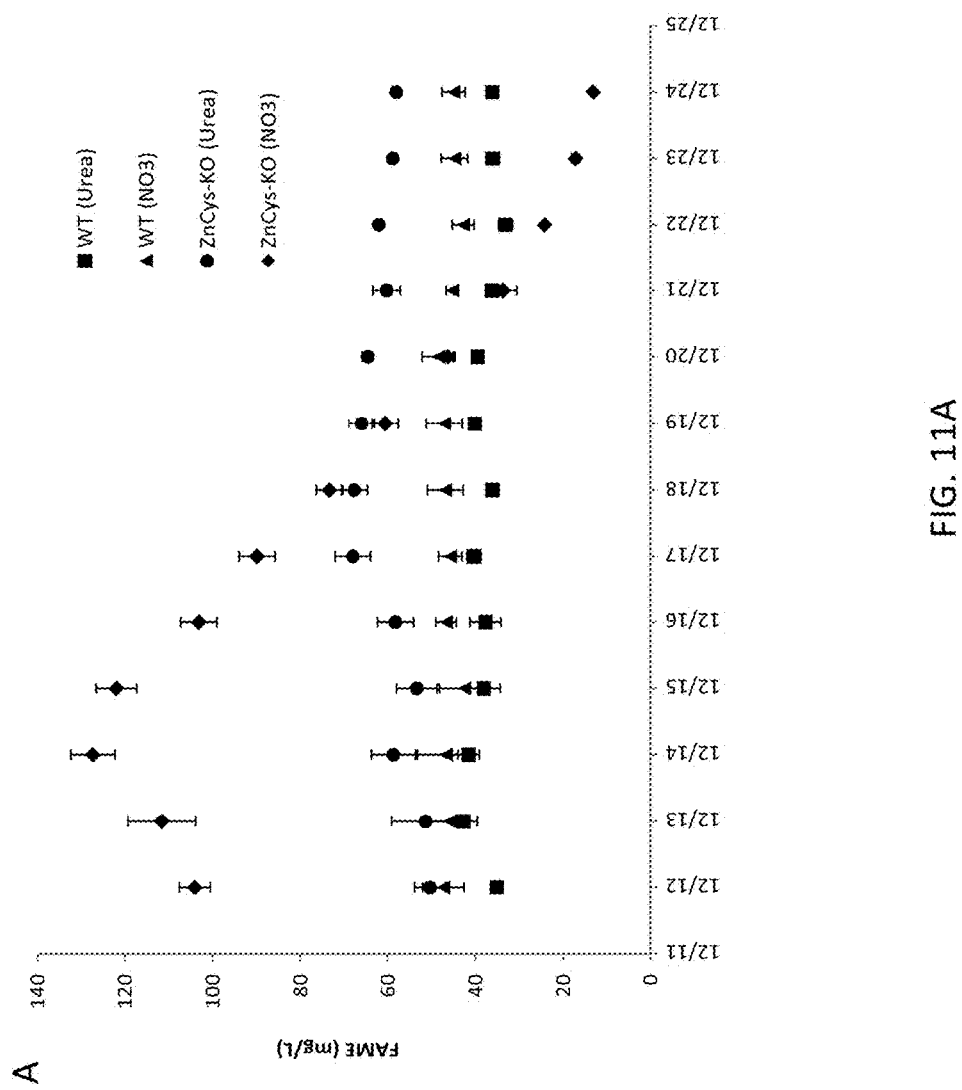
Figure 11B:
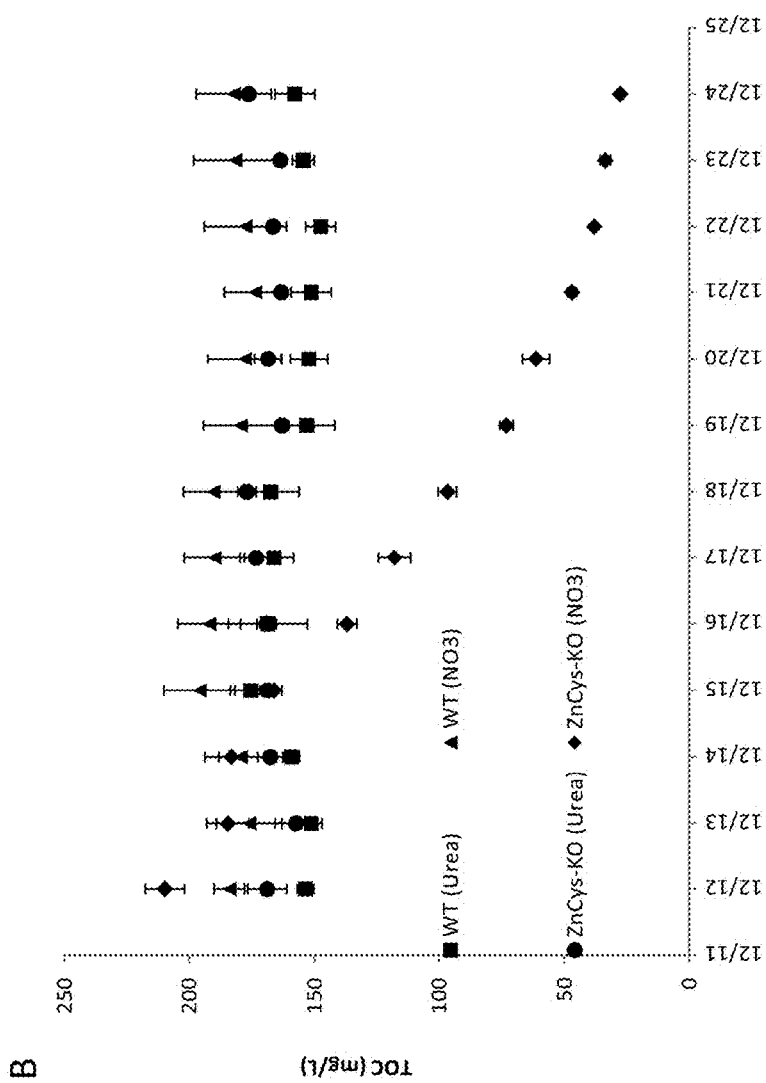
Figure 11C:
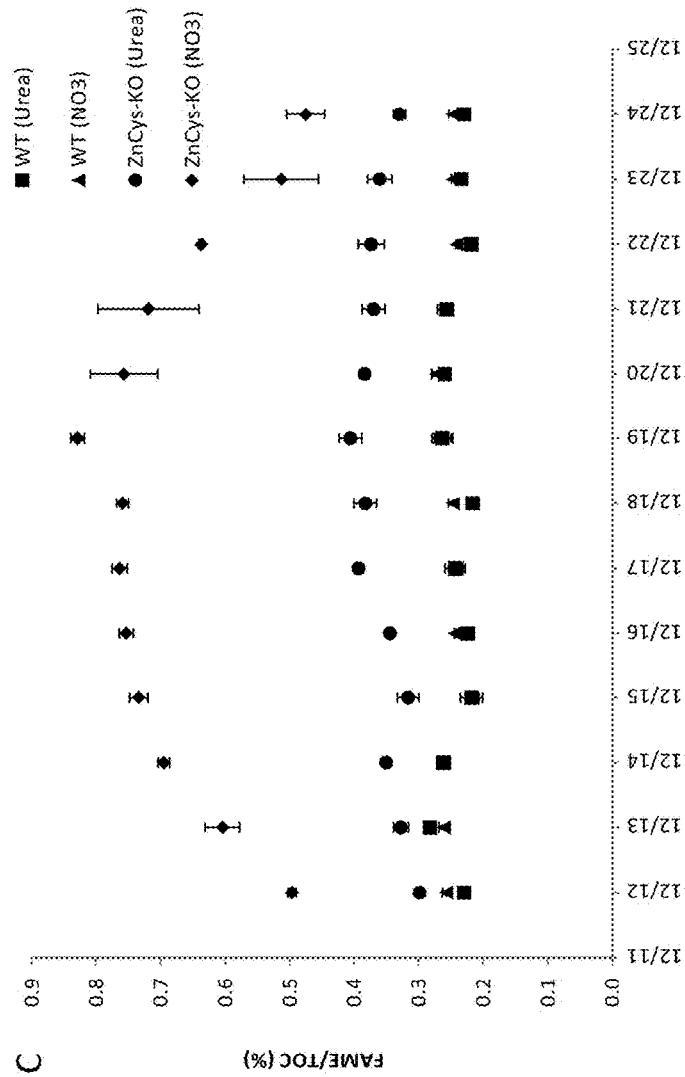

FIG. 11A-11C provides graphs depicting productivities of the *N. gaditana* wild type strain and GE-8564 knockout strain in a semi-continuous assay in which the culture medium includes urea as the sole nitrogen source. A) shows daily FAME productivity over thirteen days of the assay; B) shows daily TOC productivity over thirteen days of the assay; and C) provides the FAME/TOC ratios for each day of the assay. Error bars in graphs represent the standard deviation of the three independent cultures (biological replicates). Symbols used in graphs: squares represent wild type WT-3730 cultured in urea-only medium PM125, triangles represent wild type WT-3730 cultured in nitrate-only medium PM074, circles represent ZnCys-2845 knockout mutant GE-8564 cultured in urea-only medium PM125, and diamonds represent ZnCys-2845 knockout mutant GE-8564 cultured in nitrate-only medium PM074.

FIG. 12A-B A) is a schematic depiction of the ZnCys-2845 gene with the positions of the nuclear localization signal (NLS), Zn(2)Cys(6) domain (Zn) and PAS3 domain shown as boxes and arrows depicting the sites of CRISPR-targeted mutations, B) shows the relative transcript levels of the corresponding CRISPR-targeted mutants (position of primers used for transcript assessment shown in A). Normalized expression levels are relative to the average wild type level which was set to 1.0.

Figure 13A:
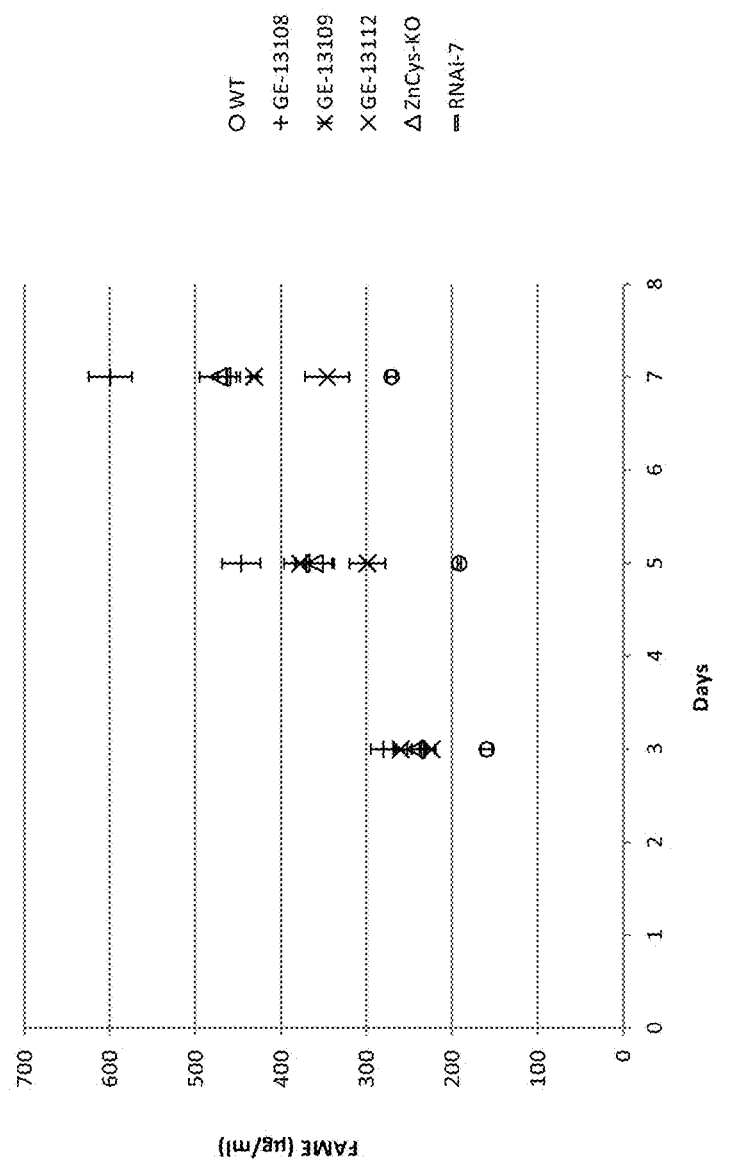
Figure 13B:
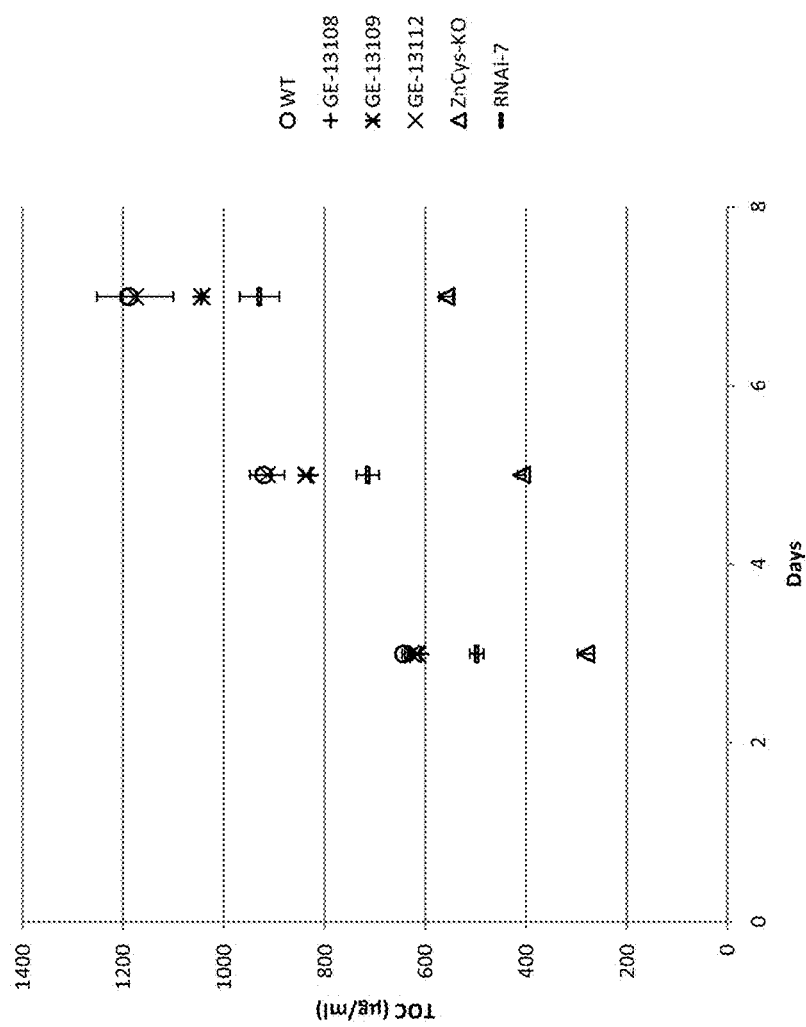
Figure 13C:
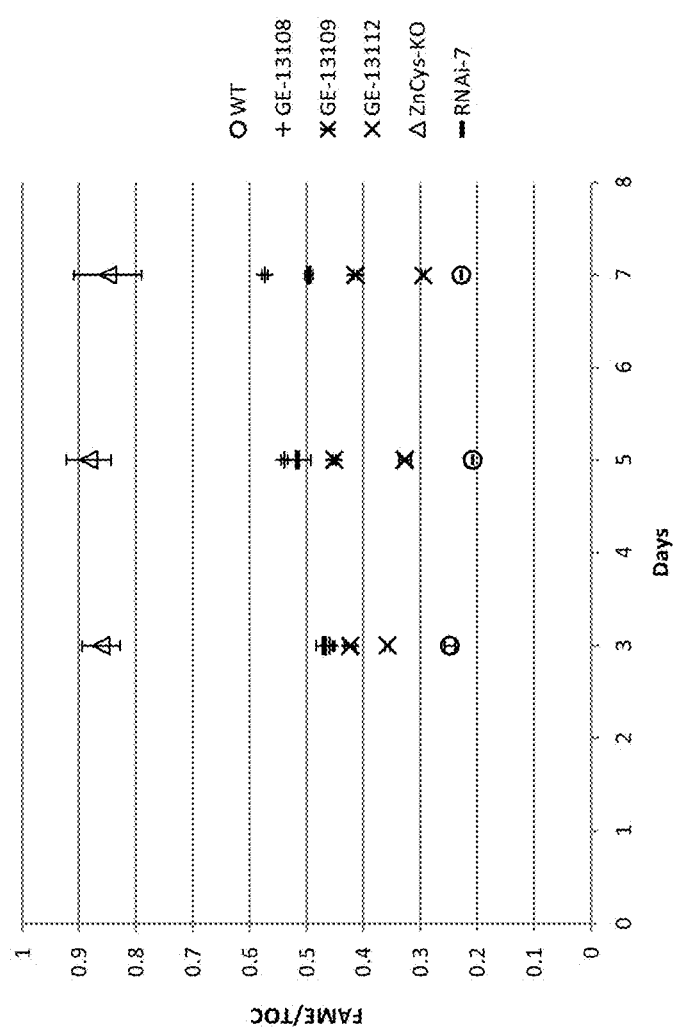

FIG. 13A-13C, A) is a graph depicting FAME productivity of wild-type and ZnCys-2845 knockdown *N. gaditana* cells cultured in batch mode in nitrate-only medium; B) is a graph depicting TOC values for the odd days of the screen (days 1-3 and days 3-5); C) is a graph providing FAME/TOC ratios of the cultures calculated on days 3, 5, and 7. Symbols used in graphs: open circles represent wild type WT-3730, a plus sign represents knockout mutant GE-13108, "BASH2"; an asterisk represents knockout mutant GE-13109, "BASH3"; Xs represent knockout mutant GE-13112, "BASH12"; open triangles represent ZnCys-2845 knockout mutant GE-8564; and dashes represent RNAi-7 strain GE-13103. The Error bars represent the standard deviation of two calculated productivity values of two separate cultures.

FIG. 14A-14C, A) provides the modular structure and salient features of the ZnCys locus. Abbreviations: NLS, nuclear localization sequence; $Zn_2Cys_6$, Zn(II)2Cys6 binuclear cluster domain (Pfam id: PF00172). The approximate location of the insertion in the original ZnCys-KO mutant is indicated with a black arrow. Patterned arrows indicate locations of successful Cas9 insertional mutants in putative 5'UTR (BASH-3 (strain GE-13109) ~65 bp from the predicted start site) and 3'UTR regions (BASH-12 (strain GE-13112), approximately 30 bp from the predicted stop codon). Black horizontal arrows show the approximate location of the qRT-PCR primers used for assessing gene expression levels in panel B. The RNAi hairpin designed to silence ZnCys spanned the conserved $Zn_2Cys_6$ domain was homologous to the sequence denoted by the dotted double arrow. The figure is not to scale. B) Steady-state mRNA levels of the ZnCys locus in attenuated ZnCys lines (left to right on graph, wild type (WT) ZnCys-BASH-3, ZnCys-BASH-12, ZnCys-RNAi-7, and ZnCys-KO) relative to wild type (WT) as determined by qRT-PCR (left to right on graph, wild type (WT) ZnCys-BASH-3, ZnCys-BASH-12, ZnCys-RNAi-7, and ZnCys-KO). Expression levels were normalized to a housekeeping gene and were calculated relative to WT using the $\Delta\Delta C_T$ method. Error bars are standard errors for 3 technical replicates. C) TOC productivity and FAME/TOC values of ZnCys mutant lines assessed in batch mode in nitrate-replete medium (SM-NO3-). Individual data points used to calculate FAME/TOC and biomass productivity averages are shown in FIG. 15. Error bars are standard deviations of two biological replicates.

FIG. 15A-15B, A) batch mode assessment of FAME (mg/L) produced by ZnCys attenuated lines (ZnCys-BASH-3 (GE-13109), ZnCys-BASH-12 (GE-13112), ZnCys-RNAi-7 (GE-13103)) grown in nitrate-replete medium and B) batch mode assessment of TOC (mg/L) measurements corresponding to days 3, 5 and 7 of the screen.

FIG. 16A-16D provides graphs and a table depicting productivities of the N. gaditana wild type strain and GE-8564 knockout strain in a semi-continuous assay in which the culture medium used for daily dilution includes nitrate as the sole nitrogen source. A) shows daily FAME productivity over thirteen days of the assay (mg/L culture); B) provides the daily productivities of the cultures in g/m2/day (standard deviation of three cultures provided in parentheses), along with the average daily productivity for each culture; C) shows daily TOC productivity over thirteen days of the assay (mg/L culture); and D) provides the FAME/TOC ratios for each day of the assay Symbols used in graphs: diamonds represent wild type WT-3730 pre-cultured in nitrate-only medium; Xs represent knockdown mutant GE-13108 "BASH2" pre-cultured in nitrate plus ammonium medium; triangles represent knockdown mutant GE-13109 "BASH3" pre-cultured in nitrate plus ammonium medium; squares represent knockdown mutant GE-13112 "BASH12" pre-cultured in nitrate plus ammonium medium; open circles represent knockdown mutant GE-13103 "RNAi-7" pre-cultured in nitrate plus ammonium medium; closed circles represent knockdown mutant GE-13103 "RNAi-7" pre-cultured in nitrate-only medium; and dashes represent knockout mutant GE-8564 pre-cultured in nitrate plus ammonium medium. Error bars in graphs represent the standard deviation of the three independent cultures (biological replicates).

FIG. 17A-17B. Productivity assessment of ZnCys mutants grown in semi-continuous mode for 8 days on $NO_3^-$-containing culture medium. A) Daily FAME and B) TOC (mg/L) measurements for ZnCys mutants (ZnCys-RNAi-7, ZnCys-BASH-12 and ZnCys-BASH-3) compared to their parental lines Ng-CAS9+ and WT. Cultures were grown in semi-continuous mode at a 30% daily dilution rate on $SM-NO_3^-$. Error bars represent standard deviations for 3 biological replicates (n=3).

Figure 18:
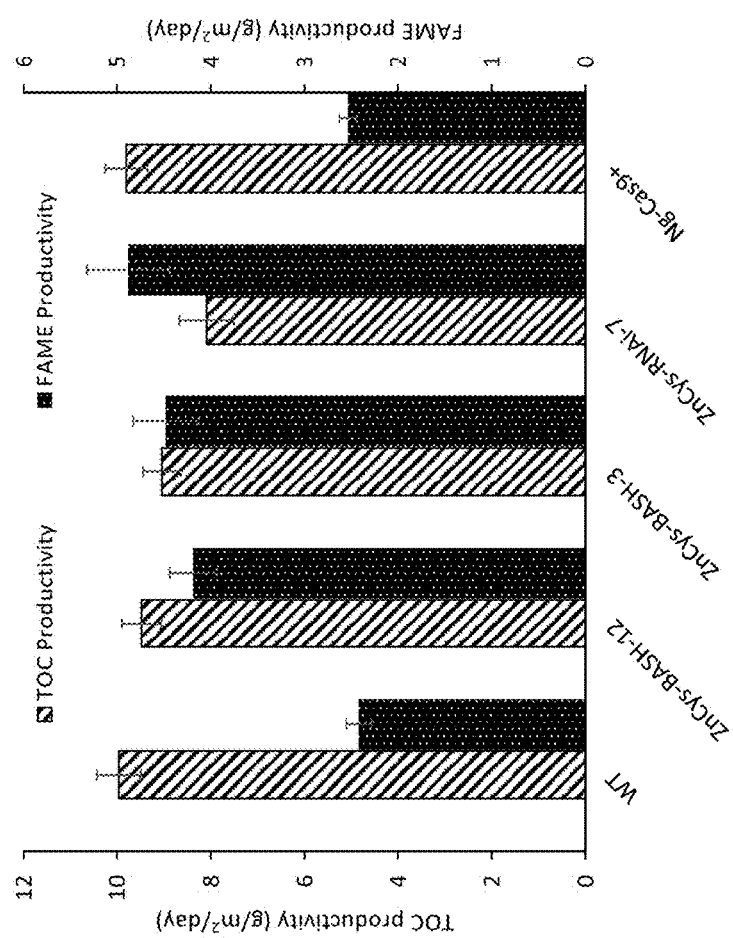

FIG. 18 provides a bar graph of FAME and TOC productivities (g/m²/day) of ZnCys mutants (ZnCys-RNAi-7 (GE-13103), ZnCys-BASH-12 (GE-13112) and ZnCys-BASH-3 (GE-13109)) compared to their parental lines Ng-CAS9+ (GE-6791) and WT in the assay whose daily FAME and TOC productivities are depicted in FIG. 17. Productivity values are 8-day averages of daily measurements (n=3).

Figure 19:
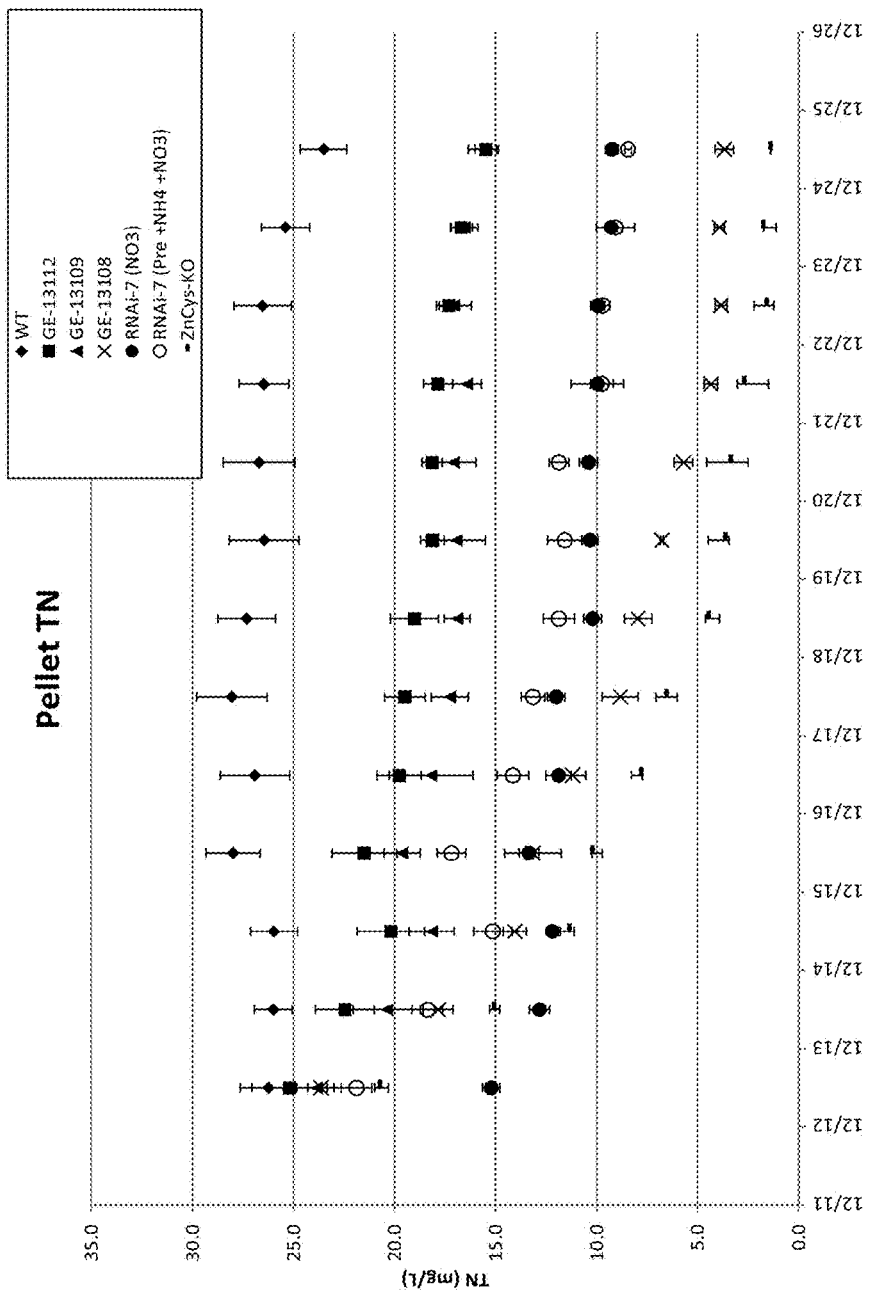

FIG. 19 provides a graph depicting the daily nitrogen content of the cells (mg/L culture, pellets only) in the semi-continuous assay whose daily FAME and TOC productivities are provided in FIGS. 16A-D. Symbols used in graphs: diamonds represent wild type WT-3730 pre-cultured in nitrate-only medium; Xs represent knockdown mutant GE-13108 "BASH2" pre-cultured in nitrate plus ammonium medium; triangles represent knockdown mutant GE-13109 "BASH3" pre-cultured in nitrate plus ammonium medium; squares represent knockdown mutant GE-13112 "BASH12" pre-cultured in nitrate plus ammonium medium; open circles represent knockdown mutant GE-13103 "RNAi-7" pre-cultured in nitrate plus ammonium medium; closed circles represent knockdown mutant GE-13103 "RNAi-7" pre-cultured in nitrate-only medium; and dashes represent knockout mutant GE-8564 pre-cultured in nitrate plus ammonium medium. Error bars in graphs represent the standard deviation of the three independent cultures (biological replicates).

Figure 20:
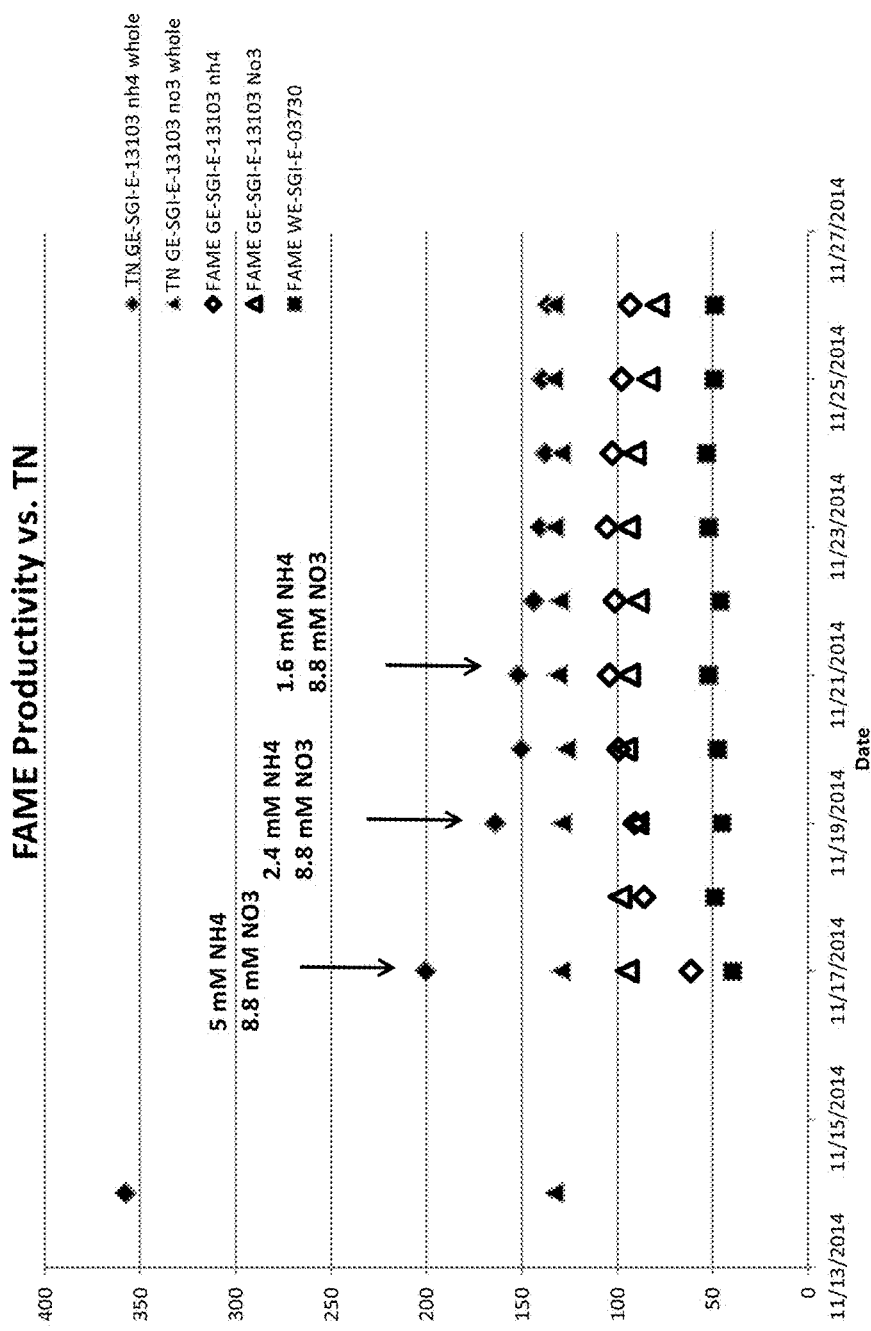

FIG. 20 provides a graph depicting total nitrogen and FAME levels of cultures of N. gaditana wild type strain WT-3730 and RNAi mutant GE-13103 in a semi-continuous assay using nitrate-only media, in which the GE-13103 knockdown strain was pre-cultured separately in either PM124 medium that included both nitrate and ammonium or in PM074 medium that included only nitrate. Wild type strain WT-3730 was pre-cultured in PM074 medium that included only nitrate. Solid diamonds and solid triangles represent the total nitrogen content of the cultures (cells plus culture medium) of GE-13103 pre-cultured in PM124 and PM074, respectively. Open diamonds and open triangles represent the FAME content of the cultures of GE-13103 pre-cultured in PM124 and PM074, respectively. Solid squares represent the FAME content of a culture of WT-3730 pre-cultured in nitrate-only medium. The calculated amount of ammonium on three days of the productivity assay is noted on the graph.

FIG. 21A-21F, provides graphs and a table depicting productivities of the N. gaditana wild type strain WT-3730 and GE-13103 knockdown strain in a semi-continuous assay in which the culture medium included three different concentrations of ammonium. A) depicts FAME productivity (mg/L) in the semi-continuous assay in culture in which the ammonium level of the media used throughout the assay was 2.5, 1.0, or 0.5 mM; B) provides daily FAME productivities (g/m²/day) (standard deviation of three cultures provided in parentheses), along with the average daily productivity for each culture condition in the semi-continuous assay in which the ammonium level of the media used throughout the assay was 2.5, 1.0, or 0.5 mM; C) depicts TOC productivity (mg/L) in the semi-continuous assay in which the ammonium level of the media used throughout the assay was 2.5, 1.0, or 0.5 mM; D) provides daily TOC productivities (g/m²/day) (standard deviation of three cultures for each ammonium concentration provided in parentheses), along with the average daily productivity for each culture condition in the semi-continuous assay in which the ammonium level of the media used throughout the assay was 2.5, 1.0, or 0.5 mM; E) depicts daily FAME/TOC ratios in the semi-continuous assay in which the ammonium level of the media used throughout the assay was 2.5, 1.0, or 0.5 mM; and F) provides daily cell counts determined by flow cytometry of cultures analyzed for FAME and TOC productivities in A-E. Symbols used in graphs: Circles: WT-3730 cultured in nitrate-only medium; Squares: RNAi knockdown strain GE-13103 cultured in nitrate-containing medium that also included 2.5 mM ammonium; Triangles: RNAi knockdown strain GE-13103 cultured in nitrate-containing medium that also included 1.0 mM ammonium; Xs: RNAi knockdown strain GE-13103 cultured in nitrate-containing medium that also included 0.5 mM ammonium. Error bars in graphs represent the standard deviation of the three independent cultures (biological replicates).

FIG. 22A-22D, Productivity assessment of ZnCys-KO and ZnCys-RNAi-7 grown in semi-continuous mode on nitrate-containing medium. A) Daily FAME (mg/L), B) Daily TOC (mg/L), and C) C/N values derived from cellular N-content. D) provides a bar graph comparing FAME and E) TOC productivities (g/m$^2$/day) for WT and ZnCys-RNAi-7 calculated for the entire 13-day assay. ZnCys-KO failed to reach steady-state at a 30% daily dilution scheme and essentially washed away as the run progressed, therefore lipid and biomass productivity values were not calculated for this line (N/A, not available). ZnCys-KO was scaled up in culture medium that included $NH_4^+$ in addition to $NO_3^-$ to obtain enough biomass for the assay.

Figure 23:
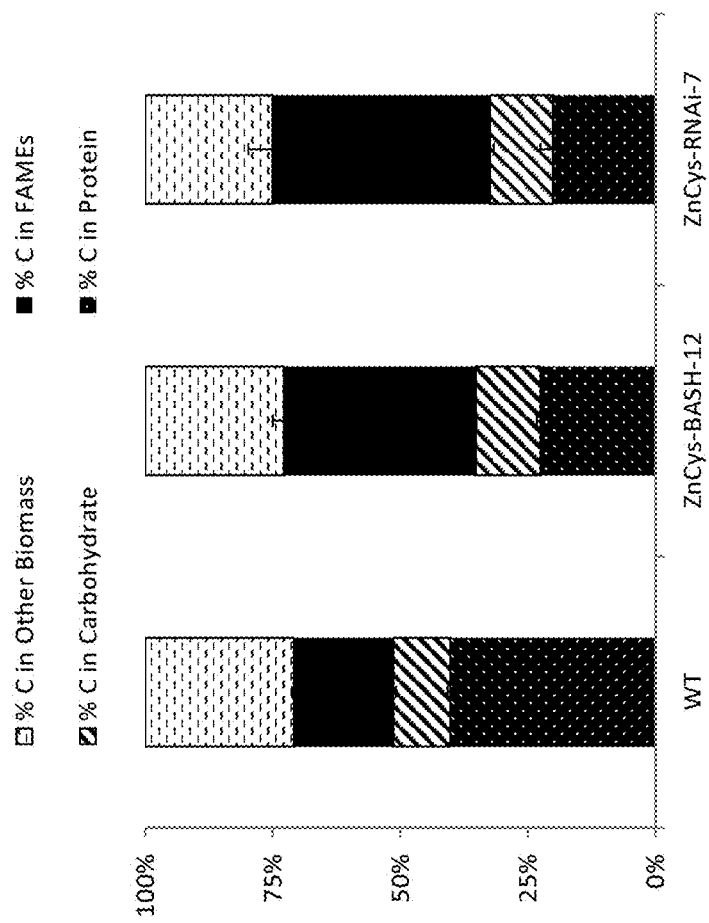

FIG. 23 is a bar graph depicting the biomolecular composition of wild type *Nannochloropsis* strain WT-3730 and two ZnCys knockdown mutants, GE-13112 (BASH 12) and GE-13130 (RNAi).

Figure 24:
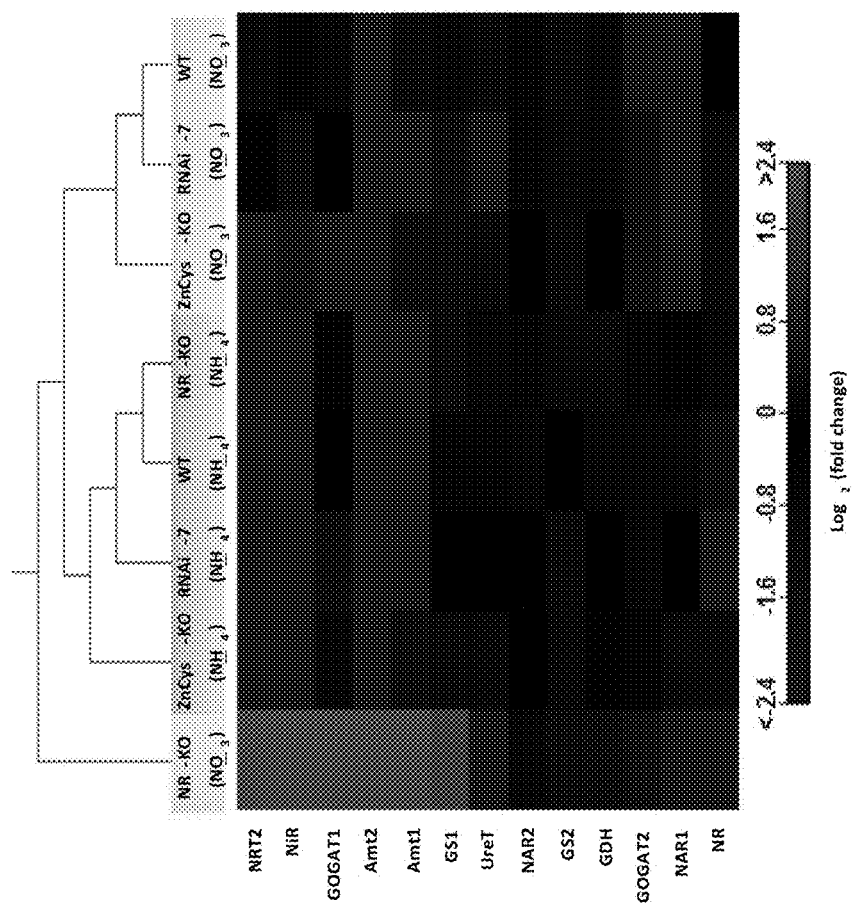

FIG. 24 depicts hierarchical clustering by Euclidian distance of transcriptional fold changes of genes encoding proteins involved in N-assimilation from biological triplicates of ZnCys-KO, the nitrate reductase knockout mutant (NR-KO), RNAi-7 and WT grown in batch mode on nitrate-only medium ($NO_3$, light green) or medium that included both ammonium and nitrate ($NH_4$, dark green). Red indicates increased expression and blue indicates reduced expression, with black being neutral (neither increased nor decreased).

Figure 25:
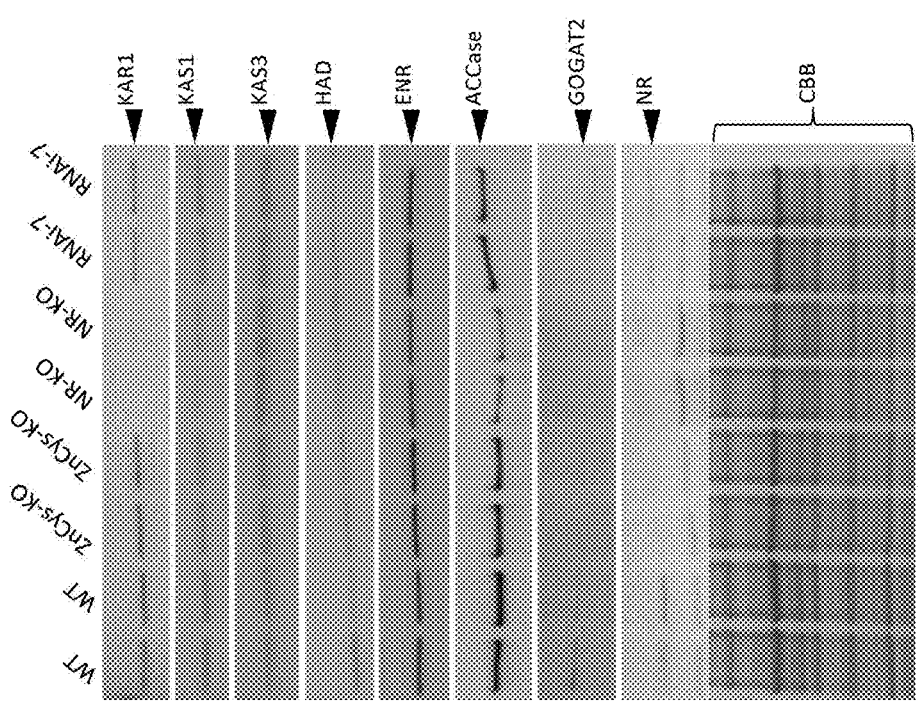

FIG. 25 provides images of immunoblot analysis of enzymes in the FAS cycle (KAR1, KAS1/3, HAD and ENR), acetyl-CoA carboxylase (ACCase), glutamate synthase (GOGAT2) and nitrate reductase (NR) for duplicate cultures grown in batch mode on nitrate-only medium (WT, ZnCys-KO and ZnCys-RNAi-7 shown as RNAi-7). Coomassie brilliant blue stain (CBB) of a protein gel used for blotting is shown as a loading reference.

DETAILED DESCRIPTION OF THE INVENTION

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All ranges provided within the application are inclusive of the values of the upper and lower ends of the range unless specifically indicated otherwise.

All publications, patents and other references mentioned herein are incorporated by reference in their entireties for all purposes as if each individual publication or patent application were specifically and individually indicated to be incorporated by reference.

The term "and/or" as used in a phrase such as "A and/or B" herein is intended to include "A and B", "A or B", "A", and "B".

"About" means either within 10% of the stated value, or within 5% of the stated value, or in some cases within 2.5% of the stated value, or, "about" can mean rounded to the nearest significant digit.

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, "gene" may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

The term "nucleic acid" or "nucleic acid molecule" refers to, a segment of DNA or RNA (e.g., mRNA), and also includes nucleic acids having modified backbones (e.g., peptide nucleic acids, locked nucleic acids) or modified or non-naturally-occurring nucleobases. The nucleic acid molecules can be double-stranded or single-stranded; a single stranded nucleic acid molecule that comprises a gene or a portion thereof can be a coding (sense) strand or a non-coding (antisense) strand.

A nucleic acid molecule may be "derived from" an indicated source, which includes the isolation (in whole or in part) of a nucleic acid segment from an indicated source. A nucleic acid molecule may also be derived from an indicated source by, for example, direct cloning, PCR amplification, or artificial synthesis from the indicated polynucleotide source or based on a sequence associated with the indicated polynucleotide source, which may be, for example, a species of organism. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other gene synthesis or molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least 65%, at least 70%, at least 75%, at least 80%, at least 85%, at least 90%, or at least 95%, sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature, or has been synthesized apart from other sequences of the chromosome, genome, or episome that it is associated with in nature, or has been synthesized apart from other sequences with which it is juxtaposed in nature.

A "purified" nucleic acid molecule or nucleotide sequence, or protein or polypeptide sequence, is substantially free of cellular material and cellular components. The purified nucleic acid molecule or protein may be substantially free of chemicals beyond buffer or solvent, for example. "Substantially free" is not intended to mean that other components beyond the novel nucleic acid molecules are undetectable.

The terms "naturally-occurring" and "wild type" refer to a form found in nature. For example, a naturally occurring or wild type nucleic acid molecule, nucleotide sequence or protein may be present in and isolated from a natural source, and is not intentionally modified by human manipulation.

As used herein "attenuated" means reduced in amount, degree, intensity, or strength with respect to a control that does not have the manipulation or mutation that results in attenuated expression or activity. Attenuated gene expression may refer to a significantly reduced amount and/or rate of transcription of the gene in question, or of translation, folding, or assembly of the encoded protein. As nonlimiting examples, an attenuated gene may be an endogenous gene of the organism that is mutated or disrupted (e.g., a gene disrupted by partial or total deletion, truncation, frameshifting, or insertional mutation) that does not encode a complete functional open reading frame or that has decreased expression due to alteration or disruption of gene regulatory sequences. An attenuated gene may also be a gene targeted by a construct that reduces expression of the gene, such as, for example, an antisense RNA, microRNA, RNAi molecule, or ribozyme. Attenuated gene expression can be gene expression that is eliminated, for example, reduced to an amount that is insignificant or undetectable, or can be gene expression the is reduced by any amount with respect to the gene expression of a control microorganism, for example reduced from about 1% to about 99%, or from about 5% to about 95% of the level of gene expression of the control microorganism. Attenuated gene expression can also be gene expression that results in an RNA or protein that is not fully functional or nonfunctional, for example, attenuated gene expression can be gene expression that results in a truncated RNA and/or polypeptide.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a cell, subjected to laboratory manipulation, and introduced or reintroduced into a host cell such that it differs in sequence or location in the genome with respect to its position in a non-manipulated organism (i.e., is juxtaposed with or operably linked to sequences it is not juxtaposed with or operably linked to in a non-transformed organism) is considered "non-native". Thus non-native genes include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering regardless of whether the amino acid sequence varies from that of a wild-type protein.

When applied to organisms, the term recombinant, engineered, or genetically engineered refers to organisms that have been manipulated by introduction of a heterologous or exogenous recombinant nucleic acid sequence into the organism, and includes gene knockouts, targeted mutations, gene replacement, and promoter replacement, deletion, or insertion, as well as introduction of transgenes or synthetic genes into the organism. Recombinant or genetically engineered organisms can also be organisms into which constructs for gene "knockdown" have been introduced. Such constructs include, but are not limited to, RNAi, microRNA, shRNA, siRNA, antisense, and ribozyme constructs. Also included are organisms whose genomes have been altered by the activity of meganucleases, zinc finger nucleases, TALENs, or cas/CRISPR systems. An exogenous or recombinant nucleic acid molecule can be integrated into the recombinant/genetically engineered organism's genome or in other instances may not be integrated into the host genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (initiate transcription in one direction) or bi-directional (initiate transcription in either direction). A promoter may be a constitutive promoter, a repressible promoter, or an inducible promoter. A promoter region can include, in addition to the gene-proximal promoter where RNA polymerase binds to initiate transcription, additional sequences upstream of the gene that can be within 1 kb, 2 kb, 3 kb, 4 kb, 5 kb or more of the transcriptional start site of a gene, where the additional sequences can influence the rate of transcription of the downstream gene and optionally the responsiveness of the promoter to developmental, environmental, or biochemical (e.g., metabolic) conditions.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g. a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

Gene and protein Accession numbers, commonly provided in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 50, less than about 40, less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix can be set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2. The preceeding parameter settings are exemplary only and other parameter settings may be used.

Thus, when referring to the polypeptide or nucleic acid sequences of the present invention, included are sequence identities of at least 40%, at least 45%, at least 50%, at least 55%, of at least 70%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 50, at least 75, at least 100, at least 125, at least 150, at least 200, or more than 200 amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

As used herein, "expression" includes the expression of a gene at least at the level of RNA production, and an "expression product" includes the resultant product, e.g., a polypeptide or functional RNA (e.g., a ribosomal RNA, a tRNA, a guide RNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production" [of a gene product] includes an increase in the amount of polypeptide expression, in the level of the enzymatic activity of a polypeptide, or a combination of both, as compared to the native production or enzymatic activity of the polypeptide.

Some aspects of the present invention include the partial, substantial, or complete deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, or other methods known in the art). The terms "eliminate," "elimination," and "knockout" can be used interchangeably with the terms "deletion," "partial deletion," "substantial deletion," or "complete deletion" and refer to substantially eliminating expression of the gene, for example, reducing the level of expression to less than 10%, less than 5%, less than 2%, or less than 1% of control levels or undetectable levels. The terms "attenuation" and "knockdown" can be used to describe mutations and manipulations resulting in a lower level of expression of a gene with respect to wild type levels of expression, or, in some cases, resulting in reduced activity of a gene product, such as by mutating a functional domain of the encoded polypeptide. Attenuation can be complete attenuation (e.g., "knockout") or can be partial attenuation, where, for example, RNA or protein levels are reduced or "knocked down" by from 1-99.5% of control levels, e.g., to a level where RNA or protein expression is detectable but reduced with respect to controls. In certain embodiments, a microorganism of interest may be engineered by site directed homologous recombination to knockout a particular gene of interest. In still other embodiments, RNAi or antisense DNA (asDNA) constructs may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified", "genetically engineered" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

As used herein, "mutant" refers to an organism that has a mutation in a gene that is the result of classical mutagenesis, for example, using gamma irradiation, UV, or chemical mutagens. "Mutant" as used herein also refers to a recombinant cell that has altered structure or expression of a gene as a result of genetic engineering that many include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild type polypeptide, and/or dominant negative polypeptides); gene attenuation via RNAi, antisense RNA, or ribozymes, or the like; and genome engineering using meganucleases, TALENs, and/or CRISPR technologies, and the like. A mutant is therefore not a naturally-occurring organism. A mutant organism of interest will typically have a phenotype different than that of the corresponding wild type or progenitor strain that lacks the mutation, where the phenotype can be assessed by growth assays, product analysis, photosynthetic properties, biochemical assays, etc. When referring to a gene "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region, e.g., within 2 kb of the transcriptional start site or within 3 kb of the translational start site. As nonlimiting examples, a mutant gene can be a gene that has an insertion within the promoter region that can either increase or decrease expression of the gene; can be a gene that has a deletion, resulting in production of a nonfunctional protein, truncated protein, dominant negative protein, or no protein; can be a gene that has one or more point mutations leading to a change in the amino acid of the encoded protein or results in aberrant splicing of the gene transcript, etc.

The term "Pfam" refers to a large collection of protein domains and protein families maintained by the Pfam Consortium and available at several sponsored world wide web sites, including: pfam.xfam.org/ (European Bioinformatics Institute (EMBL-EBI). The latest release of Pfam is Pfam 30.0 (June 2016). Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) *Nucleic Acids Research* 26, 320-322; Bateman (2000) Nucleic Acids Research 26, 263-266; Bateman (2004) *Nucleic Acids Research* 32, Database Issue, D138-D141; Finn (2006) *Nucleic Acids Research* Database Issue 34, D247-251; Finn (2010) *Nucleic Acids Research* Database Issue 38, D211-222). By accessing the Pfam database, for example, using the above-referenced website, protein sequences can be queried against the HMMs using HMMER homology search software (e.g., HMMER2, HMMER3, or a higher version, hmmer.org). Significant matches that identify a queried protein as being in a pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be double stranded or single stranded and can be, for example, the complement of the mRNA sequence. In preferred examples, a cDNA does not include one or more intron sequences that occur in the naturally-occurring gene that the cDNA corresponds to (i.e., the gene as it occurs in the genome of an organism). For example, a cDNA can have sequences from upstream of an intron of a naturally-occurring gene juxtaposed to sequences downstream of the intron of the naturally-occurring gene, where the upstream and downstream sequences are not juxtaposed in a DNA molecule in nature (i.e., the sequences are not juxtaposed in the naturally occurring gene). A cDNA can be produced by reverse transcription of mRNA molecules, or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences or compiled from the sequences multiple partial cDNAs.

Reference to properties that are "substantially the same" or "substantially identical" without further explanation of the intended meaning, is intended to mean the properties are within 10%, and preferably within 5%, and may be within 2.5%, within 1%, or within 0.5% of the reference value. Where the intended meaning of "substantially" in a particular context is not set forth, the term is used to include minor and irrelevant deviations that are not material to the characteristics considered important in the context of the invention.

Although methods and materials similar or equivalent to those described herein can be used in practice or testing of the present invention, suitable methods and materials are described below. The materials, methods, and examples are illustrative only and are not intended to be limiting. Other features and advantages of the invention will be apparent from the detailed description and from the claims.

A "control cell" or "control microorganism" is a cell or microorganism that is substantially identical to the manipulated, recombinant, or mutant cell referred to, with the exception that the control cell does not have the modification of the manipulated, recombinant, or mutant cell. A control cell can be a wild type cell, for example a wild type cell of the strain from which the manipulated, recombinant, or mutant cell is directly or indirectly derived.

"The same conditions" or "the same culture conditions", as used herein, means substantially the same conditions, that is, any differences between the referenced conditions are minor and not relevant to the function or properties of the microorganism that are material to the invention, e.g., lipid production or biomass production.

"Nitrogen replete" conditions, with respect to a particular cell type, are conditions under which the cell does not experience growth deficiency due to insufficient nitrogen.

As used herein "lipid" or "lipids" refers to fats, waxes, fatty acids, fatty acid derivatives such as fatty alcohols, wax esters, alkanes, and alkenes, sterols, monoglycerides, diglycerides, triglycerides, phospholipids, sphingolipids, saccharolipids, and glycerolipids. "FAME lipids" or "FAME" refers to lipids having acyl moieties that can be derivatized to fatty acid methyl esters, such as, for example, monoacylglycerides, diacylglycerides, triacylglycerides, wax esters, and membrane lipids such as phospholipids, galactolipids, etc. Lipid productivity can be assessed as FAME productivity in milligrams per liter (mg/L) over a given time period (e.g., per day) and for algae, may be reported as areal productivity, for example grams per meter$^2$ per day (g/m$^2$/day). In the semi-continuous assays provided herein, mg/L/day values are converted to g/m2/day by taking into account the area of incident irradiance (the SCPA flask rack aperture of 1½"×3⅜", or 0.003145 m$^2$) and the volume of the culture (550 ml). To obtain productivity values in g/m2/day, mg/L/day values are multiplied by the daily dilution rate (30%) and a conversion factor of 0.175. Where lipid or subcategories thereof (for example, TAG or FAME) are referred to as a percentage, the percentage is a weight percent unless indicated otherwise.

"Biomass" refers to cellular mass, whether of living or dead cells, and can be assessed, for example, as aspirated pellet weight, but is more preferably dry weight (e.g., lyophilate of a culture sample or pelleted cells), ash-free dry weight (AFDW), or total organic carbon (TOC), using methods known in the art. Biomass increases during the growth of a culture under growth permissive conditions and may be referred to as "biomass accumulation" in batch cultures, for example. In continuous or semi-continuous cultures that undergo steady or regular dilution, biomass that is produced that would otherwise accumulate in the culture is removed during culture dilution. Thus, daily biomass productivity (increases in biomass) by these cultures can also be referred to as "biomass accumulation". Biomass productivity can be assessed as TOC productivity in milligrams per liter (mg/L) per given time period (e.g., per day) and for algae, may be reported as grams per meter$^2$ per day (g/m$^2$/day). In the semi-continuous assays provided herein, mg/L values are converted to g/m2/day by taking into account the area of incident irradiance (the SCPA flask rack aperture of 1½"×3⅜", or 0.003145 m$^2$) and the volume of the culture (550 ml). To obtain productivity values in g/m2/day, mg/L values are multiplied by the daily dilution rate (30%) and a conversion factor of 0.175. Where biomass is expressed as a percentage, the percentage is a weight percent unless indicated otherwise.

In the context of the invention, a "nitrogen source" is a source of nitrogen that can be taken up and metabolized by the subject microorganism and incorporated into biomolecules for growth. For example, compounds including nitrogen that cannot be taken up and/or metabolized by the microorganism for growth (e.g., nitrogen-containing biological buffers such as Hepes, Tris, etc.) are not considered nitrogen sources in the context of the invention.

"Reduced nitrogen", as used herein, is nitrogen in the chemical form of ammonium, ammonia, urea, or an amino acid that can be metabolized by the microorganism being cultured to provide a source of nitrogen for incorporation into biomolecules, thereby supporting growth. For example, in addition to ammonium/ammonia and urea, reduced nitrogen can include various amino acids where the amino acid(s) can serve as a nitrogen source to the subject microorganism. Examples of amino acids can include, without limitation, glutamate, glutamine, histidine, lysine, arginine, asparagine, alanine, and glycine. "Non-reduced nitrogen" in the context of a nitrogen source that can be present in a culture medium for microorganisms refers to nitrate or nitrite that must be reduced prior to assimilation into organic compounds by the microorganism.

"The sole source of nitrogen [in the culture medium]" is used interchangeably with "substantially the sole source of nitrogen" and indicates that no other nitrogen source is intentionally added to the culture medium and/or that no other nitrogen source is present in an amount sufficient to significantly increase the growth of the microorganisms or cells cultured in the referenced medium. Throughout this application, for brevity, the terms "nitrate-only" and "urea-only" are used to characterize culture media in which nitrate is the substantially the sole source of nitrogen that is available to the microorganisms for supporting growth or urea is the only source of nitrogen that is available to the microorganisms for supporting growth, respectively.

Similarly, "the sole source of carbon [in the culture medium]" is used interchangeably with "substantially the sole source of carbon" and indicates that where inorganic carbon is substantially the sole source of carbon in the culture medium no other carbon source is present in an amount sufficient to increase the productivity or growth of the microorganisms or cells cultured in the referenced medium or any other carbon source that may be present is not significantly incorporated into biomolecules such as lipids produced by the microorganisms or cells. "Inorganic carbon" refers to carbon dioxide, carbonate and carbonate salts, and carbonic acid.

Disclosed herein are methods for manipulating, assaying, culturing, and analyzing microorganisms. The invention set forth herein also makes use of standard methods, techniques, and reagents for cell culture, transformation of microorganisms, genetic engineering, and biochemical analysis that are known in the art.

All headings are for the convenience of the reader and do not limit the invention in any way.

Mutant Microorganisms Having Increased Lipid Productivity

The invention provides mutant microorganisms having at least 45% of the biomass productivity of a control microorganism and higher lipid productivity (e.g., higher productivity per day, preferably averaged over the culture period) with respect to the control microorganism when both the mutant microorganism and control microorganism are cultured under identical conditions in which the control microorganism culture is producing biomass. Biomass productivity can be assessed, for example, as ash-free dry weight (AFDW) production or productivity (i.e., amount produced per day) or total organic carbon (TOC) productivity. A mutant microorganism as provided herein can demonstrate greater lipid productivity than a control microorganism and at least 45% of the biomass productivity of the control microorganism over a culture period of at least three days, for example, a culture period of at least four, at least five, at least six, at least seven, at least eight, at least nine, at least ten, at least eleven, at least twelve, at least thirteen, at least fourteen, at least fifteen, at least twenty, at least thirty, or at least sixty days when the mutant microorganism and the control microorganism are cultured under conditions that support growth of the control microorganism, i.e., under conditions in which the control microorganism culture produces biomass. In some examples the culture period in which a mutant microorganism as provided herein produces at least 45% of the biomass and produces more lipid with respect to a control microorganism can be less than 180 days, less than 120 days, or less than 90 days. In some examples, a mutant microorganism as provided herein produces higher amounts of lipid with respect to a control microorganism under culture conditions in which both the mutant and control microorganism are producing biomass and the mutant produces at least 45%, at least 50%, at least 55%, at least 60%, at least 65%, at least 70%, at least 75%, at least 80%, at least 85%, at least 90%, at least 95%, at least 100%, at least 105%, at least 110%, or at least 120% of the biomass produced by a control microorganism on a daily basis. In some examples, a mutant microorganism as provided herein produces higher amounts of lipid with respect to a control microorganism and at least 45% of the biomass but less than 300% or less than 325%, or less than 200% of the biomass produced by the control microorganism. In some examples, a mutant microorganism as provided herein produces higher amounts of lipid with respect to a control microorganism under culture conditions in which both the mutant and control microorganism are producing biomass and actively dividing.

Methods of measuring the amount of lipid produced by microorganisms are well-known in the art and provided in the examples herein. Total extractable lipid can be determined according to Folch et al. (1957) *J. Biol. Chem.* 226: 497-509; Bligh & Dyer (1959) *Can. J. Biochem. Physiol.* 37: 911-917; or Matyash et al. (2008) *J. Lipid Res.* 49:1137-1146, for example, and the percentage of biomass present as lipid can also be assessed using Fourier transform infrared spectroscopy (FT-IR) (Pistorius et al. (2008) *Biotechnol & Bioengin.* 103:123-129). Additional references for gravimetric analysis of FAME and TAGs are provided in U.S. Pat. No. 8,207,363 and WO 2011127118 for example, each incorporated herein by reference in its entirety. FAME analysis methods can also be found for example as American Oil Chemists' Society Methods Ce 1b-89 and Ce 1-62 (aocs.org/Methods/).

Biomass can be assessed by measuring total organic carbon (TOC) or by other methods, such as measuring ash-free dry weight (AFDW). Methods for measuring TOC are known in the art (e.g., U.S. Pat. No. 8,835,149) and are provided herein. Methods of measuring AFDW are also well-known and can be found, for example, in U.S. Pat. No. 8,940,508, incorporated herein by reference in its entirety.

A mutant microorganism can produce, for example, at least 25% more lipid than a control microorganism and at least 45% as much biomass as the control microorganism during a culture period of at least three, four, five, six, seven, eight, nine, ten, eleven, twelve, thirteen, fourteen, fifteen, twenty, thirty, or sixty days during which both the mutant and control microorganisms produce biomass. For example, the average daily lipid productivity can be at least 25% greater than the average daily lipid productivity of a control microorganism and the average daily biomass productivity can be at least 45% as much as the biomass productivity of the control microorganism during a culture period of at least three, four, five, six, seven, eight, nine, ten, eleven, twelve, thirteen, fourteen, fifteen, twenty, thirty, or sixty days. In additional examples, a mutant microorganism can produce at least about 50% more lipid than is produced by a control microorganism and at least 45% as much biomass as the control microorganism, i.e., can exhibit no more than a 55% reduction in biomass with respect to the control microorganism, under conditions in which the control microorganism is producing biomass. A mutant can in some examples produce less than 400% or less than 300% more lipid than a control microorganism while accumulating at least 45% as much biomass as the control microorganism during a culture period of at least three, four, five, six, seven, eight, nine, ten, eleven, twelve, thirteen, fourteen, fifteen, twenty, thirty, or sixty days.

The culture conditions under which a mutant as provided herein produces at least 25% or at least about 50% more FAME while producing at least 50% of the amount of TOC as a control microorganism can be nutrient replete, and can be nitrogen replete with respect to the control microorganism, that is, the culture conditions can be sufficient in nutrients with respect to the control microorganism such that additional nutrients do not increase the growth rate of the microorganism (where all other culture conditions and ingredients remain the same). For example, the culture conditions can be sufficient in nitrogen with respect to the control microorganism such that additional nitrogen do not increase the growth rate of the microorganism (where all other culture conditions and ingredients remain the same). Alternatively, in some embodiments the culture conditions under which a mutant as provided herein produces at least 25% or at least 50% more FAME (which can be the average daily FAME productivity) while producing at least 45% of the amount of TOC (e.g. the average daily TOC productivity) as a control microorganism can include nitrogen that supports biomass production, but at a lower rate than fully nitrogen replete culture media. For example, the culture conditions may allow for biomass (TOC or AFDW) production at at least 60%, at least 65%, at least 70%, at least 75%, at least 80%, at least 85%, at least 90%, or at least 95% the rate of biomass production in fully nitrogen replete culture media.

Mutant microorganisms disclosed herein can produce at least 25% more lipid, e.g., 25% more FAME, as is produced by a control microorganism, while producing at least 45% of the biomass of the control microorganism under conditions that support biomass production that is comparable to the levels of biomass of the control microorganism under nitrogen-replete conditions. For example, biomass production of the control microorganism can be within 20% or within 15% of the biomass production of the control microorganism under nitrogen-replete conditions. Alternatively or in addition, a mutant as provided herein can produce at least 45% of the biomass of the control microorganism while producing at least 25% more lipid than the control microorganism, where the mutant and control microorganism are cultured under conditions that are nitrogen replete with respect to the control microorganism. In various examples, the mutant can produce at least 45% of the biomass produced by a control cell and at least 25% more lipid than the control cell over the same time period in a culture that includes one or more of nitrate or urea, and in some examples can further optionally include less than about 5 mM ammonium, such as less than about 2.5 mM, ammonium, less than about 2 mM ammonium, less than about 1.5 mM ammonium, ammonium, less than about 1 mM ammonium, about 0.5 mM ammonium, or less than 0.5 mM ammonium.

In particular nonlimiting examples, a microorganism can be an algal or heterokont microorganism and can produce at least 25% more FAME while producing at least 45% of the amount of TOC as is produced by a control algal or heterokont microorganism in a culture medium that includes less than about 5 mM, less than about 4.5 mM, less than about 4 mM, less than about 3.5 mM, less than about 3 mM, less than about 2.5 mM, less than about 1 mM, or less than about 0.5 mM ammonium. For example, the ammonium concentration may be at a concentration ranging from about 0 to about 5 mM, from about 0 to about 4.0 mM, from about 0 to about 3 mM, from about 0 to about 2.5 mM, from about 0 to about 2.0 mM, from about 0 to about 1.5 mM, from about 0 to about 1.0 mM, or from about 0 to about 0.5 mM. The ammonium concentration may be at a concentration ranging from about from about 0.5 to about 5 mM, from about 0.5 to about 4 mM, from about 0.5 to about 3 mM, 0.5 to about 2.5 mM, from about 0.5 to about 2.0 mM, from about 0.5 to about 1.5 mM, about 0.5 to about 1 mM, or from about 1 to about 5 mM, about 1 to about 2.5 mM, or from about 0.1 to about 1 mM, from about 0.1 to about 1.5 mM, or from about 0.1 to about 2 mM. In further examples, the ammonium concentration may be at a concentration ranging from about 1 mM to about 2.5 mM or from about 0.2 to about 1.5 mM.

In some examples, a mutant microorganism can be an algal or heterokont cell that produces at least 25% more FAME while producing at least 45% of the amount of TOC as a control microorganism in a culture medium that includes about 2.5 mM ammonium or less, about 2.0 mM ammonium or less, about 1.5 mM ammonium or less, about 1.0 mM ammonium or less, about 0.5 mM ammonium or less, or substantially no ammonium, and can optionally include, for example, at least 1.0 mM, at least 2.0 mM, at least 3.0 mM, at least 4.0 mM, at least 5.0 mM, at least 6.0 mM, at least 7.0 mM, at least 8.0 mM, or at least 10.0 mM nitrate and/or urea. In further nonlimiting examples, a microorganism can be an algal or heterokont cell and can produce at least 50% more FAME while producing at least 45% of the amount of TOC as a control microorganism on a culture medium that includes less than about 5 mM, less than about 2.5 mM, less than about 1 mM, or less than about 0.5 mM ammonium. For example, a microorganism can be an algal or heterokont cell that produces at least 50% more FAME while producing at least 45% of the amount of TOC as a control microorganism in a culture medium that includes about 2.5 mM ammonium or less, about 1.0 mM ammonium or less, about 0.5 mM ammonium or less, or substantially no ammonium, and can include, for example, at least 1.0 mM, at least 2.0 mM, at least 3.0 mM, at least 4.0 mM, at least 5.0 mM, at least 6.0 mM, at least 7.0 mM, at least 8.0 mM, or at least 10.0 mM nitrate and/or urea.

The mutant microorganisms provided herein can have greater partitioning of carbon to lipid with respect to a control microorganism cultured under identical conditions in which both the control microorganism and the mutant microorganism are producing biomass. A mutant having increased partitioning of carbon to lipid with respect to a control microorganism can have increased partitioning of carbon to total extractable lipid, to total neutral lipids, to triglycerides, and/or to FAME-derivatizable lipids. For example, a mutant microorganism as provided herein can have a ratio of the amount of FAME-derivatizable lipids ("FAME") produced to biomass (TOC or ash-free dry weight (AFDW), for example) produced that is at least 50% higher than that of a control microorganism. Lipid and biomass production and/or production can be assessed, for example, by gravimetric analysis as known in the art and demonstrated in the examples herein. For example, a mutant microorganism as provided herein can have a ratio of FAME to TOC that is at least 50%, at least 55%, at least 60%, at least 65%, at least 70%, at least 75%, at least 80%, at least 85, at least 90%, at least 95%, at least 100%, at least 110%, at least 120%, at least 130%, at least 140%, at least 150%, at least 160%, at least 170%, at least 180%, at least 190%, at least 200%, or at least 250% higher than the FAME/TOC ratio of a control microorganism when both the mutant microorganism and the control microorganism are cultured under conditions in which both the culture of the mutant microorganism and the culture of the control microorganism produce biomass. In some example, the FAME/TOC ratio of a mutant microorganism as provided herein can be increased with respect to the FAME/TOC ratio of a control microorganism cultured under identical conditions by less than about 300%.

In various examples a mutant microorganism as provided herein can have a ratio of the amount of FAME produced to TOC produced that is at least 50%, at least 55%, at least 60%, at least 65%, at least 70%, at least 75%, at least 80%, at least 85, at least 90%, at least 95%, at least 100%, at least 110%, at least 120%, at least 130%, at least 140%, at least 150%, at least 160%, at least 170%, at least 180%, at least 190%, at least 200%, or at least 250% higher than the FAME/TOC ratio of a control microorganism when both the mutant microorganism and the control microorganism are cultured under conditions in which the control culture produces biomass (e.g., TOC) and the mutant culture produces at least 45%, at least 50%, at least 60%, at least 70%, at least 80%, at least 90%, or at least 95% of the amount of biomass that is produced by the control culture. In various examples, the FAME/TOC ratio of a mutant as provided herein can be at least 0.30, at least 0.35, at least 0.40, at least 0.45, at least 0.50, at least 0.55, at least 0.60, at least 0.65, at least 0.7, or at least 0.75 when cultured under conditions in which the mutant microorganism culture produces at least 45%, at least 50%, at least 60%, at least 65%, at least 70%, at least 75%, at least 80%, at least 85, at least 90%, or at least 95% as much biomass (e.g., TOC) as a control microorganism culture, under conditions where both the control and mutant cultures produce biomass. In various examples, the FAME/TOC ratio of a mutant as provided herein can be at least 0.30, at least 0.35, at least 0.40, at least 0.45, at least 0.50, at least 0.55, at least 0.60, at least 0.65, at least 0.7, or at least 0.75 when cultured under conditions in which the mutant culture produces at least about 50%, at least 60%, at least 65%, at least 70%, at least 75%, at least 80%, at least 85, at least 90%, at least 95%, or at least 100% as much biomass (e.g., TOC) as a control microorganism produces when cultured under nitrogen replete conditions.

In some examples, a mutant microorganism as provided herein can produce at least 50% more FAME while producing at least 80%, at least 85%, or at least 90% of the TOC produced by a control cell (such as a wild type cell) when cultured under conditions in which both the control and mutant microorganism produce biomass, and the FAME/TOC ratio of the mutant microorganism is at least 40%, at least 50%, at least 60%, at least 70%, or at least 75% higher than the FAME/TOC of the control microorganism. The FAME/TOC ratio of the mutant microorganism can be, for example, at least 0.30, at least 0.35, or at least 0.40. The culture conditions can include, for example, a culture medium that includes less than 5 mM, less than 2.5 mM, less than 2 mM, less than 1.5 mM, less than 1.0 mM, or less than 0.5 mM ammonium and can include at least 2 mM, at least 4 mM, or at least 6 mM urea or nitrate. In additional examples a mutant microorganism as provided herein can produce at least 60%, at least 70%, or at least 80% more FAME while producing at least 85%, at least 90%, or at least 95% of the TOC produced by a control cell (such as a wild type cell) when cultured under conditions in which both wild type and mutant microorganism are producing biomass, and the FAME/TOC ratio of the mutant microorganism is at least 50%, at least 60%, at least 70%, or at least 75% greater than the FAME/TOC ratio of the control microorganism. The FAME/TOC ratio of the mutant microorganism can be, for example, at least 0.35, at least 0.40, or at least 0.45. The culture conditions can include, for example, a culture medium that includes less than 2.5 mM, less than 1.0 mM, or less than 0.5 mM ammonium and can include at least 2 mM, at least 4 mM, or at least 6 mM urea or nitrate. The culture conditions can in some examples include substantially no ammonium, and in some examples can include substantially no reduced nitrogen as a nitrogen source.

In yet further examples a mutant microorganism as provided herein can produce at least 85%, at least 90%, at least 95%, at least 100%, at least 105%, at least 110%, or at least 115% more FAME while producing at least 70%, at least 75%, at least 80%, or at least 85% of the TOC produced by a control cell (such as a wild type cell) when cultured under conditions in which both wild type and mutant microorganism are producing biomass, and the FAME/TOC ratio of the mutant microorganism is at least 100%, at least 110%, at least 120%, at least 130%, at least 140%, at least 150%, at least 160%, at least 170%, or at least 180% greater than the FAME/TOC ratio of the control microorganism. FAME and TOC production can be assessed as average daily FAME productivity over the culture period, for example over a culture period of at least three, at least five, at least ten, at least twenty, at least thirty, or at least sixty days, or a culture period of between three and sixty days, or between three and thirty days, for example between three and fifteen days or between five and fifteen days. The FAME/TOC ratio of the mutant microorganism can be, for example, at least 0.50, at least 0.55, at least 0.60, at least 0.65, at least 0.70, or at least 0.75. The culture conditions can include, for example, a culture medium that includes less than 2.5 mM, less than 1.0 mM, or less than 0.5 mM ammonium and can include at least 2 mM, at least 4 mM, or at least 6 mM urea or nitrate.

In additional examples, a mutant microorganism can produce at least about 70% of the biomass produced by a wild type or control microorganism and at least 90% more lipid than is produced by a wild type or control microorganism when the mutant microorganism and wild type or control microorganism are cultured under the same conditions. FAME and TOC production can be assessed as average daily FAME productivity over the culture period, for example over a culture period of at least three, at least five, at least ten, at least twenty, at least thirty, or at least sixty days. For example the wild type and control microorganism can be cultured in batch, semi-continuous, or continuous culture for at least three, four, five, six, seven, eight, nine, ten, eleven, twelve, thirteen, fourteen, fifteen, twenty, thirty, or sixty days. In some examples the concentration of ammonium in the culture medium may be less than about 5 mM or less than about 2.5 mM. In some examples the culture medium may include at least 2 mM nitrate or at least 2 mM urea. The mutant microorganism can produce, in some examples, at least about 75% or at least about 80% of the biomass produced by a wild type or control microorganism and at least 100% or at least 110% more lipid than is produced by a wild type or control microorganism when the mutant microorganism and wild type or control microorganism are cultured under the same conditions. The FAME/TOC ratio can be at least 80%, at least 100%, at least 120%, or at least 150% greater than the FAME/TOC ratio of a wild type microorganism cultured under the same conditions. In some examples, the mutant microorganism can produce at least about 70% or at least about 75% of the biomass produced by a wild type or control microorganism and at least 100% or at least 120% more FAME lipids than are produced by a wild type or control microorganism when the mutant microorganism and wild type or control microorganism are cultured under the same conditions, and the mutant microorganism can have a FAME/TOC ratio at least 100% or at least 120% greater than the FAME/TOC ratio of a wild type microorganism cultured under the same conditions.

In various embodiments, a mutant microorganism as provided herein, e.g., a mutant microorganism such as any described herein that produces at least about 50% of the biomass and at least about 50%, at least 55%, at least 60%, at least 70%, at least 75%, at least 80%, at least 85%, at least 90%, at least 95%, at least 100%, at least 110%, at least 120%, at least 125%, or at least 130% more lipid than is produced by a control microorganism cultured under the same conditions, where the conditions support daily biomass accumulation by the control microorganism, can have a higher carbon to nitrogen (C:N) ratio than a control microorganism. For example, the C:N ratio can be from about 1.5 to about 2.5 the C:N ratio of a control microorganism when the mutant microorganism and the control microorganism are cultured under conditions in which both the mutant and the control microorganisms accumulate biomass, and the mutant produces at least 50%, at least 60%, at least 70%, at least 80%, at least 90% or at least 100% more lipid that the control microorganism and at least 50%, at least 60%, at least 70%, at least 80%, or at least 85% of the TOC of the control microorganism. In some embodiments the C:N ratio of a mutant as provided herein is between about 7 and about 20 or between about 8 and about 17, or between about 10 and about 15 during the culturing in which mutant produces at least 50% more lipid that a control microorganism while producing at least 50% as much biomass as the control microorganism. A control microorganism in any of the embodiments or examples herein can be a wild type microorganism.

Alternatively or in addition, mutant microorganism as provided herein, e.g., a mutant microorganism such as any described herein that produces at least about 50% of the biomass and at least about 50%, at least 55%, at least 60%, at least 70%, at least 75%, at least 80%, at least 85%, at least 90%, at least 95%, at least 100%, at least 110%, or at least 120% more lipid than is produced by a control microorganism cultured under the same conditions, where the conditions support daily biomass accumulation by the control microorganism, can have reduced protein content when compared with a control microorganism. For example, in some embodiments a mutant microorganism as provided herein can have a decrease in protein content of at least 10%, at least 20%, at least 30%, at least 40%, at least 45%, or at least 50% with respect to a control microorganism.

In various embodiments, a mutant microorganism as provided herein can have attenuated expression of a gene encoding a protein whose expression affects the expression of other genes, e.g., at least ten, at least twenty, at least thirty, at least forty, at least fifty, at least sixty, at least seventy, at least eighty, at least ninety, or at least 100 additional genes. For example, a mutant as provided herein can have at least ten genes that are upregulated with respect to a wild type microorganism and at least ten genes that are downregulated with respect to a wild type microorganism under conditions in which the mutant phenotype (greater lipid production) is expressed. A mutant as provided herein can have at least twenty, at least thirty, at least forty, at least fifty, at least sixty, at least seventy, at least eighty, at least ninety, or at least 100 genes that are upregulated with respect to a wild type microorganism and at least twenty, at least thirty, at least forty, at least fifty, at least sixty, at least seventy, at least eighty, at least ninety, or at least 100 genes that are downregulated with respect to a wild type microorganism under conditions in which the mutant phenotype (e.g., greater lipid production with respect to the wild type microorganism) is expressed. In some embodiments, genes encoding polypeptides involved in protein synthesis can be upregulated in a mutant as provided herein, for example, genes encoding ribosomal polypeptides or other polypeptides that function in translation, including, without limitation, those belonging to gene ontology (GO) groups such as "translation", "ribosome", "structural constituent of ribosome", "eukartotic translation initiation factor 3 complex", "translation initiation factor activity", "translational initiation", "small ribosomal subunit", "formation of translation preinitiation complex", regulation of translation initiation, "eukaryotic 43S preinitiation complex", and "eukaryotic 48S preinitiation complex". Alternatively or in combination with the upregulation of genes encoding polypeptides relating to protein synthesis, any of various genes encoding polypeptides involved in nitrogen assimilation such as a molybdenum cofactor biosynthesis protein, a nitrate transporter, a nitrate reductase, a nitrite reductase, a glutamate synthase, a glutamine synthase, a glutamate dehydrogenase, and an ammonium transporter can be downregulated in a mutant as provided herein. Alternatively or in combination with any of the above, a mutant as provided herein can exhibit upregulation of certain genes related to lipid biosynthesis including but not limited to a lipid droplet surface protein and/or one or more desaturases, elongases, lipases, acyltransferases, and/or glyceraldehyde-3-phosphate dehydrogenases.

The properties of a mutant as provided herein having increased lipid production are compared to the same properties of a control microorganism that may be a wild type organism of the same species as the mutant, preferably the progenitor strain of the lipid-overproducing mutant. Alternatively, a control microorganism can be a microorganism that is substantially identical to the mutant microorganism with the exception that the control microorganism does not have the mutation that leads to higher lipid productivity. For example, a control microorganism can be a genetically engineered microorganism or classically mutated organism that has been further mutated or engineered to generate a mutant having increased lipid productivity and/or increased lipid partitioning as disclosed herein.

In some examples, a control microorganism can be a microorganism that is substantially identical to the mutant microorganism, with the exception that the control microorganism does not have a mutation in a gene or attenuated expression of a gene that regulates lipid induction (i.e., the gene whose mutation results in increased lipid production under conditions in which the mutant microorganism has at least about half the biomass productivity of the progenitor strain). The properties of a lipid-overproducing mutant having a disrupted, attenuated, or otherwise directly or indirectly genetically manipulated gene (resulting in altered structure or expression of the lipid induction regulator gene) are also be compared with the same properties of a control cell that does not have a disrupted, attenuated, or otherwise directly or indirectly genetically manipulated lipid induction regulator gene resulting in altered structure or expression of the lipid induction regulator gene (regardless of whether the cell is "wild-type"). For example, a control cell may be a recombinant cell or a cell mutated in a gene other than the lipid induction regulator gene whose effects are being assessed, etc.

Heterokont species considered for use in the invention include, but are not limited to, Bacillariophytes, Eustigmatophytes, Labrinthulids, and Thraustochytrids, such as, for example, species of *Labryinthula, Labryinthuloides, Thraustochytrium, Schizochytrium, Aplanochytrium, Aurantiochytrium, Oblongichytrium, Japonochytrium, Diplophrys,* or *Ulkenia.*

Mutant microorganisms having the properties disclosed herein, such as mutant microorganisms having attenuated expression of a gene that regulates lipid biosynthesis, such as the ZnCys-2845 gene of *N. gaditana* and orthologs thereof can be, in various examples, of any eukaryotic microalgal strain such as, for example, any species of any of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phæodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox.* Non-limiting examples of particularly suitable species include, for instance, heterokont algae, such as but not limited to diatoms such as, for example, a species of any of the genera *Amphora, Chaetoceros, Cyclotella, Fragilaria, Fragilaropsis, Hantzschia, Navicula, Nitzschia, Phæodactylum,* or *Thalassiosira,* or Eustigmatophytes, e.g., *Chloridella, Chlorobptrys, Ellipsoidion, Eustigmatos, Goniochloris, Monodopsis, Monodus, Nannochloropsis, Pseudocharaciopsis, Pseudostaruastrum, Pseudotetraëdriella,* or *Vischeria*. In some examples, the mutant alga cell is a species of *Ellipsoidion, Eustigmatos, Monodus, Nannochloropsis, Pseudostaruastrum, Pseudotetraëdriella,* or *Vischeria*. In some examples, the mutant alga cell is a species of *Nannochloropsis,* e.g., *N. gaditana, N. granulata, N. limnetica N. oceanica, N oculata,* or *N. salina*.

The mutants can be spontaneous mutants, classically-derived mutants, or engineered mutants having attenuated expression of a regulator gene. For example, a mutant microorganism such as any described herein can be a mutant obtained by classical mutagenesis or genetic engineering. In particular embodiments, a mutant microorganism as provided herein is a genetically engineered mutant, for example, a microorganism into which at least one exogenous nucleic acid molecule has been introduced, e.g., into which at least one recombinant nucleic acid molecule has been introduced, where the mutant microorganism is genetically engineered to include the exogenous nucleic acid molecule and/or the exogenous nucleic acid molecule effects at least one alteration of the microorganism's genome.

In various examples, the mutant microorganism is an algal or heterokont species and has attenuated expression of a gene that encodes a polypeptide having at least 50%, at least 55%, at least 60%, at least 65%, at least 70%, at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17 and/or has a coding region having at least 50%, at least 55%, at least 60%, at least 65%, at least 70%, at least 75%, at least 80%, at least 85%, at least 90%, or at least 95% identity SEQ ID NO:1 or any of SEQ ID NOs:72-84. Alternatively or in addition, the mutant microorganism is an algal or heterokont species and has attenuated expression of a gene that encodes a polypeptide having an amino acid sequence with at least 55%, at least 60%, at least 65%, at least 70%, at least 75%, at least 80%, at least 85%, at least 90%, or at least 95% identity to amino acids 1-200 of SEQ ID NO:20 or to SEQ ID NO:18 or SEQ ID NO:19. The mutant microorganism can in certain embodiments further include a domain having at least 55%, at least 60%, at least 65%, at least 70%, at least 75%, at least 80%, at least 85%, at least 90%, or at least 95% identity to any of SEQ ID NOs:21-25. The domain can be a PAS3 domain. The mutant microorganism can be engineered to attenuate expression of at least one gene encoding a polypeptide as set forth herein by any gene attenuation method, such as any disclosed herein or equivalents thereof.

The polypeptide encoded by the gene whose expression is attenuated can be a transcription factor protein of the Zn(II)2Cys6 fungal-type DNA-binding domain protein family. The polypeptide encoded by the gene whose expression is attenuated can include a Zn(2)Cys(6) domain, categorized as conserved domain cd00067 by the NCBI conserved domain database (ncbi.nlm.nih.gov/Structure/cdd/cdd.shtml), referred to as the "GAL4-like Zn2Cys6 binuclear cluster DNA-binding domain" that is found in transcription factors such as GAL4, also characterized as smart00066: "GAL4-like Zn(II)2Cys6 (or C6 zinc) binuclear cluster DNA-binding domain". This domain, which may be referred to herein as a Zn2Cys6, $Zn_2Cys_6$, or Zn(2)Cys(6) domain or simply a ZnCys domain, occurs at amino acids 190-219 of SEQ ID NO:2, is also characterized as pfam PF00172 ("Zn_Clus" or "Fungal Zn(2)-Cys(6) binuclear cluster domain") with a gathering cutoff for this family of 20.8. In some embodiments, a mutant as provided herein can have attenuated expression of a gene encoding a polypeptide having a Zn(2)Cys(6) domain having at least 50%, at least 55%, at least 60%, at least 65%, at least 70%, at least 75%, at least 80%, at least 85%, at least 90%, or at least 95% identity to SEQ ID NO:3.

Alternatively or in addition, the gene whose expression is attenuated can encode a polypeptide having a PAS_3 domain (pfam 08447, having a gathering cutoff of 25.6) also called "PAS fold domain" or simply a PAS domain, such as, for example, a PAS domain having at least at least 55%, at least 60%, at least 65%, at least 70%, at least 75%, at least 80%, at least 85%, at least 90%, or at least 95% identity to any of SEQ ID NOs:21-25.

The mutant microorganism having attenuated expression of a gene that regulates lipid production can be a "knockout" mutant, for example, in which the reading frame of the polypeptide is disrupted such that a functional protein is not produced. For example, the gene can include an insertion, deletion, or mutation in the reading frame that results in no functional protein being made. The insertion, deletion, or mutation can be made by various means, such as, for example, homologous recombination constructs, RNA-guided endonucleases that employ guide RNAs, optionally in combination with donor DNA fragments, etc. In other examples, the mutant microorganism can be a "knockdown" mutant in which expression of the gene is reduced with respect to a wild type cell. For example, transcript levels of the target gene, which may be, for example, a gene encoding a Zn(2)-C6 fungal-type DNA-binding domain protein, can be reduced between about 5% and about 95% or between about 10% and about 90% with respect to the transcript level in a control microorganism, such as a wild type microorganism. Knockdowns can be mutants in which a mutation, insertion, or deletion occurs in a non-coding region of the gene or can be effected by expressing constructs in the cells that reduce expression of the targeted gene, such as ribozyme, RNAi, or antisense constructs. In some embodiments gene attenuation can be effected by insertion of a DNA fragment into a noncoding region of the gene, such as a 5'UTR or 3' UTR. Insertion of a DNA fragment can optionally be by use of an RNA-guided endonuclease, e.g., a cas protein. The mutant microorganism having attenuated expression of a gene that regulates lipid production can include, for example, one or more of an RNAi construct for expressing RNAi or one or more RNAi molecules, an antisense construct for expressing antisense RNA or one or more antisense molecules, a ribozyme construct for expressing a ribozyme or one or more ribozymes, one or more guide RNAs, one or more constructs for expressing a guide RNA, one or more donor fragments for cas-mediated insertion, one or more homologous recombination constructs, one or more genes encoding a cas enzyme, or a cas enzyme, one or more genes encoding a TALEN, or one or more TALENs, or one or more meganucleases.

Thus, provided herein are microorganisms that have attenuated expression of a gene encoding a polypeptide of the Zn(II)2Cys6 family, i.e., a polypeptide that includes a "GAL4-like Zn2Cys6 binuclear cluster DNA-binding domain" (NCBI conserved domain cd00067) and/or recruits to pfam PF00172 ("Zn_Clus" or "Fungal Zn(2)-Cys(6) binuclear cluster domain") with a bit score greater than the gathering cutoff for this family of 20.8. Alternatively or in addition a mutant microorganism as provided herein may have attenuated expression of a gene encoding a polypeptide that includes a PAS domain (e.g., a "PAS3 domain" or "PAS fold domain") that may be characterized as PF08447 or PF00989. The mutant can produce more lipid that a control microorganism under culture conditions in which both the mutant and the control microorganism produce biomass and in which the mutant microorganism produces at least 50% of the biomass as is produced by the control microorganism. For example, the mutant microorganism can produce at least 25%, at least 30%, at least 35%, at least 40%, at least 45%, at least 50%, at least 60%, at least 70%, at least 80%, at least 90%, at least 100%, at least 110% or at least 120% more lipid that a control microorganism under culture conditions in which both the mutant and the control microorganism produce biomass and in which the mutant microorganism produces at least 50% of the biomass as is produced by the control microorganism. In various embodiments the microorganism that has attenuated expression of a gene encoding a polypeptide of the Zn(II)2Cys6 family and/or having a PAS domain produces at least 50% more the lipid and at least 50% of the biomass as is produced by a control microorganism on a daily basis for at least five, at least six, at least seven, at least eight, at least nine, at least ten, at least eleven, or at least twelve-days of culturing. The mutant can include any of the properties described hereinabove, including, without limitation, increased FAME/TOC ratio under conditions in which the mutant produces more lipid that a control microorganism. The culture conditions under which the mutant produces a higher amount of lipid while producing at least 50% of the biomass as control microorganism can include less than 2.5 mM, less than 1.5 mM, less than 1 mM, or about 0.5 mM or less ammonium. The culture conditions under which the mutant produces a higher amount of lipid while producing at least 50% of the biomass as control microorganism can include a culture medium that includes nitrate, such as at least 2, 3, 4, or 5 mM nitrate. Alternatively or in addition, the culture conditions can include a culture medium that includes urea, such as at least 2, 3, 4, or 5 mM urea. The culture in some examples can provide nitrate as substantially the sole source of nitrogen available to the mutant and control microorganism. The control microorganism can be a wild type microorganism of the same species as the mutant, e.g., can be a wild type strain from which the mutant was derived. The microorganism can be an alga or a heterokont, and in some examples is a heterokont alga such as, but not limited to, a diatom or eustigmatophyte. In various examples lipid can be measured as FAME lipids, and biomass can be measured as, for example, TOC.

Alternatively or in addition, a mutant microorganism as provided herein having attenuated expression of a gene encoding a polypeptide of the Zn(II)2Cys6 family can demonstrate a FAME/TOC ratio that is at least 50%, at least 55%, at least 60%, at least 65%, at least 70%, at least 75%, at least 80%, at least 85, at least 90%, at least 95%, at least 100%, at least 110%, at least 120%, at least 130%, at least 140%, at least 150%, at least 160%, at least 170%, at least 180%, at least 190%, at least 200%, or at least 250% higher than the FAME/TOC ratio of a control microorganism when both the mutant microorganism and the control microorganism are cultured under conditions in which the control culture produces biomass (e.g., TOC) and the mutant culture produces at least 45%, at least 50%, at least 60%, at least 70%, at least 80%, at least 90%, or at least 95% of the amount of biomass that is produced by the control culture. In an exemplary embodiment, a ZnCys attenuation strain can exhibit about twice the lipid productivity of a control strain (e.g., a wild type strain), while allocating approximately 35-70% of its carbon to lipid, for example, while allocating from about 40% to about 65% of its carbon to lipid, such as about 45%, 50%, 60%, or 65% of its carbon to lipid in a semicontinuous or continuous culture system. Further additionally or alternatively, a mutant microorganism as provided herein, e.g., a mutant microorganism having attenuated expression of a gene encoding a polypeptide of the Zn(II)2Cys6 family that produces at least about 50% of the biomass and at least about 50% more lipid than is produced by a control microorganism cultured under the same conditions, where the conditions support daily biomass accumulation by the control microorganism, can have a higher carbon to nitrogen (C:N) ratio than a control microorganism. For example, the C:N ratio can be from about 1.5 to about 2.5 the C:N ratio of a control microorganism when the mutant microorganism and the control microorganism are cultured under conditions in which both the mutant and the control microorganisms accumulate biomass, and the mutant produces at least 50%, at least 60%, at least 70%, at least 80%, at least 90% or at least 100% more lipid that the control microorganism and at least 50%, at least 60%, at least 70%, at least 80%, or at least 85% of the TOC of the control microorganism.

The gene whose expression is attenuated in a mutant that has higher lipid productivity than a control microorganism can be a gene encoding a polypeptide of the Zn(II)2Cys6 family that has at least 50%, at least 55%, at least 60%, at least 65%, at least 70%, at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18. Alternatively or in addition, the gene whose expression is attenuated can encode a polypeptide having a PAS3 domain (pfam08447), such as, for example, a PAS3 domain having at least at least 55%, at least 60%, at least 65%, at least 70%, at least 75%, at least 80%, at least 85%, at least 90%, or at least 95% identity to any of SEQ ID NOs:21-25.

A mutant microorganism as provided herein can be designed by targeting an endogenous gene of a microorganism of interest that encodes a polypeptide that includes a Zn2Cys6 domain as disclosed herein and/or a PAS3 domain as disclosed herein. Such genes can be identified in a microorganism of interest by bioinformatics methods, molecular biology techniques and combinations thereof. For example, a gene encoding a polypeptide that includes a Zn2Cys6 domain and/or a PAS3 domain can be identified using Southern hybridization, screening of cDNA libraries by hybridization or PCR, for example, using degenerate probes and/or primers. Genome sequences available in public or proprietary databases can be searched by any of a number of programs that perform sequence matching (blast programs) or analyze domain structures of encoded amino acid sequences. For example, hmmer.org provides software for analyzing structural and functional domains encoded by genes that can be used to scan genome sequences, including, for example, hmmsearch and hmmscan. Such searches can be done online. Programs such as MUSCLE and hmmalign can also be used to search for orthologs of proteins such as the proteins disclosed herein (e.g., ZnCys-2845 and orthologs) by constructing phylogenetic trees to determine relationships among proteins. In addition, sequence-based searches, including blastp, blastn, and tblastn (protein sequence queried against translated nucleotide sequence). Gene targeting can make use of the obtained sequences from the genome of the microorganism of interest. It is not necessary to resolve the complete structure of a gene to target the gene for attenuation. For example, using methods disclosed herein, including, without limitation, cas/CRISPR genome editing, RNAi constructs, antisense constructs, homologous recombination constructs, and ribozyme constructs, only a portion of a gene sequence can be employed in gene attenuation constructs and techniques.

Gene Attenuation

A mutant microorganism having attenuated expression of a gene that regulates lipid biosynthesis can be a mutant generated by any feasible method, including but not limited to UV irradiation, gamma irradiation, or chemical mutagenesis, and screening for mutants having increase lipid production, for example using the assays disclosed herein or by staining with lipophilic dyes such as Nile Red or BODIPY (e.g., Cabanelas et al. (2015) *Bioresource Technology* 184: 47-52). Methods for generating mutants of microbial strains are well-known.

A mutant as provided herein that produces at least 25% more lipid while producing at least 50% of the biomass as the progenitor cell can also be a genetically engineered mutant, for example, a mutant in which a regulatory gene such as Zn(2)-C(6) fungal-type DNA-binding domain protein (e.g., ZnCys-2845 or an ortholog thereof, e.g. a gene encoding a polypeptide having at least 55%, at least 60%, at least 65%, at least 70%, at least 75%, at least 80%, at least 85%, at least 90%, or at least 95% identity to SEQ ID NO:2 or any of SEQ ID NOs:5-18) has been targeted by homologous recombination for knock-out or gene replacement (for example with mutated form of the gene that encodes a polypeptide having reduced activity with respect to the wild type polypeptide). For example, a microbial strain of interest may be engineered by site directed homologous recombination to insert a sequence into a genomic locus and thereby alter a gene and/or its expression, where the insertion can be, as nonlimiting examples, in the coding region of the gene, in an intron of the gene, in the 3' UTR or the gene, in the 5' UTR of the gene, or upstream of the transcriptional start site, i.e., in the promoter region of the gene.

For example, gene knockout or replacement by homologous recombination can be by transformation of a homologous recombination nucleic acid construct, i.e., a nucleic acid (e.g., DNA) fragment that includes a sequence homologous to the region of the genome to be altered, where the homologous sequence is interrupted by a foreign sequence, typically but not necessarily by a selectable marker gene that allows selection for the integrated construct. The genome-homologous flanking sequences on either side of the foreign sequence or mutated gene sequence can be for example, at least 20, at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides in length. A gene knockout or gene "knock in" construct in which a foreign sequence is flanked by target gene sequences, can be provided in a vector that can optionally be linearized, for example, by cleavage at a site outside of the region that is to undergo homologous recombination, or can be provided as a linear fragment that is not in the context of a vector, for example, the knock-out or knock-in construct can be an isolated or synthesized fragment, including but not limited to a PCR product. In some instances, a split marker system can be used to generate gene knock-outs by homologous recombination, where two DNA fragments can be introduced that can regenerate a selectable marker and disrupt the gene locus of interest via three crossover events (Jeong et al. (2007) *FEMS Microbiol Lett* 273: 157-163).

In one aspect the invention provides genetically modified organisms, e.g. microorganisms having one or more genetic modifications for attenuating expression of a lipid regulator gene such as a gene encoding a Zn(2)-C(6) fungal-type DNA-binding domain protein, that additionally may have at least 55% identity to any of SEQ ID NO:2 or SEQ ID NOs:5-18. As used herein "attenuating expression of a lipid regulator gene" means reducing or eliminating expression of the gene in any manner that reduces production of the fully functional lipid regulator protein. As used herein, "lipid regulator gene" refers to a gene whose attenuated expression in an organism or cell results in altered regulation of at least 50, at least 100, at least 200, or at least 300 genes in the organism or cell with respect to a control organism or cell and results in altered lipid productivity by the organism or cell. In an exemplary embodiment, a lipid regulator gene is a gene encoding a Zn(2)-C(6) fungal-type DNA-binding domain protein. Means for attenuating a lipid regulator gene include, for example, homologous recombination constructs; CRISPR systems, including one or more guide RNAs, a cas enzyme such but not limited to a Cas9 enzyme or a gene encoding a cas enzyme, and optionally, one or more donor fragments for insertion into a targeted site; RNAi constructs; shRNAs; antisense RNA constructs; ribozyme constructs; TALENS or genes encoding TALENs, Zinc Finger nucleases or genes encoding Zinc Finger nucleases; and meganucleases or genes encoding Zinc Finger nucleases.

For example, a recombinant microorganism engineered to have attenuated expression of a lipid regulator gene can have a disrupted lipid regulator gene that includes as least one insertion, mutation, or deletion that reduces or abolishes expression of the gene such that a fully functional lipid regulator gene is not produced or is produced in lower amounts than is produced by a control microorganism that does not include a disrupted lipid regulator gene. The disrupted lipid regulator gene can be disrupted by, for example, an insertion or gene replacement mediated by homologous recombination and/or by the activity of a meganuclease, zinc finger nuclease (Perez-Pinera et al. (2012) *Curr. Opin. Chem. Biol.* 16: 268-277), TALEN (WO 2014/207043; WO 2014/076571), or a cas protein (e.g., a Cas9 protein) of a CRISPR system.

CRISPR systems, reviewed recently by Hsu et al. (*Cell* 157:1262-1278, 2014) include, in addition to the cas nuclease polypeptide or complex, a targeting RNA, often denoted "crRNA", that interacts with the genome target site by complementarity with a target site sequence, a trans-activating ("tracr") RNA that complexes with the cas polypeptide and also includes a region that binds (by complementarity) the targeting crRNA.

The invention contemplates the use of two RNA molecules (a "crRNA" and a "tracrRNA") that can be co-transformed into a host strain (or expressed in a host strain) that expresses or is transfected with a cas protein for genome editing, or the use of a single guide RNA that includes a sequence complementary to a target sequence as well as a sequence that interacts with a cas protein. That is, in some strategies a CRISPR system as used herein can comprise two separate RNA molecules (a "tracr-RNA" and a "targeter-RNA" or "crRNA", see below) and referred to herein as a "two RNA molecule CRISPR system" "two RNA guide system" or a "Split guide RNA system". Alternatively, as illustrated in the examples, the DNA-targeting RNA can also include the trans-activating sequence for interaction with the cas protein (in addition to the target-homologous ("cr") sequences), that is, the DNA-targeting RNA can be a single RNA molecule and is referred to herein as a "chimeric guide RNA," a "single-guide RNA," or an "sgRNA." The terms "DNA-targeting RNA" and "gRNA" are inclusive, referring both to a two RNA guide system and to single-molecule DNA-targeting RNAs (i.e., sgRNAs). Both single-molecule guide RNAs and two RNA guide systems have been described in detail in the literature and for example, in U.S. Patent Application Publication No. US 2014/0068797, incorporated by reference herein in its entirety, and both are considered herein.

Any cas protein can be used in the methods herein, such as but not limited to, Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. The cas protein can be a Cas9 protein, such as a Cas9 protein of *Staphylococcus pyogenes*, *S. thermophilus*, *S. pneumonia*, *S. aureus*, or *Neisseria meningitidis*, as nonlimiting examples. Also considered are the Cas9 proteins provided as SEQ ID NOs:1-256 and 795-1346 in U.S. Patent Application Publication No. US 2014/0068797, and chimeric Cas9 proteins that may combine domains from more than one cas9 protein, as well variants and mutants of identified Cas9 proteins. In additional examples, a cas protein used for genome modification can be a Cpf1 protein that uses a single RNA guide system, such as but not limited to a Cpf1 protein of *Acidaminococcus* or *Lachnospiraceae* (see for example Fagerlund et al. (2015) *Genome Biol.* 15:261; Zetsche et al. (2015) *Cell* 163:1-13); and European patent application EP3009511), as well as the C2c1, C2c2, C2c3 RNA-guided nucleases (Shmakov et al. (2015) *Molecular Cell* 60:1-13).

Cas nuclease activity cleaves target DNA to produce double strand breaks. These breaks are then repaired by the cell in one of two ways: non-homologous end joining or homology-directed repair. In non-homologous end joining (NHEJ), the double-strand breaks are repaired by direct ligation of the break ends to one another. In this case, no new nucleic acid material is inserted into the site, although some nucleic acid material may be lost, resulting in a deletion, or altered, often resulting in mutation. In homology-directed repair, a donor polynucleotide (sometimes referred to as a "donor DNA" or "editing DNA") which may have homology to the cleaved target DNA sequence is used as a template for repair of the cleaved target DNA sequence, resulting in the transfer of genetic information from the donor polynucleotide to the target DNA. As such, new nucleic acid material may be inserted/copied into the site. The modifications of the target DNA due to NHEJ and/or homology-directed repair (for example using a donor DNA molecule) can lead to, for example, gene correction, gene replacement, gene tagging, transgene insertion, nucleotide deletion, gene disruption, gene mutation, etc.

In some instances, cleavage of DNA by a site-directed modifying polypeptide (e.g., a cas nuclease, zinc finger nuclease, meganuclease, or TALEN) may be used to delete nucleic acid material from a target DNA sequence by cleaving the target DNA sequence and allowing the cell to repair the sequence in the absence of an exogenously provided donor polynucleotide. Such NHEJ events can result in mutations ("mis-repair") at the site of rejoining of the cleaved ends that can resulting in gene disruption.

Alternatively, if a DNA-targeting RNA is co-administered to cells that express a cas nuclease along with a donor DNA, the subject methods may be used to add, i.e. insert or replace, nucleic acid material to a target DNA sequence (e.g. "knock out" by insertional mutagenesis, or "knock in" a nucleic acid that encodes a protein (e.g., a selectable marker and/or any protein of interest), an siRNA, an miRNA, etc., to modify a nucleic acid sequence (e.g., introduce a mutation), and the like.

A donor DNA can in particular embodiments include a gene regulatory sequence (e.g., a promoter) that can, using CRISPR targeting, be inserted upstream of the coding regions of the gene and upstream of the presumed proximal promoter region of the gene, for example, at least 50 bp, at least 100 bp, at least 120 bp, at least 150 bp, at least 200 bp, at least 250 bp, at least 300 bp, at least 350 bp, at least 400 bp, at least 450 bp, or at least 500 bp upstream of the initiating ATG of the coding region of the lipid regulator gene. The donor DNA can include a sequence, such as for example a selectable marker or any convenient sequence, that may be interfere with the native promoter. The additional sequence inserted upstream of the initiating ATG of the lipid regulator open reading frame (e.g., in the 5'UTR or upstream of the transcriptional start site of the lipid regulator gene) can decrease or even eliminate expression of the endogenous lipid regulator gene. Alternatively or in addition, the native lipid regulator gene can have its endogenous promoter wholly or partially replaced by a weaker or differently regulated promoter, or a non-promoter sequence.

In some examples, a nucleic acid molecule introduced into a host cell for generating a high efficiency genome editing cell line encodes a cas9 enzyme that is mutated to with respect to the corresponding wild-type enzyme such that the mutated cas9 enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (an enzyme that cleaves a single strand). Other examples of mutations that render Cas9 a nickase include, without limitation, H840A, N854A, and N863A. In some embodiments, a Cas9 nickase may be used in combination with guide sequence(s), e.g., two guide sequences, which target respectively sense and antisense strands of the DNA target. This combination allows both strands to be nicked and used to induce NHEJ. Two nickase targets (within close proximity but targeting different strands of the DNA) can be used to inducing mutagenic NHEJ. Such targeting of a locus using enzymes that cleave opposite strains at staggered positions can also reduce nontarget cleavage, as both strands must be accurately and specifically cleaved to achieve genome mutation.

In additional examples, a mutant cas9 enzyme that is impaired in its ability to cleave DNA can be expressed in the cell, where one or more guide RNAs that target a sequence upstream of the transcriptional or translational start site of the targeted gene are also introduced. In this case, the cas enzyme may bind the target sequence and block transcription of the targeted gene (Qi et al. (2013) *Cell* 152:1173-1183). This CRISPR interference of gene expression can be referred to as RNAi and is also described in detail in Larson et al. (2013) *Nat. Protoc.* 8: 2180-2196.

In some cases, a cas polypeptide such as a Cas9 polypeptide is a fusion polypeptide, comprising, e.g.: i) a Cas9 polypeptide (which can optionally be variant Cas9 polypeptide as described above); and b) a covalently linked heterologous polypeptide (also referred to as a "fusion partner"). A heterologous nucleic acid sequence may be linked to another nucleic acid sequence (e.g., by genetic engineering) to generate a chimeric nucleotide sequence encoding a chimeric polypeptide. In some embodiments, a Cas9 fusion polypeptide is generated by fusing a Cas9 polypeptide with a heterologous sequence that provides for subcellular localization (i.e., the heterologous sequence is a subcellular localization sequence, e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a hemagglutinin (HA) tag; a FLAG tag; a Myc tag; and the like).

Host cells can be genetically engineered (e.g. transduced or transformed or transfected) with, for example, a vector construct that can be, for example, a vector for homologous recombination that includes nucleic acid sequences homologous to a portion of a lipid regulator gene locus of the host cell or to regions adjacent thereto, or can be an expression vector for the expression of any or a combination of: a cas protein (e.g., a cas9 protein), a CRISPR chimeric guide RNA, a crRNA, and/or a tracrRNA, an RNAi construct (e.g., a shRNA), an antisense RNA, or a ribozyme. The vector can be, for example, in the form of a plasmid, a viral particle, a phage, etc. A vector for expression of a polypeptide or RNA for genome editing can also be designed for integration into the host, e.g., by homologous recombination. A vector containing a polynucleotide sequence as described herein, e.g., sequences having homology to host lipid regulator gene sequences (including sequences that are upstream and downstream of the lipid regulator-encoding sequences), as well as, optionally, a selectable marker or reporter gene, can be employed to transform an appropriate host to cause attenuation of a lipid regulator gene.

The recombinant microorganism in some examples can have reduced but not abolished expression of the lipid regulator gene, and the recombinant microorganism can have an increase in lipid production of from about 25% to about 200% or more, for example. A genetically modified microorganism as provided herein can in some examples include a nucleic acid construct for attenuating the expression of a lipid regulator gene, such as, for example, a gene encoding a polypeptide having at least 55%, at least 60%, at least 65%, at least 70%, at least 75%, at least 80%, at least 85%, at least 90%, or at least 95% identity to SEQ ID NO:2 or any of SEQ ID NO:5-18. For example, a host microorganism can include a construct for expressing an RNAi molecule, ribozyme, or antisense molecule that reduces expression of a lipid regulator gene encoding a polypeptide having at least 55% identity to SEQ ID NO:2 or any of SEQ ID NO:5-18. In some examples, a recombinant microorganism as provided herein can include at least one introduced (exogenous or non-native) construct for reducing expression of a lipid regulator gene.

In some examples, engineered strains can be selected for expression of a lipid regulator gene that is decreased with respect to a control cell that does not include a genetic modification for attenuating lipid regulator gene expression, but not eliminated, using methods known in the art, such as, for example, RNA-Seq or reverse transcription-PCR (RT-PCR).

A genetically engineered strain as provided herein can be engineered to include a construct for attenuating gene expression by reducing the amount, stability, or translatability of mRNA of a gene encoding a lipid regulator. For example, a microorganism such as an algal or heterokont strain can be transformed with an antisense RNA, RNAi, or ribozyme construct targeting an mRNA of a lipid regulator gene using methods known in the art. For example, an antisense RNA construct that includes all or a portion of the transcribed region of a gene can be introduced into a microorganism to decrease gene expression (Shroda et al. (1999) *The Plant Cell* 11:1165-78; Ngiam et al. (2000) *Appl. Environ. Microbiol.* 66: 775-782; Ohnuma et al. (2009) *Protoplasma* 236: 107-112; Lavaud et al. (2012) *PLoS One* 7:e36806). Alternatively or in addition, an RNAi construct (for example, a construct encoding a short hairpin RNA) targeting a gene having a Zn(2)Cys(6) domain can be introduced into a microorganism such as an alga or heterokont for reducing expression of the lipid regulator gene (see, for example, Cerruti et al. (2011) *Eukaryotic Cell* (2011) 10: 1164-1172; Shroda et al. (2006) *Curr. Genet.* 49:69-84).

Ribozymes are RNA-protein complexes that cleave nucleic acids in a site-specific fashion. Ribozymes have specific catalytic domains that possess endonuclease activity. For example, U.S. Pat. No. 5,354,855 reports that certain ribozymes can act as endonucleases with a sequence specificity greater than that of known ribonucleases and approaching that of the DNA restriction enzymes. Catalytic RNA constructs (ribozymes) can be designed to base pair with an mRNA encoding a gene as provided herein to cleave the mRNA target. In some examples, ribozyme sequences can be integrated within an antisense RNA construct to mediate cleavage of the target. Various types of ribozymes can be considered, their design and use is known in the art and described, for example, in Haseloff et al. (1988) *Nature* 334:585-591.

Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A, C or U) (Thompson et al., (1995) *Nucl Acids Res* 23:2250-68). The frequency of this dinucleotide occurring in any given RNA is statistically 3 out of 16. Therefore, for a given target messenger RNA of 1,000 bases, 187 dinucleotide cleavage sites are statistically possible.

The general design and optimization of ribozyme directed RNA cleavage activity has been discussed in detail (Haseloff and Gerlach (1988) *Nature* 334:585-591; Symons (1992) *Ann Rev Biochem* 61: 641-71; Chowrira et al. (1994) *J Biol Chem* 269:25856-64; Thompson et al. (1995) supra), all incorporated by reference in their entireties. Designing and testing ribozymes for efficient cleavage of a target RNA is a process well known to those skilled in the art. Examples of scientific methods for designing and testing ribozymes are described by Chowrira et al., (1994) supra and Lieber and Strauss (1995) *Mol Cell Biol.* 15: 540-51, each incorporated by reference. The identification of operative and preferred sequences for use in down regulating a given gene is a matter of preparing and testing a given sequence, and is a routinely practiced "screening" method known to those of skill in the art.

The use of RNAi constructs is described in literature cited above as well as in US2005/0166289 and WO 2013/016267, for example. A double stranded RNA with homology to the target gene is delivered to the cell or produced in the cell by expression of an RNAi construct, for example, an RNAi short hairpin (sh) construct. The construct can include a sequence that is identical to the target gene, or at least 70%, 80%, 90%, 95%, or between 95% and 100% identical to a sequence of the target gene. The construct can have at least 20, at least 30, at least 40, at least 50, at least 100, at least 200, at least 300, at least 400, at least 500, at least 600, at least 700, at least 800, at least 900, or at least 1 kb of sequence homologous to the target gene. Expression vectors can be engineered using promoters selected for continuous or inducible expression of an RNAi construct, such as a construct that produces an shRNA.

A nucleic acid construct for gene attenuation, e.g., a ribozyme, RNAi, or antisense construct can include at least fifteen, at least twenty, at least thirty, at least forty, at least fifty, or at least sixty nucleotides having at least 80% identity, such as at least 85%, at least 90%, at least 95%, or at least 99% or complementarity to at least a portion of the sequence of an endogenous lipid regulator gene of the microorganism to be engineered. A nucleic acid construct for gene attenuation, e.g., a ribozyme, RNAi, or antisense construct can include at least fifteen, at least twenty, at least thirty, at least forty, at least fifty, or at least sixty nucleotides having at least 80%, such as at least 95% or about 100%, identity or complementarity to the sequence of a naturally-occurring gene, such as a gene having encoding a polypeptide having at least 50%, at least 55%, at least 60%, at least 65%, at least 70%, at least 75%, at least 80% or at least 85%, at least 90%, or at least 95% sequence identity to an endogenous lipid regulator gene. For example, a nucleic acid construct for gene attenuation, e.g., a ribozyme, RNAi, or antisense construct can include at least fifteen, at least twenty, at least thirty, at least forty, at least fifty, or at least sixty nucleotides having at least 80% identity or complementarity to the sequence of a naturally-occurring lipid regulator gene, such as any provided herein. The nucleotide sequence can be, for example, from about 30 nucleotides to about 3 kilobases or greater, for example, from 30-50 nucleotides in length, from 50 to 100 nucleotides in length, from 100 to 500 nucleotides in length, from 500 nucleotides to 1 kb in length, from 1 kb to 2 kb in length, or from 2 to 5 kb. For example, an antisense sequence can be from about 100 nucleotides to about 1 kb in length. For example, a nucleic acid construct for gene attenuation, e.g., a ribozyme, RNAi, or antisense construct can include at least fifteen, at least twenty, at least thirty, at least forty, at least fifty, at least sixty, or at least 100 nucleotides having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity or complementarity to an endogenous lipid regulator gene or a portion thereof.

Promoters used in antisense, RNAi, or ribozyme constructs can be any that are functional in the host organism and that are suitable for the levels of expression required for reducing expression of the target gene to a desired amount. Promoters functional in algae and heterokonts are known in the art and disclosed herein. The construct can be transformed into algae using any feasible method, include any disclosed herein. A recombinant organism or microorganism transformed with a nucleic acid molecule for attenuating lipid regulator gene expression, such as but not limited to an antisense, RNAi, or ribozyme construct, can have the properties of a lipid regulator mutant as described herein, including, for example, reduced chlorophyll, increased photosynthetic efficiency, and increased productivity in culture, with respect to a host organism or microorganism that does not include the exogenous nucleic acid molecule that results in attenuated gene expression.

In additional examples, such as disclosed in Examples herein, gene attenuation that decreases but does not eliminate expression of the target gene can be achieved through the use of homologous recombination or CRISPR/Cas9 genome editing where the donor fragment is targeted for insertion into a non-coding region of a gene. For example, a selectable marker cassette or other donor fragment can be targeted by the use of an appropriate guide RNA to the 5' UTR, 3' UTR, or an intron of a gene whose reduced expression is desired. Thus, another aspect of the invention is a method for attenuating expression of a gene the includes inserting a nucleic acid fragment into a site upstream of the translational start site or downstream of a translational termination site, wherein the expression level of the gene is reduced. As nonlimiting examples, a donor fragment insertion can be introduced into a region up to 2 kb upstream of the translational start site of a gene, or up to 2 kb downstream of the termination codon of a gene. For example, an insertion that is targeted to a site of between about 5 bp and 2 kb upstream of the translational start site, or between about 10 bp and 1.5 kb upstream of the translational start site, or between about 10 bp and about 1.2 kb upstream of the translational start site, or between about 20 bp and about 1 kb upstream of the translational start site. Alternatively or in addition, an insertion can be targeted to the 3' UTR of a gene. Alternatively or in addition, an insertion that is targeted to a site of between about 5 bp and 2 kb downstream of the translational termination site (stop codon), or between about 10 bp and 1.5 kb downstream of the stop codon, or between about 10 bp and about 1.2 kb downstream of the stop codon, or between about 20 bp and about 1 kb downstream of the stop codon. Without being limited to any particular mechanism, such insertions may reduce the rate or transcription of a gene or may reduce the stability of a resulting transcript.

Nucleic Acid Molecules and Constructs

Also provided herein are nucleic acid molecules encoding polypeptides that include amino acid sequences having at least 60%, at least 65%, at least 70%, or at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. Alternatively or in addition, a nucleic acid molecule as provided herein can include a sequence having at least 50%, at least 55%, at least 60%, at least 65%, at least 70%, at least 75%, at least 80%, at least 85%, at least 90%, or at least 95% identity to SEQ ID NO:1 or any of SEQ ID NOs:72-84. The polypeptide having at least 60% identity to an amino acid sequence selected from the group consisting of SEQ ID NO:2 and SEQ ID NOs:5-17 or encoded by SEQ ID NO:1 or any of SEQ ID NOs:72-84 can include an amino acid sequence encoding a Zn(2)Cys(6) domain, e.g., a domain belonging to pfam PF00172. For example, the polypeptide encoded by the nucleic acid molecule can include a Zn(2)Cys(6) domain having an amino acid sequence with at least 60%, at least 65%, at least 70%, or at least 75%, at least 80%, at least 85%, at least 90%, or at least 95% identity to SEQ ID NO:3. Alternatively or in addition, a polypeptide encoded by a nucleic acid molecule as provided herein can optionally further include a PAS (or PAS3) domain. For example a polypeptide encoded by a nucleic acid molecule as provided herein can include a PAS domain having at least 60%, at least 65%, at least 70%, or at least 75%, at least 80%, at least 85%, at least 90%, or at least 95% identity to any of SEQ ID NO:21-SEQ ID NO:25.

The nucleic acid molecule in various examples can be or comprise a cDNA that lacks one or more introns present in the naturally-occurring gene, or, alternatively, can include one or more introns not present in the naturally-occurring gene. The nucleic acid molecule in various examples can have a sequence that is not 100% identical to a naturally-occurring gene. For example, the nucleic acid molecule can include a mutation with respect to a naturally-occurring gene that reduces the activity of the encoded polypeptide or reduces expression of the mRNA or protein encoded by the gene.

The nucleic acid molecule in various examples can comprise a heterologous promoter operably linked to the sequence encoding a polypeptide that includes an amino acid sequence having at least 60%, at least 65%, at least 70%, or at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17 and/or can comprise a heterologous promoter operably linked to a sequence having at least 50%, at least 55%, at least 60%, at least 65%, at least 70%, at least 75%, at least 80%, at least 85%, at least 90%, or at least 95% identity to SEQ ID NO:1 or any of SEQ ID NOs:72-84. Alternatively or in addition, a nucleic acid molecule can comprise a vector that includes a sequence encoding a polypeptide that includes an amino acid sequence having at least 60%, at least 65%, at least 70%, or at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17 and/or has at least 50%, at least 55%, at least 60%, at least 65%, at least 70%, at least 75%, at least 80%, at least 85%, at least 90%, or at least 95% identity to SEQ ID NO:1 or any of SEQ ID NOs:72-84.

A further aspect of the invention is a construct designed for attenuating expression of a gene encoding a Zn(2)Cys(6) DNA-binding domain polypeptide. The construct can be or comprise, in various examples, a sequence encoding a guide RNA of a CRISPR system, an RNAi construct, an antisense construct, a ribozyme construct, or a construct for homologous recombination, e.g., a construct having one or more nucleotide sequences having homology to a naturally-occurring Zn(2)Cys(6) domain-encoding gene as disclosed herein and/or sequences adjacent thereto in the native genome from which the gene is derived. For example, the construct can include at least a portion of a gene encoding a polypeptide having a Zn(2)Cys(6) domain, e.g., a sequence homologous to at least a portion of an gene that encodes a polypeptide that includes an amino acid sequence having at least 60%, at least 65%, at least 70%, or at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17 or can include at least a portion of a nucleic acid sequence having at least 50%, at least 55%, at least 60%, at least 65%, at least 70%, or at least 75%, at least 80%, at least 85%, at least 90%, or at least 95% identity to SEQ ID NO:1 or any of SEQ ID NOs:72-84.

The construct for gene attenuation can include, for example, at least a portion of the coding region of a gene encoding a polypeptide having a Zn(2)Cys(6) domain or a polypeptide having at least 60% identity to any of SEQ ID NO:2 and SEQ ID NOs:5-17 or at least a portion of a gene having at least 50% identity to SEQ ID NO:1 or any of SEQ ID NOs:72-84, at least a portion of an intron of a gene encoding a polypeptide having a Zn(2)Cys(6) domain or a polypeptide having at least 60% identity to any of SEQ ID NO:2 and SEQ ID NOs:5-17, at least a portion of a 5'UTR of a gene encoding a polypeptide having a Zn(2)Cys(6) domain or a polypeptide having at least 60% identity to any of SEQ ID NO:2 and SEQ ID NOs:5-17, at least a portion of the promoter region of a gene encoding a polypeptide having a Zn(2)Cys(6) domain or a polypeptide having at least 60% identity to any of SEQ ID NO:2 and SEQ ID NOs:5-17, and/or at least a portion of a 3' UTR of a gene encoding a polypeptide having a Zn(2)Cys(6) domain or a polypeptide having at least 60% identity to any of SEQ ID NO:2 and SEQ ID NOs:5-17. In some examples, the construct can be an RNAi, ribozyme, or antisense construct and can include a sequence from the transcribed region of the gene encoding a polypeptide having a Zn(2)Cys(6) domain or a polypeptide having at least 60% identity to any of SEQ ID NO:2 and SEQ ID NOs:5-17 in either sense or antisense orientation.

In further examples a construct can be designed for the in vitro or in vivo expression of a guide RNA (e.g., of a CRISPR system) designed to target a gene having a sequence having at least 50%, at least 55%, at least 60%, at least 65%, at least 70%, or at least 75%, at least 80%, at least 85%, at least 90%, or at least 95% identity to at least a portion of SEQ ID NO:1 or any of SEQ ID NOs:72-84 or coding a polypeptide having a Zn(2)Cys(6) domain or a polypeptide having at least 60% identity to any of SEQ ID NO:2 and SEQ ID NOs:5-17, and can include a sequence homologous to a portion of a gene encoding a polypeptide having a Zn(2)Cys(6) domain or a polypeptide having at least 60% identity to any of SEQ ID NO:2 and SEQ ID NOs:5-17, including, for example, an intron, a 5'UTR, a promoter region, and/or a 3' UTR of a gene encoding a polypeptide having a Zn(2)Cys(6) domain or a polypeptide having at least 60% identity to any of SEQ ID NO:2 and SEQ ID NOs:5-17. In yet further examples, a construct for attenuating expression a gene encoding a Zn(2)Cys(6) domain-containing polypeptide can be a guide RNA or antisense oligonucleotide, where the sequence having homology to a transcribed region of a gene encoding a polypeptide having a Zn(2)Cys(6) domain in antisense orientation.

Further provided are guide RNAs for attenuating expression of a Zn(2)Cys(6) gene or a gene encoding a polypeptide having at least 60% identity to any of SEQ ID NO:2 and SEQ ID NOs:5-17, and DNA constructs encoding such guide RNAs. The guide RNAs can be chimeric or single guide RNAs or can be guide RNAs that include a tracr mate sequence but require an additional tracr RNA to effect genome editing. In various embodiments, provided herein is a nucleic acid molecule having at least 50%, at least 55%, at least 60%, at least 65%, at least 70%, or at least 75%, at least 80%, at least 85%, at least 90%, or at least 95% identity to at least a portion of SEQ ID NO:1 or any of SEQ ID NOs:72-84, where the nucleic acid molecule encodes a guide RNA of a CRISPR system, that can be, as nonlimiting examples, a Cas9/CRISPR system or a Cpf1 CRISPR system. The nucleic acid molecule can include, for example at least 17, at least 18, at least 19, at least 20, at least 21, at least 22, at least 23, at least 24, or at least 25 nucleotides of sequence of a naturally occurring Zn(2)Cys(6) gene, such as SEQ ID NO:1 or any of SEQ ID NOs:72-84. In exemplary embodiments, the guide RNA or nucleic acid sequence encoding the guide RNA can include any of SEQ ID NOs:51-62 or sequences having at least 88% or 93% identity to any thereof.

In addition, provided herein are antisense, ribozyme, or RNAi constructs that include at least a portion of a gene having encoding a Zn(2)Cys(6) or a polypeptide having at least 60% identity to any of SEQ ID NO:2 and SEQ ID NOs:5-17, in which a promoter, such as a heterologous promoter, is operably linked to the Zn(2)Cys(6) gene sequence and the Zn(2)Cys(6) gene sequence is in antisense orientation.

Further, provided herein are constructs for homologous recombination that include at least one sequence from a Zn(2)Cys(6) gene locus of the genome of an alga juxtaposed with a heterologous nucleic acid sequence that can be, in nonlimiting examples, a selectable marker or detectable marker gene. In some examples a construct for homologous recombination includes two nucleic acid sequences from a Zn(2)Cys(6) gene locus of the genome of an alga where the two sequences flank a heterologous sequence for insertion into the Zn(2)Cys(6) gene locus.

One skilled in the art will appreciate that a number of transformation methods can be used for genetic transformation of microorganisms and, therefore, can be deployed for the methods of the present invention. "Stable transformation" is intended to mean that the nucleic acid construct introduced into an organism integrates into the genome of the organism or is part of a stable episomal construct and is capable of being inherited by the progeny thereof. "Transient transformation" is intended to mean that a polynucleotide is introduced into the organism and does not integrate into the genome or otherwise become established and stably inherited by successive generations.

Genetic transformation can result in stable insertion and/or expression of transgenes, constructs from either the nucleus or the plastid, and in some cases can result in transient expression of transgenes. The transformation methods can also be used for the introduction of guide RNAs or editing DNAs. Genetic transformation of microalgae has been reported successful for more than 30 different strains of microalgae, which belong to at least ~22 species of green, red, and brown algae, diatoms, euglenids, and dianoflagellates (see, e.g., Radakovits et al., *Eukaryotic Cell*, 2010; and Gong et al., *J. Ind. Microbiol. Biotechnol.*, 2011). Nonlimiting examples of such useful transformation methods include agitation of cells in the presence of glass beads or silicon carbide whiskers as reported by, for example, Dunahay, *Biotechniques*, 15(3):452-460, 1993; Kindle, *Proc. Natl. Acad. Sci. U.S.A.*, 1990; Michael and Miller, *Plant J.*, 13, 427-435, 1998. Electroporation techniques have been successfully used for genetic transformation of several microalgal species including *Nannochloropsis* sp. (see, e.g., Chen et al., *J. Phycol.*, 44:768-76, 2008), *Chlorella* sp. (see, e.g., Chen et al., *Curr. Genet.*, 39:365-370, 2001; Chow and Tung, *Plant Cell Rep.* Vol. 18, No. 9, 778-780, 1999), *Chlamydomonas* (Shimogawara et al., *Genetics*, 148: 1821-1828, 1998), *Dunaliella* (Sun et al., *Mol. Biotechnol.*, 30(3): 185-192, 2005). Micro-projectile bombardment, also referred to as microparticle bombardment, gene gun transformation, or biolistic bombardment, has been used successfully for several algal species including, for example, diatoms species such as *Phaeodactylum* (Apt et al., *Mol. Gen. Genet.*, 252:572-579, 1996), *Cyclotella* and *Navicula* (Dunahay et al., *J. Phycol.*, 31:1004-1012, 1995), *Cylindrotheca* (Fischer et al., *J. Phycol.*, 35:113-120, 1999), and *Chaetoceros* sp. (Miyagawa-Yamaguchi et al., *Phycol. Res.* 59: 113-119, 2011), as well as green algal species such as *Chlorella* (El-Sheekh, *Biologia Plantarum*, Vol. 42, No. 2: 209-216, 1999), and *Volvox* species (Jakobiak et al., *Protist*, 155:381-93, 2004). Additionally, *Agrobacterium*-mediated gene transfer techniques can also be useful for genetic transformation of microalgae, as has been reported by, for example, Kumar, *Plant Sci.*, 166(3):731-738, 2004, and Cheney et al., *J. Phycol.*, Vol. 37, Suppl. 11, 2001.

A transformation vector or construct as described herein will typically comprise a marker gene that confers a selectable or scorable phenotype on target host cells, e.g., algal cells or may be co-transformed with a construct that includes a marker. A number of selectable markers have been successfully developed for efficient isolation of genetic transformants of algae. Common selectable markers include antibiotic resistance, fluorescent markers, and biochemical markers. Several different antibiotic resistance genes have been used successfully for selection of microalgal transformants, including blastocydin, bleomycin (see, for example, Apt et al., 1996, supra; Fischer et al., 1999, supra; Fuhrmann et al., *Plant J.*, 19, 353-61, 1999, Lumbreras et al., *Plant J.*, 14(4):441-447, 1998; Zaslayskaia et al., *J. Phycol.*, 36:379-386, 2000), spectinomycin (Cerutti et al., *Genetics*, 145: 97-110, 1997; Doetsch et al., *Curr. Genet.*, 39, 49-60, 2001; Fargo, *Mol. Cell. Biol.*, 19:6980-90, 1999), streptomycin (Berthold et al., *Protist*, 153:401-412, 2002), paromomycin (Jakobiak et al., *Protist*, supra.; Sizova et al., *Gene*, 277: 221-229, 2001), nourseothricin (Zaslayskaia et al., 2000, supra), G418 (Dunahay et al., 1995, supra; Poulsen and Kroger, *FEBS Lett.*, 272:3413-3423, 2005, Zaslayskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin (e.g., ZEOCIN™ pheomycin D1) resistance (Stevens, *Mol. Gen. Genet.* 251:23-30, 1996), and paramomycin and neomycin resistance (Sizova et al., 2001, supra). Other fluorescent or chromogenic markers that have been used include luciferase (Falciatore et al., *J. Mar. Biotechnol.*, 1: 239-251, 1999; Fuhrmann et al., *Plant Mol. Biol.*, 2004; Jarvis and Brown, *Curr. Genet.*, 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.*, 1:165-169, 1994), β-galactosidase (Gan et al., *J. Appl. Phycol.*, 15:345-349, 2003; Jiang et al., *Plant Cell Rep.*, 21:1211-1216, 2003; Qin et al., *High Technol. Lett.*, 13:87-89, 2003), and green fluorescent protein (GFP) (Cheney et al., 2001, supra; Ender et al., *Plant Cell*, 2002, Franklin et al., *Plant J.*, 2002; 56, 148, 210).

One skilled in the art will readily appreciate that a variety of known promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which has been used in both dinoflagellates and chlorophyta (Chow et al, *Plant Cell Rep.,* 18:778-780, 1999; Jarvis and Brown, *Curr. Genet.,* 317-321, 1991; Lohuis and Miller, *Plant J.,* 13:427-435, 1998). The SV40 promoter from simian virus has also reported to be active in several algae (Gan et al., *J. Appl. Phycol.,* 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.,* 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.,* 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., *Mar. Biotechnol.,* 1:239-251, 1999; Zaslayskaia et al., *J. Phycol.* 36:379-386, 2000) or the vcp gene encoding a eustigmatophyte violaxanthin-chlorophyll a/b binding protein (see U.S. Pat. No. 8,318,482). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272:3413-3423, 2005), thus gene expression can be switched off or on when microalgal cells are grown in the presence of ammonium/nitrate. Additional algal promoters that can find use in the constructs and transformation systems provided herein include those disclosed in U.S. Pat. No. 8,883,993; U.S. Patent Appl. Pub. No. US 2013/0023035; U.S. Patent Application Pub. No. US 2013/0323780; and U.S. Patent Application Pub. No. US 2014/0363892.

Host cells can be either untransformed cells or cells that are already transfected with at least one nucleic acid molecule. For example, an algal host cell that is engineered to have attenuated expression of a lipid regulator gene can further include one or more genes that may confer any desirable trait, such as, but not limited to, increased production of biomolecules of interest, such as one or more proteins, pigments, alcohols, or lipids.

Methods of Producing Lipids

Also provided herein are methods of producing lipid by culturing a mutant microorganism as provided herein that has increased lipid productivity with respect to a control cell while producing at least 45% of the biomass produced by a control cell under the same culture conditions. The methods include culturing a mutant microorganism as provided herein in a suitable medium to produce lipid and recovering biomass or at least one lipid from the culture. The microorganism can in some examples be an alga, and the culture can be a photoautotrophic culture. Culturing can be in batch, semi-continuous, or continuous mode.

The mutant microorganism in some examples can be cultured in a medium that comprises less than about 5 mM ammonium, for example, less than about 2.5 mM ammonium, less than about 2 mM ammonium, less than about 1.5 mM ammonium, less than or equal to about 1 mM ammonium, or less than or equal to about 0.5 mM. The culture medium can include, for example, from about 0 to about 2.5 mM ammonium, from about 0.1 to about 2.5 mM ammonium, from about 0.5 to about 2.5 mM ammonium, from about 0 to about 1.5 mM ammonium, from about 0.1 to about 1 mM ammonium, or from about 0.2 to about 1 mM ammonium. The microorganism can be cultured in a medium that includes nitrate, which in some examples may be substantially the sole nitrogen source in the culture medium or may be present in addition to less than 5 mM ammonium, less than 2.5 mM ammonium, less than 1.0 mM ammonium, or less than or equal to about 0.5 mM ammonium. Alternatively or in addition, the culture medium can comprises urea, which in some examples can be substantially the sole source of nitrogen in the culture medium.

Yet another aspect of the invention is a method of producing lipid that includes culturing a microorganism under conditions in which the FAME to TOC ratio of the microorganism is maintained between about 0.3 and about 0.8, and isolating lipid from the microorganism, the culture medium, or both. For example, the microorganisms can be cultured such that the FAME to TOC ratio is maintained at between about 0.3 and about 0.8, between about 0.4 and about 0.7, between about 0.4 and about 0.6, or between about 0.45 and about 0.55. The ratio can be maintained at between about 0.3 and about 0.8, for example between about 0.4 and about 0.8, between about 0.4 and about 0.7, between about 0.4 and about 0.6, or between about 0.45 and about 0.55 for at least 3, at least 4, at least 5, at least 6, at least 7, at least 8, at least 9, at least 10, at least 11, at least 12, at least 13, at least 15, at least 20, at least 30 days, or at least 60 days. In these methods the microorganism can be cultured under continuous or semi-continuous conditions. The method of producing lipid can include culturing a mutant microorganism such as any provided herein under conditions in which the FAME to TOC ratio of the microorganism is maintained between about 0.3 and about 0.8, between about 0.3 and about 0.8, between about 0.4 and about 0.7, between about 0.4 and about 0.6, or between about 0.45 and about 0.55. For example, the microorganism can be a mutant microorganism having attenuated expression of a gene encoding a polypeptide having at least 55%, at least 65%, at least 75%, or at least 85% identity to a polypeptide comprising an amino acid sequence selected from the group consisting of SEQ ID NO:2 and SEQ ID NOs:5-17. The FAME to TOC ratio may be adjusted, for example, by the type and concentration of nitrogen source present in the culture medium. For example, the method may include culturing a microorganism, such as a mutant microorganism as disclosed herein, in a culture medium that includes nitrate and less than 2.5 mM ammonium or less than 1.0 mM ammonium.

The culture conditions in the methods provided herein are preferably conditions in which a control microorganism (i.e., a microorganism that does not have the mutation leading to higher lipid productivity) produces biomass on a daily basis, for example, produces biomass on a daily basis for at least five, at least eight, at least ten, or at least twelve days, and in various embodiments the methods of producing lipid result in the mutant microorganism producing at least 50% more lipid than a control microorganism while exhibiting a decrease in biomass (e.g., TOC) accumulation of no more than 35%, 30%, 25%, 20%, 15%, 10%, 5%, 2%, or 1% with respect to the control microorganism. For example, the methods of producing lipid can include culturing a mutant microorganism as provided herein in a suitable medium to produce lipid and recovering biomass or at least one lipid from the culture, in which the mutant microorganism produces at least 50%, at least 55%, at least 60%, at least 65%, at least 70%, at least 75%, at least 80%, at least 85%, at least 90%, at least 95%, at least 100%, at least 110%, at least 120% more lipid than a control microorganism while producing at least 65%, 70%, 75%, 880%, 85%, 90%, 95%, 98%, or 99% of the biomass produced by the control microorganism, under conditions where both the mutant microorganism and the control microorganism are producing biomass on a daily basis. The microorganism can in some examples be an alga, and the culture can be a photoautotrophic culture. Culturing can be in batch, semi-continuous, or continuous mode.

The lipid producing microorganisms may be cultured in any suitable vessel(s), including flasks or bioreactors, where the algae may be exposed to artificial or natural light (or natural light supplemented with artificial light). The culture comprising mutant algae that are deregulated in their response to low light may be cultured on a light/dark cycle that may be, for example, a natural or programmed light/dark cycle, and as illustrative examples, may provide twelve hours of light to twelve hours of darkness, fourteen hours of light to ten hours of darkness, sixteen hours of light to eight hours of darkness, etc.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. A microorganism as provided herein may be cultured for at least five, at least six, at least seven at least eight, at least nine, at least ten, at least eleven at least twelve, at least thirteen, at least fourteen, or at least fifteen days, or at least one, two three, four, five, six, seven, eight, nine, or ten weeks, or longer.

Non-limiting examples of selected and/or controlled conditions that can be used for culturing the recombinant microorganism can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown mixotrophically, using both light and a reduced carbon source. Alternatively, the microorganism or host cell can be cultured phototrophically. When growing phototrophically, the algal strain can advantageously use light as an energy source. An inorganic carbon source, such as $CO_2$ or bicarbonate can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. A microorganism grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture.

Microorganisms and host cells that can be useful in accordance with the methods of the present invention can be found in various locations and environments throughout the world. The particular growth medium for optimal propagation and generation of lipid and/or other products can vary and may be optimized to promote growth, propagation, or production of a product such as a lipid, protein, pigment, antioxidant, etc. In some cases, certain strains of microorganisms may be unable to grow in a particular growth medium because of the presence of some inhibitory component or the absence of some essential nutritional requirement of the particular strain of microorganism or host cell.

Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae (www.sbs.utexas.edu/utex/media.aspx); Culture Collection of Algae and Protozoa (www.ccap.ac.uk); and Katedra Botaniky (botany.natur.cuni.cz/algo/caup-media.html).

The culture methods can optionally include inducing expression of one or more genes and/or regulating a metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the microorganisms having increased lipid productivity can be cultured in a "photobioreactor" equipped with an artificial light source, and/or having one or more walls that is transparent enough to light, including sunlight, to enable, facilitate, and/or maintain acceptable microorganism growth and proliferation. For production of fatty acid products or triglycerides, photosynthetic microorganisms or host cells can additionally or alternately be cultured in shake flasks, test tubes, vials, microtiter dishes, petri dishes, or the like, or combinations thereof.

Additionally or alternately, mutant or recombinant photosynthetic microorganisms or host cells may be grown in ponds, canals, sea-based growth containers, trenches, raceways, channels, or the like, or combinations thereof. In such systems, the temperature may be unregulated, or various heating or cooling method or devices may be employed As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo)bioreactor do not constitute a dangerous and/or lethal dose with respect to the growth, proliferation, and/or survival of the microorganisms.

The mutant microorganisms can include one or more non-native genes encoding a polypeptide for the production of a product, such as but not limited to a lipid.

The methods include culturing a mutant microorganism as provided herein, such as a mutant microorganism as provided herein that has increased lipid productivity with respect to a control cell while producing at least 50% of the biomass produced by a control cell under the same culture conditions to produce biomass or lipid. Lipids can be recovered from culture by recovery means known to those of ordinary skill in the art, such as by whole culture extraction, for example, using organic solvents or by first isolating biomass from which lipids are extracted (see, for example, Hussein et al. *Appl. Biochem. Biotechnol.* 175:3048-3057; Grima et al. (2003) *Biotechnol. Advances* 20:491-515). In some cases, recovery of fatty acid products can be enhanced by homogenization of the cells (Gunerken et al. (2015) *Biotechnol. Advances* 33:243-260). For example, lipids such as fatty acids, fatty acid derivatives, and/or triglycerides can be isolated from algae by extraction of the algae with a solvent at elevated temperature and/or pressure, as described in the co-pending, commonly-assigned U.S. patent application Ser. No. 13/407,817 entitled "Solvent Extraction of Products from Algae", filed on Feb. 29, 2012, which is incorporated herein by reference in its entirety.

Biomass can be harvested, for example, by centrifugation or filtering. The biomass may be dried and/or frozen. Further products may be isolated from biomass, such as, for example, various lipids or one or more proteins. Also included in the invention is an algal biomass comprising biomass of lipid regulator mutant, such as any disclosed herein, such as but not limited to a lipid regulator mutant that includes a mutation in a gene encoding a polypeptide having at least 50%, at least 55%, at least 60%, at least 65%, at least 70%, at least 75%, at least 80%, at least 85%, at least 90%, or at least 95% identity to a polypeptide comprising an amino acid sequence selected from the group consisting of SEQ ID NO:2 and SEQ ID NOs:5-17.

Additional Embodiments

Alternatively or in addition to any of the forgoing embodiments, the invention provides the following embodiments:

Embodiment 1 is a mutant microorganism that produces at least 25% more lipid and at least 45% more biomass than is produced by a control microorganism cultured under substantially identical conditions in which the control microorganism produces biomass, optionally wherein any one or more of the following are fulfilled:

(a) the control microorganism is a wild type microorganism;

(b) the mutant microorganism produces at least 45%, at least 50%, at least 55%, at least 60%, at least 65%, at least 70%, at least 75%, at least 80%, at least 85%, at least 90%, at least 95%, at least 100%, as much biomass, which can be assessed as average biomass (e.g., TOC) productivity per day, during a culture period of at least three, at least four, at least five, at least six, at least seven, at least eight, at least nine, at least ten, at least eleven, at least twelve, at least thirteen days, at least fourteen, at least fifteen, at least twenty, at least thirty, or at least sixty days;

(c) the mutant microorganism produces at least 25%, at least 30%, at least 55%, at least 40%, at least 45%, at least 50%, at least 55%, at least 60%, at least 70%, at least 75%, at least 80%, at least 85%, at least 90%, at least 95%, at least 100%, at least 110%, at least 115%, at least 120%, at least 150% more lipid, or at least 200% more lipid, which can be assessed as average lipid (e.g., FAME) productivity per day, than is produced by a control microorganism during a culture period of at least at least three, at least four, at least five, at least six, at least seven, at least eight, at least nine, at least ten, at least eleven, at least twelve, at least thirteen days, at least fourteen, at least fifteen, at least twenty, at least thirty, or at least sixty days;

(d) the substantially identical conditions in which the control microorganism produces biomass comprise a culture medium that comprises less than about 5 mM, less than about 4 mM, less than about 3 mM, less than 2.5 mM ammonium, less than 2 mM ammonium, less than 1.5 mM ammonium, less than or equal to about 1 mM ammonium, or less than or equal to about 0.5 mM ammonium;

(e) the substantially identical conditions in which the control microorganism produces biomass comprise a culture medium that comprises nitrate or urea; and/or (f) the microorganism is a heterokont or alga.

Embodiment 2 is a mutant microorganism according to embodiment 1 in which the mutant has attenuated expression of a regulator gene wherein the regulator gene encodes a polypeptide having at least 50, at least 55%, at least 60%, at least 65%, at least 70%, at least 75%, at least 80%, at least 85%, at least 90%, at least 95%, at least 96%, at least 97%, at least 98%, or at least 99% to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18 and/or regulator gene encodes a polypeptide that includes a Zn(2)Cys(6) domain, optionally wherein the polypeptide further includes a PAS3 domain.

Embodiment 3 is a mutant microorganism according to embodiment 1 or embodiment 2, wherein the mutant is a spontaneous mutant, a classically-derived mutant, or an engineered mutant, optionally wherein the mutant is an engineered mutants that:

(a) has a disrupted gene, optionally wherein the gene is disrupted in a noncoding region;

(b) is deleted in all or a portion of a gene;

(c) includes an antisense construct, an RNAi construct, or a ribozyme construct that targets a gene;

(d) includes an insertion, optionally wherein the insertion is generated by CRISPR/cas genome editing; and/or (e) includes a mutation generated by CRISPR/cas genome editing.

Embodiment 4 is a mutant microorganism according to any of embodiments 1-3, wherein:

(a) the mutant produces at least 50% or at least 80% or at least 100% more FAME (e.g., average productivity per day) while producing at least 85% or at least 90% or at least 95% of the TOC produced by a control cell, e.g., TOC productivity on a per day basis, when cultured under conditions in which both the control and mutant microorganism produce biomass; and/or (b) wherein the FAME/TOC ratio of the mutant microorganism is at least 40%, at least 50%, at least 60%, at least 70%, or at least 75% higher than the FAME/TOC of the control microorganism while producing at least 85% or at least 90% of the TOC produced by a control cell (such as a wild type cell) when cultured under conditions in which both the control and mutant microorganism produce biomass; and/or (c) the FAME/TOC ratio of the mutant microorganism is at least 0.30, at least 0.35 at least 0.40, at least 0.5, or between about 0.3 and about 0.8 when cultured under conditions in which both the control and mutant microorganism produce biomass and/or (d) wherein the FAME/TOC ratio is maintained between about 0.3 and about 0.7 for a culture period of at least five, at least six, at least seven, at least eight, at least nine, at least ten, at least eleven, at least twelve, or at least thirteen days during which the mutant microorganism produces at least 50%, at least 60%, at least 70%, or at least 75%, at least 80% or at least 85% of the biomass produced by a control microorganism cultured under the same conditions in which the control microorganism accumulates biomass.

Embodiment 6 is a mutant microorganism according to any of embodiments 1-3, wherein:

(a) the mutant produces at least 85%, at least 90%, at least 95%, at least 100%, at least 105%, at least 110%, or at least 115% more FAME (e.g., on an average per day basis) while producing at least 70%, at least 75%, at least 80%, or at least 85% of the TOC produced (e.g., on an average per day basis) by a control microorganism (such as a wild type cell) when cultured under conditions in which both wild type and mutant microorganism are producing biomass; and/or (b) the FAME/TOC ratio of the mutant microorganism is at least 100%, at least 110%, at least 120%, at least 130%, at least 140%, at least 150%, at least 160%, at least 170%, or at least 180% greater than the FAME/TOC ratio of a control microorganism when cultured under conditions in which both wild type and mutant microorganism are producing biomass; and/or (c) the FAME/TOC ratio of the mutant microorganism is at least 0.50, at least 0.55, at least 0.60, at least 0.65, at least 0.70, or at least 0.75 and the mutant microorganism produces at least 70%, at least 75%, at least 80%, or at least 85% of the TOC produced by a control microorganism when cultured under conditions in which the wild type accumulates biomass.

Embodiment 7 is a mutant microorganism according to any of embodiments 1-6, wherein:

(a) the culture conditions under which the mutant microorganism produces more lipid is batch, semi-continuous, or continuous culture; and/or (b) the daily lipid productivity of the mutant is greater than the daily lipid productivity of the control microorganism throughout the culture period.

Embodiment 8 is a mutant microorganism according to any of embodiments 1-7 in which the mutant microorganism comprises a mutation in a non-coding region of a gene that reduces expression of the gene, optionally wherein the mutation is an insertion.

Embodiment 9 is a mutant microorganism according to any of embodiments 1-7 in which the mutant microorganism comprises a construct that reduces expression of a gene, wherein the construct encodes an RNAi, antisense transcript, or ribozyme.

Embodiment 10 is a mutant microorganism according to any of embodiments 1-9, wherein the mutant microorganism is a *Labyrinthulomycte* species, (a) optionally wherein the mutant microorganism is a species belonging to any of the genera *Labryinthula, Labryinthuloides, Thraustochytrium, Schizochytrium, Aplanochytrium, Aurantiochytrium, Oblongichytrium, Japonochytrium, Diplophrys,* or *Ulkenia*; or wherein the mutant microorganism is an algal species, (b) optionally a species belonging to any of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phæodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox*.

Embodiment 11 is biomass comprising any of the mutant microorganisms of any of embodiments 1-10.

Embodiment 12 is a nucleic acid molecule comprising a sequence encoding a polypeptide having at least 60%, at least 65%, at least 70%, or at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17;

wherein any one or more of the following are satisfied:

(a) the polypeptide includes an amino acid sequence encoding a Zn(2)Cys(6) domain, optionally wherein the Zn(2)Cys(6) domain has at least 60%, at least 65%, at least 70%, or at least 75%, at least 80%, at least 85%, at least 90%, or at least 95% identity to SEQ ID NO:3;

the polypeptide includes an amino acid sequence encoding a PAS domain, optionally wherein the PAS domain has at least 60%, at least 65%, at least 70%, or at least 75%, at least 80%, at least 85%, at least 90%, or at least 95% identity to any of SEQ ID NO:21-SEQ ID NO:25;

(b) the nucleic acid molecule in various examples comprises a cDNA that lacks one or more introns present in the naturally-occurring gene or is a gene construct that includes one or more introns not present in the naturally-occurring gene;

(c) the nucleic acid molecule in various examples can have a sequence that is not 100% identical to a naturally-occurring gene;

(d) the nucleic acid molecule has at least 50%, at least 55%, at least 60%, at least 65%, at least 70%, or at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17;

(e) the nucleic acid molecule comprises a heterologous promoter operably linked to the sequence; and/or (f) the nucleic acid molecule comprises a vector.

Embodiment 13 is a nucleic acid molecule construct for attenuating expression of a gene encoding a polypeptide according to having at least 60%, at least 65%, at least 70%, or at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17;

a sequence encoding a guide RNA of a CRISPR system, an RNAi construct, an antisense construct, a ribozyme construct, or a construct for homologous recombination, e.g., a construct having one or more nucleotide sequences having homology to a naturally-occurring Zn(2)Cys(6) domain-encoding gene as disclosed herein and/or sequences adjacent thereto in the native genome from which the gene is derived.

Embodiment 14 is method of engineering a cell for increased lipid production comprising attenuating expression of a gene encoding a polypeptide having at least 60%, at least 65%, at least 70%, or at least 75%, at least 80%, at least 85%, at least 90%, or at least 95% identity to SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17, optionally a gene encoding a polypeptide having an amino acid sequence having at least 55%, at least 60%, at least 65%, at least 70%, or at least 75%, at least 80%, at least 85%, at least 90%, or at least 95% identity to any of SEQ ID NOs:21-25, into a microorganism to produce a mutant microorganism having higher lipid productivity than the progenitor microorganism, optionally wherein attenuating expression of the gene comprises introducing a nucleic acid molecule according to embodiment 13 into the microorganism.

Embodiment 15 is method for producing lipid comprising culturing a mutant according to any of embodiments 1-10 to produce lipid, optionally wherein any one or more of the following are satisfied:

(a) the culture medium includes nitrate or urea;

(b) the culture medium includes less than 5 mM, less than 4 mM, less than 3 mM, less than 2.5 mM ammonium, less than 2 mM ammonium, less than or equal to about 1.5 mM ammonium, less than or equal to about 1 mM ammonium, or less than or equal to about 0.5 mM ammonium;

(c) the culture is a batch, semi-continuous, or continuous culture;

(d) the culture period is at least 5, 7, 8, 9, 10, 11, 12, 13 day, at least 15, 20, 30, 40, 50, or 60 days;

(e) the mutant is an algal mutant and the culture is photoautotrophic;

(f) the mutant produces at least 25% more lipid, such as at least 50% more lipid, preferably FAME lipid, and at least 65% of the biomass of a control microorganism during the culture period;

(g) the mutant produces more lipid, preferably FAME lipid, on each day of the culture period; and/or (h) the mutant accumulates biomass on each day of the culture period.

Embodiment 16 is method for producing lipid comprising culturing a microorganism under conditions in which the FAME/TOC ratio is maintained at between about 0.3 and about 0.8 throughout the culture period, optionally wherein any one or more of the following are satisfied:

(a) the culture medium includes nitrate or urea;

(b) the culture medium includes less than 5 mM, less than 4 mM, less than 3 mM, less than 2.5 mM ammonium, less than 2 mM ammonium, less than or equal to about 1.5 mM ammonium, less than or equal to about 1 mM ammonium, or less than or equal to about 0.5 mM ammonium;

(c) the culture is a batch, semi-continuous, or continuous culture;

(d) the culture period is at least 5, 7, 8, 9, 10, 11, 12, 13 day, at least 15, 20, 30, 40, 50, or 60 days;

(e) the microorganism is an algal microorganism and the culture is photoautotrophic;

(f) the microorganism accumulates biomass on each day of the culture period; and/or (g) the microorganism is a mutant microorganism according to any of embodiments 1-1

EXAMPLES

Media Used in Examples

The following media are used in the Examples.

PM066 medium (Example 1) includes 8.8 mM nitrate as the sole nitrogen source. PM066 medium included 10 mM nitrate ($NO_3$) and 0.417 mM phosphate ($PO_4$) along with trace metals and vitamins in Instant Ocean salts. PM066 media was made by adding 5.71 ml of a 1.75 M $NaNO_3$ stock solution (148.7 g/L), and 5.41 ml of a 77 mM $K_2HPO_4.3H_2O$ stock solution (17.57 g/L) to 981 mls of Instant Ocean salts solution (35 g/L) along with 4 ml of Chelated Metals Stock Solution and ml of 4 ml Vitamin Stock Solution. Chelated Metals Stock Solution was prepared by adding to 400 mls of water 2.18 g $Na_2EDTA.2H_2O$; 1.575 g $FeCl_3.6H_2O$; 500 µl of 39.2 mM stock solution (0.98 g/100 ml) $CuSO_4.5H_2O$; 500 µl of 77.5 mM stock solution (2.23 g/100 ml) $ZnSO_4.7H_2O$; 500 µl of 42.0 mM stock solution (1.00 g/100 ml) $CoCl_2.6H_2O$; 500 µl of 910.0 mM stock solution (18.0/100 ml) $MnCl_2.4H_2O$; 500 µl of 26.0 mM stock solution (0.63 g/100 ml) $Na_2MoO_4.2H_2O$; bringing up to 500 ml final volume, and filter sterilizing. Vitamin Stock Solution was prepared by adding to 400 mls of water 0.05 g Thiamine HCl; 500 µl of 0.37 mM stock solution (0.05 g/100 ml) of cyanocobalamin; and 2.5 ml of 0.41 mM stock solution (0.01 g/100 ml) of biotin, bringing up to a final volume of 500 mls, and filter sterilizing.

PM067 medium included no nitrogen source (no nitrate, ammonium, or urea), and 0.417 mM phosphate ($PO_4$) along with trace metals and vitamins in Instant Ocean salts. PM067 media was made by adding 5.41 ml of a 77 mM $K_2HPO_4.3H_2O$ stock solution (17.57 g/L) to 987 mls of Instant Ocean salts solution (35 g/L) along with 4 ml of Chelated Metals Stock Solution and ml of 4 ml Vitamin Stock Solution. Chelated Metals Stock Solution was prepared by adding to 400 mls of water 2.18 g $Na_2EDTA.2H_2O$; 1.575 g $FeCl_3.6H_2O$; 500 µl of 39.2 mM stock solution (0.98 g/100 ml) $CuSO_4.5H_2O$; 500 µl of 77.5 mM stock solution (2.23 g/100 ml) $ZnSO_4.7H_2O$; 500 µl of 42.0 mM stock solution (1.00 g/100 ml) $CoCl_2.6H_2O$; 500 µl of 910.0 mM stock solution (18.0/100 ml) $MnCl_2.4H_2O$; 500 µl of 26.0 mM stock solution (0.63 g/100 ml) $Na_2MoO_4.2H_2O$; bringing up to 500 ml final volume, and filter sterilizing. Vitamin Stock Solution was prepared by adding to 400 mls of water 0.05 g Thiamine HCl; 500 µl of 0.37 mM stock solution (0.05 g/100 ml) of cyanocobalamin; and 2.5 ml of 0.41 mM stock solution (0.01 g/100 ml) of biotin, bringing up to a final volume of 500 mls, and filter sterilizing.

PM074 is a nitrogen replete ("nitrate-only") medium (includes nitrate as substantially the sole nitrogen source) that is 10×F/2 made by adding 1.3 ml PROLINE® F/2 Algae Feed Part A (Aquatic Eco-Systems) and 1.3 ml PROLINE® F/2 Algae Feed Part B (Aquatic Eco-Systems) to a final volume of 1 liter of a solution of Instant Ocean salts (35 g/L) (Aquatic Eco Systems, Apopka, Fla.). Proline A and Proline B together include 8.8 mM $NaNO_3$, 0.361 mM $NaH_2PO_4.H_2O$, 10×F/2 Trace metals, and 10×F/2 Vitamins (Guillard (1975) Culture of phytoplankton for feeding marine invertebrates. in "Culture of Marine Invertebrate Animals." (eds: Smith W. L. and Chanley M. H.) Plenum Press, New York, USA. pp 26-60).

PM123 medium is PM074 medium supplemented with additional Proline B so that the concentration of nitrate was increased from approximately 8.8 mM to approximately 15 mM. This is also a "nitrate only" medium.

PM124 medium is PM074 supplemented with 5 mM ammonium and 10 mM HEPES pH 8.0. It is made by adding 10 mls of 1 M HEPES pH 8 and 5 mls of $NH_4Cl$ to the PM074 recipe (final volume of 1 L). In some examples, additional media with controlled ammonium levels was made by adjusting the ammonium concentration of PM074 and adding additional Hepes buffer.

PM125 medium (Example 5): includes 7.5 mM urea as the only source of nitrogen available to the cells. To 1× instant ocean was added (while mixing): 3.75 ml 2M Urea stock solution, 0.32 ml 1 M NaH$_2$PO$_4$ stock solution, 4 ml of Chelated Metals Stock Solution and ml of 4 ml Vitamin Stock Solution (see above). The media was filter sterilized through <0.1 μm filter and stored at room temperature.

Example 1

Identification of a Zinc-Cys Domain Polypeptide Downregulated During Nitrogen Starvation Various strains of *Nannochloropsis* accumulate high levels of triacylglycerols (TAG) storage lipid during nitrogen deprivaton and correlations between increased TAG production and correlations between TAG accumulation and presumed underlying changes in gene expression in different metabolic pathways leading to TAG synthesis have been reported (Radakovits et al. (2012) *Nat Commun* 3: 686; Li et al. (2014) *The Plant Cell* 26: 1645-1665; Corteggiani Carpinelli et al. (2014) *Mol Plant* 7:1645-1665). To identify genes encoding regulators that influence lipid biosynthesis and accumulation, the early transcriptional response of *Nannochloropsis* cells subjected to N-deprivation (−N) was analyzed. A comparative transcriptomics experiment was performed in which the RNA transcript levels of genes of *Nannochloropsis gaditana* cells under nitrogen starvation, during which *Nannochloropsis* induces storage lipid biosynthesis, were compared with the levels of RNA transcripts of the same strain of *Nannochloropsis gaditana* grown under identical conditions except that the amount of nitrogen in the growth medium was not limiting.

Figure 1:
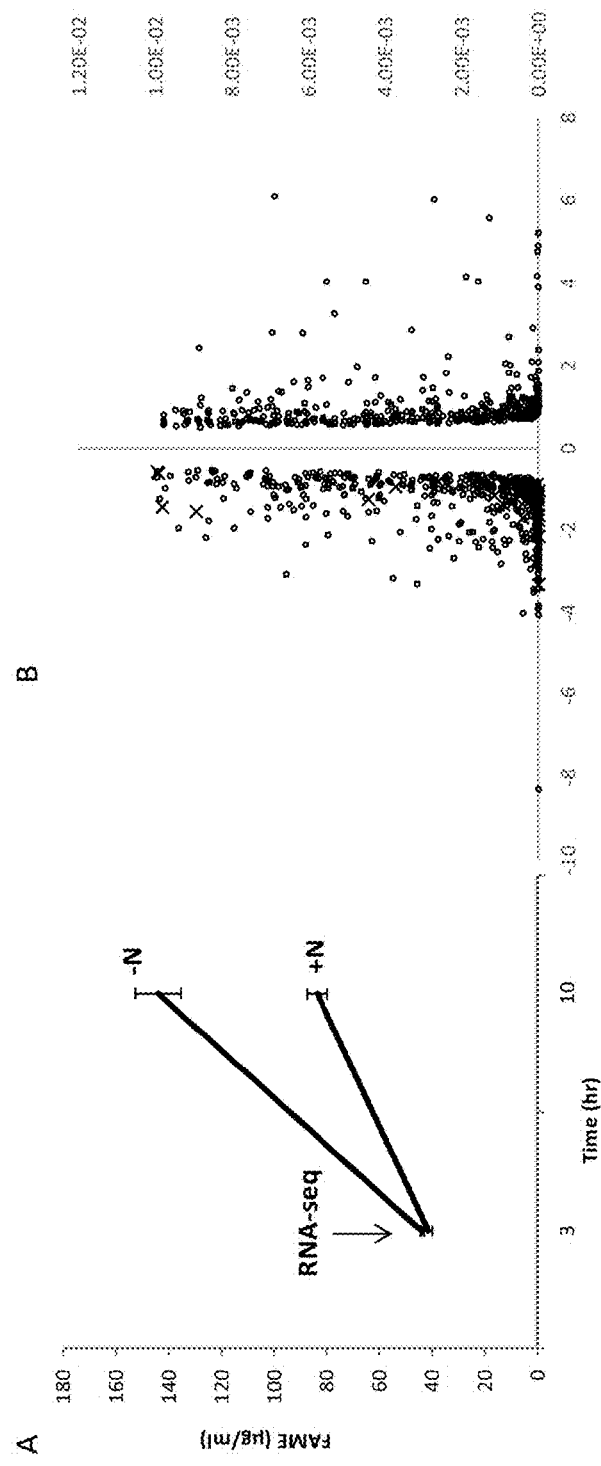
FIG. 1A-1B, A) provides a graph showing lipid (FAME) accumulation of wild-type *Nannochloropsis* cultures grown in N replete (+N) and deplete (−N) conditions. The 3 hour time point samples were subjected to transcriptomic analysis (RNA-seq). B) provides a plot of the differentially expressed genes in cells transferred to −N medium compared to cells provided with N replete medium. The genes (represented as dots) are plotted versus fold change ($\log_2$) in −N treated cells compared to replete cells. Putative transcription factors are represented as Xs. Genes present in the right side of the y-axis are upregulated and genes on the left side of the y-axis are downregulated. Only genes with a false discovery rate (FDR) less than or equal to 0.01 are displayed on the graph.

Wild type *N. gaditana* (WT-3730) cells were grown in nutrient replete medium under a 16 hour light (120 μE)/8 hour dark cycle to light limitation (to O.D. of 1.25) and at the beginning of the photoperiod were spun down and resuspended in either nitrogen replete medium PM066 or culture medium lacking a nitrogen source ("nitrogen deplete" or "−N" medium PM067) and incubated under the provided light conditions. RNA was isolated from samples removed at various time intervals after resuspension of the cells in nitrogen replete (+N) or nitrogen deplete (−N) medium. Lipid accumulation was determined from samples taken throughout the assay. Lipid accumulation (measured as FAME as described in Example 4) was indistinguishable between nitrogen deplete and nitrogen replete cultures at the 3 h timepoint, but at 10 h FAME accumulation in the nitrogen deplete culture was double that of the nitrogen replete culture (FIG. 1A). Treatments were performed in biological triplicates. Under the assumption that transcriptional changes should precede metabolic changes, the 3 h time-point was selected for mRNA sequencing. Two samples for each treatment were sequenced.

RNA was isolated by spinning down 10 mLs of each algal cell culture (4000×g for 5 minutes) and decanting the supernatant. The pellets were resuspended in 1.8 mL Buffer A (5 mL TLE Grinding Buffer, 5 mL phenol, 1 mL 1-bromo-3-chloropropane and 20 mercaptoethanol, where TLE Grinding Buffer includes 9 mL of 1M Tris pH 8, 5 mL of 10% SDS, 0.6 mL of 7.5 M LiCl, and 450 μl 0.5 M EDTA in a final volume of 50 mL) and transferred to 2 mL microcentrifuge tubes containing approximately 0.5 mL of 200 μm zirconium beads. The tubes were vortexed vigorously for 5 min at 4° C. and then centrifuged for 2 min at 11.8×g. The aqueous layers were then removed and pipetted into new 2 mL tubes, to which 1 mL 25:24:1 phenol extraction buffer (25 mL phenol pH 8.1; 24 mL 1-bromo-3-chloropropane, and 1 mL isoamyl alcohol) was added. The tubes were shaken vigorously and centrifuged for 2 min at 11.8×g. After centrifugation, the aqueous layer was removed and pipetted into new 2 mL centrifuge tubes, to which 1 ml 1-bromo-3-chloropropane was added. The tubes were shaken and again centrifuged for 2 min at 11.8×g. The aqueous layer was removed to a new tube and 0.356 volumes of 7.5 M LiCl were added. The tubes were inverted 10-12 times and stored at −20° C. overnight. The next day, samples were allowed to come to room temperature without mixing and were centrifuged at 16,000×g for 30 minutes. The supernatants were removed and the pellets were washed with 1 mL of ice cold 80% ethanol. The tubes were centrifuged for 30 min at 16,000×g and allowed to air dry after the supernatants had been removed. Finally, the RNA pellets were resuspended in 50 μl ultrapure water. The RNA quality was assessed by on-chip gel electrophoresis using an Agilent 2100 Bioanalyzer and RNA6000 LabChip according to manufacturer instructions.

Next-generation sequencing libraries were prepared from the isolated RNA utilizing the TruSeq Stranded mRNA Sample Prep Kit (Illumina, San Diego, Calif.) following manufacturer instructions. The TruSeq libraries were sequenced using sequencing-by-synthesis (Illumina MiSeq) to generate 100 bp paired-end reads using the mRNA-Seq procedure (described in Mortazavi et al. (2008) *Nature Methods* 5:621-628). Mappable reads were aligned to the *N. gaditana* reference genome sequence using TopHat (tophat.cbcb.umd.edu/). Expression levels were computed for every annotated gene using the Cuffdiff component of the Cufflinks software (cufflinks.cbcb.umd.edu). TopHat and Cufflinks are described in Trapnell et al. (2012) *Nature Protocols* 7: 562-578. Differential expression analysis was performed using the R package edgeR (McCarthy et al. (2012) *Nucl. Acids Res.* 40:doi:10/1093/nar/gks042)). Expression levels in units of fragments per kilobase per million (FPKM) were reported for every gene in each sample using standard parameters. FPKM is a measure of relative transcriptional levels that normalizes for differences in transcript length.

Global analysis of the transcriptome of −N and +N cultures at 3 h revealed 1064 differentially expressed genes having a difference in expression of greater than 1 fold and a false discovery rate (FDR) of less than 0.01. These genes are depicted as dots and Xs in the plot of FIG. 1B. Of these genes, 363 were upregulated (right side of the plot) and 701 were down-regulated in the −N condition (left side of the plot). The list of differentially expressed genes was compared with a bioinformatically curated list of putative *Nannochloropsis* transcription factors previously generated by mining the *Nannochloropsis* genome for proteins containing DNA binding domains and other conserved pfam domains typical of characterized transcription factors using the Plant Transcription Factor Database as a reference (Perez-Rodriguez et al. (2010) *Nucl. Acids Res.* 38: D822-D827; Jin et al. (2013) *Nucl. Acids Res.* 42: D1182-D1187). We found 20 transcription factors, represented as Xs in FIG. 1B and listed in Table 1, that were represented only in the down-regulated set of transcription factors. No transcription factors were found to be upregulated at the 3 h timepoint. *N. gaditana* gene identifiers are based on the genome sequence described in Corteggiani Carpinelli et al., *Mol Plant* 7, 323-335 (2014).

TABLE 1

Transcripton factors targeted for knockout by Cas9

| N. gaditana id | Gene Description | Fold Change (log 2) | FDR† | PCR Positive Lines/ Lines Screened | Success†† |
|---|---|---|---|---|---|
| Naga_100055g29 | CCT domain protein | −3.3 | 5.4E−15 | 13/31 | Y |
| Naga_100104g18 | Zn(2)-C6 fungal-type DNA-binding domain protein | −2.5 | 1.5E−19 | 19/29 | Y |
| Naga_100043g41 | RpoD family RNA polymerase sigma factor SigA | −1.6 | 5.3E−10 | 0/31 | N |
| Naga_100146g3 | Fungal Zn(2)-Cys(6) binuclear cluster domain | −1.6 | 1.7E−02 | 24/31 | Y |
| Naga_101321g2 | Zinc finger, CCCH-type | −1.5 | 4.5E−03 | 9/30 | Y |
| Naga_100489g1 | Zinc finger, TAZ-type | −1.4 | 3.6E−05 | 1/6 | Y |
| Naga_100042g29 | SANT/Myb domain protein | −1.4 | 1.1E−03 | 17/32 | Y |
| Naga_100248g8 | Winged helix-turn-helix transcription repressor DNA-binding | −1.3 | 3.1E−04 | 3/23 | Y |
| Naga_100066g21 | CCT motif family protein | −1.3 | 9.6E−06 | 5/30 | Y |
| Naga_100084g18 | Myb-like DNA-binding shaqkyf class family protein | −1.2 | 8.6E−06 | 17/32 | Y |
| Naga_100339g1 | Nucleic acid-binding protein | −1.2 | 1.6E−04 | 0/8 | N |
| Naga_100087g2 | Activating transcription factor 6 | −1.1 | 9.0E−05 | 16/29 | Y |
| Naga_100249g5 | Fungal Zn(2)-Cys(6) binuclear cluster domain | −1.1 | 4.1E−06 | 19/31 | Y |
| Naga_100329g4 | Fungal specific transcription factor domain-containing region | −1.1 | 9.1E−04 | 14/31 | Y |
| Naga_100028g52 | Zn(2)-C6 fungal-type transcription factor | −0.9 | 2.5E−03 | 10/31 | Y |
| Naga_100019g66 | Winged helix-turn-helix transcription repressor | −0.9 | 1.1E−03 | 22/31 | Y |
| Naga_100146g5 | Fungal Zn(2)-Cys(6) binuclear cluster domain | −0.9 | 9.9E−04 | 14/31 | Y |
| Naga_100086g13 | Myb-like dna-binding domain containing protein | −0.9 | 7.7E−04 | 25/32 | Y |
| Naga_100001g82 | Fungal Zn(2)-Cys(6) binuclear cluster domain | −0.9 | 3.6E−03 | 2/32 | Y |
| Naga_100001g77 | Aureochrom1-like protein | −0.5 | 3.9E−02 | 16/32 | Y |

†FDR, False discovery rate
††Y, successful insertion of the selection cassette;
N, unsuccessful insertion, as determined by PCR genotyping Example 2

Knockout of Transcription Factor Genes in *Nannochloropsis*

All 20 transcription factor genes that were discovered to be differentially regulated under nitrogen deprivation (Table 1) were targeted for insertional knockout mutagenesis via the development of a high-efficiency Cas9-expressing editor line in *Nannochloropsis* (see WO 2016/109840 and corresponding U.S. application Ser. No. 14/986,492, filed Dec. 31, 2015, incorporated herein by reference in its entirety). As described in U.S. Ser. No. 14/986,492, a highly efficient *Nannochloropsis* Cas9 Editor line, *N. gaditana* strain GE-6791, expressing a gene encoding the *Streptococcus pyogenes* Cas9 nuclease, was used as a host for transformation with a chimeric guide RNA and donor DNA for insertional knockout.

Figure 2:
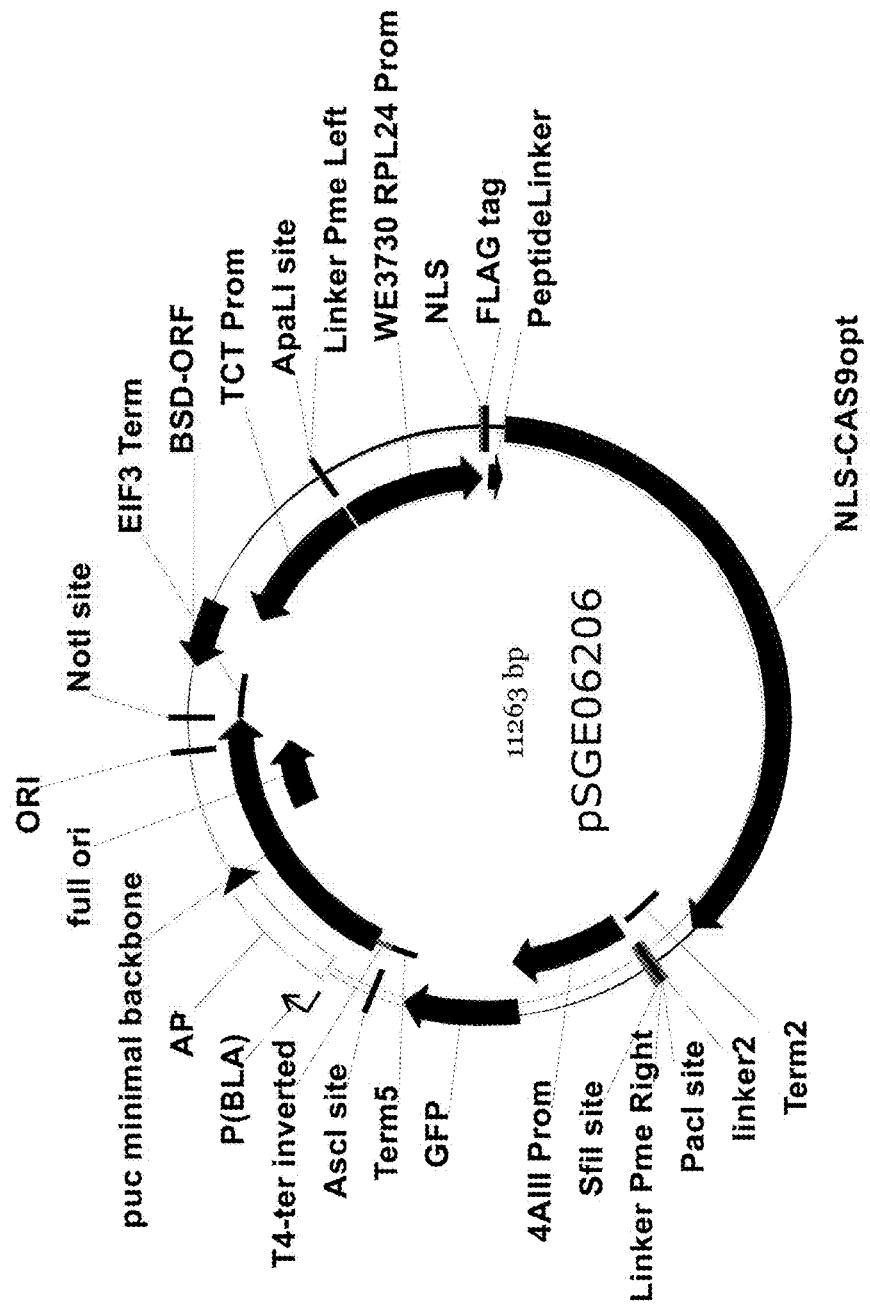
FIG. 2 is a schematic map of vector pSGE-6206 used to introduce the Cas9 gene into the *N. gaditana* Editor line.

To produce the high efficiency *Nannochloropsis* Cas9 Editor line, a *Nannochloropsis* strain was engineered and isolated that exhibited expression of the introduced cas9 gene in essentially 100% of the cell population of a growing culture. The vector pSGE-6206 (FIG. 2; SEQ ID NO:26), used to transform wild type *N. gaditana* strain WT-3730 included the following three elements: 1) a Cas9 expression cassette which contained a Cas9 gene from *Streptococcus pyogenes* codon optimized for *Nannochloropsis gaditana* (SEQ ID NO:27) that also included sequences encoding an N-terminal FLAG tag (SEQ ID NO:28), nuclear localization signal (SEQ ID NO:29), and peptide linker (entire FLAG, NLS, and linder sequence provided as SEQ ID NO:30), driven by the *N. gaditana* RPL24 promoter (SEQ ID NO:31) and terminated by *N. gaditana* bidirectional terminator 2 or "FRD" terminator (SEQ ID NO:32); 2) a selectable marker expression cassette, which contained the blasticidin deaminase ("blast" or "BSD") gene from *Aspergillus terreus* codon optimized for *N. gaditana* (SEQ ID NO:33), driven by the *N. gaditana* TCTP promoter (SEQ ID NO:34) and followed by the EIF3 terminator (SEQ ID NO:35); and 3) a GFP reporter expression cassette, which contained the TurboGFP gene (Evrogen, Moscow, Russia) codon optimized for *Nannochloropsis gaditana* (SEQ ID NO:36), driven by the *N. gaditana* 4A-III promoter (SEQ ID NO:37) and followed by the *N. gaditana* bidirectional terminator 5 or "GNPDA" terminator (SEQ ID NO:38). The Cas9 expression construct was assembled according to the Gibson Assembly® HiFi 1 Step Kit (Synthetic Genomics, La Jolla, Calif.) into a minimal pUC vector backbone; the confirmed DNA sequence of this plasmid is provided as SEQ ID NO:26.

The ZraI-linearized Cas9 expression construct (FIG. 3A) was transformed into *Nannochloropsis* cells by electroporation. 1×10$^9$ cells were transformed in a 0.2 cm cuvette using a field strength of 7,000 V/cm delivered with the Gene Pulser II (Biorad, Carlsbad, Calif., USA). The transformation mixture was plated onto PM074 agar medium containing 100 mg/L of blasticidin. Resulting colonies were patched onto selection media for analysis and archiving. A small amount of biomass was taken from the patches and completely resuspended in 300 µl of 1× Instant Ocean Salts solution (Aquatic Eco Systems; Apopka, Fla.). Care was taken to not add too much biomass so that a light green resuspension was obtained. This suspension was directly analyzed by flow cytometry using a BD Accuri C6 flow cytometer, using a 488 nm laser and 530/10 nm filter to measure GFP fluorescence per cell. 10,000-30,000 events were recorded for each sample using the slow fluidics setting. A strain having a single fluorescence peak that was shifted to a fluorescence level higher than that demonstrated by wild-type cells (FIG. 3B) and also demonstrating cas9 protein expression by Western blotting using an anti-FLAG antibody (Sigma #A9469) (FIG. 3C), designated strain GE-6791, was selected as a cas9 Editor strain and used in mutant generation by cas9/CRISPR genome editing as described herein. The Ng-Cas9 Editor line was found to be equivalent to wild-type in FAME and TOC productivity (see for example FIG. 18).

Generation of Targeted Insertional Mutants in the Ng-Cas9 Editor Line.

All 20 identified transcription factors that were found to be downregulated under nitrogen starvation (Table 1) were targeted for knockout in the Cas9 Editor line. Guide RNAs (see Table 2 for the target sequences used for knockout of each of the 23 transcription factors) were synthesized in vitro according to (Cho et al. (2013) *Nature Biotechnol.* 31: 230-232) and described in Example 3, and co-electroporated with a PCR amplified expression cassette (pHygR, SEQ ID NO:45) containing a codon optimized hygromycin resistance gene (HygR, SEQ ID NO:44) driven by endogenous the EIF3_promoter (SEQ ID NO:46) and followed by *N. gaditana* NADH-dependent fumarate reductase bidirectional terminator (SEQ ID NO:32) in inverted orientation. Approximately 1 µg each of the guide RNA targeting the particular transcription factor and the pHygR donor fragment (FIG. 4A) were added to the cuvette and electroporation was performed as described above. In general, loss-of-function "knockout" mutants were generated by selecting a guide RNA target locus in the first half of exonic coding sequence. Selection of HygR transformants was as above except that 500 mg/L hygromycin was added to agar plates instead of blasticidin. Targeted insertion of the pHygR fragment via NHEJ-mediated repair of the double stranded DNA break catalyzed by Cas9 in loci targeted by guide RNAs was assessed by colony PCR using primers that flanked the guide RNA target site by ~200 bp on either side (Table 3). Using these primers, PCR amplification of wild-type loci would result in ~400 bp products, whereas pHygR targeted insertional mutants would result in ~2800 bp products—accounting for the insertion of the 2400 bp pHygR fragment. PCR products were sequence-confirmed for all mutants allowing for the determination of insert orientation and detection of any loss of chromosomal and/or insert DNA, or the gain of small insertions generated during the NHEJ-mediated dsDNA break repair process (see FIG. 4B and FIG. 4C for a diagram of the insertion process and exemplary colony PCR results).

Eighteen of the 20 targeted transcription factors (Table 1) were disrupted at the intended locus as confirmed by PCR genotyping. Based on the high overall editing efficiency observed it is likely that the remaining 2 loci were essential for viability. To test the knockouts for effects on lipid induction, two independent mutants per locus were screened for lipid and biomass productivities by assessing FAME and TOC levels throughout multiple time-points of a 7-day culture as described in detail in Example 4, below.

TABLE 2

Guide RNA sequences and screening primers used in Cas9-mediated mutagenesis

| N. gaditana id | Target Description | Sequence Adjacent to PAM (NGG) |
|---|---|---|
| Naga_100055g29 | CCT domain protein | TTCCGAAGTACTGGTTC (SEQ ID NO: 87) |
| Naga_100104g18 | Zn(2)C6 fungal-type DNA-binding domain protein (ZnCys-2845) | AGTAGGCCATTCCCGGAG (SEQ ID NO: 88) |
| Naga_100489g1 | Zinc finger, TAZ-type | TGTGGCAGACGCCGACGG (SEQ ID NO: 89) |
| Naga_100043g41 | RpoD family RNA polymerase sigma factor SigA | GTACTGCCTGACAAACTAGG (SEQ ID NO: 90) |
| Naga_100146g3 | Fungal Zn(2)-Cys(6) binuclear cluster domain | TGAGCAGTCGTACGAAA (SEQ ID NO: 91) |
| Naga_101321g2 | Zinc finger, CCCH-type | CGAAGTCAACCATGGGGC (SEQ ID NO: 92) |
| Naga_100248g8 | Winged helix-turn-helix transcription repressor DNA-binding | TCCTGTGACTTGACGGTG (SEQ ID NO: 93) |
| Naga_100042g29 | SANT/Myb domain protein | GGCAATACAAGCAGTGGAAG (SEQ ID NO: 94) |
| Naga_100066g21 | CCT motif family protein | CTGATCTCGAGATGGCTG (SEQ ID NO: 95) |
| Naga_100329g4 | Fungal specific transcription factor domain-containing protein | GTGAAGATTGGTCCCACT (SEQ ID NO: 96) |

TABLE 2-continued

Guide RNA sequences and screening primers used in Cas9-mediated mutagenesis

| N. gaditana id | Target Description | Sequence Adjacent to PAM (NGG) |
|---|---|---|
| Naga_100084g18 | Myb-like DNA-binding shaqkyf class family protein | GGACGCTACGACCGTGCGGG (SEQ ID NO: 97) |
| Naga_100339g1 | Nucleic acid-binding protein | CTGCACCAGACACAAATT (SEQ ID NO: 98) |
| Naga_100087g2 | Activating transcription factor 6 | GGGAAATATTAAGACTGGAG (SEQ ID NO: 99) |
| Naga_100249g5 | Fungal Zn(2)-Cys(6) binuclear cluster domain | TCACGGGAGATGTCCTGT (SEQ ID NO: 100) |
| Naga_100028g52 | Zn(2)-C6 fungal-type transcription factor | AGGACTCTCCTCAGCTGA (SEQ ID NO: 101) |
| Naga_100019g66 | Winged helix-turn-helix transcription repressor | TCTTCATCTGCGACAACG (SEQ ID NO: 102) |
| Naga_100146g5 | Fungal Zn(2)-Cys(6) binuclear cluster domain | ACGTCCGAATATACCGAA (SEQ ID NO: 103) |
| Naga_100086g13 | Myb-like dna-binding domain containing protein | GTAGAACAAGCGTTAGACC (SEQ ID NO: 104) |
| Naga_100001g82 | Fungal Zn(2)-Cys(6) binuclear cluster domain | CGCCACCCTCGCACGTGTC (SEQ ID NO: 105) |
| Naga_100001g77 | Aureochrome1-like protein | GGCACCATCCCCACCGGTTT (SEQ ID NO: 106) |
| Naga_100104g18 | ZnCys-2845 (Guide targets 5'UTR resulting in strain ZnCys-2845 BASH-3) | GGGACTGTCCCATTGTGC (SEQ ID NO: 54) |
| Naga_100104g18 | ZnCys-2845 (Guide targets 3'UTR resulting in strain ZnCys-2845 BASH-12) | AACTCGCTCGTCGATCAC (SEQ ID NO: 62) |
| Naga_100699g1 | Nitrate Reductase | GGGTTGGATGGAAAAAGGCA (SEQ ID NO: 193) |

TABLE 3

Screening primers used in Cas9-mediated mutagenesis

| N. gaditana id | Genotyping Primer (Sense) | Genotyping Primer (Antisense) |
|---|---|---|
| Naga_100055g29 | AAGTGCGCAAGACGCTCCAG (SEQ ID NO: 107) | TTTGAATATCTGCACATGCA (SEQ ID NO: 108) |
| Naga_100104g18 ZnCys-2845 | ACCTCCTTGTCACTGAGCAG (SEQ ID NO: 109) | GATCCCAAAGGTCATATCCGT (SEQ ID NO: 110) |
| Naga_100489g1 | ACTCTGTGCTACCAATTGCTG (SEQ ID NO: 111) | CGTCAGCAAATCTTGCACCA (SEQ ID NO: 112) |
| Naga_100043g41 | GAGATGCTGTCCGAGACACG (SEQ ID NO: 113) | GTATCTCGGACAGGGCACTG (SEQ ID NO: 114) |
| Naga_100146g3 | ATCCATGTAAAGACGATGTGC (SEQ ID NO: 115) | TGATATCACATGCTCAAGGTC (SEQ ID NO: 116) |
| Naga_101321g2 | AGATGAGGATCAAGCACCGAGCCA (SEQ ID NO: 117) | GGAAGAAATAGTAGTTGCGTG (SEQ ID NO: 118) |
| Naga_100248g8 | AGGCGCTCTGATTGCTGTGGC (SEQ ID NO: 119) | TCTTCCACGTCGGATGGCCAG (SEQ ID NO: 120) |
| Naga_100042g29 | ATTGTGGAGGGTAACAAACTACG (SEQ ID NO: 121) | TGAGTCCCGTGGAGAGGAGTCG (SEQ ID NO: 122) |

TABLE 3-continued

Screening primers used in Cas9-mediated mutagenesis

| N. gaditana id | Genotyping Primer (Sense) | Genotyping Primer (Antisense) |
|---|---|---|
| Naga_100066g21 | AGGTTCCAATGGAGGCCGCA (SEQ ID NO: 123) | CACTTTCCTTCGTACGCTCAGC (SEQ ID NO: 124) |
| Naga_100329g4 | CTCGAGGTAGGTGGTGAAAG (SEQ ID NO: 125) | GTGATTCGCATGGACGAAC (SEQ ID NO: 126) |
| Naga_100084g18 | ATGGGTACGGACTTGTTCG (SEQ ID NO: 127) | ACAGCGATACGGACAGTGAC (SEQ ID NO: 128) |
| Naga_100339g1 | GACGTTGCATGAGAAAGGAG (SEQ ID NO: 129) | GATGCACAGGTGCTTGTTAG (SEQ ID NO: 130) |
| Naga_100087g2 | TGCAAAGCCTATTTCCGACG (SEQ ID NO: 131) | CTCATTCGTGAGGTGACCAT (SEQ ID NO: 132) |
| Naga_100249g5 | GAGCAAACTGACATTGATAC (SEQ ID NO: 133) | GTACCACACATACACATG (SEQ ID NO: 134) |
| Naga_100028g52 | CACATCCACCATCATTCCAC (SEQ ID NO: 135) | GAGTGTTCCCAGTGAGCCAG (SEQ ID NO: 136) |
| Naga_100019g66 | CTGACAAGAAGATGGACATG (SEQ ID NO: 137) | CTTTAGTTATACGTCTGAAG (SEQ ID NO: 138) |
| Naga_100146g5 | GAGAGGATAGTTCTCAGAG (SEQ ID NO: 139) | GTCCCACAATCTATTGTG (SEQ ID NO: 140) |
| Naga_100086g13 | ATGAGTACTTGCGCGCTTTG (SEQ ID NO: 141) | GCATGCCTCCGTCACAGAGT (SEQ ID NO: 142) |
| Naga_100001g82 | ATCCATTGAGCATGCCGACG (SEQ ID NO: 143) | GCAACATGTTAATGCATCGT (SEQ ID NO: 144) |
| Naga_100001g77 | TCGTCCTCGAACTCTTCCTC (SEQ ID NO: 145) | CGGGAACAACCAAGGTGTAA (SEQ ID NO: 146) |
| Naga_100104g18 ZnCys-2845 BASH-3 | TAGCAGAGCAGGCTCATCAC (SEQ ID NO: 147) | GAATATGTGGTCTAGCTCGT (SEQ ID NO: 148) |
| Naga_100104g18 ZnCys-2845 BASH-12 | ATGGCTCCACCCTCTGTAAG (SEQ ID NO: 149) | CTGACTACAGCTAGCACGAT (SEQ ID NO: 150) |
| Naga_100699g1 | AAGACTTTGGAGGATGTCTGAGTGG (SEQ ID NO: 151) | ACGAAGCTACATCCAGTGCAAGG (SEQ ID NO: 152) |

Example 3

ZnCys-2845 Knockout Mutant

The ZnCys-2845 gene (Naga_100104g18, second row of Table 1) was targeted for disruption by first making a DNA construct for producing a guide RNA in which the construct included the sequence of a chimeric guide engineered downstream of a T7 promoter. The chimeric guide sequence included an 18 bp target sequence (SEQ ID NO:39) homologous to a sequence within the ZnCys-2845 gene sequence that was immediately upstream of an S. pyogenes cas9 PAM sequence (NGG), and also included the transactivating CRISPR (tracr) sequence. The chimeric guide sequence was synthesized by first making a DNA template made up of complementary DNA oligonucleotides that included the T7 promoter sequence (SEQ ID NO:40 and SEQ ID NO:41, made by SGI-DNA, La Jolla, Calif.) that incorporated the T7 promoter sequence and were annealed to create a double-stranded DNA template which was used in in vitro transcription reactions using the MEGAshortscript™ T7 Kit (Life Technologies #AM1354M) according to the manufacturer's instructions to synthesize the guide RNA. The resulting RNA was purified using Zymo-Spin™ V-E columns (Zymo Research #C1024-25) according to manufacturer's protocol.

The donor fragment for insertion into the targeted ZnCys-2845 locus (SEQ ID NO:44) included a selectable marker cassette that included the hygromycin resistance gene (HygR, SEQ ID NO:45) downstream of the N. gaditana EIF3 promoter (SEQ ID NO:46) and followed by N. gaditana bidirectional terminator 2 (SEQ ID NO:32), with the entire promoter-hygromycin resistance gene-terminator sequence flanked by 27 base pair identification sequences on the 5' (SEQ ID NO:47 5'ID) and 3' (SEQ ID NO:48 3'ID) ends to yield the DNA fragment referred to as the "Hyg Resistance Cassette" (SEQ ID NO:44, HygR Cassette).

For targeted knockout of the ZnCys-2845 (Naga_100104g18) locus, Cas9 Editor line GE-6791 was transformed by electroporation using 5 μg of purified chimeric guide RNA targeting the ZnCys-2845 gene and 1 μg of the selectable donor DNA (Hyg Resistance Cassette; SEQ ID NO:44, shown in FIG. 4A) essentially as described in US 2014/0220638. Following electroporation, cells were plated on PM124 agar media containing hygromycin to select for transformants that incorporated the hygromycin resistance cassette. Transformants were patched onto a fresh plate and screened by colony PCR for insertion of the donor fragment into the ZnCys-2845 gene.

For colony PCR screening, a small amount of cells from a colony to be screened was suspended into 100 µl of 5% Chelex 100 Resin (BioRad)/TE solution and the suspension was boiled for 10 minutes at 99° C., after which the tubes were briefly spun. One microliter of the lysate supernatant was added to a PCR reaction mix, in which the PCR mixture and reactions were set up and performed according to the QIAGEN Fast Cycling PCR Master Mix Protocol from the manufacturer (Handbook available at qiagen.com). The primers used to detect the insertion of the donor fragment into the targeted locus of the ZnCys-2845 gene were SEQ ID NO:49 and SEQ ID NO:50. Based on the PCR-based colony screening, two knockout strains, GE-8564 and GE-8565, were tested in productivity assays.

As described below, mutants harboring the HygR cassette in the coding sequence of genome locus Naga_100104g18 had an insertion of the donor cassette in a gene encoding a predicted Zn(II)2Cys6 binuclear cluster domain protein (Pfam PF00173, see FIG. 5) and is referred to as ZnCys-2845. These mutants exhibited a marked increase in lipid accumulation with respect to wild type as assessed by FAME/TOC (Example 4, FIG. 7C). As described below, the lipid accumulation phenotype in these ZnCys-2845 KO mutants was further confirmed to be similar to that observed in nitrogen-starved wild type cells by the appearance of prominent lipid droplets (FIGS. 7 F-H).

Example 4

ZnCys-2845 Knockout Mutants in Batch Productivity Assay

To determine the effect of knocking out the ZnCys-2845 gene on growth and lipid production, ZnCys-2845 knockout strain GE-8564 and the wild type progenitor strain WT-3730 were cultured in a batch productivity assay in nitrogen replete medium PM123 that included 15 mM nitrate as the sole nitrogen source available to the cells, i.e., the culture medium had no source of reduced nitrogen. Because it had been determined that the ZnCys-2845 mutant does not grow in the absence of reduced nitrogen, the production cultures were inoculated to an initial OD730 of 0.5 from seed (scale-up) cultures that were grown in PM124 medium that included 5 mM ammonium in addition to 8.8 mM nitrate.

After inoculation, ZnCys knockout strain GE-8564 and wild type strain WT-3730 were grown in triplicate cultures in a batch assay in 75 cm² rectangular tissue culture flasks containing 175 ml of PM123 medium, which includes 15 mM nitrate as the sole nitrogen source, for seven days. The flasks were positioned with their narrowest "width" dimension against an LED light. The culture flasks were masked with an opaque white plastic to provide a 21.1 cm² rectangular opening for irradiance to reach the cultures. Incident irradiance was programmed at a 16 h light:8 hour dark cycle with a linear ramp up of irradiance from 0 to 1200 uE over 4 hours, after which the irradiance was held at for six hours at 1200 uE, and then a linear ramp down in irradiance from 1200 to 0 uE over a 4 h period (increasing in 15 min intervals) (FIG. 6A). Deionized $H_2O$ was added to the cultures daily to replace evaporative losses. The temperature of the cultures was regulated by a water bath set at 25° C. Cultures were inoculated at OD730 of 0.5 on day 0 and samples (5 mls) were removed on days 3, 5, and 7 for assessing cell density, fatty acid methyl esters (FAME) as a measure of lipid, and total organic carbon (TOC). Sampling was done 30 minutes prior to the end of the light cycle. FAME analysis was performed on 2 mL samples that were dried using a GeneVac HT-4X. To each of the dried pellets the following were added: 500 µL of 500 mM KOH in methanol, 200 µL of tetrahydrofuran containing 0.05% butylated hydroxyl toluene, 40 µL of a 2 mg/ml C11:0 free fatty acid/C13:0 triglyceride/C23:0 fatty acid methyl ester internal standard mix and 500 µL of glass beads (425-600 µm diameter). The vials were capped with open top PTFE septa-lined caps and placed in an SPEX GenoGrinder at 1.65 krpm for 7.5 minutes. The samples were then heated at 80° C. for five minutes and allowed to cool. For derivatization, 500 µL of 10% boron trifluoride in methanol was added to the samples prior to heating at 80° C. for 30 minutes. The tubes were allowed to cool prior to adding 2 mL of heptane and 500 µL of 5 M NaCl. The samples were vortexed for five minutes at 2K rpm and finally centrifuged for three minutes at 1K rpm. The heptane layer was sampled using a Gerstel MPS Autosampler. Quantitation used the 80 µg of C23:0 FAME internal standard. The samples were run on an Agilent 7890A gas chromatography system using an Agilent 127-3212 DB-FFAP, 10 m×100 µm×100 nm column and an FID detector at 260° C. The flow rate was 500 µL/minute using $H_2$ as a carrier with constant flow control. The oven was set at 90° C. for 0.98 min, then 15.301° C./minute to 230° C. and held for 1.66 min. The inlet contained a 4 mm glass wool packed liner (Agilent P/N 5183-4647), and was set at 250° C. and used a split ratio of 40:1. The injection volume was 900 nL.

Total organic carbon (TOC) was determined by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of $r^2 > 0.999$.

The results of these analyses are shown in Tables 4-6. Values provided for wild type and knockout GE-8564 mutant are the average of three cultures with standard deviations (sd). The "% increase" column refers to the percentage increase of the ZnCys knockout mutant with respect to wild type values.

TABLE 4

Lipid (FAME) Produced by ZnCys-2845 Knockout Mutant and Wild Type Cultures in Batch Assay with Nitrate-only Culture Medium.

| Day | WT-3730 (NO3) | | ZnCys-KO GE-8564 (NO₃) | | |
|---|---|---|---|---|---|
| | µg/ml | sd | µg/ml | sd | % increase |
| 3 | 105.03 | 9.71 | 188.56 | 6.52 | 79.53 |
| 5 | 140.01 | 13.48 | 223.41 | 0.28 | 59.57 |
| 7 | 198.49 | 2.04 | 250.76 | 3.22 | 26.33 |

TABLE 5

Biomass (TOC) Produced by ZnCys-2845 Knockout Mutant and Wild Type Cultures in Batch Assay with Nitrate-only Culture Medium.

| Day | WT-3730 (NO3) | | ZnCys-KO GE-8564 (NO3) | | |
|---|---|---|---|---|---|
| | µg/ml | s.d. | µg/ml | s.d. | % diff |
| 3 | 375.6 | 10.18 | 261.7 | 7.07 | −30.3 |
| 4 | 474.6 | 8.34 | 283.95 | 3.61 | −40.2 |
| 5 | 534.45 | 43.20 | 269.5 | 3.68 | −49.6 |
| 6 | 644.8 | 48.65 | 311.75 | 3.18 | −51.7 |
| 7 | 804.35 | 36.13 | 329.3 | 1.70 | −59.1 |

TABLE 6

FAME/TOC ratios of ZnCys-2845 Knockout Mutant and Wild Type Strains in Batch Assay with Nitrate-only Culture Medium.

| Day | WT-3730 (NO3) | | ZnCys-KO GE-8564 (NO3) | | |
|---|---|---|---|---|---|
| | | s.d. | | s.d. | % increase |
| 3 | 0.28 | 0.018 | 0.72 | 0.044 | 157 |
| 5 | 0.26 | 0.004 | 0.83 | 0.012 | 219 |
| 7 | 0.25 | 0.009 | 0.76 | 0.006 | 204 |

The same batch productivity assay was performed on ZnCys-2845 cas9 knockout mutant GE-8564 using PM124 medium that included 5 mM ammonium in addition to 8.8 mM nitrate. Samples were removed as described and analyzed for FAME and TOC as provided above. The "% difference" column refers to the percentage difference of the ZnCys knockout mutant with respect to wild type values.

TABLE 7

FAME Produced by ZnCys-2845 Knockout Mutant and Wild Type Cultures in Batch Assay with Nitrate plus Ammonium Culture Medium.

| DAY | WT-3730 (NO3 + NH4) | | ZnCys-KO GE-8564 (NO3 + NH4) | | |
|---|---|---|---|---|---|
| | µg/ml | s.d. | µg/ml | s.d. | % diff |
| 3 | 93.03 | 6.943 | 88.43 | 1.827 | −4.9 |
| 4 | 120.14 | 8.427 | 124.41 | 0.472 | 3.6 |
| 5 | 121.31 | 0.7895 | 123.31 | 3.702 | 1.6 |
| 6 | 169.70 | 6.0668 | 181.6 | 3.397 | 7.0 |
| 7 | 198.11 | 7.954 | 225.6 | 4.548 | 13.88 |

TABLE 8

Biomass (TOC) Produced by ZnCys-2845 Knockout Mutant and Wild Type Cultures in Batch Assay with Nitrate plus Ammonium Culture Medium.

| DAY | WT-3730 (NO3 + NH4) | | ZnCys-KO GE-8564 (NO3 + NH4) | | |
|---|---|---|---|---|---|
| | µg/ml | s.d. | µg/ml | s.d. | % diff |
| 3 | 321.5 | 35.07 | 302.7 | 6.36 | −5.8 |
| 4 | 392.3 | 16.69 | 415.65 | 11.10 | 6.0 |
| 5 | 464 | 4.384 | 502.3 | 5.80 | 8.3 |
| 6 | 556.45 | 20.15 | 637.65 | 14.21 | 14.59 |
| 7 | 679.95 | 6.01 | 728.6 | 32.10 | 7.15 |

TABLE 9

FAME/TOC Ratios of ZnCys-2845 Knockout Mutant and Wild Type Strains in Batch Assay with Nitrate plus Ammonium Culture Medium.

| Day | WT-3730 (NO3 + NH4) | | ZnCys-KO GE-8564 (NO3 + NH4) | | |
|---|---|---|---|---|---|
| | | s.d. | | s.d. | % diff |
| 3 | 0.29 | 0.0100 | 0.29 | 0.0001 | 0 |
| 4 | 0.31 | 0.0085 | 0.30 | 0.0091 | −3.2 |
| 5 | 0.26 | 0.0008 | 0.25 | 0.0045 | −3.8 |
| 6 | 0.31 | 0.0220 | 0.29 | 0.0117 | −6.5 |
| 7 | 0.29 | 0.0091 | 0.31 | 0.0074 | 6.9 |

Figure 7A:
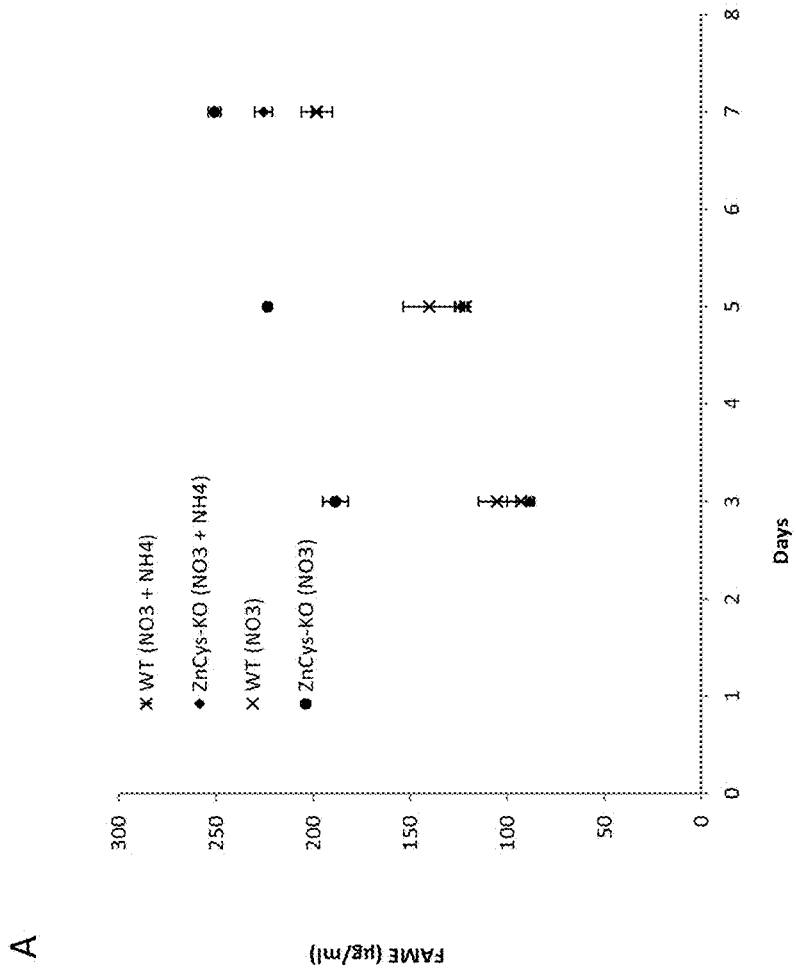
Figure 7B:
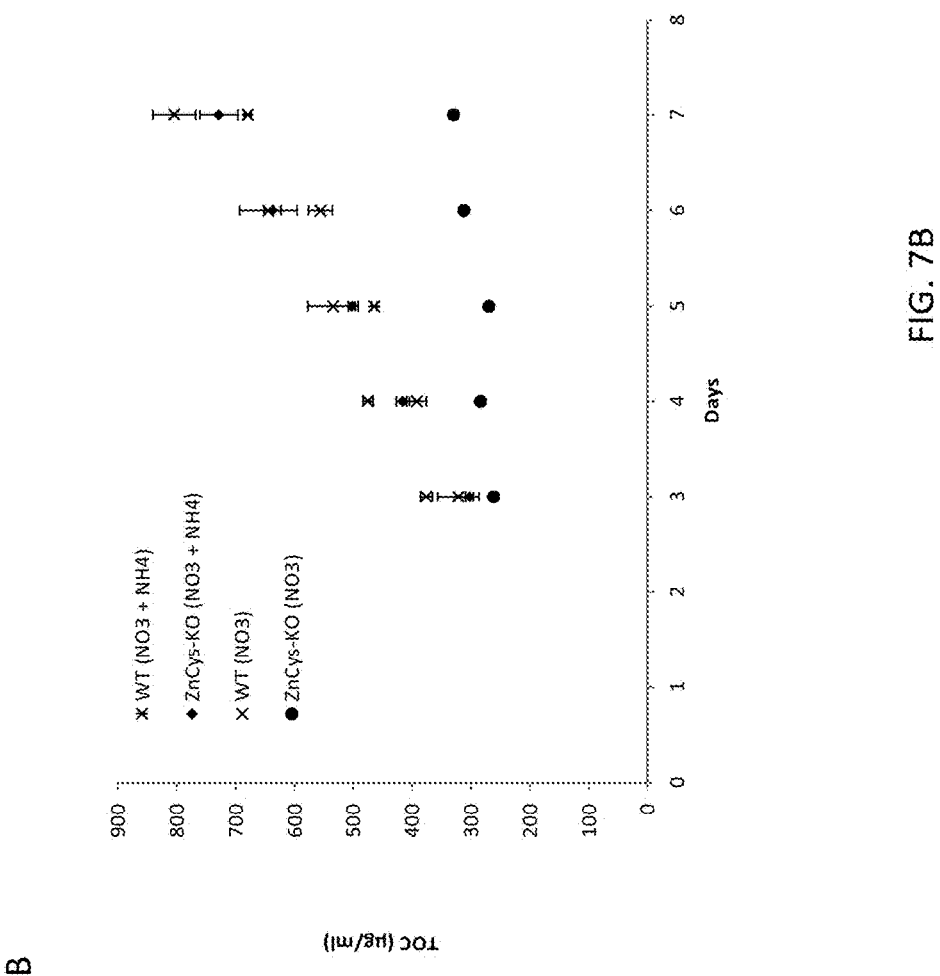

The graphs in FIGS. 7A-D show the results of this analysis. FIG. 7A demonstrates that cultures of ZnCys-2845 knockout strain GE-8564 (average values for triplicate cultures depicted as circles on the graph) grown in a medium that included only nitrate as a nitrogen source had higher FAME content than wild type cultures every day tested. As can be seen in Table 4, these FAME values were considerably higher than wild type on a volumetric basis. Although the FAME content of the ZnCys-2845 knockout mutant culture in nitrate-only medium was at a higher level on day 3 of the culture, which was the first day assayed, as well as on days 5 and 7 (Table 4 and FIG. 7A), the increase in FAME per day between days 3 and 7 was less for the ZnCys-2845 knockout strain than for the wild type strain. FIG. 7B demonstrates that over this time period the ZnCys-2845 gene disruption mutant cultured in nitrate-only medium (circles) increased its total organic carbon very little as compared to wild type (Xs), which showed steady growth as assessed by TOC accumulation (as also seen in Table 5). Thus, the ZnCys-2845 knockout strain, when cultured in a medium that included nitrate as the sole nitrogen source, behaved as though it were in nitrogen starvation, increasing lipid production but also decreasing in biomass accumulation. FIG. 7C confirms this, demonstrating that over the course of the one week productivity assay, the FAME/TOC ratio of the ZnCys-2845 knockout strain GE-8564 was elevated over wild type (approximately three-fold that of wild type, Table 6), with greater than 60% (and up to at least about 80%) of TOC being allocated to FAME lipids. FIG. 7D shows that the C16 and C18 fatty acids that were overproduced in knockout strain GE-8564 (black bars) with respect to wild type in nitrogen replete conditions (diagonally striped bars), while C20 fatty acids were underrepresented with respect to their abundance in wild type cells, as expected for selective overproduction of storage lipids (i.e., triglycerides). The fatty acid profile of the GE-8564 knockout strain was very similar to that of wild type cells under nitrogen starvation (dotted bars).

Direct demonstration of TAG production was determined by analysis of extracted lipids. Extracted lipids of knockout mutant GE-8564 and wild type progenitor strain WT-3730 from samples taken on Day 7 of the batch assay in the nitrate-only PM074 medium were identified and quantitated by HPLC. For HPLC analysis of lipids, 2 mL samples of each culture were spun down at maximum speed for 5 minutes, the supernatants were removed, and pellets were re-suspended in 400 µL of $H_2O$. The cell suspensions (approximately 500 µL) were transferred to 4 mL glass vials with Teflon lined caps. 500 µL of glass beads (212-300 µm diameter) were added to each of the cell suspensions, after which 50 µL of 50% $H_2SO_4$ and 100 µL of 5M NaCl were added. Bead beating was performed for 5 minutes at 1 krpm, then 2 mL of hexane was added to each sample, and bead beating was repeated for 5 minutes at 1 krpm. The samples were loaded onto a multi-tube vortexer and shaken for 30 minutes at 1 krpm, and then vortexed for 30 seconds at 2.5 krpm. 500 µL of the organic layer was transferred to an HPLC vial, and 50 µL of internal standard solution (1 mg/mL 6-ketocholestanol in toluene) was added to each vial. Standards were from NuCheck, Sigma-Aldrich, or Supelco. The vials were capped and vortexed briefly (5 seconds at 2.5 krpm) prior to HPLC analysis. The HPLC was run at a flow rate of 2 mL/minute on a Chromegasphere SI-60 150 mm×4.6 mm×10 µm column (ES Industries), with a column compartment set at 40° C. The injection volume was 25 µL with a draw and eject speed of 200 µL/minute. Eluent A was hexane and Eluent B was a 80:10:10:1 mixture of hexane, isopropanol, ethyl acetate, and 10% formic acid in isopropanol, run as a gradient program as follows: 2% B at 0.0 min; 2% B at 1.0 min; 25% B at 5.0 min; 98% B at 5.5 min; 98% B at 8.99 min; 2% B at 9.00 min; stop time: 9.0 minutes; 4 minutes post time. The detector was ELSD at 30° C. and 3.5 bar $N_2$, with a gain of 5.

Figure 7E:
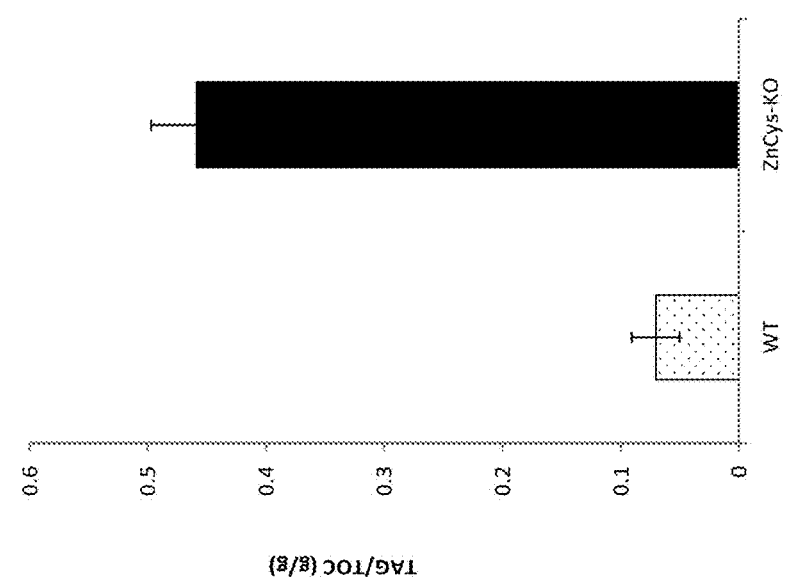

FIG. 7E shows that the amount of TAG in the ZnCys-2845 knockout cells in nitrate only medium was more than 5-fold that of the wild type cells, that is, the observed increase in FAME lipid could be attributed to the increase in TAGs. Electron microscopy also showed the dramatic lipid accumulation characteristic of the nitrogen starvation response. FIG. 7F shows a wild type cell grown under nitrogen replete conditions (nitrate-only culture medium), with a prominent nucleus (N), chloroplast (Ch), and mitochondrion (M), as well as a few small lipid droplets (LD). FIG. 7G shows the ZnCys knockout mutant grown in nitrate-only medium, in which a prominent lipid droplet (LD) is the largest cellular structure visible, a cellular morphology highly similar to the nitrogen starved wild type cell shown in FIG. 7H. Thus, the ZnCys-2845 polypeptide acts as a negative regulator of lipid biosynthesis, as attenuating expression of the ZnCys-2845 gene results in increased lipid production.

The increase in FAME exhibited by the ZnCys-2845 knockout strain cultured in nitrate-only medium was not apparent when the ZnCys-2845 knockout strain was grown in a culture medium that also included ammonium however (Table 7). In this case, the amount of FAME produced was very similar to that produced by wild type cells grown in nitrate plus ammonium medium, with lipid production of the knockout mutant increasing somewhat relative to wild type toward the end in the run, probably indicating depletion of ammonium from the batch culture (Table 7). FIG. 8A shows that the amount of FAME produced by wild type (diamonds) and the ZnCys-2845 knockout strain (circles) cultured in ammonium-only medium was virtually identical over the one week batch assay, as was TOC accumulation, shown in FIG. 8B (also evident from Table 8). FAME/TOC values of the wild-type and ZnCys-2845 knockout strain were correspondingly similar (FIG. 8C, Table 9).

Thus, the ZnCys-2845 gene disruption mutant behaved like the wild type strain when ammonium was replete in the culture medium (Tables 7-9 and FIGS. 8A-8C), but appeared to be impaired in nitrate assimilation, behaving as though the cells were in nitrogen depleted medium when nitrate was the sole source of nitrogen present by inducing storage lipid biosynthesis (FIGS. 7A-H).

Example 5

Bioinformatic Analysis of the ZnCys-2845 Protein: Domains and Orthologs

As described in Example 1, the ZnCys-2845 gene at locus Naga 100104g18 that was differentially expressed between the N-replete and N-deplete samples was a gene (cDNA sequence provided as SEQ ID NO:1) encoding a polypeptide (SEQ ID NO:2) that appeared on a bioinformatics-generated *Nannochloropsis* putative transcription factor list. The polypeptide was observed to have a Zinc(2)Cys(6) domain characteristic of some transcription factors and is therefore classified as a Zn(2)-C(6) fungal-type DNA-binding domain protein. In addition to the Zn(2)-Cys(6) domain, the *Nannochloropsis* polypeptide ZnCys-2845 contains a distinct nuclear localization sequence with a confidence score of 1.0 (which equates to 100% confidence), consistent with its characterization as transcription factor (FIG. 5).

ZnCys-2845 is a 1065 amino acid protein (SEQ ID NO:2) identified by transcriptomics analysis of genes differentially regulated during lipid induction and annotated as a putative transcription factor due to the Zn(2)-Cys(6) binuclear cluster domain extending from amino acid 190 to 219 (SEQ ID NO:3). The protein recruits to Pfam PF00172 ("Zn_Clus" or "Fungal Zn(2)-Cys(6) binuclear cluster domain" with a bit score of 25.2 (the gathering cutoff for this family is 20.8) and an e value of 1.1 e-05. Thus, ZnCys-2845 is a member of the Zn(II)2Cys6 fungal-type DNA-binding domain protein family. Members of this family contain the well-conserved motif $CysX_2CysX_6CysX_{5-12}CysX_2CysX_{6-8}Cys$ (a cysteine residue followed by two amino acid residues of any identity, followed by second cysteine residue followed by six amino acid residues of any identity, followed by a third cysteine residue followed by between five and twelve amino acid residues of any identity, followed by a fourth cysteine residue followed by two amino acid residues of any identity, followed by a fifth cysteine residue followed by between six and eight amino acid residues of any identity, followed by a sixth cysteine residue; SEQ ID NO:4). It has been demonstrated that the cysteine residues can bind two zinc atoms, which coordinate folding of the domain involved in DNA binding. Other identifiers for this domain include the conserved domain database (cdd) domain cd00067, the interpro protein domain database domain IPR001138, the SMART protein domain 'GAL4', and the PROSITE protein domain PS00463.

This class of "ZnCys" transcription factors was originally thought to be exclusively fungal, but more recently members have been identified among chromalveolates, in particular stramenopiles/heterokonts (including non-photosynthetic labyrinthulomycetes or "chytrids") and haptophytes (e.g., *E. huxleyi*). The first and best studied protein in this family is Gal4p, a *Saccharomyces* transcriptional activator of genes involved in galactose catabolism (Leverentz & Reece (2006) *Biochem Soc Transac* 34:794-797; Breunig (2000) *Food Technol. Biotechnol.* 38:287-293). The terms "Zn(2)-C(6) fungal-type DNA-binding domain protein", "Zn(II)2Cys6 fungal-type DNA-binding domain protein", "Zn(2)-Cys(6) domain polypeptide", "Zn(2)Cys(6) protein/polypeptide" and "Zn2Cys6 protein/polypeptide" are used interchangeably herein.

Examination of genome databases revealed genes encoding polypeptides having Zn(2)-Cys(6) domains in plants and fungi. Interestingly, several heterokont species were found to include Zn(2)-Cys(6) domain polypeptides, including labyrinthulomycete species such as from the genera *Schizochytrium* and *Aplanochytrium* and diatom species, including members of the *Navicula, Cyclotella, Thalassiosira, Phaeodactylum, Fragilariopsis* genera.

TABLE 10

Putative orthologs of *N. gaditana* lipid regulator ZnCys-2845

| Species | Library | Translation ID | SEQ ID NO |
|---|---|---|---|
| *Phaeodactylum tricornutum* | Phatr2_2 | 337562 | 5 |
| *Navicula* sp. | wt0229_cDNA_clc | 4242909 | 6 |
| *Navicula* sp. | wt0229_cDNA_clc | 4243087 | 7 |
| *Navicula* sp. | wt0229_cDNA_clc | 4238609 | 8 |
| *Cyclotella* sp. | wt0293_nuclear_v1.3 | 5077789 | 9 |
| *Cyclotella* sp. | wt0293_nuclear_v1.3 | 5083384 | 10 |
| *Cyclotella* sp. | wt0293_nuclear_v1.3 | 5084316 | 11 |
| *Thalassiosira pseudonana* | thaps3_2 | 322124 | 12 |
| *Thalassiosira pseudonana* | thaps3_2 | 326683 | 13 |
| *Thalassiosira pseudonana* | thaps3_2 | 326937 | 14 |
| *Fragilariopsis cylindrus* | fracy1_2 | 386612 | 15 |
| *Fragilariopsis cylindrus* | fracy1_2 | 386837 | 16 |
| *Nannochloropsis oceanica* | Wt-5473 | | 17 |

The *N. oceanica* gene (coding sequence provided as SEQ ID NO:84, encoded polypeptide provided as SEQ ID NO:17) was found by scanning the predicted protein set of a proprietary *Nannochloropsis* genome for matches to the PF00172 HMM model using hmmsearch (hmmer.org) and the trusted cutoff for the match score; however, no additional *Nannochloropsis* orthologs were found by scanning *Nannochloropsis* genomes downloaded from singlecellcenter.org/en/NannoRegulationDatabase/Download/S11.zip, probably due to incomplete protein sets of the genomes. Additional putative orthologs of the *Nannochloropsis gaditana* ZnCys-2845 protein (SEQ ID NO:2) were found by BLAST (tblastn) against public genome assemblies of *Nannochloropsis* strains and species, including *N. gaditana* strain CCMP526, *N. oceanica* strain IMET1, *N. oceanica* strain CCMP531, *N. oculata* strain CCMP525, *N. salina* strain CCMP537, and *N. granulata* strain CCMP529. However, in each case the alignment matches were observed to break within the PF00172 Zn_Clus domain, such that all of the sequences were found to be incomplete, lacking the 5' end of the coding region and N-terminal sequence of the proteins. An additional conserved region, approximately 170 amino acids in length from the ZnCys-2845 polypeptide (positions 345-51 of SEQ ID NO:27), was clearly identified in all *Nannochloropsis* genomes analyzed and examined further. The delta-blast tool in NCBI was used to evaluate the highly conserved region between *N. gaditana* WT-3730 ZnCys-2845 (SEQ ID NO:2) putative orthologs in other *Nannochloropsis* species.

This domain, a PAS3_fold domain (pfam PF08447), is found in many signaling proteins where it functions as a signal sensor. Using this approach putative matches to ZnCys-28345 could be clearly identified in each of the six *Nannochloropsis* genomes searched. Unfortunately, the alignment matches in all cases appeared to break within the putative match to the PF00172 Zn_Clus domain. However, from the blast alignments, an approximately 170 aa region from ZnCys-28345 (positions 345-517) was observed and clearly identifiable across all strains (single copy). An alignment of the PAS3 domains in the identified ZnCys-2845 orthologs from *Nannochloropsis* is provided in FIG. 9, where the high degree of conservation of the domain sequence among different *Nannochloropsis* species is evident. The PAS3 domain of ZnCys-2845 (identified in the gene diagram of FIG. 12A) extends from amino acid 345 to amino acid 517 of SEQ ID NO:2, and is provided as SEQ ID NO:21. SEQ ID NO:21 also represents the sequence of the PAS3 domain of *N. gaditana* strain CCMP526. The sequence of the PAS3 domain of *N. oceanica* strain WT-5473, *N. oceanica* strain IMET1, and *N. oceanica* strain CCMP531 ZnCys-2845 orthologs is provided as SEQ ID NO:22. The *N. oceanica* ZnCys-2845 ortholog PAS3 domain (SEQ ID NO:22) is 86% identical in sequence to the *N. gaditana* PAS3 domain (SEQ ID NO:21). The PAS3 domain of the *N. salina* strain CCMP537 ZnCys-2845 ortholog is provided as SEQ ID NO:23, which is 98% identical to the *N. gaditana* ZnCys-2845 PAS3 domain (SEQ ID NO:21). The PAS3 domain of the *N. oculata* strain CCMP539 ZnCys-2845 ortholog is provided as SEQ ID NO:24, and it demonstrates 86% sequence identity to the PAS3 domain of *N. gaditana* ZnCys-2845 (SEQ ID NO:21). As provided above, the PAS3 domain of the ZnCys-2845 ortholog of *N. granulata* strain CCMP529 is provided as SEQ ID NO:22, which is approximately 86% identical to the PAS3 domain of *N. gaditana* ZnCys-2845 (SEQ ID NO:21).

An alignment of the amino acid sequence encoded by the *N. gaditana* ZnCys-2845 gene and the amino acid sequence (SEQ ID NO:17) encoded by the *N. oceanica* strain WT-5473 ortholog of the ZnCys-2845 gene, both of which were determined by in-house genome sequencing and gene assignment, is provided in FIG. 10. Genome sequences of three additional *Nannochloropsis* species, *N. granulata* strain CCMP529, *N. oculata* strain CCMP539, and *N. salina* strain CCMP537, were further examined to attempt to stitch together protein-encoding sequences of putative ZnCys-28545 orthologs as characterized by the PAS3 domains. The six *Nannochloropsis* genomes were curated to find regions of homology extending outward from the PAS3 domains. Blastn was utilized to identify homologous sequences, which were linked together with gaps introduced to maximize homology.

The Zn(2)-Cys(6) domain of *N. oceanica* is identical to the Zn(2)-Cys(6) domain of *N. gaditana* (SEQ ID NO:3). The polypeptides encoded by the two genes (*N. gaditana* ZnCys-2845 and the *N. oceanica* ortholog) have 56% identity across the entire deduced polypeptide sequence, and 71% identity across the first 517 amino acids of *N. gaditana* ZnCys-2845 (SEQ ID NO:2), a portion of the amino acid sequence that extends from the N-terminus of the protein through the Zn(2)-Cys(6) domain and through the PAS3 domain (see FIG. 5). Amino acids 1-200 encoded by the *N. salina* ZnCys-2845 homologous sequence (SEQ ID NO:20) have approximately 98% identity to corresponding amino acid sequence of *N. gaditana* ZnCys-2845 (SEQ ID NO:2); whereas the incomplete polypeptide sequence of a putative ortholog of *N. granulata* (SEQ ID NO:18) is approximately 61% identical to *N. gaditana* ZnCys-2845 (SEQ ID NO:2) and the incomplete polypeptide sequence of a putative ortholog of *N. oculata* (SEQ ID NO:19) is approximately 61% identical to *N. gaditana* ZnCys-2845 (SEQ ID NO:2). These partial polypeptide sequences do not include the PAS3 domains of the *Nannochloropsis* orthologs, which, as noted above, have much higher % identities to the PAS3 domain of *N. gaditana* ZnCys-2845 (SEQ ID NO:21).

Example 6

Growth and Lipid Biosynthesis of ZnCys-2845 Knockout Mutant in Semi-Continuous Production System Using Urea Nitrogen Source To determine whether the ZnCys-2845 gene disruption knockout mutant could utilize other sources of nitrogen, a semi-continuous productivity assay was set up in which the culture medium included urea as the sole nitrogen source.

For assays in cultures that included urea as the sole nitrogen source, seed cultures (also referred to as "starter cultures" or "scale-up cultures") of ZnCys-2845 knockout strain GE-8564 and wild type strain WT-3730 were grown in PM125 medium that included 7.5 mM urea as the sole nitrogen source. For assays in which wild type cells were cultured in nitrate-only medium (PM074), the wild type cells were scaled up in cultures that included the PM074 nitrate-only medium. The GE-8564 ZnCys-2845 knockout mutants were scaled up in cultures that included the PM124 medium that included both nitrate (8.8 mM) and ammonium (5 mM) for the semi-continuous assays that included only nitrate as the nitrogen source in the assay culture medium.

The scale-up cultures were used to inoculate 225 cm² rectangular tissue culture flasks, each of which contained a final total volume of 550 ml of culture after inoculation. The cultures were inoculated so that each 550 ml culture had an initial $OD_{730}$ of 0.9. A typical inoculum volume was approximately 200 ml of scale-up culture that was added to approximately 350 ml of assay culture medium, which was either PM074 (nitrate-only medium) or PM125 (urea-only medium). Cultures were diluted daily at mid-day, when the light intensity was at its peak, by removing 30% of the volume (165 mls) and replacing it with the same volume of the assay medium (either PM074 or PM125) plus an additional 10 ml of deionized water to make up for evaporation (included in the make-up medium). Semi-continuous assays were typically run for 10-14 days. Daily lipid and biomass productivities were only calculated for cultures that had reached steady state (where the increase in growth was equal to the dilution factor for the assay).

Three cultures were initiated per strain. The flasks included stir bars and had stoppers having inserted tubing connected with syringe filters for delivering $CO_2$ enriched air (1% $CO_2$, flow rate, 300 ml per min) that was bubbled through the cultures. The flasks were set in a water bath programmed to maintain a constant temperature of 25° C. on stir plates set to 575 rpm during the assay period. Culture flasks were masked with an opaque white plastic to provide a 31.5 cm² rectangular opening for irradiance to reach the culture. The flasks were aligned with the width (narrowest dimension) against an LED light bank that was programmed with a light/dark cycle and light profile that increased until "solar noon" and then declined to the end of the light period. The light profile was designed to mimic a spring day in Southern California: 14 h light:10 h dark, with the light peaking at approximately 2000 µE (FIG. 6B). The flasks included stir bars and had stoppers with inserted tubing connected with syringe filters for delivering $CO_2$ enriched air (1% $CO_2$, flow rate, 300 ml per min). The flasks were set in a water bath programmed to maintain a constant temperature of 25° C. on stir plates set to 575 rpm during the assay period.

Cultures were diluted daily at mid-day, when the light intensity was at its peak by removing 30% of the volume (165 ml) and replacing it with the same volume of the assay medium plus an additional 10 ml of deionized water to make up for evaporation. A 30% dilution rate was empirically determined as the most productive dilution rate for *Nannochloropsis*, as 50, 30, and 15% daily dilutions resulted in average TOC productivities of 6.5, 9 and 8 g/m²/day, respectively. Semi-continuous assays were typically run for 7-14 days. Daily lipid (FAME) and biomass (TOC) productivities were calculated from cultures that had reached steady state standing crop TOC and FAME density. Volumetric FAME and TOC productivities in (mg/L/day) were calculated by multiplying the volumetric FAME and TOC amounts by the 30% dilution rate. Aerial productivities (g/m2/day) were calculated by dividing the total productivity of the culture by the size of the aperture through which irradiance was permitted:

$$\frac{\text{(volumetric productivity)mg}}{L*\text{day}} * \frac{0.55 \text{ L}}{0.00315 \text{ m}^2} * \frac{g}{1000 \text{ mg}} = \frac{g}{m^2 * \text{day}}$$

FIG. 11A shows that the ZnCys-2845 knockout mutant GE-8564, when cultured in the semi-continuous assay where nitrate is the sole source of nitrogen (diamonds), showed a large induction of lipid production at the outset of the assay which subsequently declined steeply after day 3 of the assay such that lipid production fell below that of the non-induced wild type culture by day 10 of the assay, after which it declined to even lower levels. This pattern is consistent with the results of the batch assay of Example 4 which indicated the ZnCys-2845 knockout mutant GE-8564 is induced for lipid production in nitrate-only media.

In contrast, the cultures of the GE-8564 mutant having a disrupted ZnCys-2845 gene cultured in urea-only medium (FIG. 11A, circles) had consistently higher daily FAME productivity than the wild type strain cultured in either nitrate only medium (triangles) or urea-only medium (squares), both of which are conditions in which the wild type strain is not induced for lipid production (as evidenced by the FAME/TOC ratios of these cultures throughout the assay, see FIG. 11C and Table 14, below). Table 11 provides the daily amounts of FAME produced on an areal basis by all strains in the semi-continuous assay along with the percentage increase of the amount of FAME produced by the knockout mutant GE-8564 strain over wild type FAME levels when both were cultured in urea-only culture medium also provided. Average areal FAME productivity for each strain, expressed as g/m²/day, is provided in Table 12. The increase in FAME productivity of the knockout mutant strain GE-8564 over the wild type strain averaged 58% over the course of the thirteen day assay when both strains were cultured in urea-only medium. It can also be seen that wild type cells cultured in urea-only medium showed, on average, 16% less FAME productivity than wild type cells in nitrate-only medium. The GE-8564 knockout mutant in nitrate-only medium showed increased FAME production with respect to wild type in the first 8 days of the assay and then experienced declines in daily FAME production as the assay progressed, consistent with a nitrogen depletion response.

TABLE 11

FAME (g/m²/day) Produced by ZnCys Knockout and Wild type Strains Cultured with Nitrate or Urea as Nitrogen Source in Semi-continuous Assay.

| DAY | WT/ NO3 | ZnCys-KO/ NO3 | ZnCys-KO % difference NO3 | WT/ UREA | ZnCys-KO/ UREA | ZnCys-KO % increase UREA |
|---|---|---|---|---|---|---|
| 1 | 2.48 | 5.46 | 120% | 1.84 | 2.64 | 43% |
| 2 | 2.41 | 5.86 | 143% | 2.24 | 2.70 | 20% |
| 3 | 2.45 | 6.68 | 172% | 2.18 | 3.08 | 41% |
| 4 | 2.23 | 6.40 | 187% | 2.00 | 2.80 | 40% |
| 5 | 2.45 | 5.41 | 121% | 1.98 | 3.05 | 54% |
| 6 | 2.40 | 4.72 | 97% | 2.12 | 3.57 | 69% |
| 7 | 2.46 | 3.85 | 57% | 1.90 | 3.55 | 87% |
| 8 | 2.47 | 3.18 | 28% | 2.11 | 3.46 | 64% |
| 9 | 2.54 | 2.43 | −5% | 2.07 | 3.39 | 64% |
| 10 | 2.38 | 1.77 | −26% | 1.90 | 3.16 | 66% |
| 11 | 2.25 | 1.27 | −43% | 1.74 | 3.25 | 87% |
| 12 | 2.35 | 0.90 | −62% | 1.89 | 3.09 | 63% |
| 13 | 2.09 | 0.69 | −67% | 1.90 | 3.05 | 60% |
| Avg. | 2.38 | 3.74 | 57% | 1.99 | 3.14 | 57% |

Table 12 provides the average daily FAME productivities of the cultures over the thirteen day semi-continuous culture. The average daily FAME productivity for the ZnCys knockout GE-8564 grown in a urea-only medium was 32% higher than the average daily FAME productivity of the wild type strain (WT-3730) grown in nitrate medium (rightmost column). The high FAME productivity value of the ZnCys-2435 knockout in nitrate-only medium is due to the very high FAME production in the first 7 days of the culture. The daily FAME productivity is already declining by day 5 of the culture however, after which it declines well below wild type cultured in nitrate-only medium (FIG. 11A).

TABLE 12

Average Daily FAME Productivity of Semi-Continuous Cultures in Urea-only or Nitrate-only Media

| Strain | g/m²/day FAME | Avg change v. WT (NO3) |
|---|---|---|
| WT-3730 (NO3) | 2.38 | 0% |
| WT-3730 (Urea) | 1.99 | −16% |
| ZnCys-KO GE-8564 (Urea) | 3.14 | 32% |
| ZnCys-KO GE-8564 (NO3) | 3.74 | 57% |

FIG. 11B shows that the ZnCys-2845 knockout mutant (GE-8564) cultured in the semi-continuous assay in a nitrate-only medium (diamonds) demonstrated a precipitous drop in biomass production over the course of the assay, declining to levels that were only a fraction of the biomass produced by wild type cells cultured in nitrate medium by the end of the assay. In contrast, during this semi-continuous productivity assay, there was little decline in biomass (TOC) productivity in the ZnCys-2845 gene disruption mutant cultured in urea medium (circles) with respect to the wild type strain cultured in nitrate medium (triangles), and the ZnCys-2845 knockout mutant even demonstrated slightly better productivity than wild type cultured in urea medium (squares), all three of which remained in fairly consistent over the entire course of the assay.

Table 13 provides the TOC content of these semi-continuous cultures and the percentage difference in the daily amount of TOC produced between the ZnCys-2845 knockout mutant cultured in nitrate-only medium with respect to wild type cells cultured in nitrate-only medium, and the percentage difference in daily TOC produced between the ZnCys-2845 knockout mutant cultured in urea medium with respect to wild type cells cultured in urea medium. In Table 13 the reduction in the amount of biomass produced on a daily basis can be seen in ZnCys-2845 knockout mutant cultured in nitrate only medium as the assay progresses. The biomass production levels of the other cultures, including the ZnCys-2845 knockout mutant cultured in urea medium that had a 58% increase in daily FAME productivity with respect to wild type in urea medium, remains quite consistent throughout the thirteen day assay, and has a slightly better average TOC productivity than does the wild type strain cultured in urea medium. Thus, the ZnCys-2845 knockout mutant was able to accumulate biomass at levels at least equivalent to the wild type strain while demonstrating nearly 60% higher daily FAME productivity when cultured in a medium that included urea as the sole source of nitrogen.

TABLE 13

Biomass (g/m²/day TOC) produced by strains grown in nitrate or urea in a semi-continuous assay

| DAY | WT/ NO3 medium | ZnCys-KO/ NO3 medium | ZnCys-KO % difference NO3 medium | WT/ UREA medium | ZnCys-KO/ UREA medium | ZnCys-KO % increase, UREA medium |
|---|---|---|---|---|---|---|
| 1 | 9.65 | 11.00 | 14% | 8.06 | 8.86 | 10% |
| 2 | 9.24 | 9.69 | 5% | 7.94 | 8.25 | 4% |
| 3 | 9.42 | 9.61 | 2% | 8.35 | 8.80 | 5% |

TABLE 13-continued

Biomass (g/m²/day TOC) produced by strains grown in nitrate or urea in a semi-continuous assay

| DAY | WT/ NO3 medium | ZnCys-KO/ NO3 medium | ZnCys-KO % difference NO3 medium | WT/ UREA medium | ZnCys-KO/ UREA medium | ZnCys-KO % increase, UREA medium |
|---|---|---|---|---|---|---|
| 4 | 10.28 | 8.72 | −15% | 9.21 | 8.86 | −4% |
| 5 | 10.08 | 7.19 | −29% | 8.85 | 8.88 | 0% |
| 6 | 9.97 | 6.18 | −38% | 8.72 | 9.09 | 4% |
| 7 | 9.99 | 5.07 | −49% | 8.79 | 9.29 | 6% |
| 8 | 9.42 | 3.83 | −59% | 8.03 | 8.55 | 6% |
| 9 | 9.34 | 3.22 | −66% | 7.99 | 8.84 | 11% |
| 10 | 9.12 | 2.46 | −73% | 7.94 | 8.57 | 8% |
| 11 | 9.32 | 2.00 | −79% | 7.74 | 8.74 | 13% |
| 12 | 9.53 | 1.77 | −81% | 8.11 | 8.59 | 6% |
| 13 | 9.57 | 1.45 | −85% | 8.28 | 9.25 | 12% |
| Avg | 9.61 | 5.55 | −42% | 8.31 | 8.81 | 6% |

In fact, despite the increased lipid production by the ZnCys-2845 knockout mutant in urea-only medium with respect to wild type cells in nutrient replete (nitrate-only) medium (FIG. 11A and Table 11) the average amount of TOC produced throughout the course of the assay by the ZnCys knockout mutant in urea-containing medium was at least 90% that of wild type cells cultured in nitrate medium, i.e., only about 10% less than that of nitrogen replete wild type cells.

FIG. 11C shows the daily FAME to TOC ratios of the cultures in the semi-continuous assay. These ratios stay fairly consistent for all samples with the exception of the ZnCys-2845 gene disruption mutant ("ZnCys-KO") cultured in nitrate-only medium (diamonds), which shows FAME to TOC ratios climbing from the first day of culturing up to day 8, after which the ratio begins to decline. These FAME:TOC ratios of the ZnCys-2845 gene disruption mutant cultured in nitrate-only medium are far higher than the FAME:TOC ratios of wild type cultured in both nitrate-only and urea-only medium and the ZnCys-2845 knockout mutant cultured in urea-only medium and are indicative of the classic lipid induction response to nitrogen depletion. FAME to TOC ratios of the mutant and wild type semicontinuous assay cultures are provided in Table 14.

TABLE 14

FAME/TOC ratios of cultures cultured in nitrate or urea.

| DAY | WT/ NO3 | ZnCys-KO/ NO3 | WT/ UREA | ZnCys-KO/ UREA |
|---|---|---|---|---|
| 1 | 0.3 | 0.5 | 0.2 | 0.3 |
| 2 | 0.3 | 0.6 | 0.3 | 0.3 |
| 3 | 0.3 | 0.7 | 0.3 | 0.3 |
| 4 | 0.2 | 0.7 | 0.2 | 0.3 |
| 5 | 0.2 | 0.8 | 0.2 | 0.3 |
| 6 | 0.2 | 0.8 | 0.2 | 0.4 |
| 7 | 0.2 | 0.8 | 0.2 | 0.4 |
| 8 | 0.3 | 0.8 | 0.3 | 0.4 |
| 9 | 0.3 | 0.8 | 0.3 | 0.4 |
| 10 | 0.3 | 0.7 | 0.3 | 0.4 |
| 11 | 0.2 | 0.6 | 0.2 | 0.4 |
| 12 | 0.2 | 0.5 | 0.2 | 0.4 |
| 13 | 0.2 | 0.5 | 0.2 | 0.3 |

The ZnCys-2845 gene disruption mutant cultured in urea-only shows consistently higher FAME:TOC ratios with respect to wild type cells cultured in either nitrate-only or urea only medium, but the FAME:TOC ratio is fairly stable throughout the culture period, in the range of 0.3 to less than 0.5, representing an increase of on average about 45% over wild type. Thus, when urea was used as the sole source of reduced nitrogen in the assay, the ZnCys-2845 gene disruption mutant demonstrated significantly increased partitioning of carbon to lipid (Table 14, FIG. 11C) without a substantial loss of overall carbon assimilation (Table 13, FIG. 11B), resulting in an approximately 57% increase in FAME produced on a daily basis and only an approximately 6% decrease in TOC produced with respect to wild type cells cultured under the same (urea-only) conditions over the course of the assay.

Example 7

Cas9 ZnCys-2845 Knockdown Constructs

Since the ZnCys-2845 knockout line exhibited a significant deficit in TOC productivity concomitant with increased carbon partitioning to lipid in batch growth (Example 4, FIG. 7B), we next investigated whether varying the degree of attenuation of ZnCys-2845 expression would result in engineered strains in which lipid and TOC productivity were better optimized. Additional mutant strains were engineered to have decreased expression of the ZnCys-2845 gene using Cas9/CRISPR genome engineering. Twelve chimeric guide RNAs were designed to target sequences upstream of the ATG, within an intron of the gene, in the 3' end of the gene but still within the coding sequence, or in the 3' untranslated region of the gene (FIG. 12A). These constructs described here as "Bash Knockdown constructs" or simply "Bash constructs" because they are designed to insert the donor fragment into a site in a region of the gene where the insertion is expected to allow the targeted gene to be expressed at a lower level than in wild type. (Correspondingly, the strains that include such insertions are referred to as "Bash strains", "Bashers", or "Bash Knockdown mutants".) The twelve 18-nucleotide sequences having homology to the ZnCys-2845 gene (target site sequences) are provided in Table 15.

TABLE 15

Target and Chimeric Guide Sequences for Attenuating ZnCys-2845 Expression

| "Bash" Gene Attenuation Target Site | Gene Region Targeted | Target Sequence (18 nt) |
|---|---|---|
| −1 | 5' UTR | SEQ ID NO: 51 |
| 1 | 5' UTR | SEQ ID NO: 52 |
| 2 | 5' UTR | SEQ ID NO: 53 |
| 3 | 5' UTR | SEQ ID NO: 54 |
| 4 | 5' UTR | SEQ ID NO: 55 |
| 6 | Intron in PAS3 domain sequence | SEQ ID NO: 56 |
| 7 | Intron in PAS3 domain sequence | SEQ ID NO: 57 |
| 8 | C-terminus | SEQ ID NO: 58 |
| 9 | C-terminus | SEQ ID NO: 59 |
| 10 | C-terminus | SEQ ID NO: 60 |
| 11 | 3' UTR | SEQ ID NO: 61 |
| 12 | 3' UTR | SEQ ID NO: 62 |

Chimeric guide DNA constructs were synthesized as two complementary strands that were annealed to produce a double-stranded construct with a T7 promoter positioned upstream of the guide sequence (that included the 18 nucleotide target sequence in addition to the tracr sequence), and used to produce the chimeric guide RNAs by in vitro transcription and purified as described in Example 3. SEQ ID NO:42 is an example of a generic "sense" strand for producing a guide RNA and SEQ ID NO:43 is an example of a generic "complementary" strand that would be annealed to the sense strand (where the target sequence is again represented by 18 Ns) for producing the guide RNA by in vitro transcription.

In the present experiments, each chimeric guide RNA was individually transformed into Nannochloropsis Editor strain GE-6791 along with the donor fragment that included a Hyg resistance ("HygR") cassette (FIG. 4A, SEQ ID NO:44) as described in Example 3. Hygromycin resistant colonies were selected and screened by colony PCR as described using primers adjacent to the targeted regions of the ZnCys-2845 gene. Primers MA-ZnCys-FP (SEQ ID NO:49) and MA-ZnCys-RP (SEQ ID NO:50) were used to confirm the knockout (GE-8564) and donor fragment insertion into introns; primers MA-5'Bash-ZnCys-FP (SEQ ID NO:63) and MA-5'Bash-ZnCys-RP (SEQ ID NO:64) were used to confirm the insertion of the donor fragment into the 5' regions of the ZnCys-2845 gene; and primers MA-3'Bash-ZnCys-FP (SEQ ID NO:65) and MA-3'Bash-ZnCys-RP (SEQ ID NO:66) were used to confirm the insertion of the donor fragment into the 3' regions of the ZNCys-2845 gene. Eleven of the twelve guide RNAs resulted in isolates that by colony PCR appeared to have the Hyg gene inserted at the targeted locus (insertion into 5' UTR target site-1 was not observed.)

Quantitative reverse transcription-PCR (qRT-PCR) was performed on RNA isolated from the knockdown lines to determine whether expression of the ZnCys-2845 gene was in fact reduced in these lines. The ZnCys-2845 Bash Knockdown strains were grown under standard nitrogen replete conditions (PM074 (nitrate-only) medium) and harvested during early stationary phase. Total RNA was isolated from ZnCys-2845 Bash Knockdown cells, using methods provided in Example 1, above. RNA was converted to cDNA BioRad's iScript™ Reverse Transcription Supermix kit according to the manufacturer's protocol. For PCR, Ssofast EvaGreen Supermix (Bio-Rad, Hercules, Calif.) was used along with gene-specific primers. The PCR reaction was carried out on C1000 Thermal Cycler coupled with a CFX Real-time System (BioRad). Primer and cDNA concentrations were according to the manufacturer's recommendation. Primers for amplifying a sequence of the ZnCys-2845 transcript were SEQ ID NO:67 and SEQ ID NO:68. Transcript levels for each sample were normalized against a housekeeping gene with consistent expression levels under different culture conditions (1T5001704; SEQ ID NO:69) and relative expression levels were calculated using the ddCT method using BioRad's CFX Manager software.

FIG. 12B shows that several of the strains had reduced levels of ZnCys-2845 transcript. Of these, strains GE-13108 (ZnCys-2845 Bash-2) and GE-13109 (ZnCys-2845 Bash-3), targeting the 5' end of the ZnCys-2845 gene, and strain GE-13112 (ZnCys-2845 Bash-12), targeting the 3' end of the ZnCys-2845 gene, were selected for productivity assays.

Example 8

RNAi Knockdown Construct

In another strategy to determine whether decreasing expression of the ZnCys-2845 gene would allow the cells to accumulate more carbon than the Cas9 knockout while still producing increased amounts of lipid with respect to wild type, an interfering RNA (RNAi) construct was designed for expression in Nannochloropsis cells. The construct included a sequence designed to form a hairpin that included a sequence homologous to a region of the ZnCys-2845 gene (SEQ ID NO:70), followed by a loop sequence and then followed by the inverse sequence to the ZnCys-2845 gene-homologous sequence, driven by the N. gaditana EIF3 promoter (SEQ ID NO:46) and followed by N. gaditana "terminator 9" (SEQ ID NO:71). The construct also included a gene encoding GFP codon optimized for Nannochloropsis (SEQ ID NO:36) under the control of the Nannochloropsis 4AIII promoter (SEQ ID NO:37) and followed by "terminator 5" (SEQ ID NO:38), as well as a gene conferring hygromycin resistance (SEQ ID NO:45) driven by the TCTP promoter (SEQ ID NO:34) and terminated by the EIF3 terminator (SEQ ID NO:35). The construct was linearized and transformed into wild type Nannochloropsis gaditana WT-3730 by electroporation as described.

Hygromycin resistant colonies were screened for the presence of the RNAi construct and positive strains were further screened by qRT-PCR as described in Example 7 for knockdown of the ZnCys-2845 transcript levels.

Example 9

Knockdown Constructs in Batch Assay

ZnCys-2845 RNAi strain GE-13103 and ZnCys-2845 knockdown "basher" strains GE-13108, GE-13109, and GE-13112 were tested in the batch productivity assay described in Example 4 by scaling up the cultures in culture medium PM124 (which includes both $NH_4$ and $NO_3$ as nitrogen sources) and by carrying out the assay in PM123 culture medium that includes nitrate as the sole nitrogen source. The ZnCys-2845 Knockout strain GE-8564 and the wild type background strain were run in the same assay as controls.

The results, provided in Tables 16-18 and shown in FIGS. 13A-C, were startling. All gene attenuation mutants, including original knockout mutant GE-8564 (triangles), produced FAME in amounts greater than wild type (circles) when cultured with nitrate as the sole nitrogen source on all days sampled (FIG. 13A, data provided in Table 16). However, while the original knockout strain GE-8564 (triangles) had a significantly reduced rate of total organic carbon accumulation with respect to wild type (FIG. 13B), in these conditions, the attenuated knockdown strains—the "bash" strains and RNAi strain having reduced expression of the ZnCys-2845 gene—had rates of TOC accumulation close to or (for example in the case of GE-13112 (represented as Xs)) essentially identical to, wild type (FIG. 13B, data provided in Table 17). Remarkably, these ZnCys-2845 knockdown mutants demonstrated FAME to TOC ratios that were significantly enhanced with respect to wild type (FIG. 13C and Table 18), although not as high as the FAME to TOC ratios of the ZnCys-2845 knockout mutant GE-8564, i.e., the carbon partitioning to lipid in these knockdown attenuation strains was intermediate between that of wild type and the ZnCys-2845 knockout strain.

vided in Example 7. The ZnCys BASH-3 strain GE-13109 demonstrated an approximately 20% reduction in ZnCys-2845 transcript level, the ZnCys BASH-12 strain GE-13112 demonstrated an approximately 50% reduction in ZnCys-2845 transcript level, and the ZnCys-2845 RNAi isolate (GE-13103) demonstrated an approximately 70% reduction in ZnCys-2845 transcript level. FIG. 14C provides a graph of the FAME/TOC ratio and TOC productivity of each strain based on a batch assay in nitrate-only medium as described above, except that in the assay of FIG. 14C, the ZnCys-2845 knockout strain GE-8564) was not precultured in the presence of ammonium but in nitrate-only medium. As summarized in FIG. 14C, in batch growth with no nitrate, all three ZnCys-2845 gene attenuation lines exhibited increases in carbon partitioning to lipid evident at FAME/TOC ratios (see also Table 18) that were intermediate between wild type and ZnCys knockout (strain GE-8564) FAME/TOC ratios. TOC accumulation in the knockdown mutants were nearly equivalent to wild type (the ZnCys RNAi-7 strain GE-13103 having the greatest impairment of only about 20%), showing

TABLE 16

FAME productivity of ZnCys-2845 Knockdown Strains Compared to Wild Type in Batch Assay with $NO_3$-containing Culture Medium (mg/L culture)

| Day | WT | BASH-2 (GE-13108) | % incr | BASH-3 (GE-13109) | % incr | BASH-12 (GE-13112) | % incr | RNAi-7 (GE-13103) | % incr | ZnCys-KO (GE-8564) | % incr |
|---|---|---|---|---|---|---|---|---|---|---|---|
| 3 | 159.22 | 279.72 | 75.68 | 260.14 | 233.36 | 233.36 | 40.64 | 233.36 | 46.56 | 242.05 | 52.02 |
| 5 | 191.33 | 446.40 | 133.31 | 377.8 | 368.41 | 368.41 | 55.98 | 368.41 | 92.55 | 360.89 | 88.67 |
| 7 | 270.37 | 599.06 | 121.57 | 431.41 | 460.69 | 460.69 | 27.96 | 460.69 | 70.39 | 473.53 | 75.14 |

TABLE 17

TOC productivity of ZnCys-2845 Knockdown Strains Compared to Wild Type in Batch Assay with $NO_3$-containing Culture Medium (mg/L culture)

| Day | WT | BASH-2 (GE-13108) | % diff | BASH-3 (GE-13109) | % diff | BASH-12 (GE-13112) | % diff | RNAi-7 (GE-13103) | % diff | ZnCys-KO (GE-8564) | % diff |
|---|---|---|---|---|---|---|---|---|---|---|---|
| 3 | 642.4 | 608.1 | −5.34 | 615.05 | −4.26 | 627.2 | −2.37 | 497.4 | −22.57 | 281.5 | −56.18 |
| 5 | 920.75 | 827.9 | −10.09 | 836.9 | −9.11 | 913.95 | −0.74 | 713.4 | −22.52 | 408.8 | −55.01 |
| 7 | 1188 | 1044.5 | −12.08 | 1044 | −12.12 | 1175.5 | −1.05 | 929.2 | −21.78 | 558.15 | −53.18 |

TABLE 18

FAME/TOC ratios of ZnCys-2845 Knockdown Strains Compared to Wild Type in Batch Assay with $NO_3$-containing Culture Medium

| Day | WT-3730 | s.d. | BASH-2 (GE-13108) | s.d. | BASH-3 (GE-13109) | s.d. | BASH-12 (GE-13112) | s.d. | RNAi-7 (GE-13103) | s.d. | ZnCys-KO (GE-8564) | s.d. |
|---|---|---|---|---|---|---|---|---|---|---|---|---|
| 3 | 0.2478 | 0.0092 | 0.4599 | 0.0090 | 0.4229 | 0.0096 | 0.3570 | 0.0043 | 0.4690 | 0.0146 | 0.8608 | 0.0334 |
| 5 | 0.2078 | 0.0012 | 0.5391 | 0.0059 | 0.4514 | 0.0025 | 0.3263 | 0.0106 | 0.5161 | 0.0230 | 0.8824 | 0.0393 |
| 7 | 0.2276 | 0.0012 | 0.5735 | 0.0051 | 0.4132 | 0.0036 | 0.2942 | 0.0033 | 0.4959 | 0.0069 | 0.8491 | 0.0593 |

FIG. 14A provides a diagram of the ZnCys-2845 gene and FIG. 14B provides a graph showing normalized ZnCys-2845 RNA levels in cultured strains having insertional BASH mutations ("basher" strains GE-13109 and GE-13112), the RNAi construct (ZnCys-2845 RNAi strain GE-13103), or the knockout (KO) mutation (ZnCys-2845 knockout mutant GE-8564) as quantitated by PCR using the methods proa substantial improvement over the reduction shown in the ZnCys-2845 knockout mutant which demonstrates an approximately 85% reduction in average daily TOC productivity (FIG. 14C). The daily FAME and TOC values of the batch assay from which the data of FIG. 14C is derived are provided in the graphs of FIGS. 15A and 15B.

Example 10

ZnCys-2845 Knockdown Mutants in the Semi-Continuous Productivity Assay

ZnCys-2845 RNAi strain GE-13103, BASH2 strain GE-13108, BASH3 strain GE-13109, and BASH12 strain GE-13112 were then assayed in the semi-continuous productivity assay described in Example 6, except that in this case the assay medium, PM074, included nitrate as the sole nitrogen source and the knockdown strains were pre-cultured in PM124 medium that included 5 mM ammonium in addition to 8.8 mM nitrate. For the GE-13103 ZnCys-2845 RNAi strain, productivity was assayed in two ways: a first set of semi-continuous assay cultures was inoculated using starter cultures that included the PM074 nitrate-only culture medium, and a second set of GE-13103 semi-continuous assay cultures was inoculated using starter cultures that included 5 mM ammonium in addition to 8.8 mM nitrate (PM124 medium).

The starter cultures were used to inoculate 225 cm$^2$ rectangular tissue culture flasks, each of which contained a final total volume of 550 ml of culture after inoculation. The cultures were inoculated so that each 550 ml culture had an initial $OD_{730}$ of 0.9. A typical inoculum volume was approximately 200 ml of scale-up culture that was added to approximately 350 ml of assay culture medium, which was PM074 (nitrate-only medium). Cultures were diluted daily at mid-day, when the light intensity was at its peak, by removing 30% of the volume (165 mls) and replacing it with the same volume of the assay medium (PM074) plus an additional 10 ml of deionized water to make up for evaporation (included in the make-up medium). Thus, assay cultures inoculated from scale-up ZnCys-2845 RNAi cultures that included 5 mM ammonium in the culture medium (PM124 medium) started out with a significant amount of ammonium (e.g., about 2 mM ammonium or less) that progressively declined and was diluted out further during the course of the assay. Semi-continuous assays were typically run for 10-14 days. Daily lipid and biomass productivities were only calculated for cultures that had reached steady state (where the increase in growth was equal to the dilution factor for the assay).

During the course of the semi-continuous assay, daily 30% dilutions were with nitrate-only medium (PM074) for all cultures. In these assays, much more lipid was produced on a daily basis by the GE-13103 RNAi knockdown cells scaled up in nitrate-only medium in the semi-continuous assay (filled-in circles, FIG. 16A) as compared with wild type cells, which were in nitrogen replete conditions (diamonds). The amount of lipid produced on a daily basis by the GE-13103 strain was even higher when the scale-up culture medium included ammonium in addition to nitrate (open circles in FIG. 16A). BASH2 strain GE-13108 (Xs), BASH3 strain GE-13109 (triangles), and BASH12 strain GE-13112 (squares) also produced considerably more FAME in the semi-continuous assay than did the wild type strain.

Figure 16A:
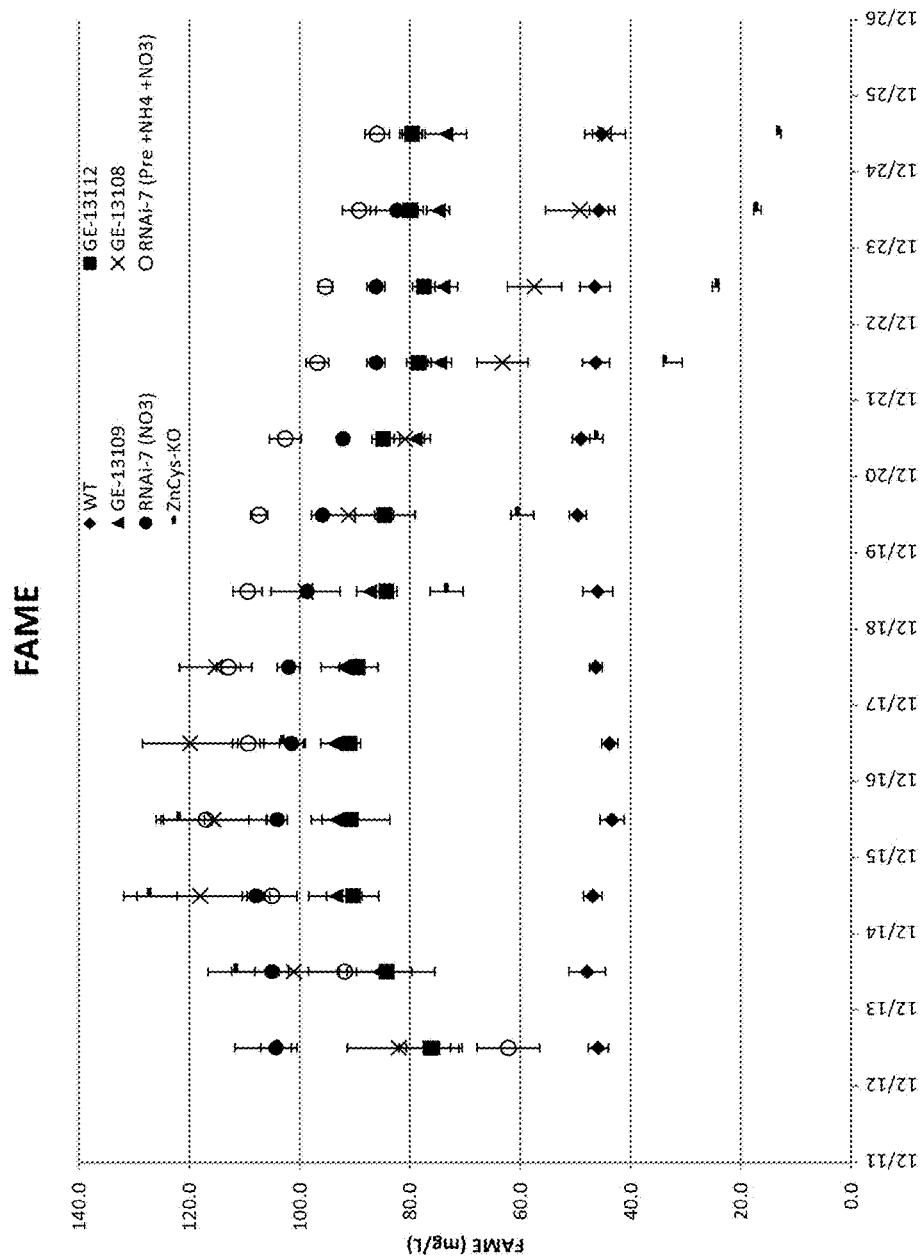
Figure 16C:
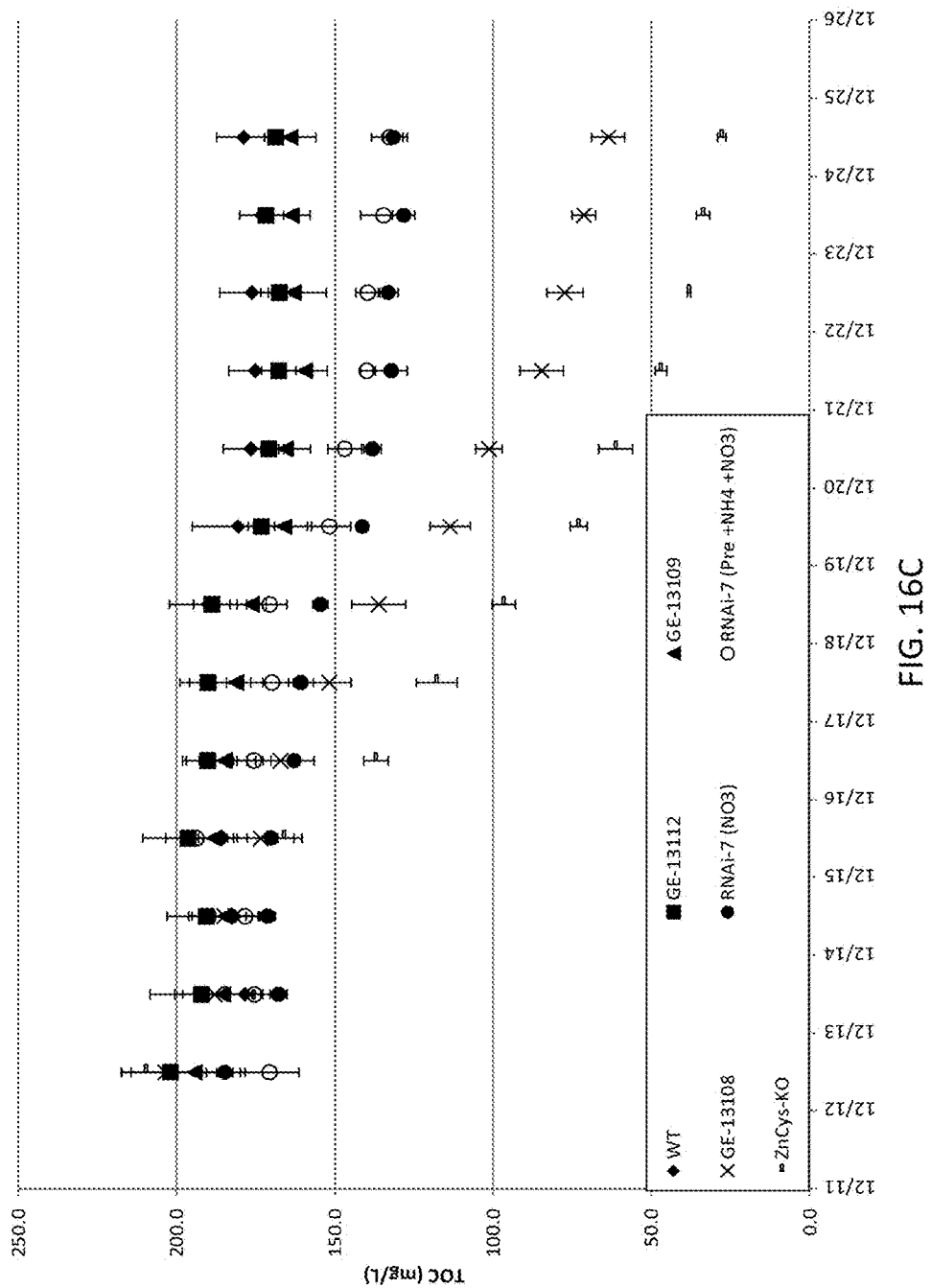

FIG. 16B provides the daily amount of FAME produced by the knockdown strains in the semi-continuous assay that included nitrate as the sole nitrogen source in the culture medium (PM074 medium). The knockdown strains, which included GE-13108 (5' Bash2), GE-13109 (5' Bash3), GE-13112 (3' Bash12), and GE-13103 (RNAi-7) were pre-cultured in nitrate plus ammonium medium PM124. The RNAi knockdown strain GE-13103 was also assayed after being pre-cultured in nitrate-only medium (PM074), alongside wild type strain WT-3730 pre-cultured in nitrate-only medium (PM074) (which is a nitrogen replete medium for the wild type strain). Knockout strain GE-8564 was cultured separately in nitrate-only (PM074) medium as the culture medium used in the semi-continuous assay. The table of FIG. 16B demonstrates that all of the knockdown strains had higher productivities than the wild type strain when cultured in the semi-continuous assay with regular dilution using a culture medium in which nitrate was substantially the sole nitrogen source (PM074). In this assay, knockdown strain GE-13112 (BASH12), demonstrated production of an average daily amount of FAME that was 83% greater than wild type, and knockdown strain GE-13109 (BASH3), demonstrated production of an average daily amount of FAME that was 81% greater than wild type on nitrate. Knockdown strain GE-13108 (BASH2), demonstrated production of an average daily amount of FAME that was 88% greater than wild type diluted with the same culture medium (PM074) over the course of the assay. Thus, all of the insertional knockdown mutants targeting non-coding regions of the ZnCys-2845 gene demonstrated substantial increases in areal FAME productivity of at least 70% higher (and approximately 80%-90% higher), than wild type cells in nitrate-only culture medium, with only minimal TOC productivity decreases of approximately 5-15% in the GE-13108 (BASH2), GE-13112 (BASH12), and RNAi-7 GE-13103 strains compared to the wild type strain (FIG. 16C). The RNAi-7 strain GE-13103 pre-cultured in nitrate-only medium produced on average is 107% more FAME on a daily basis than wild type cultured under the same conditions. The RNAi-7 strain GE-13103 pre-cultured in a medium that included both ammonium plus nitrate produced on average is 122% more FAME on a daily basis than wild type cultured under the same conditions. Thus, the GE-13103 gene attenuation mutant produced at least twice as much lipid as wild type in a semi-continuous assay in which the cultures were regularly diluted with nitrate-only medium, regardless of the nitrogen source in the pre-culture medium. The knockout mutant, GE-8564, also produced somewhat more FAME than wild type in the assay, although the increase was not as great as for the knockdown mutants (approximately 40% greater than when both were cultured in nitrate-only medium). The amount of FAME produced by knockout mutant GE-8564 cultured in nitrate-only medium fell off drastically beginning at about day 6 of the culture, reflecting large losses in biomass (Table 20).

These improvements in FAME productivity by the knockdown strains are presented as a percentage increase over wild type, averaged over the duration of the culture, in Table 19. All of the knockdown strains (GE-13103, GE-13108, GE-13109, and GE13112) had increases in FAME productivity (i.e, g/m$^2$/day) with respect to wild type over the course of the culture, ranging from 81% to 122% over the course of the entire culture, with even greater productivity increases seen in the first four days of culturing, ranging from 100% (i.e., twice the wild type productivity) to 160%. GE-13103, the RNAi knockdown strain, had the largest productivity increase with respect to wild type over the course of the semi-continuous culture, approximately 100% improvement (when pre-cultured in PM074) and approximately 120% improvement (when pre-cultured in PM124).

TABLE 19

FAME productivity of Knockdown and Knockout Strains (g/m2/day)

| Strain | Day 1-Day 4 | | | Day 8-Day 11 | | | Day 1-Day 11 | |
|---|---|---|---|---|---|---|---|---|
| | | s.d. | % impr | | s.d. | % impr | | % impr |
| WT-3730 | 2.37 | 0.11 | — | 2.41 | 0.08 | — | 2.43 | — |
| GE-13112 (BASH-12) | 4.75 | 0.20 | 100% | 4.14 | 0.10 | 72% | 4.44 | 83% |
| GE-13109 (BASH-4) | 4.89 | 0.16 | 107% | 3.90 | 0.13 | 62% | 4.39 | 81% |
| GE-13108 (BASH-3) | 6.15 | 0.43 | 160% | 2.84 | 0.46 | 18% | 4.55 | 88% |
| GE-13103 (RNAi-7) (pre-cultured in NO3) | 5.45 | 0.17 | 130% | 4.39 | 0.19 | 82% | 4.95 | 104% |
| GE-13103 (RNAi-7) (pre-cultured in NH4 + NO3) | 5.83 | 0.32 | 146% | 4.82 | 0.26 | 100% | 5.40 | 122% |
| GE-8564 (ZnCys-KO) Urea medium | 2.98 | 0.20 | 26% | 3.14 | 0.12 | 30% | 3.22 | 33% |
| GE-8564 (ZnCys-KO) Nitrate medium | 5.80 | 0.84 | 145% | 1.16 | 0.43 | −52% | 3.39 | 40% |

The amount of TOC accumulated on a daily basis by the knockdown strains was only slightly to modestly less than the TOC accumulated by wild type in knockdown cultures, GE-13109 (5' Bash-3), and GE13112 (3' Bash-12) although it was significantly lower in GE-13108 (5' Bash-2) and knockout strain GE-8564 cultured in nitrate-only medium (FIG. 16C and Table 20). Nevertheless, the TOC productivity in the RNAi knockdown strain (GE-13103) that exhibited an approximately 100% increase in FAME productivity over 11 days (and approximately 120% increased when precultured with ammonium) was only about 18% reduced with respect to wild type, and the TOC productivities of BASH-12 and BASH-4 knockdown mutant strains GE-13112 and GE-13109 (that demonstrated increases of at least 80% in FAME productivity over eleven days) were decreased by only 5% or less.

TABLE 20

Daily Average TOC productivity of Knockdown and Knockout Strains

| Strain | g/m²/day | s.d. | % diff |
|---|---|---|---|
| WT | 9.50 | 0.30 | 0% |
| GE-13112 (BASH-12) | 9.43 | 0.60 | −1% |
| GE-13109 (BASH-3) | 9.06 | 0.56 | −5% |
| GE-13108 (BASH-2) | 6.33 | 2.32 | −33% |
| GE-13103 (RNAi-7) (pre-cultured in NO3) | 7.75 | 0.87 | −18% |
| GE-13103 (RNAi-7) (pre-cultured in NH4 + NO3) | 8.27 | 1.09 | −13% |
| GE-8564 (ZnCys-KO) Cultured in Urea | 8.86 | 0.26 | −7% |
| GE-8564 (ZnCys-KO) Cultured in NO3 | 4.68 | 2.88 | −51% |

Figure 16D:
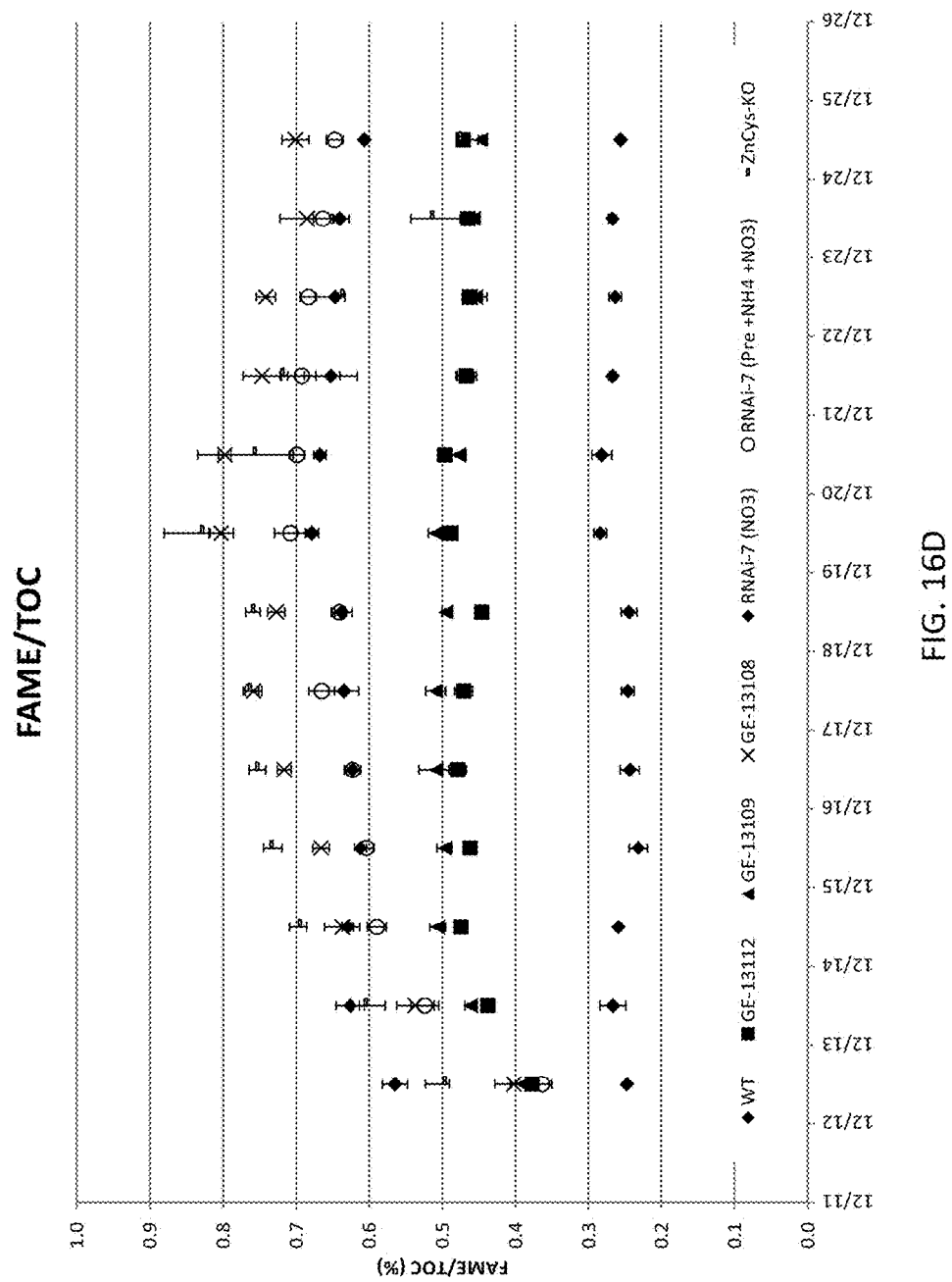

The ZnCys-2845 knockdown and knockout cultures all demonstrated increased FAME to TOC ratios as compared to wild type (solid diamonds) in the semicontinuous assay in nitrate medium (FIG. 16D and Table 21). When scaled up in nitrate only medium, the RNAi knockdown strain GE-13103 (closed circles) demonstrated a greater than 100% increase, approximately a 150% increase, in FAME/TOC ratio with respect to wild type and the same GE-13103 strain scaled up in nitrate plus ammonium medium (open circles) demonstrated an 153% increase in their FAME to TOC ratio in the semi-continuous productivity assay (Table 21).

TABLE 21

FAME/TOC Ratios of Knockdown and Knockout Strains

| Strain | fame/toc | s.d. | % impr |
|---|---|---|---|
| WT-3730 | 0.26 | 0.02 | 0% |
| GE-13112 (BASH-12) | 0.47 | 0.01 | 82% |
| GE-13109 (BASH-3) | 0.48 | 0.02 | 87% |
| GE-13108 (BASH-2) | 0.73 | 0.05 | 180% |
| RNAi-7 (precultured in NO3) | 0.64 | 0.02 | 147% |
| RNAi-7 (precultured in NO3 + NH4) | 0.66 | 0.04 | 153% |
| GE-8564 (ZnCys-KO) Cultured in Urea | 0.36 | 0.03 | 41% |
| GE-8564 (ZnCys-KO) Cultured in NO3 | 0.69 | 0.11 | 168% |

These genetically engineered knockdown cells were able to partition more of their carbon to lipid than wild type (FIG. 16D). The increased FAME/TOC ratios were particularly notable in the ZnCys RNAi attenuation strain GE13103, as it had only modest reductions in TOC (between about 15% and about 20%, Table 20) coupled with increased FAME with respect to wild type throughout the assay (greater than 100% increase, an approximately 120% increase, Table 19).

Graphs of volumetric FAME and TOC productivities of wild type, Cas9 Editor line GE-6791, and ZnCys-2845 knockdown lines GE-13112 (BASH-12A), GE-13109 (BASH-3A), and GE-13108 (BASH-2A) assayed in a separate semicontinuous assay using nitrate-only medium are provided in FIGS. 17A and 17B (data provided in Table 22 and Table 23), and the average areal (g/m²/day) TOC and FAME productivities of the wild type strain and Cas9 editor line (as controls) and the BASH-3, BASH-12, and RNAi mutants (all pre-cultured in nitrate-only medium) in this assay are summarized in the graph of FIG. 18, where it can be seen that the RNAi strain has the highest FAME productivity of the tested mutants.

TABLE 22

Average Daily FAME Productivity of Knockdown Strains in Semi-continuous Assay using Nitrate-only Medium

| STRAIN | AV DAILY FAME PRODUCTIVTY (sd) | % INCREASE FROM WT |
|---|---|---|
| WT | 2.42 (0.13) | 0 |

TABLE 22-continued

Average Daily FAME Productivity of Knockdown Strains in Semi-continuous Assay using Nitrate-only Medium

| STRAIN | AV DAILY FAME PRODUCTIVTY (sd) | % INCREASE FROM WT |
|---|---|---|
| ZnCys-BASH-12 | 4.19 (0.25) | 73.1 |
| ZnCys-BASH-3 | 4.48 (0.35) | 85.1 |
| ZnCys-RNAi-7 | 4.88 (0.44) | 101.7 |
| Ng-Cas9+ | 2.53 (0.10) | 4.5 |

TABLE 23

Average Daily FAME Productivity of Knockdown Strains in Semi-continuous Assay using Nitrate-only Medium

| STRAIN | AV DAILY TOC PRODUCTIVITY (sd) | % DECREASE FROM WT |
|---|---|---|
| WT | 9.96 (0.47) | 0 |
| ZnCys-BASH-12 | 9.48 (0.42) | 4.8 |
| ZnCys-BASH-3 | 9.04 (0.40) | 9.2 |
| ZnCys-RNAi-7 | 8.09 (0.58) | 18.8 |
| Ng-Cas9+ | 9.80 (0.45) | 1.6 |

The increases in FAME/TOC were significantly less at the outset of the culture period in the ZnCys RNAi attenuation cultures that had been pre-cultured in a medium containing a mixture of nitrate and ammonium than in the ZnCys RNAi attenuation cultures that had been pre-cultured in a medium containing only nitrate (FIG. 16D). Thus it appeared that strains pre-cultured in nitrate plus ammonium media included reduced nitrogen (ammonium) from the pre-culture that was introduced into the assay cultures, and this residual ammonium repressed lipid biosynthesis to some degree. This effect disappeared by the fifth day of the assay (see FIG. 16A, open circles (RNAi strain precultured with ammonium in the medium) versus solid circles (RNAi strain precultured with only nitrate in the medium)), by which time the rate of production of lipid by the ZnCys RNAi attenuation strain did not significantly differ between cultures that had been inoculated with a seed culture that included ammonium and nitrate and cultures that had been inoculated with a seed culture that included only nitrate as a nitrogen source. At this point presumably the cultures that had been pre-cultured in medium that included ammonium ran out of their reduced nitrogen source and induced lipid biosynthesis to approximately the same degree as the cultures that had not been pre-cultured in an ammonium-containing medium. This interpretation was supported by analysis of the nitrogen present in the cultures. For total nitrogen (TN) analysis of cell pellets, 10 ml culture samples were spun down, the media removed from the pellets, and each pellet was resuspended in 1 ml nanopure $H_2O$, which was then transferred to a 22 ml vial, to which 19 ml of nanopure $H_2O$ was added. Total nitrogen analysis was performed using a Shimadzu TOC-$V_{CSH}$/VN$_{M-1}$ analyzer. FIG. 19 shows that the amount of total nitrogen in the cell pellets was significantly higher in the GE-13103 cultures that had been inoculated with a pre-culture that included ammonium in the medium (open circles) than in the cultures that had been inoculated with a pre-culture that included only nitrate ($NO_3$) (e.g., closed circles). Thus it appeared that the ZnCys RNAi attenuation cells, while able to utilize nitrate for growth (as evidenced by continued TOC accumulation, e.g., FIG. 16C), still induced lipid biosynthesis as long as ammonium was present at low concentrations, for example, of less than about 2 mM or less than about 1.5 mM.

The relationship between the amount of ammonium present in the ZnCys-2845 RNAi strain GE-13103 cultures during semi-continuous assays was investigated in semi-continuous productivity assays performed as described above in which daily samples were analyzed for nitrogen content of the whole culture (culture medium plus cells) as well as FAME content as described in the examples above.

FIG. 20 shows the amount of FAME and nitrogen present in the culture on successive days of semi-continuous culture graphically. Whole culture total nitrogen (TN) was determined by removing a 2 ml sample of the culture to a 22 ml vial, to which 18 ml of nanopure $H_2O$ was added, and analyzing the sample using a Shimadzu TOC-$V_{CSH}$/VN$_{M-1}$ analyzer. The amount of nitrate that could be accounted for in the PM074 medium was subtracted from the total nitrogen of the sample to arrive at the amount of nitrogen present as ammonium indicated in FIG. 19. Because the ammonium present in the PM124 starter culture was progressively diluted out of the cultures that were inoculated with PM124 ($NH_4$+$NO_3$) starter cultures, it can be seen that for this sample, FAME production (open diamonds) rises as ammonium concentration (solid diamonds) falls. Ammonium levels in the culture below about 2.5 mM, and especially below about 2 mM, appeared to result in induction of FAME production in the attenuated RNAi strain (open diamonds).

Example 11

Relationship of Productivity of ZnCys-2845 Attenuation Mutants to Available $NH_4$ Concentration The relationship between nitrogen availability and FAME productivity in the ZnCys-2845 RNAi strain GE-13103 was further investigated in a semi-continuous productivity assay as described in Example 10 except that the semi-continuous assay was performed in three separate culture media in which the concentration of ammonium was held constant at three different levels. Wild type *Nannochloropsis gaditana* (WT-3730) was also included in the assay, where the wild type strain was cultured in the standard PM074 medium that included no ammonium (but included 8.8 mM nitrate as the sole source of nitrogen).

In this experiment, starter cultures that included culture medium containing either 0.5 mM, 1.0 mM, or 2.5 mM ammonium in addition to 8.8 mM nitrate were used to inoculate assay flasks that included culture media that included the corresponding amount of ammonium (in addition to 8.8 mM nitrate). After reaching steady state the cultures were diluted back daily with the ammonium-supplemented media, such that one set of triplicate cultures in which the assay medium included 0.5 mM ammonium was inoculated from a seed culture that included 0.5 mM ammonium and was diluted daily with a medium containing 0.5 mM ammonium throughout the assay, another set of triplicate cultures was inoculated from a seed culture that included 1.0 mM ammonium and included 1.0 mM throughout the assay, and a third set of triplicate cultures was inoculated from a seed culture that included 2.5 mM ammonium and included 2.5 mM ammonium throughout the assay. In each case, the medium was PM074 that includes 8.8 mM nitrate as the sole source of nitrogen that can be used by the microorganisms, supplemented with the appropriate amount of $NH_4Cl$ as well as with 5 mM Hepes, pH 7.5. The results can be seen in Tables 22-24. All samples were assayed in triplicate, and provided values are the average of the three cultures.

Figure 21A:
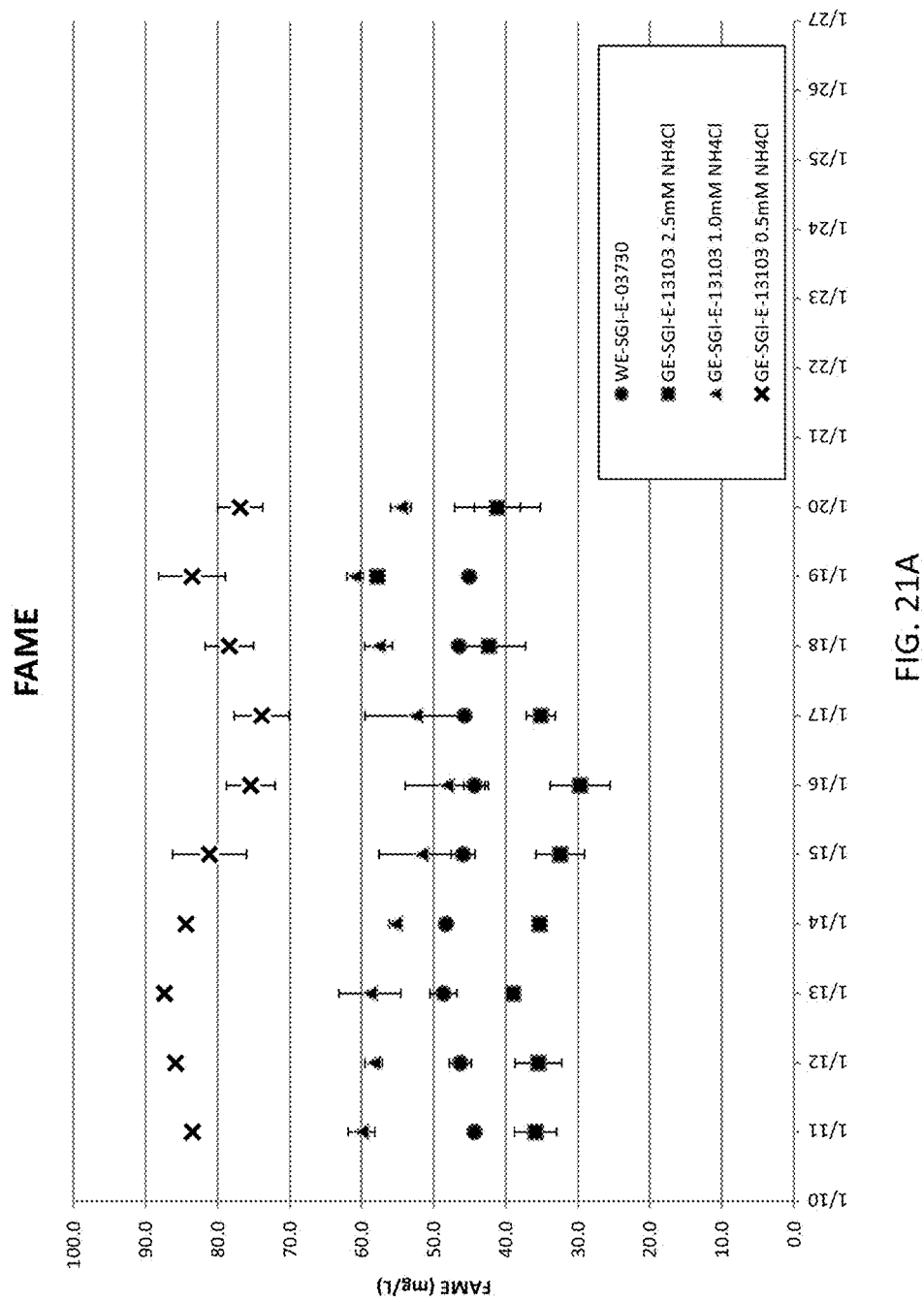

FIG. 21A shows the amount of FAME present in the culture on successive days of semicontinuous culture for cultures held at 0.5 mM, 1.0 mM, and 2.5 mM ammonium (solid diamond and triangles, representing RNAi symbols). It can be clearly seen that reducing the ammonium concentration of the culture from 2.5 mM (squares) to 1.0 mM (triangles) increases FAME productivity, which is increased even further when the ammonium concentration is maintained at 0.5 mM (Xs) (see also Table 24).

The FAME productivity is provided in the table of FIG. 21B. The FAME productivity of the GE13103 knockdown strain in 2.5 mM $NH_4$ medium is reduced by about 15% with respect to wild type FAME productivity in nitrate-only medium (which does not induce lipid production in the wild type strain). At lower ammonium concentrations however, the knockdown mutant shows greater FAME productivity over the course of the assay than does the wild type strain. For example, in culture medium in which the ammonium concentration is 1 mM, the knockdown mutant strain demonstrates an increased average daily FAME productivity of 22%, while at 0.5 mM ammonium, GE-13103 demonstrates an increased average daily FAME productivity of 77% with respect to the wild type strain, that is, the GE-13103 knockdown strain at very low ammonium concentration produces almost twice as much FAME lipids as wild type.

Figure 21C:
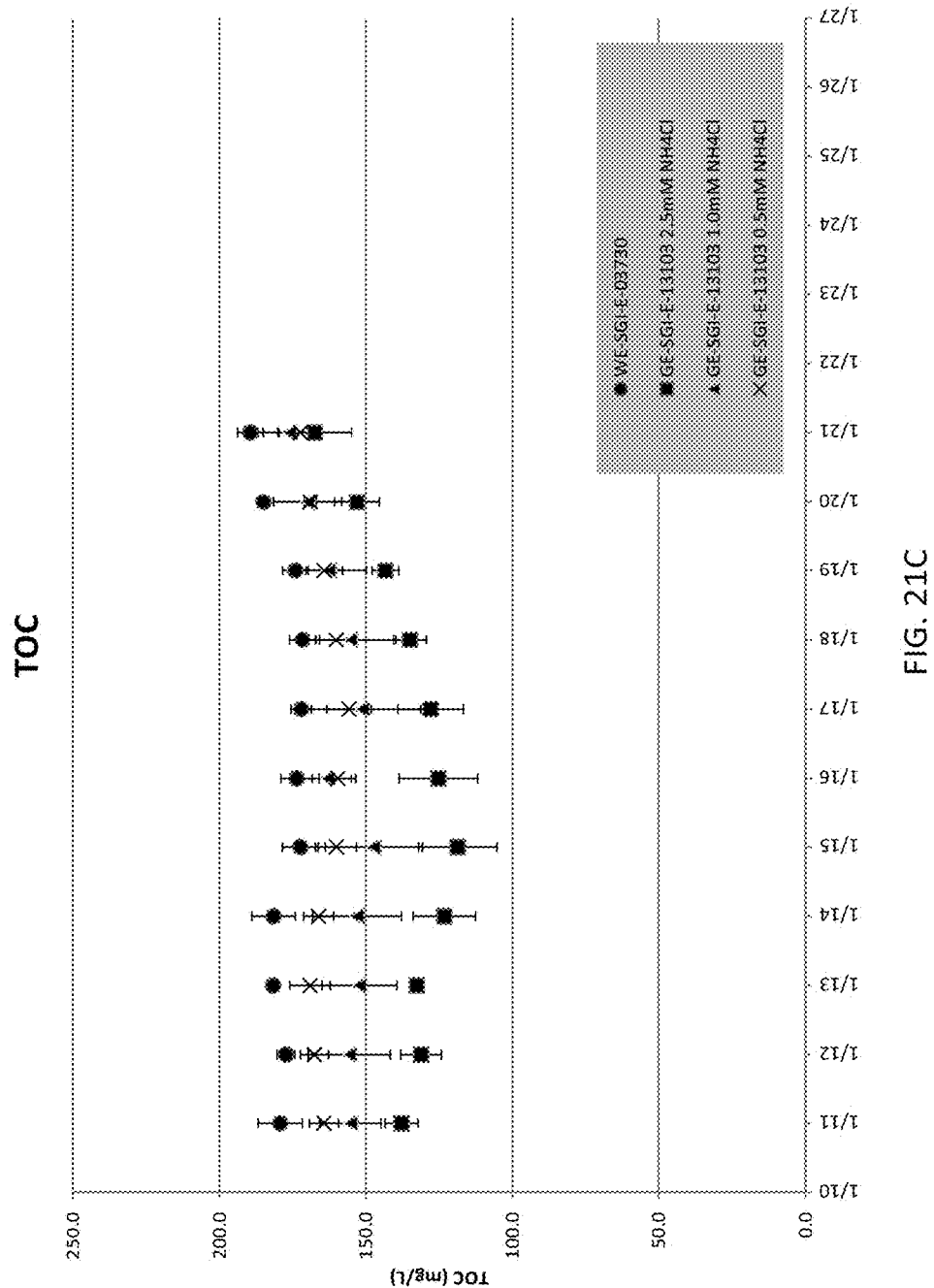

Nevertheless, FIG. 21C shows that reducing the ammonium concentration of the culture medium below 2.5 mM $NH_4$ does not have a major effect on TOC accumulation by the GE13103 knockdown mutant (Table 25).

For example, the average daily TOC productivity of the knockdown mutant strain cultured in 0.5 mM ammonium was essentially identical to that of wild type cultured under nitrogen replete (nitrate only) conditions (FIG. 21D). Thus, the GE-13103 knockdown mutant demonstrated at least 75% more lipid productivity while demonstrating no reduction in biomass productivity with respect to wild type cells in nitrogen replete conditions over a period of at least 10 days of culturing. As shown in FIG. 21F, cell counts, as determined by flow cytometry, remained reasonably consistent for a given ammonium concentration throughout the assay, indicating that the cells were actively dividing throughout the semi-continuous assay under all conditions, including conditions in which the low-ammonium cultures were induced for lipid biosynthesis, as indicated by the elevated FAME/TOC ratios of the 1 mM ammonium and 0.5 mM ammonium-containing cultures (as demonstrated in FIG. 21E).

Figure 21E:
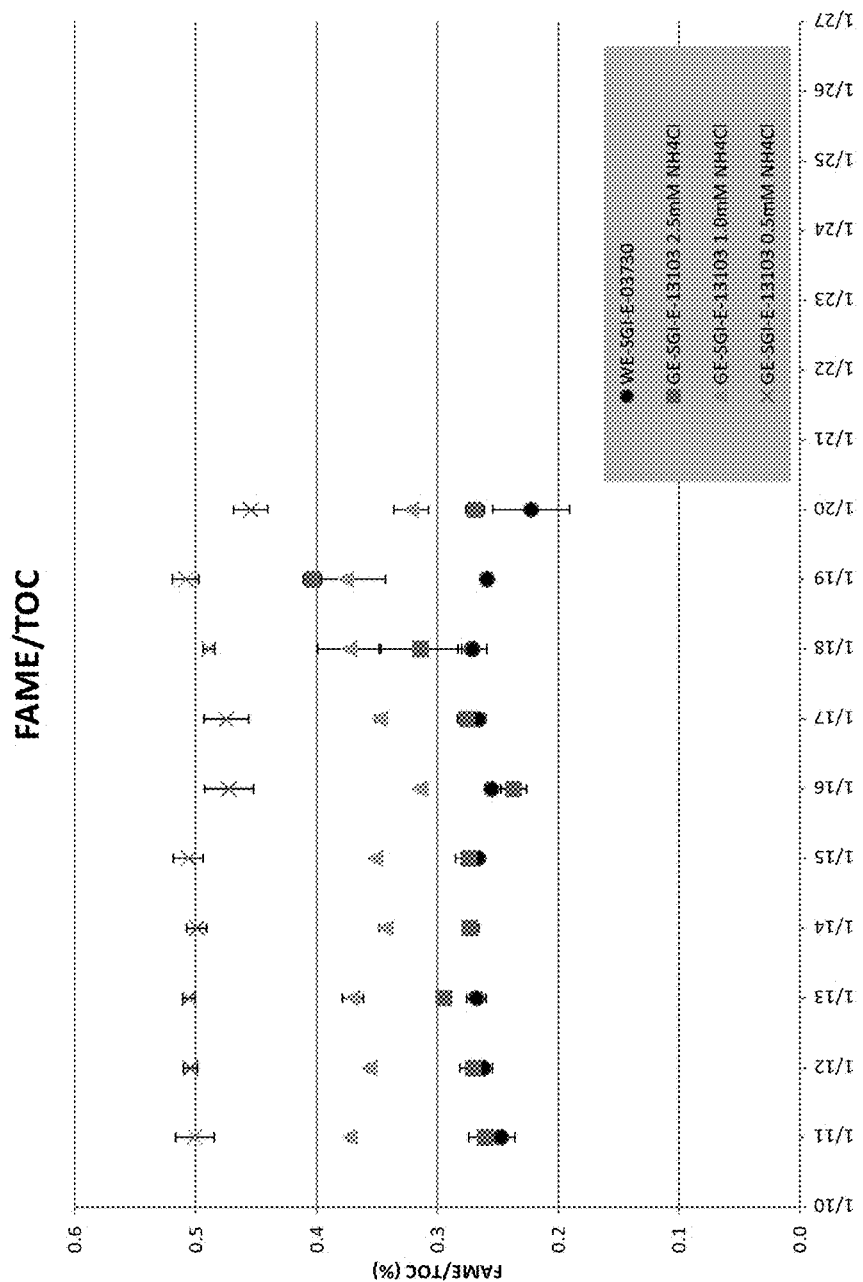
Figure 21F:
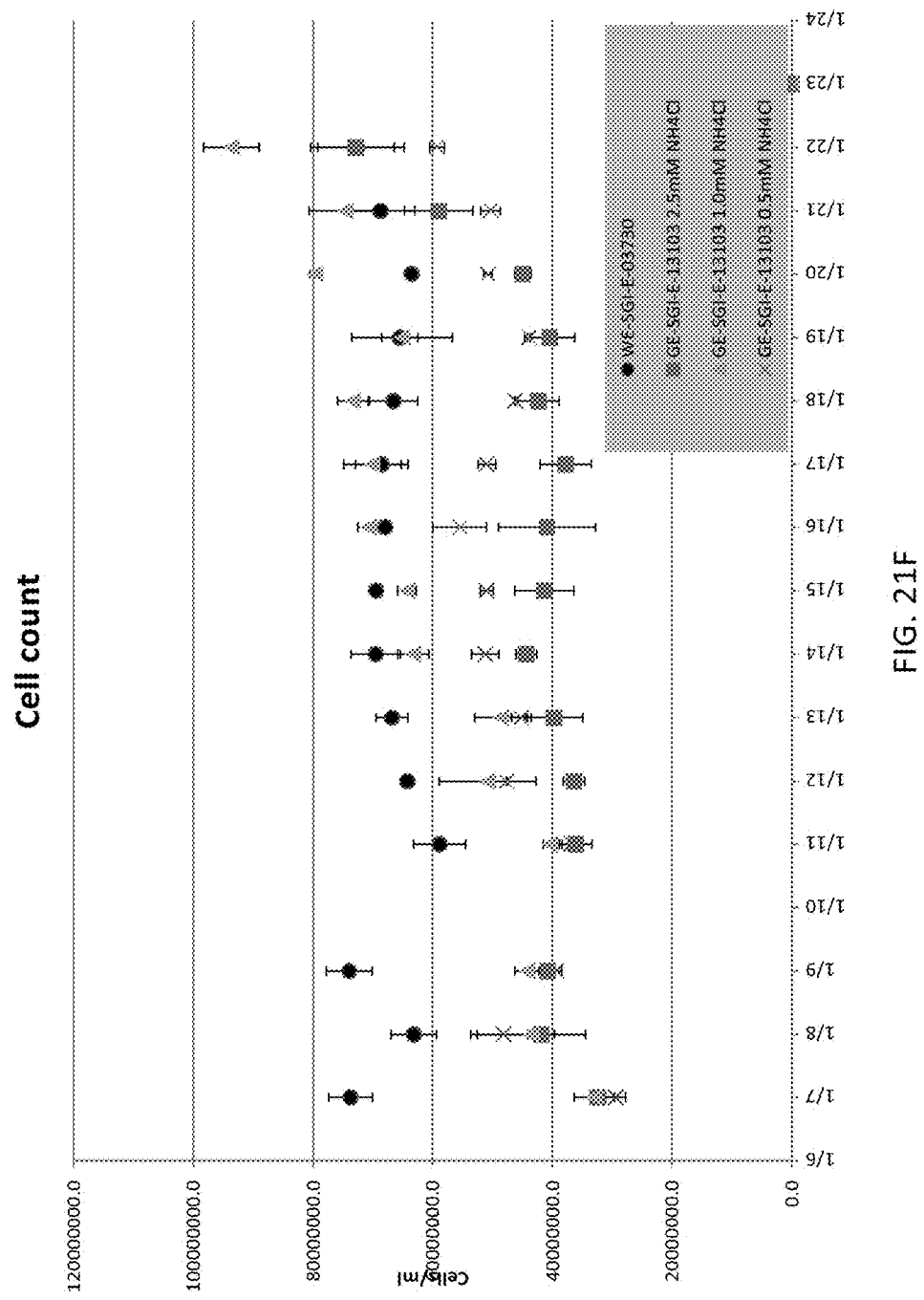

The FAME to TOC ratio of the GE-13103 knockdown mutant cultured in medium having varying ammonium concentrations is shown in FIG. 21E. The FAME to TOC ratio remains between about 0.3 and 0.4 when the ammonium concentration is between about 1 mM and about 2.5 mM, but increases further when the ammonium concentration drops from about 1.0 mM to about 0.5 mM, remaining close to 0.5 throughout the assay using 0.5 mM ammonium in the medium, for example well within the range of between about 4.0 and about 6.0, and within the region of between about 4.5 and about 5.5 (see Table 26).

TABLE 24

Daily FAME content (mg/L) of cultures: Average of Triplicate FAME Values (sd)

| Strain | Day 1 | Day 2 | Day 3 | Day 4 | Day 5 | Day 6 | Day 7 | Day 8 | Day 9 | Day 10 |
|---|---|---|---|---|---|---|---|---|---|---|
| WE-3730 | 44.3 | 46.31 | 48.63 | 48.27 | 45.91 | 44.35 | 45.73 | 46.48 | 45.07 | 41.15 |
|  | (0.32) | (1.53) | (1.87) | (0.76) | (1.66) | (1.47) | (0.16) | (0.81) | (0.91) | (5.94) |
| GE-13103 2.5 mM NH4Cl | 35.9 | 35.5 | 39.0 | 35.3 | 32.5 | 29.7 | 35.1 | 42.3 | 57.8 | 41.2 |
|  | (2.92) | 3.24 | 0.16 | 0.46 | 3.36 | 4.15 | 2.01 | 5.09 | 0.80 | 3.17 |
| GE-13103 1.0 mM NH4Cl | 60.0 | 58.3 | 58.8 | 55.3 | 51.7 | 48.2 | 52.5 | 57.6 | 60.9 | 54.5 |
|  | (1.85) | (1.20) | 94.290 | (0.79) | (5.83) | (5.75) | (6.97) | (1.92) | (1.11) | (1.41) |
| GE-13103 0.5 mM NH4Cl | 83.5 | 85.8 | 87.4 | 84.4 | 81.1 | 75.4 | 73.9 | 78.4 | 83.6 | 76.9 |
|  | (0.86) | (0.290 | (0.980 | (0.550 | (5.130 | (3.37) | (3.80) | (3.35) | (4.60) | (3.11) |

TABLE 25

Daily TOC content (g/m²/day): Average of triplicate Values (sd)

| Strain | Day 1 | Day 2 | Day 3 | Day 4 | Day 5 | Day 6 | Day 7 | Day 8 | Day 9 | Day 10 | Day 11 |
|---|---|---|---|---|---|---|---|---|---|---|---|
| WT-3730 | 179.3 | 177.35 | 181.7 | 181.57 | 172.43 | 173.7 | 172.13 | 171.67 | 174.1 | 185 | 189.47 |
|  | (7.56) | (3.04) | (1.56) | (7.38) | (6.09) | (5.36) | (3.50) | (4.44) | (4.36) | (2.19) | (4.35) |
| GE-13103 2.5 mM NH4 | 137.7 | 131.1 | 132.5 | 123.2 | 118.6 | 125.2 | 127.9 | 134.9 | 143.2 | 153.0 | 167.5 |
|  | (5.59) | (6.92) | (1.70) | (10.63) | (13.35) | (13.36) | (11.15) | (5.61) | (4.55) | (7.74) | (12.62) |
| GE-13103 1.0 mM NH4 | 155.2 | 155.7 | 152.2 | 153.0 | 147.3 | 163.2 | 151.2 | 155.3 | 162.8 | 170.0 | 176.1 |
|  | (10.53) | (14.08) | (12.84) | (15.22) | (16.67) | (8.20) | (19.97) | (15.51) | (13.06) | (11.60) | (10.77) |
| GE-13103 0.5 mM NH4 | 164.4 | 167.7 | 169.1 | 166.2 | 160.2 | 159.7 | 155.8 | 160.2 | 164.3 | 169.1 | 172.4 |
|  | (4.95) | (4.74) | (6.86) | (5.11) | 7.06) | (6.33) | (7.68) | (5.65) | (6.22) | (1.99) | (7.35) |

TABLE 26

| FAME/TOC Ratios: Average of Triplicate FAME/TOC Values (sd) | | | | | | | | | | |
|---|---|---|---|---|---|---|---|---|---|---|
| Strain | Day 1 | Day 2 | Day 3 | Day 4 | Day 5 | Day 6 | Day 7 | Day 8 | Day 9 | Day 10 |
| WT-3730 | 0.2 | 0.3 | 0.27 | 0.27 | 0.27 | 0.26 | 0.27 | 0.27 | 0.26 | 0.22 |
|  | (0.01) | (0.01) | (0.01) | (0.01) | (0.00) | (0.00) | (0.01) | (0.01) | (0.00) | (0.03) |
| GE-13103 2.5 mM NH4Cl | 0.3 | 0.3 | 0.3 | 0.3 | 0.3 | 0.2 | 0.3 | 0.3 | 0.4 | 0.3 |
|  | (0.01) | (0.01) | (0.00) | (0.00) | (0.01) | (0.01) | (0.01) | (0.03) | (0.01) | (0.01) |
| GE-13103 1.0 mM NH4Cl | 0.4 | 0.4 | 0.4 | 0.3 | 0.4 | 0.3 | 0.3 | 0.4 | 0.4 | 0.3 |
|  | (0.00) | (0.00) | (0.01) | (0.01) | (0.00) | (0.00) | (0.00) | (0.03) | (0.03) | (0.01) |
| GE-13103 0.5 mM NH4Cl | 0.5 | 0.5 | 0.5 | 0.5 | 0.5 | 0.5 | 0.5 | 0.5 | 0.5 | 0.5 |
|  | (0.02) | (0.01) | (0.01) | (0.01) | (0.01) | (0.02) | (0.02) | (0.00) | (0.01) | (0.01) |

Thus, the strains obtained by attenuating expression of a gene as provided here that regulates lipid biosynthesis are able to actively divide while producing considerably more lipid than wild type. The ability to sustain elevated levels of lipid production without a decline in TOC accumulation throughout the assay (FIG. 22), indicates the mutants provided herein can provide sustained high level lipid production such as in continuous and semi-continuous cultures.

Example 12

Analysis of Protein, Carbohydrate, and Lipid Content of ZnCys Mutants

In the above experiments (e.g., Example 4), FAME and TOC productivities of knockout mutant strain GE-8564 were found to be essentially equal to those of the wild type strain when both were cultured in the presence of ammonium (FIGS. 8A-C), suggesting that a bottleneck in nitrate assimilation led to the marked phenotypes of increased lipid production that were observed only when nitrate was used as the sole nitrogen source. Knockdown mutants of ZnCys-2845 were observed to exhibit substantial increases in FAME productivity (Table 16 and FIG. 13A as well as FIGS. 16A and 16B) with minimal TOC decreases of from about 1% to about 33% (Table 17 and FIG. 13B; FIG. 16C). FAME and TOC productivities for a semi-continuous assay that included wild-type, ZnCys-2845 BASH-3, ZnCys-2845 BASH-12, and ZnCys-2845 RNAi strain GE-13103 are shown in the graphs of FIGS. 17A and 17B, respectively. ZnCys BASH-3, ZnCys BASH-12, and ZnCys RNAi all exhibited substantial increases in aerial FAME productivity (up to 103% for ZnCys RNAi-7) with only minimal TOC decreases of approximately 5-15% compared to the wild type strain and the Cas9 progenitor line (FIG. 18). To determine how carbon was allocated to major categories of biomolecules, the strains were grown in the semi-continuous assay system as described in Example 10, where the PM074 dilution medium included nitrate as the sole nitrogen source. In this assay the RNAi line demonstrates increased FAME productivity and the knockout line is unable to maintain growth (FIGS. 22A-D). The strains from these cultures were assessed for carbohydrate, lipid, and protein, which together accounted for about 75% of TOC.

For HPLC analysis of lipids, 2 ml samples of each culture were spun down at maximum speed for 5 minutes, the supernatants were removed, and pellets were re-suspended in 400 µL of $H_2O$. The cell suspensions (approximately 500 µL) were transferred to 4 ml glass vials with Teflon lined caps. 500 µL of glass beads (212-300 µm diameter) were added to each of the cell suspensions, after which 50 µL of 50% $H_2SO_4$ and 100 µL of 5M NaCl were added. Bead beating was performed for 5 minutes at 1 krpm, then 2 ml of hexane was added to each sample, and bead beating was repeated for 5 minutes at 1 krpm. The samples were loaded onto a multi-tube vortexer and shaken for 30 minutes at 1 krpm, and then vortexed for 30 seconds at 2.5 krpm. 500 µL of the organic layer was transferred to an HPLC vial, and 50 µL of internal standard solution (1 mg/ml 6-ketocholestanol in toluene) was added to each vial. Standards were from NuCheck, Sigma-Aldrich, or Supelco. The vials were capped and vortexed briefly (5 seconds at 2.5 krpm) prior to HPLC analysis. The HPLC was run at a flow rate of 2 ml/minute on a Chromegasphere SI-60 150 mm×4.6 mm×10 µm column (ES Industries), with a column compartment set at 40° C. The injection volume was 25 µL with a draw and eject speed of 200 µL/minute. Eluent A was hexane and Eluent B was an 80:10:10:1 mixture of hexane, isopropanol, ethyl acetate, and 10% formic acid in isopropanol, run as a gradient program as follows: 2% B at 0.0 min; 2% B at 1.0 min; 35% B at 8.0 min; 98% B at 8.5 min; 98% B at 11.5 min; 2% B at 11.6 min; stop time: 11.6 minutes; 5 minutes post time. The detector was ELSD at 30° C. and 3.5 bar N2, with a gain of 5.

Total carbohydrate analysis was conducted on ~0.7 mg TOC equivalent of cell culture concentrated to 0.5 ml in phosphate buffered saline (PBS) after three centrifugations followed by washing with PBS. Acid hydrolysis was used to convert carbohydrates to their constituent monomers by the addition of 0.5 ml deionized $H_2O$ and 1 ml 6 N HCl and U-$^{13}$C-glucose and -galactose as internal standards at a final concentration of 50 µg/ml each. Samples were heated at 105° C. for one hour in glass vials with PTFE-lined capped. One hundred µl aliquots of the room temperature cooled, 3,000 g centrifuged (1 min) samples were dried in an EZ-2 Genevac (Stoneridge, N.Y.) and derivatized with MSTFA/TMCS and analyzed by GC-MS according to Ruiz-Matute et al. (2011) *J. Chromatogr B Analyt Technol Biomed Life Sci* 879: 1226-1240. Internal $^{13}$C labeled standards were used to quantify the concentration of the major carbohydrate monomers, glucose and galactose, and estimate the concentration of less abundant sugars (arabinose, rhamnose, xylose, and mannose). These were summed to yield a total saccharide concentration in ug/ml which was converted to the carbon content of total carbohydrates by a multiplication factor of 0.45 (i.e. ~45% of carbohydrate mass is represented by carbon. This value was divided by the amount of TOC detected in an identical aliquot of concentrated cell culture to estimate the percent of carbon allocated to carbohydrate.

Total amino acid analysis was conducted by derivatization of whole amino acid hydrolysate to propoxycarbonyl propyl esters using a modified method according to the EZ:faast kit from Phenomenex (Torrance, Calif.). Briefly, to 0.5 ml concentrated cells (as described for carbohydrate analysis above) 800 ul of 6 N HCl containing 200 µl/ml thioglycolic acid, 10 ul of β-mercaptoethanol, and 200 ul of 2 mM norvaline (internal standard) were added and the vortexed sample was incubated at 110° C. for 24 h. Samples cooled to room temperature were centrifuged at 1,500 g for 1 minute and a 50 µl aliquot was transferred to a fresh 2 ml GC vial. Aliquots were derivatized and analyzed by GC-MS according to the EZ-faast manual and (8). This method allowed for the quantification of Ala, Gly, Val, Leu, Ile, Pro, Asp+Asn, Met, Glu+Gln, Phe, Lys, Tyr, and Cys; Trp, Thr, Ser, Arg, and His were excluded. Volumetric concentrations of each detected hydrolyzed amino acid was converted to the carbon content present in that amount. These values were summed to and normalized to TOC as described for total carbohydrates above to give an estimate of carbon allocated to protein.

The results are seen in FIG. 23, where it can be seen that both attenuated ZnCys mutants ZnCys-BASH-12 and ZnCys RNAi had decreases of approximately 45-50% in protein compared to the wild type strain, accompanying an approximately 90-125% increase in lipids in the strains. Consistently, the ZnCys knockout strain were observed to have the highest C:N ratios while ZnCys RNAi displayed more intermediate levels (FIG. 22C), suggesting there may be a threshold C:N value that maximizes lipid productivity. The ZnCys knockout strain appears to be beyond that threshold, partitioning so much carbon into lipid that overall biomass and lipid productivity are negatively affected. In contrast, in this set of gene attenuation mutants, the ZnCys RNAi appears to have the optimal C:N value for lipid productivity in the range of about 10-15.

TABLE 27

Protein, Carbohydrate, and Lipid (FAME) % Composition of Wild type and ZnCys Knockdown Strains

| STRAIN | Protein | Change from wt | Carb | Change from wt | FAME | Change from wt | Other | Change from wt |
|---|---|---|---|---|---|---|---|---|
| WT | 40.2 (0.55) | 0 | 11.2 (0.50) | 0 | 19.6 (0.32) | 0 | 29.1 (0.27) | 0 |
| ZnCys-BASH-12 | 22.5 (0.70) | −44% | 12.7 (0.12) | +13% | 37.6 (2.19) | +92% | 27.2 (2.94) | −6.5% |
| ZnCys-RNAi-7 | 20.1 (2.43) | −50% | 12.7 (0.70) | +13% | 42.7 (4.73) | +118% | 24.9 (1.59) | −14% |

BASH-12 strain GE-1112 allocated approximately 38% of its carbon to FAME lipids, and approximately 22% of its carbon to protein, while RNAi strain GE-13103 allocated approximately 43% of its carbon to lipid, and approximately 20% of its carbon to protein. This is distinguished from wild type cells in nitrate-only medium that allocate approximately 20% of carbon to lipid, and approximately 40% of carbon to protein. (In both mutants and wild type cells, approximately 10-15% of carbon is allocated to carbohydrates.) Thus both ZnCys gene attenuation ("knockdown") mutants increased carbon allocation to lipid by 90-120% (doubling lipid productivity with respect to wild type) largely at the expense of allocation of carbon to protein, which dropped by about 40-50% with respect to the carbon allocation to protein in wild type cells cultured under the same conditions.

Example 13

Transcriptomic Analysis of the ZnCys-2845 Knockout and Knockdown Mutants

The ability of ZnCys-2845 knockout strain GE-8564 to accumulate FAME and TOC at levels essentially identical to wild type cells when the culture medium was supplemented with ammonium (Tables 7-9, FIG. 8), indicated the mutant was impaired in nitrate assimilation. To further investigate nitrogen assimilation in these mutants, steady-state mRNA levels of key N-assimilation genes by qRT-PCR were determined to gain a better understanding of N-deficiency in the mutants under induced (nitrate-only medium) and non-induced (ammonium supplementation) conditions.

A nitrate reductase mutant was engineered using the same Cas9 Editor line described in Example 2. Briefly, a guide RNA was designed having the target sequence of a portion of the coding region of the *N. gaditana* nitrate reductase gene Naga_100699g1. The guide RNA (having target sequence SEQ ID NO:193) was synthesized as disclosed in Example 3, and transformed into the Cas9 editor line along with the donor fragment (SEQ ID NO:44) as described in Example 2. The resulting nitrate reductase knockout strain (NR-KO) served as a control for the inability to assimilate nitrate, as a functional nitrate reductase enzyme is necessary to assimilate nitrogen when nitrate is the sole nitrogen source. Effectively, the NR-KO strain is under nitrogen starvation when cultured in nitrate-only medium.

Steady-state mRNA levels of key N-assimilation genes were assessed by qRT-PCR to gain a better understanding of N-deficiency in the mutants under induced ($NO_3^-$) and non-induced ($NH_4^+$) conditions, where the nitrate reductase mutant (NR-KO) created by Cas9-mediated mutagenesis was used as an N-starvation control under growth on $NO_3^-$. When grown on medium that included ammonium all strains shared similar gene expression profiles for the N-assimilation gene set, consistent with their wild type phenotype with regard to biomass and FAME accumulation when cultured with ammonium-containing medium (FIG. 24, ammonium transcriptional profiles of the ZnCys knockout, the ZnCys RNAi knockdown, wild type, and the NR knockout shown in columns 2-5).

TABLE 28

Primer sequences for transcripts measured by quantitative real-time PCR

| Gene | Description | *N. gaditana* genome ID | qRT-PCR sense primer/ qRT-PCR antisense primer |
|---|---|---|---|
| NAR1 | Formate Nitrite Transporter | Naga_100100g7 | GCCAACCTGCCAGTAAAATTC (SEQ ID NO: 153) AGAGCGGGATTCTGTTCTTG (SEQ ID NO: 154) |
| Amt2 | Ammonium Transporter | Naga_100099g15 | AGAACGTGGGTAAGATGCAAC (SEQ ID NO: 155) ACCAGCCAAACCAGAGAAG (SEQ ID NO: 156) |
| GS2 | Glutamine Synthase | Naga_100003g119 | GGCATACCTATTCATCCGCTAG (SEQ ID NO: 157) CAAATGACCAAGCACCAACTC (SEQ ID NO: 158) |
| NAR2 | Nitrite Transporter (NAR1) | Naga_100046g36 | GCGAGGCATCTTGTGAATTG (SEQ ID NO: 159) ACGGAGTGTTCAAATCCCAG (SEQ ID NO: 160) |
| GS1 | Glutamine Synthase | Naga_100056g25 | CATGGACTCATTCTCCTACGG (SEQ ID NO: 161) ATCCTCGAAATATCCGCACC (SEQ ID NO: 162) |
| GOGAT1 | Glutamate Synthase | Naga_101084g2 | TGGATGCAAACGAGATGCTAG (SEQ ID NO: 163) AGGAAAGCGGGAATAGTGTG (SEQ ID NO: 164) |
| GDH | Glutamate Dehydrogenase | Naga_100063g22 | GGGACTCGTTGGAAGGTAAG (SEQ ID NO: 165) CATTTCCACAAGTTTCTCCGC (SEQ ID NO: 166) |
| GOGAT2 | Glutamate Synthase (plastid) | Naga_100005g23 | AAGGGAATGTCTTGGAACCG (SEQ ID NO: 167) AGTGGGTAGACAGTGGAGAG (SEQ ID NO: 168) |
| NRT2 | Nitrate high affinity Transporter | Naga_100699g1 | AGTGCTATGGAGTTTTGCGG (SEQ ID NO: 169) TTGGGATTTGGTCAAGGAGAG (SEQ ID NO: 170) |
| NiR | Nitrite Reductase | Naga_100852g1 | GCCGATCCTTTCTTGCAAAC (SEQ ID NO: 171) AGCGTTCAATCAGGTCCAAG (SEQ ID NO: 172) |
| NR | Nitrate Reductase | Naga_100699g1 | GCTATATTGGAGAATCCGGCG (SEQ ID NO: 173) GGGAACGTCAACAGTGATAGTG (SEQ ID NO: 174) |
| Amt1 | Ammonium Transporter AmtB-like protein | Naga_100551g3g1 | CCTTCGGTGCCTATTTCGG (SEQ ID NO: 175) CATGTCGCTGGTATAGGATGC (SEQ ID NO: 176) |
| UreT | Urea active transporter-like protein | Naga_100311g2 | ATGGCAGTAGAAATGGACCC (SEQ ID NO: 177) AGTAAGAGAACGAAAAGGGCG (SEQ ID NO: 178) |
| qRT-PCR control | Protein of Unknown Function | Naga_100004g25 | CTCTCCTATTGCTTTCCCTCG (SEQ ID NO: 179) CTACCAACACCTCTACACTTCC (SEQ ID NO: 180) |

However, when grown on nitrate as the sole nitrogen source, NR-KO showed a radically different expression profile from the ZnCys mutant lines (FIG. 24, column 1 compared with columns 6 & 7 showing transcriptional profiles of the ZnCys-2845 knockout and RNAi knockdown mutants). Consistent with previous reports on N-deprived *N. gaditana* (Radakovitz et al. 2012), a large number of genes involved in N-assimilation were severely upregulated in the NR-KO (shown in red color), including two ammonium transporters (AMT1 and AMT2), a glutamate synthase (GOGAT1), a $NO_3^-$ transporter (NRT2) and nitrite reductase (NiR). Interestingly, this response was not observed for ZnCys mutants. In fact, gene expression profiles for the ZnCys-2845 knockout and the ZnCys-2845 RNAi knockdown engineered mutants more closely resembled wild type under these conditions, though NiR and NRT2 were significantly down regulated in the ZnCys-2845 knockout with respect to wild type, thus offering a possible explanation to the N-deficiency of the cells (FIG. 22C). Analysis of protein levels by Western blotting showed that nitrate reductase could not be detected in extracts of ZnCys-2845 knockout strain GE-8564, while a signal was detected in ZnCys-2845 RNAi knockdown strain GE-13103 extracts as well as wild-type extracts (FIG. 25). Likewise, a very weak signal was observed for the nitrogen assimilation enzyme glutamine oxoglutarate aminotransferase (GOGAT1) in GE-8564, while it was more apparent for GE-13103.

Protein level changes in the plastid lipid biosynthetic machinery were also assessed using specific peptide antibodies against ACCase and fatty acid synthesis (FAS) pathway components (FIG. 25). For antibody production, two peptides (#1 and #2 in Table 29) were synthesized and injected into rabbits. Terminal cysteines are shown for reference.

Compared to wild type, levels of these enzymes were not noticeably higher in ZnCys mutants, and in the case in NR-KO, ACCase and KAR1 were reduced. These data suggest that under N-replete conditions the plastid lipid biosynthetic machinery is already present at a capacity that is capable of at least double the flux to fatty acid given the ~100% increase in FAME productivity observed in ZnCys-2845 RNAi knockdown strain GE-13103. This conclusion is consistent with transcriptional changes observed for N-deprived *Nannochloropsis*, where pathways involved in providing carbon precursors to lipid biosynthesis appear to be more differentially expressed than "core" lipid biosynthetic pathways (Radakovitz et al 2012, Carpinelli et al 2014, Li et al 2014).

In order to gain further insight into the mechanisms that allow for ZnCys-2845 attenuated lines to constitutively produce lipid and sustain growth, we analyzed the global transcriptional profiles of ZnCys-2845 RNAi strain GE-13103 during steady-state growth conditions (e.g., FIG. 17). Using a 2-fold cut-off and FDR<0.05, 1118 genes were found to be differentially expressed between ZnCys-RNAi-7 and wild type in nitrate-only culture medium. Of these, 790 were up-regulated and 328 down-regulated in the mutant. Analysis of the down-regulated gene set for enriched gene ontology (GO) categories by "molecular function", "biological process" or "cellular component" revealed that genes involved in photosynthesis and light harvesting were overrepresented in the mutant with respect to the wild type (Table 30).

TABLE 29

Peptide sequences used to generate antibodies detecting fatty acid biosynthesis enzymes in *N. gaditana*.

| Gene | Description | *N. gaditana* genome ID | Peptide #1 | Peptide #2 |
|---|---|---|---|---|
| ACCase | Acetyl-CoA Carboxylase | Naga_100605g1 | C-FKFADTPDEESPLR (SEQ ID NO: 181) | C-AENFKEDPLRRDMR (SEQ ID NO: 182) |
| HAD | 3-Hydroxyacyl ACP Dehyrase | Naga_100113g7 | C-TANEPQFTGHFPER (SEQ ID NO: 183) | C-IDGVFRKPVVPGD (SEQ ID NO: 184) |
| ENR | Enoyl-ACP Reductase | Naga_101053g1 | C-PEDVPEAVKTNKRY (SEQ ID NO: 185) | C-AIGGGEKGKKTFIE (SEQ ID NO: 186) |
| KAR | β-Ketoacyl- ACP Reductase | Naga_100037g12 | C-VAIKADMSKPEEVE (SEQ ID NO: 187) | C-SDMTEKLDLDGIKK (SEQ ID NO: 188) |
| KAS1 | β-Ketoacyl- ACP Synthase 1 | Naga_100002g173 | C-YMRGSKGQIYMKEK (SEQ ID NO: 189) | C-DAKPYFKDRKSAVR (SEQ ID NO: 190) |
| KAS3 | β-Ketoacyl- ACP Synthase 3 | NG_scf10:19284..18979 | MGKRSTASSTGLAY-C (SEQ ID NO: 191) | C-PPSIREVTPYKGKY (SEQ ID NO: 192) |

TABLE 30

Overrepresented Gene Ontology categories corresponding to genes that are down-regulated in ZnCys_RNAi-7

| Category | Ontology[†] | GO Term | # genes DE[††] | # genes in category | Over-represented pvalue | FDR adjusted pvalue[†††] |
|---|---|---|---|---|---|---|
| GO:0009765 | BP | photosynthesis, light harvesting | 15 | 17 | 4.3E−11 | 7.4E−08 |
| GO:0016168 | MF | chlorophyll binding | 15 | 22 | 4.3E−08 | 2.4E−05 |
| GO:0018298 | BP | protein-chromophore linkage | 15 | 22 | 4.3E−08 | 2.4E−05 |
| GO:0009523 | CC | photosystem II | 18 | 39 | 1.3E−06 | 5.7E−04 |
| GO:0003824 | MF | catalytic activity | 98 | 399 | 2.6E−05 | 8.9E−03 |

[†]BP, Biological process; CC, cellular component; MF, molecular function
[††]DE, Differentially expressed genes
[†††]FDR, False Discovery Rate The same analysis conducted on the up-regulated gene set revealed that components of protein synthesis were significantly enriched for in the attenuated ZnCys-2845 RNAi strain GE-13103 (Table 31). Considering that our analysis of biomass composition indicated an approximately 45% decrease in total protein content in GE-13103 (FIG. 23), the up-regulation of translation machinery and down-regulation of photosynthetic apparatus is likely a response to that deficit.

TABLE 31

Overrepresented Gene Ontology (GO) categories corresponding to genes that are up-regulated in ZnCys-2845 RNAi strain GE-13103

| Category | Ontology[†] | GO Term | #genes DE[††] | # genes in category | Over-represented pvalue | FDR adjusted pvalue[†††] |
|---|---|---|---|---|---|---|
| GO:0006412 | BP | translation | 88 | 175 | 1.9E−26 | 3.1E−23 |
| GO:0005840 | CC | ribosome | 77 | 160 | 5.1E−24 | 4.4E−21 |
| GO:0003735 | MF | structural constituent of ribosome | 68 | 138 | 1.2E−22 | 6.5E−20 |
| GO:0005622 | CC | intracellular | 85 | 226 | 1.1E−11 | 4.6E−09 |
| GO:0005737 | CC | cytoplasm | 70 | 183 | 3.4E−07 | 1.2E−04 |
| GO:0000166 | MF | nucleotide binding | 175 | 525 | 5.5E−07 | 1.4E−04 |
| GO:0005524 | MF | ATP binding | 206 | 636 | 5.6E−07 | 1.4E−04 |
| GO:0005852 | CC | eukaryotic translation initiation factor 3 complex | 10 | 11 | 2.2E−06 | 4.6E−04 |
| GO:0003743 | MF | translation initiation factor activity | 26 | 55 | 1.5E−05 | 2.8E−03 |
| GO:0005694 | CC | chromosome | 12 | 18 | 2.3E−05 | 3.5E−03 |
| GO:0006413 | BP | translational initiation | 26 | 56 | 2.3E−05 | 3.5E−03 |
| GO:0030529 | CC | Ribonucleo-protein complex | 34 | 109 | 2.9E−05 | 4.1E−03 |
| GO:0006260 | BP | DNA replication | 20 | 37 | 1.1E−04 | 1.4E−02 |
| GO:0015935 | CC | small ribosomal subunit | 8 | 13 | 2.0E−04 | 2.4E−02 |
| GO:0005874 | CC | microtubule | 17 | 30 | 4.3E−04 | 4.3E−02 |
| GO:0001731 | BP | formation of translation preinitiation complex | 5 | 5 | 4.9E−04 | 4.3E−02 |
| GO:0006446 | BP | regulation of translational initiation | 5 | 5 | 4.9E−04 | 4.3E−02 |
| GO:0016282 | CC | eukaryotic 43S preinitiation complex | 5 | 5 | 4.9E−04 | 4.3E−02 |

TABLE 31-continued

Overrepresented Gene Ontology (GO) categories corresponding to
genes that are up-regulated in ZnCys-2845 RNAi strain GE-13103

| Category | Ontology[†] | GO Term | #genes DE[††] | # genes in category | Over-represented pvalue | FDR adjusted pvalue[†††] |
|---|---|---|---|---|---|---|
| GO:0033290 | CC | eukaryotic 48S preinitiation complex | 5 | 5 | 4.9E−04 | 4.3E−02 |
| GO:0051082 | MF | unfolded protein binding | 14 | 28 | 5.4E−04 | 4.4E−02 |
| GO:0007155 | BP | cell adhesion | 8 | 10 | 5.5E−04 | 4.4E−02 |

[†]BP, Biological process; CC, cellular component; MF, molecular function
[††]DE, Differentially expressed genes
[†††]FDR, False Discovery Rate Consistent with our qRT-PCR findings (FIG. 24), analysis of N-assimilation genes revealed a few key down-regulated genes that could account for the low N-levels in the mutant, including nitrite reductase, two glutamine synthetases (GS1 and GS2), an ammonium transporter (AMT1) and a key enzyme involved in molybdenum cofactor biosynthesis (MoeA/CNX1), a cofactor that is essential for nitrate reductase activity (Table 29).

TABLE 32

Average transcript levels and fold changes of differentially expressed genes involved in N-assimilation

| Gene Alias | N. gaditana id | Description | WT (FPKM)[†] | ZnCys RNAi-7 (FPKM)[†] | FC[††] (log$_2$) | FDR[††] |
|---|---|---|---|---|---|---|
| Amt3 | Naga_102173g1 | Ammonium transporter AmtB-like protein | 2.3 | 14.7 | 2.5 | 3.8E−06 |
| Amt2 | Naga_100099g15 | Ammonium transporter | 635.9 | 841.4 | 0.4 | 5.5E−02 |
| NAR2 | Naga_100100g7 | Formate nitrite transporter | 40.3 | 42.7 | 0.1 | 8.3E−01 |
| UreT | Naga_100311g2 | Urea active transporter-like protein | 6.4 | 6.5 | −0.1 | 7.9E−01 |
| NAR1 | Naga_100046g36 | Nitrite transporter | 137.1 | 128.2 | −0.1 | 5.2E−01 |
| GOGAT2 | Naga_100005g23 | Glutamate synthase (plastid) | 54.1 | 48.9 | −0.2 | 5.0E−01 |
| GOGAT1 | Naga_101084g2 | Glutamate synthase | 8.7 | 7.2 | −0.3 | 7.3E−01 |
| NR | Naga_100699g1 | Nitrate reductase | 336.1 | 283.2 | −0.3 | 2.4E−01 |
| NRT2 | NG_SCF17:5277-7851 | Nitrate high affinity transporter | 1650.0 | 1368.4 | −0.3 | 1.0E−02 |
| GS1 | Naga_100056g25 | Glutamine synthetase | 2084.4 | 1529.3 | −0.5 | 3.4E−03 |
| GDH1 | Naga_100063g22 | Glutamate dehydrogenase | 317.5 | 205.4 | −0.7 | 9.7E−06 |
| GS2 | Naga_100003g119 | Glutamine synthetase | 6.5 | 3.9 | −0.7 | 4.3E−02 |
| NiR | Naga_100852g1 | Nitrite reductase | 783.2 | 499.2 | −0.7 | 2.3E−04 |
| MoeA/CNX1 | Naga_101167g3 | Molybdenum cofactor biosynthesis protein | 207.0 | 83.0 | −1.4 | 6.2E−14 |
| Amt1 | Naga_100551g3 | Ammonium transporter AmtB-like protein | 126.9 | 16.7 | −2.9 | 7.9E−36 |

[†]FPKM, Fragments per kilobase of transcript per million mapped reads
[††]FC, Fold change of genes in ZnCys-RNAi-7 relative to WT
[†††] FDR, False Discovery Rate The GO category analysis did not find a statistical enrichment for genes involved in lipid biosynthesis. However, when the list was manually curated, 26 genes related to glycerolipid biosynthesis were identified as upregulated using the same filtering criterium as above (Table 30). These genes included six fatty acid desaturases, elongases, lipases and acyltransferases of unknown substrate specificity, and the lipid droplet surface protein (LDSP) which is believed to be the main structural component of the lipid droplet (Vieler et al. (2012) *Plant Physiol.* 158:1562-1569).

TABLE 33

Average transcript levels and fold changes of differentially expressed genes involved in glycerolipid biosynthesis

| N. gaditana id | Description | WT (FPKM)[†] | ZnCys-RNAi-7 (FPKM)[†] | FC[††]($\log_2$) | FDR[†††] |
|---|---|---|---|---|---|
| Naga_100092g4 | Omega-6 fatty acid desaturase delta-12 | 1.0 | 13.8 | 4.0 | 1.0E−11 |
| Naga_100004g102 | Elongation of fatty acids protein (EC 2.3.1.199) | 19.6 | 120.0 | 2.6 | 2.9E−14 |
| Naga_100086g4 | Lipid droplet surface protein | 280.3 | 1608.6 | 2.5 | 7.4E−34 |
| Naga_100040g9 | Acyl transferase/acyl hydrolase/lysophospholipase | 0.7 | 2.0 | 2.2 | 7.9E−04 |
| Naga_100042g43 | Nadp-dependent glyceraldehyde-3-phosphate dehydrogenase | 14.2 | 63.0 | 2.1 | 5.2E−08 |
| Naga_100042g12 | Delta 5 fatty acid desaturase | 11.3 | 46.8 | 2.0 | 5.0E−11 |
| Naga_100035g27 | CDP-diacylglycerol pyrophosphatase | 1.0 | 4.3 | 2.0 | 3.2E−06 |
| Naga_100162g4 | Elongation of fatty acids protein (EC 2.3.1.199) | 7.3 | 28.5 | 1.9 | 5.9E−07 |
| Naga_100257g1 | Glyceraldehyde-3-phosphate dehydrogenase (EC 1.2.1.12) | 20.0 | 74.9 | 1.8 | 2.2E−14 |
| Naga_100937g1 | Acyltransferase 3 (Fragment) | 1.6 | 6.2 | 1.8 | 1.9E−04 |
| Naga_100273g7 | Delta 5 fatty acid desaturase | 12.2 | 42.2 | 1.8 | 2.4E−08 |
| Naga_100001g58 | Glyceraldehyde-3-phosphate dehydrogenase (EC 1.2.1.12) | 25.8 | 87.8 | 1.7 | 4.8E−17 |
| Naga_100426g5 | Lipase, class 3 | 1.0 | 4.6 | 1.7 | 7.5E−05 |
| Naga_100012g35 | Lipase domain-containing protein | 0.3 | 1.6 | 1.6 | 2.8E−03 |
| Naga_100226g14 | Acyltransferase 3 | 2.3 | 6.6 | 1.6 | 6.5E−07 |
| Naga_100241g4 | Lipase | 0.7 | 2.6 | 1.4 | 2.0E−03 |
| Naga_100075g9 | Delta(5) fatty acid desaturase B | 6.0 | 16.1 | 1.4 | 9.0E−05 |
| Naga_100115g11 | Stearoyl-CoA 9-desaturase | 23.8 | 63.1 | 1.4 | 4.0E−14 |
| Naga_102092g1 | Acyl-CoA Synthase | 5.3 | 13.1 | 1.3 | 8.5E−04 |
| Naga_100063g13 | Delta 3 fatty acid desaturase | 25.6 | 59.7 | 1.2 | 6.0E−09 |
| Naga_100530g1 | Lipase-like protein | 1.7 | 3.9 | 1.1 | 2.1E−02 |
| Naga_100028g54 | Acetyl-coenzyme A synthetase (EC 6.2.1.1) | 16.9 | 36.8 | 1.1 | 1.3E−10 |
| Naga_101607g1 | Triglyceride lipase-cholesterol esterase | 53.7 | 115.3 | 1.1 | 1.9E−06 |
| Naga_100247g4 | Patatin-like phospholipase domain-containing protein 2 | 114.3 | 54.5 | −1.1 | 2.0E−09 |
| Naga_100529g6 | Lipase, class 3 (Fragment) | 291.2 | 134.6 | −1.1 | 2.1E−13 |
| Naga_100771g2 | Acyltransferase 3 | 14.1 | 3.6 | −2.0 | 5.4E−15 |

[†]FPKM, Fragments per kilobase of transcript per million mapped reads
[††]FC, Fold change of genes in ZnCys-RNAi-7 relative to WT
[†††]FDR, False Discovery Rate (transcript levels are shown for genes with FDR < 0.05)

Consistent with our Western blot data for ACCase and FAS (FIG. 25), transcripts encoding these enzymes were not found to be differentially expressed in the mutant with respect to wild type, nor was differential regulation of genes encoding diacylglycerol acyltransferases (DGATs) or other enzymatic steps leading to TAG biosynthesis observed.

Although the invention has been described with reference to the above examples, it will be understood that modifications and variations are encompassed within the spirit and scope of the invention. Accordingly, the invention is limited only by the following claims.

What is claimed is:

1. A classical mutagenesis derived or genetically engineered mutant algal or heterokont microorganism that produces at least 50% more fatty acid methyl ester-derivatizable lipids (FAME lipids) than a control algal or heterokont microorganism and at least 70% of the amount of biomass produced by the control microorganism when the mutant microorganism and control microorganism are cultured under identical conditions under which the control microorganism is producing biomass, wherein the mutant microorganism has attenuated expression of a gene encoding a polypeptide comprising an amino acid sequence having at least 80% identity to the amino acid sequence of SEQ ID NO:2 or SEQ ID NO:17.

2. A mutant algal or heterokont microorganism according to claim 1, wherein the mutant microorganism and control algal or heterokont microorganism are cultured under identical conditions which are nitrogen replete with respect to the control microorganism.

3. A mutant algal or heterokont microorganism according to claim 1, wherein the control algal or heterokont microorganism is a wild type microorganism.

4. A mutant algal or heterokont microorganism according to claim 1, wherein the mutant microorganism produces at least 50% more FAME lipids than a control algal or heterokont microorganism while accumulating at least 70% the amount of biomass accumulated by the control microorganism over a culture period of at least five days.

5. A mutant algal or heterokont microorganism according to claim 4, wherein the mutant microorganism produces at least 50% more FAME lipids than a control algal or heterokont microorganism while accumulating at least 70% the amount of biomass accumulated by the control microorganism over a culture period of at least ten days.

6. A mutant algal or heterokont microorganism according to claim 4, wherein the mutant microorganism accumulates at least 80% the amount of biomass accumulated by the control algal or heterokont microorganism.

7. A mutant algal or heterokont microorganism according to claim 6, wherein the mutant microorganism accumulates at least 90% the amount of biomass accumulated by the control algal or heterokont microorganism.

8. A mutant algal or heterokont microorganism according to claim 7, wherein the mutant microorganism accumulates at least 95% the amount of biomass accumulated by the control algal or heterokont microorganism.

9. A mutant algal or heterokont microorganism according to claim 4, wherein the mutant microorganism produces at least 75% more FAME lipids than the algal or heterokont wild type microorganism.

10. A mutant algal or heterokont microorganism according to claim 9, wherein the mutant microorganism produces at least 100% more FAME lipids than the control algal or heterokont microorganism.

11. A mutant algal or heterokont microorganism according to claim 1, wherein the mutant microorganism exhibits a Fatty Acid Methyl Esters/Total Organic Carbon (FAME/TOC) ratio at least 30% higher than the FAME/TOC ratio of the control algal or heterokont microorganism.

12. A mutant algal or heterokont microorganism according to claim 1, wherein the polypeptide further comprises a PAS3 domain.

13. A mutant algal or heterokont microorganism according to claim 12, wherein the PAS3 domain has at least 65% identity to a sequence selected from the group consisting of SEQ ID NO:21, SEQ ID NO:22, SEQ ID NO:23, SEQ ID NO:24, and SEQ ID NO:25.

14. A mutant heterokont microorganism according to claim 1, wherein the heterokont microorganism is a *Labyrinthulomycite* species of *Labyinthula, Labyrinthuloides, Thraustochytrium, Schizochytrium, Aplanochytrium, Aurantiochytrium, Oblongichytrium, Japonochytrium, Diplophrys*, or *Ulkenia*.

15. A mutant algal microorganism according to claim 1, wherein the algal microorganism is an *algal* species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Plurodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, or *Volvox*.

16. A method of producing lipid, comprising culturing the microorganism of claim 1 and isolating lipid from the microorganism, the culture medium, or both.

17. A method of producing lipid, comprising culturing a microorganism according to claim 1 under conditions in which the FAME to TOC ratio of the microorganism is maintained between 0.3 and 0.9, and isolating lipid from the microorganism, the culture medium, or both.

18. A method according to claim 17, wherein the FAME to TOC ratio is maintained between about 0.4 and about 0.8.

* * * * *

SEQUENCE LISTING

```
<160> NUMBER OF SEQ ID NOS: 193

<210> SEQ ID NO 1
<211> LENGTH: 3198
<212> TYPE: DNA
<213> ORGANISM: Nannochloropsis gaditana
<220> FEATURE:
<221> NAME/KEY: misc_feature
<223> OTHER INFORMATION: ZnCys-2845 protein-encoding sequence (cDNA)

<400> SEQUENCE: 1
atgaccacct tcttgaatcc aggcccggca agggagaaac tcgtgggcag tggcgtcttt     60
ttcgaaggca gcatcggggt cgtcgggcac gagtcaggcg ggggagttgg gagccaggac    120
gagatggaca cggaccattt caacgagcta gaccacatat tcgacttgtc gtacagcgcg    180
```

```
gaacaggacc cttttggctc gggcagcggg cacgcgcaga gtcagggcac tgggtatggg    240
catccgcccc agacgcagct cggggggcgcc agtctcttga tgccccaccc acacaacagc    300
catggcgcga tcagccacga cggctctcgc atgcacaacg atggcatgga ttggcgcgcg    360
aaggatgagg actgctcgta ccacaccgcc gtggacgcca gctgccacat cgacagtagc    420
taccaccatg ttgatgcctc aggccactcc atggtcgacg cctcgggtca cagcacgata    480
gacgcgtcgg gccacgactc cctcatcgac tcaagcggcc attacgacga ctatctggcg    540 cacaagggg acgcccgcta catggagcac agttgtgaag cctgcaagcg ctcgaagaaa    600
cgatgcaacc gccgcaaccc ctgccagatc tgcacctcca ggggcatcaa gtgtgtgccg    660
caaatccggg gtcctgggcg ccccccgggc agtaaaagca gtcggggctg cacctccttg    720
tcactgagca gctcacggca tggaagctcc aggggtgaca tacgcgccgc gaacggaagc    780
gggcagagcc acaacagcag tgccacgaca tcggccgcct cctccacctc ctcctccttg    840
tcccgctccc tctccgggaa tggcctactc caacagggcc aggagttggc cgtcggcgcc    900
cggcggcact ctccccccg cgaccctgg cactgtcgct ttttcttcga ggccgcccgc    960
cactgcaaag aggccttcct gcggacgtgg cacgataacg agctggacac cgccaagtgc    1020
atcatgctca ggaatttgtg gacgaaagtc tcgtcgcaac tggcctctgg cacggatatg    1080
acctttggga tctgcgacca gctgcaagag gtggtgggc cgcccccac gggctctggt    1140 cccatggccg ggagccccgc cacgcgctcc aagagccacg cggcgcagca ggcgcaactc    1200
ctcacgcacc ccggttcgaa agaggccatg ggccctcact gcctgcccct ggacttgcga    1260
agaatggagg acggcgtctc catgctgtgc ggcttcatgt tcttgcagga cgagcttttc    1320
gtctacacgg acgagcgttt cgcggccacc ttcatgacgc gggaagaggt ggagtccaag    1380
gtcggctccc tcgcggtgct gcccatcctc ctgctcgcgg agatcttcca ccccgacgac    1440
ctccctgaca tctacgcggc catcggtgct tactggtttt ctcgccgctc tctaccacg    1500 tcagagagcg ggagcagcag cagcagcagc acaaacagca gtgtcagcag tgcggggagt    1560
cgggagtcgg cggcctcggc cacaggcacc ccggaggcgt cctggatctg caaatgcatc    1620
gacaaggcga acacggaagt gacggccttc gtgcgcttcc gctctttcgt cgcacctgcg    1680
gagggctacc ccggggcggc catgctctcc atcctgccct taaaaccgag caagtatctc    1740
gcggacccgg acactaaggg gagtgtcagg tctggggtgt cgtcgcgctt gcagatgagg    1800
gacaccttcg gagccttgcc cacagccctg ccggagcaag acgacgagga ccttggcgac    1860
gatttggtcg gcggcgacc gtcggtggat cgcatggagg gctgggggcc cggggccggg    1920
gagggccagg accctgagag cgacgacgcc ttattccggc cccttcggag gggcatgacc    1980 gtgctctcg atgagacgag cgggccgcag gctgtgcctg tcgcaaagca ggtttcagac    2040
cccggcgtac agcaccagga tcacgcctgc tacagccagc ctaccataca catatcccag    2100
ctgtcgagcg cccttcggag cacgtgggc ttgtcgtggg ggggagggg gaccgaccgc    2160 agtggggaat cttttccatc gtcgcagttc tcctcccatg ctcagacgca aggtggacaa    2220
tcatcttctg gtctcccgca agatggcaaa agctgtggtg gttaccctgc ctcggatgat    2280
ggtcgtgggg gggacatgac ggacgggggtt ctgcccattg cacaacttac caaggcccaa    2340
attttccttc tgcaagaaga gggtggtgtt tctggtcgag acctcccgc tgccggcgac    2400 aattcatcat atggcgattt agccagcggg agagagggcc aagggggtcg ccgtcatcaa    2460
cgaaaggaac aagagtcgcg gaagcaccct gaccctcggg atggacacac cctccctgca    2520
```

-continued

```
agtggattga cgatggacga ggaggataca ggaagcgtgg ttacagactt tgagatttac    2580
ggctccagtc ccagtccgga gcccggccag tcccttaata cttcctcacg aggctcggca    2640
aggttgcaga tgcaggcctc gagccagggg gggcaccaaa cgtactttgg acgacacgag    2700
cacatggaaa agcaaaatcg agaggaggtg cagcgactgc cgatggctcc accctctgta    2760
agtttcgccc aggcggggga gctatccagt gatcgacgag cgagttgcgc gggcttgagc    2820
atcctaggcg gacctgctgg gaaagtggaa ggctccaggg gatccctgag ccacagtaag    2880
agtaacaacg acctggacat atcgtgtcat gggcccgccg atcccaacgg ctacggtggg    2940
ttgcagtgga cgccggctcc actggcgtct ctgctggggg ccaagggcct actagaggcg    3000
gggaacgggg tgggcgatca cgcgatctcg tcggttcacg ccaatcaggg gcctgcccac    3060
cagaagcgtc ggacgagccg cgcggggtcg cggaccgttc ctgccaacaa tggtggcgat    3120
aataccgcgg ggagcgcagc gatcgcgggc gcgaaggatg aagaggcgga gccaggcttt    3180
cttgcccgct ctttgtga                                                  3198
```

<210> SEQ ID NO 2
<211> LENGTH: 1065
<212> TYPE: PRT
<213> ORGANISM: Nannochloropsis gaditana
<220> FEATURE:
<221> NAME/KEY: misc_feature
<223> OTHER INFORMATION: ZnCys-2845 protein sequence

<400> SEQUENCE: 2

```
Met Thr Thr Phe Leu Asn Pro Gly Pro Ala Arg Glu Lys Leu Val Gly
1               5                   10                  15

Ser Gly Val Phe Phe Glu Gly Ser Ile Gly Val Gly His Glu Ser
            20                  25                  30

Gly Gly Gly Val Gly Ser Gln Asp Glu Met Asp Thr Asp His Phe Asn
        35                  40                  45

Glu Leu Asp His Ile Phe Asp Leu Ser Tyr Ser Ala Glu Gln Asp Pro
    50                  55                  60

Phe Gly Ser Gly Ser Gly His Ala Gln Ser Gln Gly Thr Gly Tyr Gly
65                  70                  75                  80

His Pro Pro Gln Thr Gln Leu Gly Gly Ala Ser Leu Leu Met Pro His
                85                  90                  95

Pro His Asn Ser His Gly Ala Ile Ser His Asp Gly Ser Arg Met His
            100                 105                 110

Asn Asp Gly Met Asp Trp Arg Ala Lys Asp Glu Asp Cys Ser Tyr His
        115                 120                 125

Thr Ala Val Asp Ala Ser Cys His Ile Asp Ser Ser Tyr His His Val
    130                 135                 140

Asp Ala Ser Gly His Ser Met Val Asp Ala Ser Gly His Ser Thr Ile
145                 150                 155                 160

Asp Ala Ser Gly His Asp Ser Leu Ile Asp Ser Ser Gly His Tyr Asp
                165                 170                 175

Asp Tyr Leu Ala His Lys Gly Asp Ala Arg Tyr Met Glu His Ser Cys
            180                 185                 190

Glu Ala Cys Lys Arg Ser Lys Lys Arg Cys Asn Arg Arg Asn Pro Cys
        195                 200                 205

Gln Ile Cys Thr Ser Arg Gly Ile Lys Cys Val Pro Gln Ile Arg Gly
    210                 215                 220

Pro Gly Arg Pro Pro Gly Ser Lys Ser Ser Arg Gly Cys Thr Ser Leu
225                 230                 235                 240
```

```
Ser Leu Ser Ser Ser Arg His Gly Ser Ser Arg Gly Asp Ile Arg Ala
                245                 250                 255

Ala Asn Gly Ser Gly Gln Ser His Asn Ser Ser Ala Thr Thr Ser Ala
            260                 265                 270

Ala Ser Ser Thr Ser Ser Ser Leu Ser Arg Ser Leu Ser Gly Asn Gly
        275                 280                 285

Leu Leu Gln Gln Gly Gln Glu Leu Ala Val Gly Ala Arg Arg His Ser
    290                 295                 300

Pro Pro Arg Asp Pro Trp His Cys Arg Phe Phe Glu Ala Ala Arg
305                 310                 315                 320

His Cys Lys Glu Ala Phe Leu Arg Thr Trp His Asp Asn Glu Leu Asp
                325                 330                 335

Thr Ala Lys Cys Ile Met Leu Arg Asn Leu Trp Thr Lys Val Ser Ser
            340                 345                 350

Gln Leu Ala Ser Gly Thr Asp Met Thr Phe Gly Ile Cys Asp Gln Leu
        355                 360                 365

Gln Glu Val Val Gly Pro Ala Pro Thr Gly Ser Gly Pro Met Ala Gly
    370                 375                 380

Ser Pro Ala Thr Arg Ser Lys Ser His Ala Ala Gln Gln Ala Gln Leu
385                 390                 395                 400

Leu Thr His Pro Gly Ser Lys Glu Ala Met Gly Pro His Cys Leu Pro
                405                 410                 415

Leu Asp Leu Arg Arg Met Glu Asp Gly Val Ser Met Leu Cys Gly Phe
            420                 425                 430

Met Phe Leu Gln Asp Glu Leu Phe Val Tyr Thr Asp Glu Arg Phe Ala
        435                 440                 445

Ala Thr Phe Met Thr Arg Glu Glu Val Glu Ser Lys Val Gly Ser Leu
    450                 455                 460

Ala Val Leu Pro Ile Leu Leu Ala Glu Ile Phe His Pro Asp Asp
465                 470                 475                 480

Leu Pro Asp Ile Tyr Ala Ala Ile Gly Ala Tyr Trp Phe Ser Arg Arg
                485                 490                 495

Ser Ser Thr Thr Ser Glu Ser Gly Ser Ser Ser Ser Ser Thr Asn
            500                 505                 510

Ser Ser Val Ser Ser Ala Gly Ser Arg Glu Ser Ala Ala Ser Ala Thr
        515                 520                 525

Gly Thr Pro Glu Ala Ser Trp Ile Cys Lys Cys Ile Asp Lys Ala Asn
    530                 535                 540

Thr Glu Val Thr Ala Phe Val Arg Phe Arg Ser Phe Val Ala Pro Ala
545                 550                 555                 560

Glu Gly Tyr Pro Gly Ala Ala Met Leu Ser Ile Leu Pro Leu Lys Pro
                565                 570                 575

Ser Lys Tyr Leu Ala Asp Pro Asp Thr Lys Gly Ser Val Arg Ser Gly
            580                 585                 590

Val Ser Ser Arg Leu Gln Met Arg Asp Thr Phe Gly Ala Leu Pro Thr
        595                 600                 605

Ala Leu Pro Glu Gln Asp Asp Glu Asp Leu Gly Asp Leu Val Gly
    610                 615                 620

Arg Arg Pro Ser Val Asp Arg Met Glu Gly Leu Gly Pro Gly Ala Gly
625                 630                 635                 640

Glu Gly Gln Asp Pro Glu Ser Asp Asp Ala Leu Phe Arg Pro Leu Arg
                645                 650                 655
```

-continued

```
Arg Gly Met Thr Val Leu Ser Asp Glu Thr Ser Gly Pro Gln Ala Val
            660                 665                 670

Pro Val Ala Lys Gln Val Ser Asp Pro Gly Val Gln His Gln Asp His
            675                 680                 685

Ala Cys Tyr Ser Gln Pro Thr Ile His Ile Ser Gln Leu Ser Ser Ala
            690                 695                 700

Leu Arg Ser Thr Val Gly Leu Ser Trp Gly Gly Gly Thr Asp Arg
705                 710                 715                 720

Ser Gly Glu Ser Phe Pro Ser Ser Gln Phe Ser His Ala Gln Thr
            725                 730                 735

Gln Gly Gly Gln Ser Ser Ser Gly Leu Pro Gln Asp Gly Lys Ser Cys
            740                 745                 750

Gly Gly Tyr Pro Ala Ser Asp Asp Gly Arg Gly Gly Asp Met Thr Asp
            755                 760                 765

Gly Val Leu Pro Ile Ala Gln Leu Thr Lys Ala Gln Ile Phe Leu Leu
            770                 775                 780

Gln Glu Glu Gly Gly Val Ser Gly Arg Asp Leu Pro Ala Ala Gly Asp
785                 790                 795                 800

Asn Ser Ser Tyr Gly Asp Leu Ala Ser Gly Arg Glu Gly Gln Gly Gly
            805                 810                 815

Arg Arg His Gln Arg Lys Glu Gln Glu Ser Arg Lys His Pro Asp Pro
            820                 825                 830

Arg Asp Gly His Thr Leu Pro Ala Ser Gly Leu Thr Met Asp Glu Glu
            835                 840                 845

Asp Thr Gly Ser Val Val Thr Asp Phe Glu Ile Tyr Gly Ser Ser Pro
850                 855                 860

Ser Pro Glu Pro Gly Gln Ser Leu Asn Thr Ser Ser Arg Gly Ser Ala
865                 870                 875                 880

Arg Leu Gln Met Gln Ala Ser Ser Gln Gly His Gln Thr Tyr Phe
            885                 890                 895

Gly Arg His Glu His Met Glu Lys Gln Asn Arg Glu Glu Val Gln Arg
            900                 905                 910

Leu Pro Met Ala Pro Pro Ser Val Ser Phe Ala Gln Ala Gly Glu Leu
            915                 920                 925

Ser Ser Asp Arg Arg Ala Ser Cys Ala Gly Leu Ser Ile Leu Gly Gly
930                 935                 940

Pro Ala Gly Lys Val Glu Gly Ser Arg Gly Ser Leu Ser His Ser Lys
945                 950                 955                 960

Ser Asn Asn Asp Leu Asp Ile Ser Cys His Gly Pro Ala Asp Pro Asn
            965                 970                 975

Gly Tyr Gly Gly Leu Gln Trp Thr Pro Ala Pro Leu Ala Ser Leu Leu
            980                 985                 990

Gly Ala Lys Gly Leu Leu Glu Ala Gly Asn Gly Val Gly Asp His Ala
            995                 1000                1005

Ile Ser Ser Val His Ala Asn Gln Gly Pro Ala His Gln Lys Arg
            1010                1015                1020

Arg Thr Ser Arg Ala Gly Ser Arg Thr Val Pro Ala Asn Asn Gly
            1025                1030                1035

Gly Asp Asn Thr Ala Gly Ser Ala Ala Ile Ala Gly Ala Lys Asp
            1040                1045                1050

Glu Glu Ala Glu Pro Gly Phe Leu Ala Arg Ser Leu
            1055                1060                1065
```

```
<210> SEQ ID NO 3
<211> LENGTH: 30
<212> TYPE: PRT
<213> ORGANISM: Nannochloropsis gaditana
<220> FEATURE:
<221> NAME/KEY: misc_feature
<223> OTHER INFORMATION: Zn(2)-Cys(6) binuclear cluster domain of ZnCys-
      2845

<400> SEQUENCE: 3

His Ser Cys Glu Ala Cys Lys Arg Ser Lys Lys Arg Cys Asn Arg Arg
1               5                   10                  15

Asn Pro Cys Gln Ile Cys Thr Ser Arg Gly Ile Lys Cys Val
            20                  25                  30

<210> SEQ ID NO 4
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Conserved motif of Zn(2)-Cys(6) binuclear
      cluster domain
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 4

Cys Xaa Xaa Cys Xaa Xaa Xaa Xaa Xaa Xaa Cys Xaa Cys Xaa Xaa Cys
1               5                   10                  15

Xaa Cys

<210> SEQ ID NO 5
<211> LENGTH: 696
<212> TYPE: PRT
<213> ORGANISM: Phaeodactylum tricornutum

<400> SEQUENCE: 5

Met Asn Glu Asp Ser Thr Glu Asp Pro Asp Asp Gly Ser Val Ala Leu
1               5                   10                  15

Cys Ala Ser Cys Asp Arg Cys Arg Ser Arg Lys Thr Lys Cys Asp Gly
            20                  25                  30

Gln Arg Pro Cys Gly Asn Cys Leu Ala Lys Tyr Met Lys Lys Asn Lys
        35                  40                  45

Leu Ser Ser Ala Asp Gly Ile Asp Phe Thr Glu Cys Glu Cys Val Tyr
    50                  55                  60

Ser Pro Ala Lys Arg Arg Gly Pro Ile Pro Gly Arg Thr Ala Gly Gln
65                  70                  75                  80
```

-continued

Ala Arg Lys Ala Thr Glu Leu Gln His His Gln Gln Gln Gln Pro Asn
                85                  90                  95

Asp Trp Pro Gln Asn Tyr His Asn Asn Pro Ser Thr Gly Val Asn Leu
            100                 105                 110

Asn Gly Thr Gly Leu Asp Ala Gln Met Thr Ala Ala Leu Phe Ser Gly
        115                 120                 125

Gln Thr Glu Gln Ala Ser Leu Gln Gln Lys Leu Asn Phe Leu Gln Ser
    130                 135                 140

Leu Gln Asn Gln Asp Glu Asp His Leu Met Met Gln Gln Gln Gln Gln
145                 150                 155                 160

Gln His Gln Met Asp Glu Pro Ala Asn Arg Arg Val Lys Arg Glu Asp
                165                 170                 175

Ala Gly Gln Asn Thr Ser Thr Asn Gly Ile Pro Arg Thr Ile Thr Thr
            180                 185                 190

His Thr His Leu Leu Glu Arg Ser Asn Pro Asp Gly Ala Arg Leu Arg
        195                 200                 205

Ala Tyr Tyr Gln Leu Ser Ile Asp Glu Leu Tyr Arg Leu Pro Pro Ile
    210                 215                 220

Pro Thr Asp Glu Glu Tyr Cys Ala Arg Leu Asn Val Pro Gly Met Thr
225                 230                 235                 240

Pro Gln Met Ile Pro Gly Pro His Leu Ala Ala Leu Ser Ala Ala Arg
                245                 250                 255

Phe Ala Glu Ile Ala Leu Gly Ala Leu Val His Asn Glu Val Ser Leu
            260                 265                 270

Ala Met Glu Leu Cys Asn Ala Val Val His Cys Leu Arg Glu Ser Val
        275                 280                 285

Gln Glu Pro Val Gln Thr Pro Val Met Phe Glu Val Ala Lys Ala Tyr
    290                 295                 300

Phe Leu Leu Gly Val Phe Arg Ala Cys Arg Gly Asp Met Glu Arg Tyr
305                 310                 315                 320

Phe Lys Tyr Arg Arg Val Cys Met Thr Tyr Leu Ala Lys Leu Glu Asn
                325                 330                 335

Asp Asp Lys Thr Ala Val Leu Leu Ala Ala Val Ala Tyr Leu Asp Ser
            340                 345                 350

Trp Ala Pro Tyr Ala Thr Gln Thr Glu Leu Lys Tyr Asp Val Lys Leu
        355                 360                 365

Asp Ala Gly Ala Ile Ala Ser Asp Pro Lys Asn Gln Asn Trp Ile Gln
    370                 375                 380

Gly Ala Pro Pro Val Tyr Leu Asn Asn Glu Ala Pro Leu His Ala Arg
385                 390                 395                 400

Ala Leu Asp Ala Leu Ala Cys Ala Val Arg Thr Cys Cys Asp Gln Ala
                405                 410                 415

Asn Ser Arg Phe Ala Leu Ile Ser Lys Glu Ala Asn Ile Glu Gly Leu
            420                 425                 430

Asp Thr Ile Pro Ser Glu Ser Ile Ser Ser Ala Thr Tyr Asn Ala Val
        435                 440                 445

Leu Ser His Glu Asn Glu Leu Cys Ser Arg Asn Ile Val Leu Ser Ala
    450                 455                 460

Tyr Thr Leu Met Gln Gln His Glu Ser Thr Asp Ser Ser Arg His Lys
465                 470                 475                 480

Asn Glu Gly Gln His Met Val Ile Ser Ala Met Asp Ala Phe Leu Glu
                485                 490                 495

Asn Ser Asp Glu Asp Gly Asn Gly Gly Phe Thr Asp Ser Gln Ile Gln

```
                500                 505                 510
    Ser Leu Leu Ser Val Cys Asn Thr Ala Ile Glu Asn Pro Phe Leu Leu
        515                 520                 525

His His Ala Gly Pro Thr Tyr His Met Val Ser Asn Ala Ala Val Leu
        530                 535                 540

Leu Cys His Leu Leu Asn Gly Leu His Met Ala Lys Met Asn Gly Gln
    545                 550                 555                 560

Asp Phe Gly Arg Met Glu Gln Ser Met Phe Glu Glu Val Phe Asp Ala
                    565                 570                 575

Phe Ile Ser Ile Arg Lys Leu Leu Thr Ile His Arg Arg Lys Leu Pro
                580                 585                 590

Val Lys Leu Arg Cys His Ala Ile Pro Arg Pro Ser Met Asp Gly Leu
            595                 600                 605

Lys Glu Gly Gln Pro Leu Ile Asp Leu Gly Glu Thr Ile Leu Cys Ala
            610                 615                 620

Cys Arg Gly Cys Gln Gly Phe Val Leu Met Ala Cys Ser Pro Cys Val
    625                 630                 635                 640

Ala Ala Glu Arg Ala Gln Ala Ala Gln His Asp Leu Ser Val Glu Ala
                    645                 650                 655

Ala Lys Glu Ala Glu Ala Ile Glu Met Gly Glu Leu Asp Asn Glu Leu
                660                 665                 670

Asp Asn Leu Gly Ala Glu Phe Asp Met Asp Asp Met Leu Leu Gly
            675                 680                 685

Met Ile Ser Asn Leu Ile Ser Ser
        690                 695

<210> SEQ ID NO 6
<211> LENGTH: 248
<212> TYPE: PRT
<213> ORGANISM: Navicula sp.

<400> SEQUENCE: 6

Met Ala Cys Thr Ala Cys His Leu Ala Lys Arg Lys Cys Asp Lys Lys
1               5                   10                  15

Ser Pro Cys Ser Arg Cys Ile Ser Lys Ser Leu Glu Cys Ile Pro His
            20                  25                  30

Ile Ser Arg Gln Gly Lys Lys Val Arg Val Glu Glu Lys Lys
        35                  40                  45

Asp Asp Gly Leu Asp Arg Leu Leu Glu Gln Leu Thr Gly Thr Glu
    50                  55                  60

Pro Val Gln Gly His Thr His His Phe Gly Leu Lys Tyr Leu Val Arg
65                  70                  75                  80

Ser Trp Ile Ser Phe Ala Phe Lys Arg Arg Ser Phe Phe Leu Met Gln
                85                  90                  95

Arg Gly Cys Ala Leu Ala Ile Lys Val Gly Phe Ser Met Asp Glu Ile
            100                 105                 110

Phe Cys Glu Gln Ser Asn Ser Arg Glu Met Asp Phe Leu Lys Asn Ile
        115                 120                 125

Ile Leu Val Pro Lys Glu Ala Gln His Leu Tyr Val Pro Thr Pro Leu
    130                 135                 140

Gln Trp Thr Glu Ile Pro Glu Arg Leu Leu Arg Asn Thr Asp Thr Ile
145                 150                 155                 160

Gly Ser Ser Gly Asn Arg Glu Gly Arg Trp Ile Trp Met Arg Glu Met
                165                 170                 175
```

```
Ile Lys Gly Glu Ser Arg Tyr Leu Val Ser Glu Ala Phe Glu Arg Asp
            180                 185                 190

Val Ala Pro Trp Ser Ser Leu His Lys Ala Trp Glu Asp Asn Arg Gly
            195                 200                 205

Ala Val Ile Asp Leu Phe Val Ile Glu Glu Asp Lys His Lys His Thr
    210                 215                 220

Lys Ser Phe Ala His Gln Ile Ser Leu Tyr Lys Gln Ala Val Asn
225                 230                 235                 240

Gly Glu Gly Asn Arg Leu Thr Arg
                245

<210> SEQ ID NO 7
<211> LENGTH: 333
<212> TYPE: PRT
<213> ORGANISM: Navicula sp.

<400> SEQUENCE: 7

Met Val Cys Ile Gly Cys His Glu Ser Lys Lys Cys Asp Lys Gln
1               5                   10                  15

Thr Pro Cys Ser Arg Cys Leu Lys Leu Gly Ile Pro Cys Ile Pro His
            20                  25                  30

Leu Ser Gln Gln Gly Lys Arg Lys Arg Gly Ser Pro Asp Glu Thr Pro
            35                  40                  45

Glu Asp Val Thr Ile Leu Arg Gln Val Ser Leu Pro Lys Asp His Tyr
    50                  55                  60

Gly Leu Cys His Leu Ile Arg Ser Trp Ile Ser Ile Ala Phe Val Arg
65                  70                  75                  80

Arg Ser Phe Pro Leu Leu Asn Lys Ala Thr Thr Met Ala Asn Gln Leu
                85                  90                  95

Gly Val Thr Met Asp Glu Ile Met Ser Arg Ser Met Thr Gln Gln Gly
            100                 105                 110

Met His Trp Leu Gly Pro Val Val Ala Thr Pro Gln Ser Glu Gln Met
        115                 120                 125

Ala Gly Gly Pro Arg Leu Gln Trp Asn Glu Leu Pro Glu Gly Leu Leu
    130                 135                 140

Val Ala Thr Arg Thr Leu His Ser Val Asp Cys Glu Ala Arg Trp Ile
145                 150                 155                 160

Trp Ile Arg Glu Leu Ser Gln Gly Arg Ser Arg Tyr Leu Val Thr Gln
                165                 170                 175

Ala Phe Glu Arg Asp Ile Ala Thr Trp Ala Leu Val Gln Ser Thr Trp
            180                 185                 190

Asn Glu Asn Arg Ile Ser Val Val Asp Leu Phe Leu Asp Gly Ala Ala
        195                 200                 205

Arg Glu Lys His Ala Lys Ser Val Ala His Gln Tyr Ser Leu His Ala
    210                 215                 220

Lys Pro Pro Thr Pro His Ser Ala Arg Cys Ser Arg Gln Arg Ser Gln
225                 230                 235                 240

Val Lys Leu Arg Asn Gly Asp Met Ile Ser Val Glu Ile Ser Cys
                245                 250                 255

Met Asp Phe Val His Met Asp Leu Ser Tyr His Phe Glu Tyr Val
            260                 265                 270

Pro Val Cys Ile Gln Pro Ile Arg Ser Gln Ala Cys Ile Gln Asn Lys
        275                 280                 285

Val Gln Ser Thr Gln Ser Leu Phe Gln Glu Met Ser Lys Val Met Trp
    290                 295                 300
```

```
Asp Asp Tyr Pro Leu Met Val Asn Val Asp Asp Ile Pro Ala Glu Gly
305                 310                 315                 320

Asn Glu Leu Asp Gln Ile Leu Gln Leu Leu Asn Gly Gly
                325                 330

<210> SEQ ID NO 8
<211> LENGTH: 729
<212> TYPE: PRT
<213> ORGANISM: Navicula sp.

<400> SEQUENCE: 8

Met Glu Asp Phe Asn Asn Asn Thr Gln Gln Ala Asp Asp Glu Lys
1               5                   10                  15

Leu Cys Ala Ser Cys Asp Arg Cys Arg Ser Arg Lys Thr Lys Cys Asp
                20                  25                  30

Gly Lys Arg Pro Cys Gly Asn Cys Val Ala Lys Tyr Met Lys Lys Tyr
            35                  40                  45

Lys Val Met Ser Val Glu Gly Val Pro Glu Ser Ala Phe Glu Cys Val
50                  55                  60

Tyr Ser Pro Ala Lys Arg Arg Gly Pro Val Pro Gly Arg Thr Pro Ser
65                  70                  75                  80

Gln Ala Arg Ser Leu Asn Asp Val Thr Gly Gly Asn Met Asn Val Asn
                85                  90                  95

Met Thr Gly Gly Asn Asn Phe Asp Trp Asn Met Asp Leu Met Ser Gln
            100                 105                 110

Gln Gln Gln Gln Gln His His Gln Gln Gln Gln Pro Met Met Ser
        115                 120                 125

Ser Leu Ile Gly Gly Leu Asp Gly Asn Asn Ile Leu Asn Gln Phe Asn
130                 135                 140

Leu Met Arg Gln Met Gln Leu Gln Gln Gln Leu Pro Leu Gln Pro Gln
145                 150                 155                 160

Gln Met Ala Met Gln Gln His Met Met Asp Thr Ser Glu Val Gly Glu
                165                 170                 175

Arg Ser Ala Arg Arg Met Lys Met Glu Asp Val Pro Ser Ala Pro Gly
            180                 185                 190

Gly Val Pro Arg Thr Val Ser Asp His Thr His Leu Leu Asp Arg Asn
        195                 200                 205

Asp Pro Asp Gly Ser Arg Leu Phe Ser Tyr Phe Lys Leu Ser Ile Asp
    210                 215                 220

Glu Leu Phe Arg Leu Pro Pro Thr Pro Thr Asp Glu Glu Tyr Cys Leu
225                 230                 235                 240

Arg Leu Asn Ile Pro Gly Met Thr Pro Arg Met Ile Pro Gly Thr His
                245                 250                 255

Leu Ala Ala Leu Ser Ala Ala Arg Phe Ala Glu Ile Ala Leu Gly Ala
            260                 265                 270

Met Val His Asn Glu Ile Ser Leu Ala Met Glu Leu Cys Asn Ala Val
        275                 280                 285

Val His Cys Leu Arg Glu Ser Val Lys Glu Pro Val Gln Thr Pro Ile
    290                 295                 300

Met Leu Glu Val Ser Lys Ala Tyr Phe Leu Gly Val Phe Arg Ala
305                 310                 315                 320

Cys Arg Gly Asp Met Ala Arg Tyr Phe Lys Tyr Arg Arg Val Cys Met
                325                 330                 335

Thr Tyr Leu Gly Lys Leu Glu Asn Ser Ser Arg Thr Ala Thr Leu Thr
```

```
               340                 345                 350
Ser Ala Ile Ser Tyr Leu Asp Ala Trp Ala Tyr Met Ile Tyr Asn Gly
            355                 360                 365

Asn Glu Lys Gln Val Pro Asp Val Arg Thr Leu Pro Pro Ser
        370                 375                 380

Gly Cys Ala Thr Asn Gly Met Ile Asn Pro Ile Glu Ala Lys Tyr Asn
385                 390                 395                 400

Thr Lys Thr Ser Val Pro Ala Val Val Ser Asp Pro Lys Asn Lys Asn
                405                 410                 415

Trp Ile Gln Gly Ala Pro Pro Val Tyr Leu Asn Asn Glu Ala Pro Pro
            420                 425                 430

His Ala Arg Ser Leu Asp Ala Leu Ala Cys Ala Val Arg Ser Cys Cys
            435                 440                 445

Asp Gln Ala Asn Ser Arg Phe Ala Gln Met Met Lys Thr Glu Gly Asn
        450                 455                 460

Pro Ser Asp Asn Thr Met Ile Pro Gln Ser Thr Ile Thr Pro Thr
465                 470                 475                 480

Ala Thr Ala Val Met Asn His Glu Asn Glu Leu Cys Ser Arg Asn Met
                485                 490                 495

Val Leu Ser Ala Tyr Thr Leu Met Gln Gln Gln Ser Ser Thr Lys
            500                 505                 510

Gly Arg His His Ser Glu Gly His Gln Met Val Ile Ser Ala Met Asp
            515                 520                 525

Ala Phe Leu Glu Asn Ser Asp Glu Asp Gly Thr Gly Phe Thr Asp
        530                 535                 540

Ser Gln Ile Gln Ser Leu Leu Ser Val Cys Asn Thr Ala Ile Ala Asn
545                 550                 555                 560

Pro Phe Leu Leu His His Ala Gly Pro Thr Tyr His Met Val Thr Asn
                565                 570                 575

Ala Thr Ile Leu Leu Cys His Leu Leu Asn Ala Met His Ala Met Lys
            580                 585                 590

Gln Ser Gly Gln Val Glu Asp Met Glu Val Ala Met Phe Glu Glu Val
            595                 600                 605

Leu Asp Thr Phe Ile Ala Ile Arg Lys Leu Leu Thr Ile His Arg Arg
        610                 615                 620

Lys Leu Pro Val Lys Leu Arg Cys His Gly Ile Pro Arg Pro Gln Leu
625                 630                 635                 640

Thr Asn Thr Asp Ala Ser Ala Pro Ile Val Asp Leu Gly Glu Thr Phe
                645                 650                 655

Leu Cys Ala Cys Arg Gly Cys Gln Gly Phe Val Leu Met Ala Cys Ser
            660                 665                 670

Pro Cys Val Ala Ala Glu Arg Ala Arg Asp Ala Thr Lys Arg Met Glu
            675                 680                 685

Met Glu Leu Gln His Glu Ala Gln Ala Ile Glu Met Gly Glu Leu Asp
        690                 695                 700

Thr Asp Ile Asp Asn Ile Gly Ala Glu Phe Asp Leu Asp Asp Ala
705                 710                 715                 720

Leu Leu Ser Met Ile Ser Ser Leu Ile
                725

<210> SEQ ID NO 9
<211> LENGTH: 723
<212> TYPE: PRT
<213> ORGANISM: Cyclotella sp.
```

<400> SEQUENCE: 9

Met Asp Asp Thr Val Ala Ala Glu Glu Ala Lys Glu Ala Thr Asp Leu
1               5                   10                  15

Gln Ser Ser Asp Ser Lys Pro Thr Ser Pro Ser Ser Thr Pro Leu Asn
            20                  25                  30

Arg Asp Ser Thr Ser Leu Cys Ser Ser Cys Asp Pro Cys Arg Ala Arg
        35                  40                  45

Lys Thr Lys Cys Asp Gly Leu Arg Pro Cys Arg Ala Cys Ile Ser Lys
    50                  55                  60

His Val Lys Lys His Lys Leu Ser Ser Tyr Glu Gly Ile Thr Ala Glu
65                  70                  75                  80

Asp Cys Gly Cys Thr Tyr Ser Val Ala Lys Arg Gly Pro Val Pro
                85                  90                  95

Gly Phe Lys Asn Ala Lys Asp Glu Lys Gly Asp Gly Asn Leu Ser Thr
                100                 105                 110

Ser Lys Lys Arg Gly Pro Thr Gln Asp Gly Thr Leu His Ser Tyr Pro
            115                 120                 125

Pro Lys Lys Lys Glu Lys Arg Ser Val Asp Val Leu Ala Arg Phe
130                 135                 140

Pro His Ser Ala Ala Gln Asp Ala Met Ala Ala Ser Asp Ser Ala
145                 150                 155                 160

Arg Gln Gln Leu Gly Phe Ile Glu Arg Leu Gln Gln Gln Gln Glu
                165                 170                 175

Phe Gln Arg Gln Gln Gln Gln Met Gln Met Gln Gln Met Ala Gln
            180                 185                 190

Ala Gln Asn Ala Gln Ala Met Pro Phe Met Ser Arg Asp Gly Asp Asn
        195                 200                 205

Ser Ala Ile Ser Arg Gln Met Asn Asn Asn Tyr Asn Glu Gln Val Ser
    210                 215                 220

Gly His Lys Pro Ser Gln Gln Phe Ser Ser Thr Glu Gln Thr Ser Ala
225                 230                 235                 240

Val Gly Cys Glu Lys Thr Thr Val Arg Glu Leu Leu His Val Leu Asp
                245                 250                 255

Pro Lys Asp Pro Leu Gly Ser Arg Phe Arg Ala Cys Tyr Gly Ile Ser
            260                 265                 270

Phe Gly Ser Ile Phe Gly Leu Pro Pro Ile Leu Thr Tyr Asp Glu Tyr
        275                 280                 285

Cys Arg Gln Phe Thr Pro Thr Ile Ala Ser Thr Ser Met Pro Lys Tyr
    290                 295                 300

Asp Val Ala Ala Leu Gln Ala Ala Gln Phe Ala Glu Leu Ala Leu Gly
305                 310                 315                 320

Ala Leu Ala Asp Gly Asp Arg Cys Met Met Phe Ala Leu Ile Asn Ala
                325                 330                 335

Ser Ile Phe Cys Leu Gln Asp Thr Val Lys Glu Pro Val His Arg Ser
            340                 345                 350

Cys Gln Phe Glu Leu Ala Lys Ala Phe Phe His Ser Leu Ile Arg
        355                 360                 365

Cys His Asn Gly Asp Met Glu Arg Tyr Phe Lys Tyr Arg Arg Ala Ala
    370                 375                 380

Met His Thr Leu Ala His Leu Asp Gly Tyr Pro Asn Val Glu Thr Leu
385                 390                 395                 400

Met Ala Ala Val Gly Phe Gln Asp Ala Leu Ala Phe Met Leu Tyr Asn

```
            405                 410                 415
Gly Cys Asp Asp Val Pro Asp Ile Asp Ser Asp Tyr Pro Gln Val
            420                 425                 430

Leu Asp Arg Phe Asp Thr Lys Glu Ser Ser Val Ser Phe Thr Pro
            435                 440                 445

Ser Lys Leu Ala Ser Asp Pro Thr Asn Lys Thr Trp Ile Thr Gly Pro
        450                 455                 460

Pro Met Phe Ser Ser Glu Ser Ser Ala Pro Leu Lys Ser Arg Ile Leu
465                 470                 475                 480

Asp Ile Leu Ala Cys Ala Thr Arg Ser Phe Val Glu Glu Ser Gln Phe
                485                 490                 495

Lys Lys Glu Ile Lys Ser Val Glu Thr Ser Thr Arg Lys Arg Arg Asn
                500                 505                 510

Phe Ile Thr Ala Glu Asp Lys Arg Ile Lys Tyr Lys Ile Cys Leu Gly
                515                 520                 525

His Leu Asn Glu Ala Gly Arg Leu Leu Ala Val Ala Asn Cys Lys Ser
            530                 535                 540

Ser Ser Ser Ser Ile Tyr Asp Val Tyr His Val Leu Val Met Ala Phe
545                 550                 555                 560

Arg Val Met Ile His Glu Asp Thr Ser Glu Pro Glu Ser Gln Val
                565                 570                 575

Gln Asn Ala Phe His Val Leu Lys Ala Ile Ile Arg Gln Pro Ser Leu
                580                 585                 590

Leu Asn Ile Gly Pro Ile Asn Ile Phe Val His Lys Cys Val Ile Phe
            595                 600                 605

Val Ala Arg Leu Ile Asn Lys Ser His Lys Ala Gly Leu Glu Asp Gln
            610                 615                 620

Ser Ala Arg Asp Leu Phe Glu Glu Ser Ile Asp Leu Tyr His Ala Ser
625                 630                 635                 640

Arg Thr Ile Leu Asn Ile His Asn Ser Lys Leu Pro Asp Gln Leu Arg
                645                 650                 655

Cys His Glu Ile Pro Arg Pro Lys Ser Ile Thr Ala Lys Glu Cys Asp
                660                 665                 670

Thr Ile Ile Thr Leu Gly Asp Glu Ser Met Met Pro His Arg Met Ala
            675                 680                 685

Ser Val Lys Glu Glu Thr Ser Ala Ser Thr Ser Asp Thr Glu Lys Glu
            690                 695                 700

Cys His Ile Asn Asp Lys Ala Phe Leu Val Phe Leu Ser Gly Leu Tyr
705                 710                 715                 720

Leu Ala Arg

<210> SEQ ID NO 10
<211> LENGTH: 1515
<212> TYPE: PRT
<213> ORGANISM: Cyclotella sp.

<400> SEQUENCE: 10

Met His Phe Ser Ala Gln Pro Pro Gln Gly Asn Gly Asp Met Ala Gln
1               5                   10                  15

Leu Asp Gly Val Ser Thr Ala Ser Lys Lys Thr Arg Ala Cys Thr Glu
                20                  25                  30

Cys His Arg Ala Lys Ser Lys Cys Val Phe Ser Glu Glu Gly Gln Glu
            35                  40                  45

Lys Cys Asp Arg Cys Phe Arg Leu Asn Lys Asp Cys Val Pro His Leu
```

```
            50                  55                  60
Ser Arg Gln Gly Gln Arg Lys Lys Ser Glu Lys Gly Met Met Lys
65                      70                  75                  80

Ser Ser Val Ala Thr Ser Leu Ala Glu Val Ser Lys Gly Ser Asn Val
                    85                  90                  95

Ala Ser Lys Ala Pro Met Ser Gly Glu Ser Lys Ser Thr Ser Pro Phe
                100                 105                 110

Phe Pro Asp Asn Ala Val Glu Gly Asn Arg Pro Phe Ser Phe His Ala
            115                 120                 125

Ala Ser Gln Asp Thr Ser Leu Asn Arg Leu Ala Ala Thr Ala Thr Gly
        130                 135                 140

Gly Pro Ser Met Ser Gln Met Ala Pro Leu Ala Lys Phe Ile Pro Gln
145                 150                 155                 160

Lys His Met Phe Ser Ser Asn His Pro Thr Phe His Asn Thr Gly Pro
                165                 170                 175

Cys Gly Leu Tyr Glu Ala Arg Leu Arg Arg Thr Gln Ala Gly Thr Ala
                180                 185                 190

Leu Pro Val Asp Gln Thr Asn Ile Thr Val Thr Glu Gln Arg Gln Ala
            195                 200                 205

Ala Met Ser Met Phe Ser Asn Ser Asp Arg Thr Ile Thr Asp Ser Thr
        210                 215                 220

His Gln Gly Val Thr Phe Arg Glu Asp Leu Ser Ser Ser Arg Ser Leu
225                 230                 235                 240

Pro Leu Arg Glu Trp Met Lys Cys Ala Leu Asn Ser Asn Lys Ile Arg
                245                 250                 255

Asp Ser Ser Gly Ser Ser Pro Ile Ser Ser Lys Tyr Ile Ala Ser Cys
            260                 265                 270

Leu Lys Ile Ala Leu Ser Leu Ala Lys Gln Ile Ser Asp Ala Glu Val
        275                 280                 285

Thr Ser Ser Arg Glu Ile Leu Gln Trp Leu Pro Arg Asp Ser Ile Asp
        290                 295                 300

Trp Pro Gln Tyr Ile Thr Val Lys Leu Thr Gly Asn Glu Thr Gln Val
305                 310                 315                 320

Pro Pro His Asp Ala Arg Thr Gly Ser Leu Asp His Ser Ser Val Ala
                325                 330                 335

Asp Asp Glu Leu Asp Met Leu Glu Ala Leu Leu Asp Ser Ile Cys Glu
            340                 345                 350

Glu Asn Glu Val Asp Thr Thr Asp Val Phe Asp Ile Tyr Ser Ala Ala
        355                 360                 365

Ile Leu Leu Asp Tyr Ser Lys Asn Ser Asp Asp Gly Val Asp Pro Leu
        370                 375                 380

Ser Phe Pro Gly Gln Glu Tyr Arg Ile His Ala Leu Gly Leu Val Phe
385                 390                 395                 400

Cys Glu Leu Phe Ser Gly Gly Arg Val Pro Ser Thr Glu Leu Val Ser
                405                 410                 415

Asp Gly Leu Cys Gln Asp Val Val Thr Pro Ala Ile Ser Glu Arg
            420                 425                 430

Leu Glu Phe Thr Gly Met Leu Lys Leu Glu Pro Asn Glu Asn Asp Ile
        435                 440                 445

Tyr Lys Asp Thr Ser Cys Lys Tyr Val Gly Thr Arg Lys Lys Thr Arg
        450                 455                 460

Glu Leu Asp Glu Ser Leu His Ser Ser Ile Glu Ser Leu Arg Arg Leu
465                 470                 475                 480
```

```
Gly Ile Ser Cys Pro Leu Cys Asp Leu Ile Phe Asn Ile Leu Asp Ser
            485                 490                 495

Ile Asn Gly Asp Leu Gly Arg Asp Asp Ser Tyr Arg Lys Met Ser Asp
            500                 505                 510

Val Ala Ile Asp Leu Gln Asn Met Val Asp Lys Pro Lys Thr Phe Leu
            515                 520                 525

Asn Asp Leu Asp Val Ile Thr Leu Ser Ser Thr Gly Leu Gln Leu Thr
530                 535                 540

Asp Asn Leu Phe Met Arg Asp Glu Glu Val Ala Leu Leu Gln His Ala
545                 550                 555                 560

Tyr Tyr Arg Ser Thr Leu Gly Ser Ser Glu Phe Ala Val Ile Thr Gly
            565                 570                 575

Gly Ser Gly Thr Gly Lys Ser His Leu Ala Phe Arg Leu Gly Ser His
            580                 585                 590

Ile Thr Ser His Gly Gly Ile Phe Leu Ser Val Lys Phe Asn Gln Met
            595                 600                 605

Lys Gln Ala Asp Pro Tyr Ser Ala Leu Val Ser Ala Phe Asn Glu Tyr
            610                 615                 620

Phe Asn Asn Phe Thr Met Thr Lys Gln Leu Asp Ser Met Lys Arg Ile
625                 630                 635                 640

Ala Ser Lys Leu Arg Asp Glu Leu Gly Gln Asp Ala Leu Leu Leu Ala
            645                 650                 655

Lys Val Ile Pro Asn Leu Ala Glu Val Leu Asp Phe Ala Ala Val Asp
            660                 665                 670

Thr Ala Phe Asp Gly Asp Cys Val Asn Gly His Glu Lys Met His Tyr
            675                 680                 685

Ile Leu Val Cys Phe Val Glu Val Met Ser Ala Cys Ser His Val Thr
            690                 695                 700

Leu Thr Leu Phe Leu Asp Asp Leu Gln Trp Ala Asp Ala Phe Ser Leu
705                 710                 715                 720

Ser Val Leu Gln Gln Ile Met Ile Met Pro Asp Glu His Lys Gln Phe
            725                 730                 735

Phe Phe Val Gly Cys Tyr Arg Asp Asp Gln Met Glu Asp His Pro
            740                 745                 750

Phe Lys Lys Met Ile Ser Arg Cys Gly Asp Phe Gly Val Arg Leu Thr
            755                 760                 765

Met Val Tyr Leu Glu Cys Met Asp Lys Asp Gly Met Asn Thr Met Ile
770                 775                 780

Ser Glu Leu Leu Cys Leu Pro Pro Arg Leu Val Lys Ser Leu Ser Glu
785                 790                 795                 800

Leu Val Tyr Ser Lys Thr Lys Gly Asn Pro Leu Phe Leu Ser Arg Leu
            805                 810                 815

Leu Ile Ser Leu Asn Lys Asp Gly Leu Leu Asn Leu Ser Leu Gly Arg
            820                 825                 830

Arg Arg Trp Val Trp Asp Glu Lys Gln Ile Gln Ser Lys Glu Leu Pro
            835                 840                 845

Asp Asp Val Ala Ser Phe Phe Ser Ser Arg Val Gly Lys Leu Ser Pro
850                 855                 860

Glu Val Gln Ala Ala Leu Gln Val Leu Ser Cys Phe Gly Ser Val Asn
865                 870                 875                 880

Thr Tyr Glu Leu Ser Ile Leu Glu Ser Gly Leu Ser Leu Asn Val Val
            885                 890                 895
```

```
Lys Pro Leu Glu Arg Ala Val Asn Glu Gly Phe Val Ser Lys Asn Gly
            900                 905                 910

Asn Asp Tyr Arg Phe Ser His Asp Lys Ile His Glu Ala Val Tyr Gly
        915                 920                 925

Met Val Glu Leu Glu Glu Arg Arg Phe Gln His Leu Asn Tyr Ala Ile
    930                 935                 940

Ser Leu Val Lys Phe Ala Leu Gly Gln Asp Asp Ser Ile Ile Phe Thr
945                 950                 955                 960

Ala Ile Gly Gln Ala Asn Leu Ala Gly Pro Ser Ile Thr Thr Asp Ala
                965                 970                 975

Leu Gln Ser Ala Glu Phe Ala Arg Cys Asn Met Val Ala Gly Lys Lys
            980                 985                 990

Ala Met Ser Leu Ser Asp Phe Ser Cys Ala Ala Ile Cys Phe Ser Lys
        995                 1000                1005

Gly Leu Ser Phe Leu Asp Glu Asn Arg Trp Ser Asp Tyr Tyr Asn
   1010                1015                 1020

Leu Ser Leu Glu Leu Phe Glu Leu Ala Ala Lys Cys Ala Leu Val
   1025                1030                 1035

Leu Gly Asp Phe Ala Ser Leu Ala Thr Met Ser Glu Gln Val Glu
   1040                1045                 1050

Lys His Ser Arg Cys Phe Glu Asp Lys Leu Glu Val Ser Phe Leu
   1055                1060                 1065

Val Met Cys Ser Leu Ala Tyr Ala Ser Lys Ile Ser Asp Ser Val
   1070                1075                 1080

His Ile Gly Leu Ser Ile Leu Ser Gln Leu Gly His Glu Leu Pro
   1085                1090                 1095

Thr Asn Phe Thr Arg Ala Glu Ile Ile Phe His Ile Glu Gln Thr
   1100                1105                 1110

Lys Thr Val Leu His Ser Ile Ser Asp Lys Asp Leu Met Phe Tyr
   1115                1120                 1125

Lys Lys Met Thr Asp Pro Lys His Ile Met Ala Met Arg Cys Leu
   1130                1135                 1140

Ala Lys Leu Glu Leu Ile Val Leu Gln Ile Asn Pro Asp Leu Gln
   1145                1150                 1155

Pro Ile Ile Thr Leu Lys Met Val Asn Met Thr Met Asp Leu Gly
   1160                1165                 1170

Val Ser His Met Ser Ser Val Gly Met Ala Tyr Phe Ala Gly Leu
   1175                1180                 1185

Val Ala Lys Leu Asp Glu Ile Gln Asp Gly Ile Arg Phe Ala Arg
   1190                1195                 1200

Leu Ala Lys Met Leu Leu Asp Lys Ser Gly Ser Lys Glu Ile Thr
   1205                1210                 1215

Gly Asp Val Ile Phe Thr Thr Ser Glu Val Leu Cys Phe His Glu
   1220                1225                 1230

Pro Leu Gln Ser Val Asn Glu Tyr Arg Phe Tyr Gly Gln Thr Thr
   1235                1240                 1245

Ala Leu Ala Ala Gly Asp Met Tyr Phe Ala Cys Val Leu Lys Met
   1250                1255                 1260

Ser Asn Cys Gly Thr Met Leu Trp Met Gly Ser Asn Leu Leu Ser
   1265                1270                 1275

Val Lys Asp Ala Phe Val Gln Val Ala Arg Tyr Leu Lys Ala Lys
   1280                1285                 1290

Asn His Leu Ser Thr Tyr Asn Leu Leu Leu Leu Ser Lys Arg Ser
```

```
              1295                1300                1305

Ile Leu Met Leu Met Gly Leu Ala Asp Glu Asp Glu Pro Leu Thr
    1310                1315                1320

Val Asp Gln Leu Thr Asn Pro Tyr Gln Leu Lys Tyr Phe Tyr Phe
    1325                1330                1335

Gln Lys Met Phe Gln Ser Phe Val Phe Asn Arg Asn Asp Asp Met
    1340                1345                1350

Lys Gln Tyr Thr Glu Lys Phe Leu Gln Phe Lys Met Pro Ser Trp
    1355                1360                1365

Leu Leu Leu Ser Val His Ala Arg His Glu Phe Tyr Val Gly Leu
    1370                1375                1380

Ile Ser Phe Gln Ile Tyr Arg Glu Ser Gly Ile Ser Leu Trp Phe
    1385                1390                1395

Glu Arg Gly Gln Gln Cys Lys Ser Lys Val Gln Leu Trp Lys Glu
    1400                1405                1410

Gln Gly Ser Val Trp Asn Phe Glu His Lys Leu Tyr Leu Leu Gln
    1415                1420                1425

Ala Glu Glu Tyr Tyr Cys Asn Asp Phe Glu Arg Ala Gly Glu
    1430                1435                1440

Ser Phe Lys Asn Ser Ile Thr Ser Ala Lys Ser His Lys Phe Leu
    1445                1450                1455

Asn Asp Glu Ala Leu Ala Cys Glu Leu Ala Ala Asn Phe Tyr Leu
    1460                1465                1470

Gly Thr Gly Asp Leu Thr Ser Ser Met Lys Tyr Phe Arg Leu Ala
    1475                1480                1485

His Asp Lys Tyr Asn Glu Trp Gly Ala Leu Gly Lys Ala Ala Gln
    1490                1495                1500

Leu Val Thr Phe Met Thr Glu Lys Phe Ala Ser Cys
    1505                1510                1515

<210> SEQ ID NO 11
<211> LENGTH: 873
<212> TYPE: PRT
<213> ORGANISM: Cyclotella sp.

<400> SEQUENCE: 11

Met Thr Asn His Phe Asp Asn Asn Gln Trp Ser Ser Pro Ser Pro Pro
1               5                   10                  15

Met Met Glu Ala His Asp Asp Asn Gln His Gln Gln His Glu Gly Gly
                20                  25                  30

Val Leu Leu Cys Ala Ser Cys Asp Arg Cys Arg Ala Arg Lys Thr Lys
            35                  40                  45

Cys Asp Gly Met Arg Pro Cys Gly Asn Cys Lys Thr Lys Tyr Met Lys
        50                  55                  60

Ser Lys Lys Leu Asp Ser Val Glu Gly Ile Asp Leu Ala Glu Phe Asp
65                  70                  75                  80

Cys Ile Tyr Ser Pro Ala Lys Arg Arg Gly Pro Val Pro Gly Lys Ser
                85                  90                  95

Ala Thr Arg Lys Ala Ser Glu Met Met Ser Tyr Ser Asn Pro Asp Val
            100                 105                 110

Met His Phe Gly Ala Gly Gly Gly Thr Gln Gly Gly Gly Tyr His
        115                 120                 125

Ser Gln Val Gly Phe Asp Gly Thr Met Asn Thr Gly Gly Gly Phe Asn
    130                 135                 140
```

```
Pro Gln Gln Gln Gln Gln Leu Gln Gln Phe Asn Asn Ser Ser Ala
145                 150                 155                 160

Gln Phe Ser Ala Glu Glu Leu Lys Gln Met Leu Leu Gln Gln Gln
            165                 170                 175

Leu Leu Leu Gln Gln Gln Glu Met Gln Met Gln Gln Gln Gln His
            180                 185                 190

Gln Gln Gly Leu Leu Gln Gln Leu Thr Asn Val Ala Gly Gly Asn
        195                 200                 205

Ile Asn Ile Ala Asn Thr Leu Arg Arg Ala Ser Met Asn Gly Gly Ile
    210                 215                 220

Thr Ala Asn Gly Glu Thr Met Gly Ala Met Asn Asn Asp Val Gly Ser
225                 230                 235                 240

Val Asp Arg Ser Gly Met Gly Gly Asn Gly His Val Asp Glu Gln
            245                 250                 255

Ser Leu Gln Leu Ile Gln Gln Tyr Gln Asn Gln Leu Asn Ile Gly Ser
            260                 265                 270

Asn His Gly Met Thr Ser Gly Asn Ala Ser Ile Ile Gly Ser Val Val
    275                 280                 285

Gly Gly Leu Pro Val Gln Pro Ser Pro Met Pro Ser Gln Gln Tyr Val
290                 295                 300

Gln Glu Gln Gln Pro Ala Lys Arg Ala His Arg Ile Asp Ser Ala Met
305                 310                 315                 320

Ser Ser Asn Asn Asp Gly Thr Leu Pro Lys Ser Val Ile Ser His Leu
            325                 330                 335

Pro Leu Leu Asp Arg His Asp Gly Asp Gly Asn Val Leu Arg Ala Tyr
        340                 345                 350

Tyr Asp Leu Ser Val Asn Asp Ile Leu Asn Leu Pro Pro Ile Pro Ser
        355                 360                 365

Asp Glu Glu Tyr Cys Ser Arg Leu Ala Arg Asn Asn Tyr His Cys Leu
        370                 375                 380

Pro Ser Asn Leu Pro Thr Tyr Asp His Ser Ala Leu Gln Ala Ala Arg
385                 390                 395                 400

Phe Ala Glu Leu Ala Leu Gly Ala Leu Ala Asn Asn Gln Ile Pro Leu
            405                 410                 415

Ala Leu Glu Leu Ser Asn Ala Ser Val Met Cys Met Arg Asn Cys Ala
        420                 425                 430

Glu Glu Pro Ser Asp Glu Ser Cys Met Tyr Glu Val Ala Arg Ala Tyr
            435                 440                 445

Leu Leu His Gly Ile Phe Arg Ser Phe Arg Gly Asp Phe Val Arg Tyr
    450                 455                 460

Phe Lys Tyr Arg Arg Val Cys Met Thr His Val Gly Gln Leu Ala Asn
465                 470                 475                 480

Thr Pro His Val Glu Ala Leu Leu Ala Ala Val Ser Phe His Asp Ala
            485                 490                 495

Leu Ala Tyr Met Met His Asn Ala Lys Glu Glu Ser Leu Pro Asp Ile
        500                 505                 510

Asp Gln Val Leu Pro Arg Leu Asn Pro Gly Asn Cys Asp Phe Asp Asp
        515                 520                 525

Ser Asp Glu Val Glu Ala Lys Tyr Gly Ile Ser Thr Asn Ala Lys Ser
        530                 535                 540

Val Ala Ser Asp Pro Asn Asn Gln Met Trp Ile Gln Gly Ala Pro Pro
545                 550                 555                 560

Val Phe Leu Asn Asn Glu Ala Asn Leu Ala Asn Arg Ser Leu Asp Gly
```

```
                    565                 570                 575
Leu Ala Cys Ala Ile Arg Ser Cys Cys Asp His Ala Asn Ser Gln Phe
            580                 585                 590

Glu Glu Met Ala Lys Ala Val Gly Ala Asp Phe Val Gly Gly Ser Gly
            595                 600                 605

Ser Cys Gly Met Ser Ala Thr Thr Lys Ala Val Thr Ala Asn Glu Asn
            610                 615                 620

Glu Leu Cys Ser Arg Asn Ile Val Leu Ser Ala Arg Thr Leu Leu Asp
625                 630                 635                 640

Gln Tyr Asn Gly Val Ser His Glu Lys Ala Lys His Gly Leu Gln
            645                 650                 655

Met Leu Ala Leu Ala Met Glu Ala Phe Leu Glu Asn Ser Gly Glu Ser
            660                 665                 670

Asp Gly Val Gly Gly Phe Thr Asp Lys Gln Ile Lys Asn Leu Leu Thr
            675                 680                 685

Val Cys Asp Thr Ile Val Lys Asn Pro Leu Leu Leu His Ala Pro Gly
            690                 695                 700

Pro Val Tyr His Met Met Thr Asn Ser Ala Ile Met Leu Cys His Leu
705                 710                 715                 720

Leu Asn Gly Met His Ala Asn Cys Gly Glu Gly Ser Asn Ser Ser Gly
            725                 730                 735

Lys Ser Gly Ile Glu Glu Val Leu Phe Asp Glu Val Leu Asp Ser Phe
            740                 745                 750

Met Ala Thr Arg Lys Ile Leu Asn Ala His Arg Lys Ser Leu Pro Val
            755                 760                 765

Lys Leu Arg Cys His Gly Ile Pro Arg Pro Asn Val Gly Pro Phe Lys
770                 775                 780

Lys Ser Asp Pro Glu Ala Pro Phe Val Asp Leu Gly Glu Thr Leu Leu
785                 790                 795                 800

Cys Ala Cys Arg Gly Cys Gln Gly Phe Val Leu Met Gly Cys Ser Pro
            805                 810                 815

Cys Val Ala Ala Glu Arg Ser Ala Ala Ala Lys Ala Gln His Ala
            820                 825                 830

His Ser Ser Ser Thr Asn Gly Asn Tyr Asn Glu Asp Glu Phe Glu Arg
            835                 840                 845

Glu Leu Gln Asp Met Gly Ala Phe Asp Met Asp Asp Ala Leu Leu
            850                 855                 860

Asn Val Leu Ser Arg Phe Val Gln Asn
865                 870

<210> SEQ ID NO 12
<211> LENGTH: 379
<212> TYPE: PRT
<213> ORGANISM: Thalassiosira pseudonana

<400> SEQUENCE: 12

Met Ala Thr Thr Thr Glu Val Gln Lys His Ala Val Ser Ala Pro Leu
1               5                   10                  15

Pro Ala Ser Ala Ala Thr Thr Thr Gly Gly Gly Asn Asn Glu Ser
            20                  25                  30

Thr Val Leu Cys Ala Ser Cys Asp Arg Cys Arg Ala Arg Lys Thr Lys
            35                  40                  45

Cys Asn Gly Ala His Pro Cys Ser Gly Cys Val Ser Lys Tyr Met Lys
        50                  55                  60
```

```
Lys His Lys Leu Glu Ser Phe Asp Gly Ile Asp His Ala Leu Val Glu
 65                  70                  75                  80

Cys His Tyr Ser Val Ala Arg Lys Arg Gly Pro Gln Pro Gly Ser Ser
                 85                  90                  95

Lys Ser Pro Thr Ala Pro Arg Gly Ser Ile Pro Ala Asp Gly Thr Thr
            100                 105                 110

Ile Tyr Gln Gln Pro Ala Lys Lys Pro Lys Lys Ala Lys Gln Ala
        115                 120                 125

Ala Pro Met Met His Asp Leu Ala Ala Met Ala Ser Ala Phe Gly Gly
    130                 135                 140

Gly Asn Leu Gly Gln Met Pro Leu Pro Leu Asp Pro Ala Ala Ala
145                 150                 155                 160

Leu Gln Gln Gln Ile Leu Ser Ser Leu Gly Ala Ile Gly Leu Gly Leu
                165                 170                 175

Tyr Ala Asn Phe Thr Ala Gly Gly Ser Ala Met Thr Ala Ala Ser
            180                 185                 190

Asn Asn Ala Arg Gln Gln Leu Ala Ala Val Glu Ser Leu Leu Ser Asn
        195                 200                 205

Asn Lys Ser Asp Val Asp Ser Val Thr Asn Pro Leu Ser Ser Glu Glu
    210                 215                 220

Glu Ala His Phe Arg Ala Cys Tyr Thr Leu Ser Val Gly Ser Leu Phe
225                 230                 235                 240

Gly Leu Pro Asp Val Leu Lys Lys Glu Asp Tyr Phe Pro Lys Tyr Asp
                245                 250                 255

Val Ala Val Leu Gln Ala Ala Arg Phe Ala Glu Leu Ala Ile Gly Ala
            260                 265                 270

Leu Val Asp Gly Asn Gly Ser Lys Met Thr Lys Leu Ala Asn Ala Thr
        275                 280                 285

Val Leu Cys Leu Lys Glu Ala Ala Gln Glu Pro Val His Pro Ser Cys
    290                 295                 300

Lys Phe Asp Val Ala Arg Ala Tyr Phe Leu Ala Ile Cys Glu Leu
305                 310                 315                 320

Asn Ile Gly Asp Val Glu Gly Tyr Leu Lys Tyr Arg Arg Glu Ser Met
                325                 330                 335

Arg Arg Leu Ser Glu Met Asn Asp Ala Ser Gly Ala Asp Thr Leu Leu
            340                 345                 350

Ala Ala Met Ser Leu Gln Asp Ser Phe Val Tyr Ile Leu Tyr Lys Gly
        355                 360                 365

Leu Asp Asp Thr Leu Pro Asn Ile Asp Ser Ala
    370                 375

<210> SEQ ID NO 13
<211> LENGTH: 896
<212> TYPE: PRT
<213> ORGANISM: Thalassiosira pseudonana

<400> SEQUENCE: 13

Met Ser Thr Asp Asp Asn Asn Ile Met Pro Glu Asp Trp Gln Asn Asn
 1                5                  10                  15

Pro Pro Pro Leu Pro Gln Asp Asn Trp Gln Asn Asn Glu Gln Thr Ser
                20                  25                  30

Asn Tyr Asp Asn Gly Asn Ser Asn Gly Gly Gln Tyr Ser Thr His His
            35                  40                  45

Gln Gln Gln Pro Pro Gln Glu Gln Val Asn Arg Ala Gln Ser Ser Tyr
        50                  55                  60
```

```
Asn Asn Gln Tyr Ser Thr Ser Gln Tyr Asn Ser Asn Gln Gln Gln Glu
 65                  70                  75                  80

Gln His Tyr Gln Gln Gln Gln Gln Gln Leu Gln Leu Cys Ala
                 85                  90                  95

Ser Cys Asp Arg Cys Arg Ala Arg Lys Thr Lys Cys Asp Gly Glu Arg
            100                 105                 110

Pro Cys Gly Asn Cys Val Asn Lys Leu Lys Lys Lys Leu Lys Leu Asp
        115                 120                 125

Asn Val Asp Gly Ile Asp Ile Ala Glu Phe Asp Cys Val Tyr Ser Pro
130                 135                 140

Ala Lys Arg Arg Gly Pro Ile Pro Gly Lys Thr Gly Gln Ser Arg Lys
145                 150                 155                 160

Ser Ser Glu Met Met Tyr Gln Gln Pro Gln Gln Arg Gly Gly Gly Tyr
                165                 170                 175

Leu Gly Ser Gly Gly Gly Gly Tyr Pro Gln Gln Gln His Gly Leu
            180                 185                 190

Gln Gly Gly Gly Tyr Asn Phe Gly Gly Gln Gln Gln Gln Gln Gln
        195                 200                 205

Gln Gln Trp Ile Asn Ser Asn Asn Gln Gly Ser Gln Phe Ser Ser
210                 215                 220

Glu Glu Leu Lys Gln Met Leu Ser Leu Gln Gln Gln Leu Leu Ile Gln
225                 230                 235                 240

Gln Gln Gln Met Gln Gln Gln Gln Gln Gly Met Leu Gln Gln
                245                 250                 255

Leu Ala Thr Val Thr Ser Gly Val Gly Ser Ser Gly Ile Gly Gly Ala
            260                 265                 270

Gly Gly Ile Gly Gly Met Gly Asn Thr Asn Asn Val Gln Val Glu Asn
        275                 280                 285

Gly Ala Leu Gln Leu Leu Gln Gln Tyr Gln Gln Gln Leu Asn Ser Gly
290                 295                 300

Asn Asn Thr Leu Gly Ser Ser Gly Ser Ile Asn Met Gly Leu Gly Ser
305                 310                 315                 320

Gln Pro Ser Pro Met Pro Ser Ser Ser Tyr Asn Gln Glu Gln Gln Gln
                325                 330                 335

Gln Pro Thr Lys Arg Ala His Arg Leu Glu Pro Val Leu Ser Asn Ala
            340                 345                 350

Asn Ser Thr Asn Leu Pro Asn Ser Val Ala Ser His Leu Pro Leu Leu
        355                 360                 365

Ser Leu His Asn Pro Asp Gly Asn Val Leu Arg Ser Tyr Tyr Gln Leu
    370                 375                 380

Ser Val Asn Asp Leu Leu Asn Leu Pro Pro Ile Pro Ser Asp Glu Asp
385                 390                 395                 400

Tyr Cys Thr Ile Leu Ser Gln Asn Asn Tyr Asn Cys Leu Pro Ser Asn
                405                 410                 415

Leu Pro Thr Tyr Asp Gln Ser Ala Leu Gln Ala Ala Arg Phe Ala Glu
            420                 425                 430

Leu Ala Leu Gly Ala Leu Ala Asn Asn Gln Val Pro Leu Ala Leu Glu
        435                 440                 445

Leu Ser Asn Ala Ser Val Met Cys Met Arg Asn Cys Val Glu Glu Pro
    450                 455                 460

Ser His Lys Ser Cys Ile Tyr Asp Val Ala Arg Ala Tyr Leu Leu His
465                 470                 475                 480
```

```
Gly Ile Phe Arg Ser Phe Arg Gly Asp Phe Val Arg Tyr Phe Lys Tyr
            485                 490                 495
Arg Arg Val Cys Met Ser His Leu Ser Gln Leu Asn Asn Glu Pro Asn
        500                 505                 510
Val Glu Ala Leu Leu Ala Ala Ile Ser Tyr His Asp Ala Leu Ala Tyr
    515                 520                 525
Met Met His Asn Ala Ser Glu Asp Ala Leu Pro Asp Ile Asp Glu Val
530                 535                 540
Leu Pro Arg Leu Asn Asp Cys Gly Lys Asn Asp Ser Gly Cys Asp Ile
545                 550                 555                 560
Glu Ala Lys Tyr Gly Ile Ser Thr Asn Ala Ser Ser Val Val Thr Asn
                565                 570                 575
Ala Asn Asn Gln Met Trp Met Gln Gly Ala Pro Pro Val Phe Leu Asn
            580                 585                 590
Asn Glu Ala Ser Leu Val Asn Arg Ser Leu Asp Ala Leu Ala Cys Ala
        595                 600                 605
Val Arg Ser Cys Cys Asp Gln Ala Asn Ser Ser Phe Glu Glu Met Ala
    610                 615                 620
Lys Glu Ala Gly Val Asp Leu Pro Ala Gly Gly Ser Cys Gly Thr
625                 630                 635                 640
Ser Ala Thr Thr Gln Ala Val Met Ala Asn Glu Asn Glu Leu Cys Ser
                645                 650                 655
Arg Asn Ile Val Leu Ser Ala Gln Thr Leu Leu Ser Gln His Ala Gly
            660                 665                 670
Thr Ser His Glu Lys Ser Lys Lys His Gly Leu Val Met Val Ala Thr
        675                 680                 685
Ala Met Glu Ala Phe Leu Glu Asn Gly Gly Asp Glu Glu Gly Met
690                 695                 700
Gly Gly Phe Thr Asp Lys Gln Ile Lys Asn Leu Leu Ala Val Cys Asn
705                 710                 715                 720
Thr Ile Val Lys Asn Pro Leu Leu Leu Phe Ala Pro Gly Pro Thr Tyr
                725                 730                 735
His Met Val Ser Asn Val Ala Ile Leu Leu Cys His Leu Leu Asn Gly
            740                 745                 750
Ile His Ala Asn Cys Gly Gly Ser Gly Asn Ala Lys Ser Gly Met
        755                 760                 765
Glu Glu Val Leu Phe Asp Glu Val Leu Asp Ala Phe Met Ala Ile Arg
    770                 775                 780
Lys Leu Leu Asn Leu His Arg Lys Asn Leu Pro Val Lys Leu Arg Cys
785                 790                 795                 800
His Gly Ile Pro Arg Pro Lys Leu Gly Pro Phe Lys Lys Ser Asp Pro
                805                 810                 815
Glu Thr Pro Phe Ile Asp Leu Gly Asp Thr Leu Met Cys Val Cys Arg
            820                 825                 830
Gly Cys Gln Gly Phe Val Leu Met Gly Cys Ser Pro Cys Val Ala Ala
        835                 840                 845
Glu Arg Ser Ala Ser Ser Ala Arg Met His Ala Asn Gln Ser Glu Asp
    850                 855                 860
Asp Asp Asp Glu Phe Glu Arg Glu Leu Gly Gln Leu Asp Asp Phe Asn
865                 870                 875                 880
Leu Asp Asp Asp Ala Leu Leu Ser Leu Leu Ser Arg Ile Val Gln Asn
                885                 890                 895
```

```
<210> SEQ ID NO 14
<211> LENGTH: 689
<212> TYPE: PRT
<213> ORGANISM: Thalassiosira pseudonana

<400> SEQUENCE: 14
```

| | | | | | | | | | | | | | | |
|---|---|---|---|---|---|---|---|---|---|---|---|---|---|---|
| Met | Ser | Gln | Thr | Ser | Asn | Thr | Glu | Pro | Lys | Gly | Ala | Lys | Arg | Lys | Thr |
| 1 | | | | 5 | | | | | 10 | | | | | 15 | |

Gln Ala Cys Thr Glu Cys His Lys Ser Lys Ser Lys Cys Thr Tyr Pro
             20                   25                   30

Asp Pro Thr Thr Thr Ala Ala Gly Gly Thr Ala Lys Leu Cys Cys Asn
             35                   40                   45

Arg Cys Ile Arg Leu Gly Arg Asp Cys Ile Pro His Ile Ser Gln Gln
50                      55                   60

Gly Lys Arg Asn Lys Lys Thr Glu Glu Thr Met Lys Asn Glu Lys
65                    70                75                   80

Arg Val Asn Glu Asp Asp Met Gln Asp Gly Leu Cys Lys Ser Thr Met
             85                   90                   95

Cys Ala Ala Ala Ile Gly Asn Gln Asp Lys Ile Leu Lys Glu Asn Asn
             100                  105               110

Leu Ser Leu Glu Leu Pro Arg His Ile Thr Asn Ser Met Ala Gly Gln
             115                  120               125

Phe Pro Ala Gly Gly Gly Gly Met Met Gly Gly Gln Phe Ala Gly
             130                  135               140

Arg Ser Gly Ala Gly Ile Leu His Pro Ala Asp Ile Leu Ser Gly Gly
145                     150                   155               160

Met Asn Ser Ser Gln Leu Ser Leu Met Leu Asn His Phe Ser Gly Thr
             165                  170               175

Ser Gly Gly Gln Ser Asp Thr Met Ser Thr Leu Asn Asn Ile Met Ser
             180                  185               190

Ser Ser Ala Met Gly Ala Thr Gly Pro Pro Ser Val Asp Ala Leu
             195                  200               205

Leu Met Leu Ala Ser Arg Ser Thr Ser Ile Gly Ser Asn Ser Gly Val
             210                  215               220

Asn Leu Gly Gly Thr Ala Ser Ala Ala Pro Ala Leu Pro Gly Thr Ser
225                     230                   235               240

Gln His Leu Ile Gln Gln Trp Gln His Gln Gln Asn Gln Leu Arg Tyr
             245                  250               255

Ala Val Met Gly Gly Met Gln Thr Ala Thr Met Met Gly Met Thr Gln
             260                  265               270

Ala Ser Gly Asp Gly Ser Ala Thr Gly Asn Gln Leu Asp Ser Ala Ile
             275                  280               285

Ile Thr Lys Lys Glu Arg Thr Ser Ser Phe Gly Ser Glu Asn Asp Gln
             290                  295               300

Pro Lys Asn Lys Lys Gln Lys Ala Ile Gln Glu Ala Lys Glu Trp Cys
305                     310                   315               320

Ala Gly Gly Gly Gly Asp Asp Gln Lys Gln Ser Val Leu Glu Ala Leu
             325                  330               335

Ala Ala Ala Thr Lys Asn Glu Thr Thr Pro Lys Phe Val Pro Pro His
             340                  345               350

Ile His Tyr Pro Pro Val Ser Leu Leu Ala Glu Thr Thr Thr Thr Ala
             355                  360               365

Ile Asn Asp Asn Ala Ser Ser Ser Ala Ala Ala Ala Asp Asn Thr
370                     375                   380

```
Thr Asp Thr Gln Glu Ser Gln Leu Arg Arg Ser Ser Tyr Asn Ala Gln
385                 390                 395                 400

Phe Val Thr Pro Glu Asp Ala Ile Gly Asn His Ile Thr Gly Gln Lys
            405                 410                 415

Leu Pro Cys Leu Gln Asn His Tyr Gly Leu Gln Cys Gln Ile Arg Glu
            420                 425                 430

Trp Ile Ser Met Ala Leu Val Arg Arg Ser Phe Ala Leu Leu Ser Lys
            435                 440                 445

Ala Ser Ser Leu Ala Asn Arg Cys Gly Ile Ser Met Asp Arg Ile Phe
            450                 455                 460

Cys Gly Val Val Glu Glu Val Glu Lys Lys Gly Gly Ala Glu Lys Lys
465                 470                 475                 480

Thr Lys Gly Gly Cys Lys Met Asn Val Gly Gly Lys Met Asn Tyr Leu
            485                 490                 495

Leu Ser Val Phe Leu Glu Pro Arg Thr Ala Gln Val Val Pro Met Glu
            500                 505                 510

Gln Pro Phe Glu Arg Asn Leu Leu Cys Trp Arg His Ile Ser Gln Ile
            515                 520                 525

Phe Glu Asp Asn Leu Ala Asp Gly Phe Ser Leu Met Phe Ala Lys Glu
530                 535                 540

Asp Phe Arg Arg Phe Leu Ala Cys Tyr Ala His Gln Ile Ser Ser Gln
545                 550                 555                 560

Pro Ser Ala Glu Ser Pro Ile Arg Pro Val Tyr Ala Pro Lys Ile Thr
            565                 570                 575

Val Arg Leu Leu Ser Arg Asp Trp Gly Gln Thr Glu Ala Val Thr Glu
            580                 585                 590

Glu Met Ile Glu Gly Val Gly Lys Asn Glu Ala Glu Thr Thr Glu Met
            595                 600                 605

Asp Ala Leu Phe Val Val Pro Thr Met Asp Lys Val Thr Tyr Tyr
610                 615                 620

Leu Glu Leu Phe His Pro Asn Leu Glu Ser Asp Ala Lys Asp Cys Glu
625                 630                 635                 640

Ala Asp Asp Asn Asp Glu Gly Thr Glu Thr Pro Glu Ser Asn Pro Pro
            645                 650                 655

Ala Leu Asp Thr Val Met Glu Gly Glu Asp Trp Gln Gly Ile Asp Glu
            660                 665                 670

Ile Leu Ala Ser Gly Asp Asp Met Asp Ala Leu Met Lys Ala Leu Leu
            675                 680                 685

Asp

<210> SEQ ID NO 15
<211> LENGTH: 410
<212> TYPE: PRT
<213> ORGANISM: Fragilariopsis cylindrus

<400> SEQUENCE: 15

Met Gly Thr Ser Ala Asn Arg Ala Cys Thr Glu Cys His Lys Ala Lys
1               5                   10                  15

Val Lys Cys Val Arg Asp Asp Gly Asn Ile Ile Cys Lys Arg Cys
            20                  25                  30

Glu Arg Ile Gly Leu Lys Cys Val Glu His Ile Ser Arg Gln Gly Gln
            35                  40                  45

Gly Thr Arg Arg Arg Lys Lys Val Lys Lys Glu Thr Thr Thr Ala Thr
        50                  55                  60
```

Gly Ala Ala Asn Lys Asn Asn Glu Asp Lys Thr Val Asp Glu Ala Leu
65                  70                  75                  80

Ala Ile Thr Ile Ala Leu Ser Ser Pro Ser Pro Met Pro Ser Cys Pro
                85                  90                  95

Val Ser Gly Gly Ser Asn Ile Val Phe Ser Gly Asn Gly Asn Val Asn
            100                 105                 110

Gly Val Pro Ser Ser Ala Cys Asn Ala Leu Thr Ala Met Asn Gly Gln
        115                 120                 125

Ala Met Thr Asn Asn Lys Glu Gly Leu Cys Asn Gly Met Ala Ser Leu
    130                 135                 140

Gln Val Glu Asp Ser Ile Ile Cys Lys Ser Ile Thr Asn Gly Leu Gly
145                 150                 155                 160

Lys Glu His Tyr Gly Ile His His Leu Ile Arg Met Trp Val Ala Leu
                165                 170                 175

Ser Phe Thr Arg Arg Ser Phe Ser Leu Leu Ala Arg Ala Ser Phe Ile
                180                 185                 190

Ala Ser Arg Met Gly Ile Ser Met Asp Glu Ile Ile Ser Asn Gln Ser
            195                 200                 205

Asn Phe Ala Ile Asp Ser Gly Ser Gln Pro Met Tyr Phe Leu Gly Arg
        210                 215                 220

Asp Ile Leu Val Pro Lys Ser Gln Arg Lys Thr Ile Gly Leu Pro Leu
225                 230                 235                 240

Asn Ile Glu Glu Ile Pro Trp Asp Leu Leu Glu Ala Val Gln Ile Asp
                245                 250                 255

Pro Val Arg Pro Asp Glu Thr Phe Arg Asn Arg Trp Cys Ala Ile Arg
                260                 265                 270

Met Thr Val Gln Gly Thr Ser Arg Phe Leu Thr Ser Pro Leu Phe Ser
            275                 280                 285

Arg Asp Phe Ser Ser Val Asp Glu Ile Asn Lys Val Trp Asp Glu Asn
        290                 295                 300

Lys Pro Asn Lys Glu Val Val Asp Leu Trp Met Pro Lys Ser Glu Lys
305                 310                 315                 320

Gly Asn Ile Asn Asn Asp Asn Asn Asn Asn Asn Ser Ser Asp Arg
                325                 330                 335

Asn Ser Gln Tyr Gly Gly Thr Thr Ser Ser Ala Lys Lys Arg Asp Ile
            340                 345                 350

Ile Asp Val Ala Gly Gly Thr Ser Asn Asn Glu Ile Glu Ser Asp Val
        355                 360                 365

Cys Asp Pro Ile Met His Asp Asp Gly Ile Glu Phe Thr Asp Leu Val
370                 375                 380

Val Thr Glu Glu Met Gln Glu Phe Phe Gln Leu Leu Ala Gly Asp Gln
385                 390                 395                 400

Arg Val Gln Ala Asp Leu Asn Ser Leu Phe
                405                 410

<210> SEQ ID NO 16
<211> LENGTH: 805
<212> TYPE: PRT
<213> ORGANISM: Fragilariopsis cylindrus

<400> SEQUENCE: 16

Met Thr Thr Ser Thr Arg Leu Arg Gly Lys Arg Gly Lys Lys Asp Ser
1               5                   10                  15

Arg Asn Asp Ala Val Ala Thr Ser Asp Asn Gly Val Ala Met Thr Thr
            20                  25                  30

Ala Asn Ala Val Val Val Asn Asp Glu Lys Asn Lys Gln Asp Asn
        35                  40                  45

Tyr Asn Asn Glu Gly Asp Pro Val Glu Phe Lys Val Arg Val Glu Leu
 50                  55                  60

Glu Val Glu Ala Pro Ile Asn Glu Gln Lys Ala Val Asp Asn Asn Glu
 65                  70                  75                  80

Lys Lys Lys Ser Ser Ala Glu Thr Thr Lys Ala Glu Ala Ala Val Val
                 85                  90                  95

Asn Ser Asp Glu Asp Val Asn Asp Asp Val Asn Asp Asp Val Asn Asp
                100                 105                 110

Gly Glu Asp Asp Ala Val Val Val Lys Asn Ser Lys Glu Asn Asn
            115                 120                 125

Asp Asp Asp Asn Asp Ser Asp Thr Lys Lys Met Gln Asp Ala Thr Lys
130                 135                 140

Lys Lys Met Ala Pro His Gln Asp Asp Ala Cys Val Glu Val Val
145                 150                 155                 160

Gln Val Ser Asp Arg Pro Ser Phe Leu Gly Thr Val Leu Lys Arg
            165                 170                 175

Asp Thr Val Gly Leu Gly Leu Arg Tyr Lys Thr Glu Lys Glu Lys Glu
            180                 185                 190

Lys Val His Glu Asn Asp Ile Leu Phe Ser Ser Val Asp Leu Gly Leu
            195                 200                 205

Gln Ser Gly Ser Gly Gly Ser Ser Ser Gln Phe Leu Asn His Thr
    210                 215                 220

Asp His Ser Gly Asn Lys Lys Leu Gln Ser Ile Ile Lys Ala Arg Lys
225                 230                 235                 240

Ser Asn Tyr Phe Val Asn Asp Val Thr Asn Ile Asp Ser Cys Ser Ile
                245                 250                 255

Ala Val Asn Glu Glu Glu Arg Thr Lys Ile Ala Lys Glu Ile Phe His
            260                 265                 270

Glu Ile Thr Thr Thr Thr Thr Thr Gly Lys Asp Val Gly Ile Gly
            275                 280                 285

Val Gly Arg Phe Leu Asn Phe Lys Ser Met Thr Lys Ala Lys Tyr Glu
    290                 295                 300

Asn Leu Gly Cys Asp Phe Val Trp Glu Ile Met Asp Glu Ile Thr Ser
305                 310                 315                 320

Ile Ile Lys Ile Cys Gln Thr Met Asn Tyr Ile Phe Met Ser Asp Gln
                325                 330                 335

Glu Arg Thr Glu Arg Ser Leu Ala Ile Glu Thr Gln Gln Lys Gln Gln
            340                 345                 350

Gln Asn Asp Tyr Arg Asn Glu Arg Gln Gln Lys Asn Gly Lys Thr Leu
            355                 360                 365

Ser Ser Ser Asp Lys Lys Ser Lys Thr Lys Lys Ser Thr Lys Gln Asn
    370                 375                 380

Lys Ile Leu Leu Gln Gln Arg Gln Gln Glu Gln Arg Glu Asn
385                 390                 395                 400

Ala Gln Ile Gln Glu Gln Gln Leu Gln Gln Gln Gln Gln Gln Gln
            405                 410                 415

Gln Cys Gln Gln Val Gln Met Arg Ile Tyr Gln Leu Gln Gln Leu
            420                 425                 430

Gln Gln Gln Gln Val Tyr Tyr Pro Pro Thr Pro Leu Ile Gln Gln Tyr
    435                 440                 445

```
Pro Thr Ala Met Pro Met Pro Met Pro Leu Ser Ser Pro Ser Pro Leu
    450                 455                 460

Leu Pro Lys Asp Gly Lys Lys Lys Thr Lys Gly Glu Lys Arg Lys
465                 470                 475                 480

Ala Pro Val Pro Ala Met Ala Ser Glu Arg Ser Gly Ile Ile Glu
                485                 490                 495

Gly Arg Val Ile Val Asp Thr Ile Val Gly Gly Asp Ser Asp Glu His
                500                 505                 510

Ile Gly Asn Glu Asn Leu Val Lys Leu Ile Val Lys Lys Ser Glu
                515                 520                 525

Tyr Asp Tyr Ile Glu Val Lys Asp Ile Lys Lys Leu Gly Ile Ala Arg
530                 535                 540

Val Arg Gln Asn Val Ser Leu Asn Ile Val Lys Ser Ile Val Lys Glu
545                 550                 555                 560

Asn Gly Gly Arg Phe Leu Phe Arg Arg Lys Asp Val Asp Asp Asp
                565                 570                 575

Leu Leu Glu Thr Pro Thr Val Glu Ala Thr Ile Ala Val Ile Lys Asp
                580                 585                 590

Gly Glu Asp Ala Ile Ala Arg Ala Glu Ala Ala Leu Arg Gly Glu Lys
                595                 600                 605

Thr Pro Thr Lys Thr Ser Asn Asp Ile Glu Asp Glu Asp Glu Asp
                610                 615                 620

Asn Ile Lys Asn Glu Asp Ser Gly Pro Val Val Trp Glu Glu Leu Lys
625                 630                 635                 640

Asp Glu Ser Met Ile Gln Ala Ile Val Trp Arg Cys Met Lys Asp Ile
                645                 650                 655

Tyr Glu Leu Ala Asp Glu Asn Lys Thr Glu Ile Leu Glu Lys Arg Lys
                660                 665                 670

Glu Ala Lys Lys Glu Arg Lys Arg Leu His Glu Tyr Asp His Asp Asp
                675                 680                 685

Glu Ser Ala Gly Pro Ala Ala Ala Thr Ala Arg Lys Lys Gln Ala
                690                 695                 700

Val Glu Glu Asp Pro Ser Gly Arg Lys Asn Lys Ser Cys Asp Phe Cys
705                 710                 715                 720

Arg Asp Lys Lys Leu Lys Cys Asn Arg Thr Ser Pro Cys Glu Asn Cys
                725                 730                 735

Thr Thr Lys Tyr Met Lys Asp His Asn Leu Thr Ser Glu Glu Val Glu
                740                 745                 750

Glu Ser Lys Ile Ala Asn Ser Ile Asn Ala Val Ala Val Ala Lys
                755                 760                 765

Val Glu Glu Ala Lys Lys Leu Glu Ser Met Pro Glu Thr Lys Arg Pro
770                 775                 780

Arg Thr Arg Ser Ile Phe His Phe Leu Val Phe Leu Ile Leu Glu Cys
785                 790                 795                 800

Ser Val Pro Met Glu
            805
```

<210> SEQ ID NO 17
<211> LENGTH: 1039
<212> TYPE: PRT
<213> ORGANISM: Nannochloropsis oceanica
<220> FEATURE:
<221> NAME/KEY: misc_feature
<223> OTHER INFORMATION: ZnCys-2845 Ortholog
<220> FEATURE:
<221> NAME/KEY: misc_feature
<223> OTHER INFORMATION: Strain 5473

<400> SEQUENCE: 17

```
Met Thr Thr Leu Leu Gly Gln Pro Pro Ser Leu Gly Ala Met Gly
1               5                   10                  15

Ser Ala Phe Tyr Asp Glu Asp Ala Gln Ser Val Val Ala Leu Gly Gln
            20                  25                  30

His Ala Ala Gly Ser Gly Thr Glu Asp Glu Met Asp Thr Asp His Phe
            35                  40                  45

Asp Glu Leu Asp Arg Ile Ile Phe Asp Met Pro Tyr Val Ser Glu Gln
        50                  55                  60

Asp Pro Leu Ser Ser Cys Ser Val Gly Gly Gln Ser Gln Gly Gln Thr
65                  70                  75                  80

Asn Gly Gln Gly His Gly His Gln Glu Arg Gly Ala Ser Gln His Gly
                85                  90                  95

Gly Ala Gly Leu Leu Met Pro Asn Pro His Asn Gly His Ile His Gly
            100                 105                 110

Asp Gly Gly His His Ile Asn His Asn Asn His Gly Ser Val Arg Gly
            115                 120                 125

Gly Gly Met Asp Trp His Ala Lys Glu Glu Asp Ala Ser Tyr His Thr
        130                 135                 140

Ala Val Asp Ser Ser Cys His Thr Asp Arg Ser Tyr His Arg Val Asp
145                 150                 155                 160

Ala Ser Gly His Ser Met Ile Asp Ala Ser Ser His Ser Met Met Asp
                165                 170                 175

Ala Ser Gly His Glu Ser Leu Ile Asp Ser Ser Gly His Tyr Asp Asp
            180                 185                 190

Phe Ala Ala His Lys Gly Asp Pro Arg Tyr Met Glu His Ser Cys Glu
        195                 200                 205

Ala Cys Lys Arg Ser Lys Lys Arg Cys Asn Arg Arg Asn Pro Cys Gln
        210                 215                 220

Ile Cys Thr Ser Arg Gly Ile Lys Cys Val Pro Gln Ile Arg Gly Pro
225                 230                 235                 240

Gly Arg Pro Pro Gly Ser Lys Ser Ser Arg Gly Ser Ser Ser Ser
                245                 250                 255

Ser Leu Thr Leu Gly Ser Ser Arg His Gly Gly Ser Arg Gly Asp Val
            260                 265                 270

Arg Ser Ser Leu Asn Ser Thr Gln His Ser Thr Asn Ser Ser Ala Thr
        275                 280                 285

Thr Ser Ala Ala Ser Ser Thr Ala Ser Ser Leu Ser Arg Ser Leu Ser
    290                 295                 300

Gly Asn Gly Leu Leu Gln Gln Glu Gln Asp Leu Val Val Val Ala Ala
305                 310                 315                 320

Ala Ala Ser Thr Arg Gln Ser Pro Pro Arg Asp Pro Trp His Cys Arg
                325                 330                 335

Phe Phe Phe Glu Ala Ala Arg His Cys Lys Glu Ala Phe Leu Lys Ala
            340                 345                 350

Trp His Asp Asn Glu Leu Asp Thr Ser Lys Cys Ile Met Leu Arg Asn
        355                 360                 365

Leu Trp Thr Lys Thr Ser Ser Ile Leu Ala Ser Gly Val Asp Met Thr
    370                 375                 380

Phe Gly Ile Cys Asp Gln Leu Gln Glu Val Val Gly Pro Ala Pro Thr
385                 390                 395                 400
```

```
Gly Ser Gly Pro Ile Ala Cys Ser Pro Ala Thr Arg Ser Lys Ser Gln
                405                 410                 415

Ala Ala Gln Gln Ala Gln Leu Leu Ser His Pro Gly Ser Lys Glu Gly
            420                 425                 430

Met Gly Pro Trp Asn Leu Pro Asp Asp Leu Arg Lys Met Asp Asp Gly
            435                 440                 445

Val Ser Met Leu Cys Gly Phe Met Phe Ile Gln Asp Glu Leu Phe Val
    450                 455                 460

Phe Thr Asp Glu Arg Phe Ala Ala Thr Phe Met Thr Arg Glu Glu Val
465                 470                 475                 480

Glu Gly Lys Val Glu Ser Phe Ala Val Leu Pro Ile Leu Leu Leu Ala
                485                 490                 495

Glu Ile Phe His Pro Asp Asp Leu Pro Asp Val Tyr Ala Ala Ile Gly
            500                 505                 510

Ala His Trp Phe Arg Arg Pro Ser Ser Gly Val Gly Val Gly Gly
            515                 520                 525

Ser Asn Gly Ser Ile Ser Ser Met Asn Ser Ser Ser Gly Ser Thr Ser
    530                 535                 540

Ser Arg Asp Ser Ala Ser Pro Gly Pro Val Ser Arg Glu Val Pro Glu
545                 550                 555                 560

Ala Ala Trp Ile Cys Lys Cys Ile Asp Lys Arg Asn Thr Glu Ile Thr
                565                 570                 575

Ala Leu Val Arg Phe Arg Ser Phe Ala Ala Pro Thr Glu Gly Tyr Ala
                580                 585                 590

Gly Ala Ala Met Leu Ser Ile Leu Pro Leu Thr Arg Ser Lys Tyr Ile
                595                 600                 605

Ala Asp Pro Asp Val Gln Thr Asn Met Arg Ser Gly Val Ser Ser Arg
610                 615                 620

His His Leu Arg Asp Thr Phe Gly Ala Leu Pro Thr Ala Leu Pro Glu
625                 630                 635                 640

His Asp Asp Glu Asp Asp Asp Glu His His His Leu Val Leu Glu
            645                 650                 655

Arg Arg Gly Glu Arg Val Gly Ala Ser Gly His Gly Gln Asp Leu Leu
            660                 665                 670

Asn Glu Glu Glu Asp Asp Glu Ile Phe Leu Asp Ala His Gly Asp Asp
            675                 680                 685

Ala Met Phe Arg Pro Leu Arg Arg Gly Met Thr Val Leu Ser Ala Glu
            690                 695                 700

Thr Ser Gly Pro Gln Pro Val Pro Leu Ser Lys His Ala Ser Asp Pro
705                 710                 715                 720

Leu Pro His His Asn Glu His His Phe His Ser Gln Pro Gln His Thr
                725                 730                 735

Ser Ser His Leu Ser Ser Leu Ser Ser Met Ala Ser His Gln Thr Gly
            740                 745                 750

Val Ser Trp Gly Gly Gly Arg Ile Ser Glu Cys Leu Gly Asn Gln Asn
            755                 760                 765

Arg Ser Ala Ser Gln Phe Tyr Asn Thr Val Gln His Gln Glu Arg Pro
    770                 775                 780

Lys Arg Glu Gln Glu Glu Pro His Gln Gln Arg Glu Glu Gln Gln
785                 790                 795                 800

Gln His Arg Leu Pro Gly Asn Asn Ser Leu Asp Gly Ser Ser Ser His
            805                 810                 815

Gly Gly Ala Met Asp Gln Asp Leu Pro Thr Val Gln Leu Thr Gln Ala
```

```
                820                 825                 830

Gln Leu Phe Leu Leu Gln Gly Gly Thr Gly Ser Gly Ile Gly Leu Phe
            835                 840                 845

Lys Asp Ile Gln Gln Glu Gln Gln His Met Cys Asn Gln Ile Ser Pro
850                 855                 860

Asp Gly Val Thr Ala Ala Glu Glu Ser Ala Glu Arg Val Ala Thr Glu
865                 870                 875                 880

Leu Tyr Gly Ser Ser Pro Ser Pro Glu Pro His Leu Leu Gly His Ser
                885                 890                 895

Arg His Ser Pro Thr Gln Arg Ala Gln Gln Gln Gln Gln Gln Gln Lys
            900                 905                 910

Arg Gln Gln Glu Arg Gln Gln Glu Asp Gln Gln Glu Gln Gly His
            915                 920                 925

Gln Gln Gln Gln Gln Gln Gln Gln Gln Gly Met Val Leu Pro Leu
        930                 935                 940

Pro His Leu Pro Gly Met Val Pro Ser Leu Val Arg Thr Val Ser Ser
945                 950                 955                 960

Ser Ala Met Leu Gly Ala Arg Pro Thr Thr Ile Ser Gln Gly Lys Asp
                965                 970                 975

Glu Gly Gly Arg Gly Gly Ala Leu Ser His Ser Asn Ser Ser Thr Asp
            980                 985                 990

Leu Asp Met Ser Cys His Gly Pro Ala Asp Pro Asn Gly Tyr Gly Gly
            995                1000                1005

Leu His Trp Thr Pro Ala Pro Leu Ala Ser Phe Leu Gly Val Ser
        1010                1015                1020

Ser Trp Gly Ser Arg Arg Gly Ser Arg Lys Glu Glu Arg Ser Lys
        1025                1030                1035

Asp

<210> SEQ ID NO 18
<211> LENGTH: 364
<212> TYPE: PRT
<213> ORGANISM: Nannochloropsis granulata
<220> FEATURE:
<221> NAME/KEY: misc_feature
<223> OTHER INFORMATION: ZnCys-2845 Ortholog
<220> FEATURE:
<221> NAME/KEY: misc_feature
<223> OTHER INFORMATION: Partial sequence
<220> FEATURE:
<221> NAME/KEY: misc_feature
<222> LOCATION: (211)..(211)
<223> OTHER INFORMATION: Xaa can be any naturally occurring amino acid

<400> SEQUENCE: 18

Met Thr Thr Leu Ile Gly Gln Pro Pro Ser Leu Arg Ala Met Gly
1               5                   10                  15

Ser Ala Phe Tyr Asp Glu Asp Ala Gln Ser Val Val Ala Leu Ser Gln
            20                  25                  30

His Ala Ser Gly Ser Gly Thr Glu Asp Glu Met Asp Thr Asp His Phe
        35                  40                  45

Asp Glu Leu Asp Arg Ile Ile Phe Asp Met Pro Tyr Val Ala Asp Gln
    50                  55                  60

Asp Pro Phe Ser Ser Gly Ser Gly Gly Gln Ser Gln Gly Gln Thr
65                  70                  75                  80

Asn Gly Gln Gly His Gly His Gln Gln Arg Gly Gly Ala Ser Gln His
                85                  90                  95
```

```
Gly Gly Ala Gly Leu Leu Met Pro Thr Pro His Asn Gly His Thr His
            100                 105                 110

Gly Asp Gly His His Ser Asn His Ser Asn His Gly Ser Ala Arg
        115                 120                 125

Gly Gly Gly Ile Asp Trp His Val Lys Glu Glu Asp Ala Ser Tyr His
    130                 135                 140

Thr Ala Val Asp Ser Ser Cys His Ile Asp Arg Ser Tyr His Arg Val
145                 150                 155                 160

Asp Val Ser Gly His Ser Met Ile Asp Ala Ser Gly His Ser Met Met
                165                 170                 175

Asp Ala Ser Gly His Glu Ser Leu Ile Asp Ser Ser Gly His Tyr Asp
                180                 185                 190

Asp Phe Ala Ala His Lys Gly Asp Pro Arg Tyr Met Glu His Ser Cys
            195                 200                 205

Glu Ala Xaa Pro Cys Gln Ile Cys Thr Ser Arg Gly Ile Lys Cys Val
        210                 215                 220

Pro Gln Ile Arg Gly Pro Gly Arg Pro Gly Ser Lys Ser Ser Arg
225                 230                 235                 240

Gly Ser Ser Ser Ser Ser Leu Ala Leu Ser Ser Ser Arg His Gly
                245                 250                 255

Gly Ser Arg Gly Asp Val Arg Ser Ser Leu Asn Ser Thr Gln His Ser
            260                 265                 270

Thr Asn Ser Ser Ala Thr Thr Ser Ala Ala Ser Ser Thr Ala Ser Ser
        275                 280                 285

Leu Ser Arg Ser Leu Ser Gly Asn Gly Leu Leu Gln Gln Gln Gln Glu
        290                 295                 300

Leu Ala Ala Val Ala Ala Gly Ala Ala Arg Gln Ser Pro Pro Arg Asp
305                 310                 315                 320

Pro Trp His Cys Arg Phe Phe Glu Ala Ala Arg His Cys Lys Glu
            325                 330                 335

Ala Phe Leu Lys Ala Trp His Asp Asn Glu Leu Asp Thr Ser Lys Cys
            340                 345                 350

Ile Met Leu Arg Tyr Val Leu Thr Ser Phe Gly Asp
            355                 360

<210> SEQ ID NO 19
<211> LENGTH: 333
<212> TYPE: PRT
<213> ORGANISM: Nannochloropsis oculata
<220> FEATURE:
<221> NAME/KEY: misc_feature
<223> OTHER INFORMATION: ZnCys-2845 Ortholog
<220> FEATURE:
<221> NAME/KEY: misc_feature
<223> OTHER INFORMATION: Partial sequence
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (176)..(176)
<223> OTHER INFORMATION: Xaa can be any naturally occurring amino acid
<220> FEATURE:
<221> NAME/KEY: misc_feature
<222> LOCATION: (316)..(316)
<223> OTHER INFORMATION: Xaa can be any naturally occurring amino acid

<400> SEQUENCE: 19

Met Thr Thr Leu Leu Gly Gln Pro Pro Pro Ser Leu Arg Ala Met Gly
1               5                   10                  15
```

Ser Ala Phe Tyr Asp Glu Asp Ala Gln Ser Val Val Ala Leu Ser Gln
            20                  25                  30

His Ala Ala Gly Ser Gly Thr Glu Asp Glu Met Asp Thr Asp His Phe
        35                  40                  45

Asp Glu Leu Asp Arg Ile Ile Phe Asp Met Pro Tyr Val Ala Glu Gln
 50                  55                  60

Xaa Leu Leu Met Pro Thr Pro His Asn Gly His Thr His Gly Asp Gly
 65                  70                  75                  80

Gly Tyr His Ser Asn His Ser Asn His Gly Ser Ala Arg Gly Gly Gly
                85                  90                  95

Met Asp Trp His Val Lys Glu Glu Asp Ala Ser Tyr His Thr Ala Val
            100                 105                 110

Asp Ser Ser Cys His Ile Asp Arg Ser Tyr His Arg Val Asp Ala Ser
        115                 120                 125

Gly His Ser Met Ile Asp Ala Ser Gly His Ser Met Met Asp Ala Ser
130                 135                 140

Gly His Glu Ser Leu Ile Asp Ser Ser Gly His Tyr Asp Asp Phe Ala
145                 150                 155                 160

Ala His Lys Gly Asp Pro Arg Tyr Met Glu His Ser Cys Glu Ala Xaa
                165                 170                 175

Pro Cys Gln Ile Cys Thr Ser Arg Gly Ile Lys Cys Val Pro Gln Ile
            180                 185                 190

Arg Gly Pro Gly Arg Pro Pro Gly Ser Lys Ser Ser Arg Gly Ser Ser
        195                 200                 205

Ser Ser Ser Ser Leu Ala Leu Ser Ser Ser Arg His Gly Gly Ser Arg
    210                 215                 220

Gly Asp Val Arg Ser Ser Leu Asn Asn Thr Gln His Ser Thr Asn Ser
225                 230                 235                 240

Ser Ala Thr Thr Ser Ala Ala Ser Ser Thr Ala Ser Ser Leu Ser Arg
                245                 250                 255

Ser Leu Ser Gly Asn Gly Leu Leu Gln Gln Glu Gln Glu Leu Ala Ala
            260                 265                 270

Val Ala Ala Ala Ala Ala Ala Ala Arg Gln Ser Pro Pro Arg
        275                 280                 285

Asp Pro Trp His Cys Arg Phe Phe Glu Ala Ala Arg His Cys Lys
290                 295                 300

Glu Ala Phe Leu Lys Ala Trp His Asp Asn Glu Xaa Lys Ala Trp His
305                 310                 315                 320

Asp Asn Glu Leu Asp Thr Ser Lys Cys Ile Met Leu Arg
                325                 330

<210> SEQ ID NO 20
<211> LENGTH: 255
<212> TYPE: PRT
<213> ORGANISM: Nannochloropsis salina
<220> FEATURE:
<221> NAME/KEY: misc_feature
<223> OTHER INFORMATION: ZnCys-2845 Ortholog

<400> SEQUENCE: 20

Met Thr Thr Phe Leu Asn Pro Gly Pro Ala Arg Glu Lys Leu Val Gly
 1               5                  10                  15

Ser Gly Val Phe Phe Glu Asp Ser Ile Gly Leu Val Gly His Glu Ser
            20                  25                  30

Gly Gly Gly Val Gly Ser Gln Asp Glu Met Asp Thr Asp His Phe Asn

```
              35                  40                  45
Glu Leu Asp His Ile Phe Asp Leu Ser Tyr Ser Ala Glu Gln Asp Pro
 50                  55                  60

Phe Gly Ser Gly Ser Gly His Ala Gln Ser Gln Gly Thr Gly Tyr Gly
 65                  70                  75                  80

His Pro Pro Gln Thr Gln Leu Gly Gly Ala Gly Leu Leu Met Pro His
                 85                  90                  95

Pro His Asn Ser His Gly Ala Thr Ser His Asp Gly Ser Arg Met His
                100                 105                 110

Asn Asp Gly Met Asp Trp Arg Ala Lys Asp Glu Asp Cys Ser Tyr His
            115                 120                 125

Thr Ala Val Asp Ala Ser Cys His Ile Asp Ser Ser Tyr His His Val
        130                 135                 140

Asp Ala Ser Gly His Ser Met Val Asp Ala Ser Gly His Ser Thr Ile
145                 150                 155                 160

Asp Ala Ser Gly His Asp Ser Leu Ile Asp Ser Ser Gly His Tyr Asp
                165                 170                 175

Asp Tyr Leu Ala His Lys Gly Asp Ala Arg Tyr Met Glu His Ser Cys
            180                 185                 190

Glu Ala Cys Lys Arg Ser Lys Val Arg Arg Val Ala Thr Ser Leu Trp
        195                 200                 205

Arg Ala Gln Pro Arg Arg Tyr Phe His Ala Leu Pro His Gln Ser His
    210                 215                 220

Phe Val Leu Leu Asn Pro Lys Phe Cys Val Leu Arg Asn Ile Val Ala
225                 230                 235                 240

Cys Pro Thr Ala Pro His Ser Ser Leu Tyr Phe His Ile Pro Ser
                245                 250                 255

<210> SEQ ID NO 21
<211> LENGTH: 173
<212> TYPE: PRT
<213> ORGANISM: Nannochloropsis gaditana
<220> FEATURE:
<221> NAME/KEY: misc_feature
<223> OTHER INFORMATION: PAS3 domain of ZnCys-2845

<400> SEQUENCE: 21

Asn Leu Trp Thr Lys Val Ser Ser Gln Leu Ala Ser Gly Thr Asp Met
 1                   5                  10                  15

Thr Phe Gly Ile Cys Asp Gln Leu Gln Glu Val Val Gly Pro Ala Pro
                 20                  25                  30

Thr Gly Ser Gly Pro Met Ala Gly Ser Pro Ala Thr Arg Ser Lys Ser
             35                  40                  45

His Ala Ala Gln Gln Ala Gln Leu Leu Thr His Pro Gly Ser Lys Glu
 50                  55                  60

Ala Met Gly Pro His Cys Leu Pro Leu Asp Leu Arg Arg Met Glu Asp
 65                  70                  75                  80

Gly Val Ser Met Leu Cys Gly Phe Met Phe Leu Gln Asp Glu Leu Phe
                 85                  90                  95

Val Tyr Thr Asp Glu Arg Phe Ala Ala Thr Phe Met Thr Arg Glu Glu
                100                 105                 110

Val Glu Ser Lys Val Gly Ser Leu Ala Val Leu Pro Ile Leu Leu Leu
            115                 120                 125

Ala Glu Ile Phe His Pro Asp Asp Leu Pro Asp Ile Tyr Ala Ala Ile
        130                 135                 140
```

```
Gly Ala Tyr Trp Phe Ser Arg Arg Ser Ser Thr Ser Glu Ser Gly
145                 150                 155                 160

Ser Ser Ser Ser Ser Thr Asn Ser Ser Val Ser Ser
                165                 170

<210> SEQ ID NO 22
<211> LENGTH: 173
<212> TYPE: PRT
<213> ORGANISM: Nannochloropsis oceanica
<220> FEATURE:
<221> NAME/KEY: misc_feature
<223> OTHER INFORMATION: PAS3 domain of ZnCys-2845 ortholog
<220> FEATURE:
<221> NAME/KEY: misc_feature
<223> OTHER INFORMATION: Strain IMET1

<400> SEQUENCE: 22

Asn Leu Trp Thr Lys Thr Ser Ser Ile Leu Ala Ser Gly Val Asp Met
1               5                   10                  15

Thr Phe Gly Ile Cys Asp Gln Leu Gln Glu Val Val Gly Pro Ala Pro
                20                  25                  30

Thr Gly Ser Gly Pro Ile Ala Cys Ser Pro Ala Thr Arg Ser Lys Ser
            35                  40                  45

Gln Ala Ala Gln Gln Ala Gln Leu Leu Ser His Pro Gly Ser Lys Glu
    50                  55                  60

Gly Met Gly Pro Trp Asn Leu Pro Asp Asp Leu Arg Lys Met Asp Asp
65                  70                  75                  80

Gly Val Ser Met Leu Cys Gly Phe Met Phe Ile Gln Asp Glu Leu Phe
                85                  90                  95

Val Phe Thr Asp Glu Arg Phe Ala Ala Thr Phe Met Thr Arg Glu Glu
                100                 105                 110

Val Glu Gly Lys Val Glu Ser Phe Ala Val Leu Pro Ile Leu Leu Leu
            115                 120                 125

Ala Glu Ile Phe His Pro Asp Asp Leu Pro Asp Val Tyr Ala Ala Ile
    130                 135                 140

Gly Ala His Trp Phe Arg Arg Pro Ser Ser Gly Val Gly Val Gly
145                 150                 155                 160

Gly Ser Asn Gly Ser Ile Ser Ser Met Asn Ser Ser Ser
                165                 170

<210> SEQ ID NO 23
<211> LENGTH: 173
<212> TYPE: PRT
<213> ORGANISM: Nannochloropsis salina
<220> FEATURE:
<221> NAME/KEY: misc_feature
<223> OTHER INFORMATION: Strain CCMP
<220> FEATURE:
<221> NAME/KEY: misc_feature
<223> OTHER INFORMATION: PAS3 domain of ZnCys-2845 ortholog

<400> SEQUENCE: 23

Asn Leu Trp Thr Lys Val Ser Ser Gln Leu Ala Ser Gly Thr Asp Met
1               5                   10                  15

Thr Phe Gly Ile Cys Asp Gln Leu Gln Glu Val Val Gly Pro Ala Pro
                20                  25                  30

Thr Gly Ser Gly Pro Met Ala Gly Ser Pro Ala Thr Arg Ser Lys Ser
            35                  40                  45

His Ala Ala Gln Gln Ala Gln Leu Leu Thr His Pro Gly Ser Lys Glu
    50                  55                  60
```

```
Ala Met Gly Pro His Cys Leu Pro Leu Asp Leu Arg Arg Met Glu Asp
 65                  70                  75                  80

Gly Val Ser Met Leu Cys Gly Phe Met Phe Leu Gln Asp Glu Leu Phe
                 85                  90                  95

Val Tyr Thr Asp Glu Arg Phe Ala Ala Thr Phe Met Thr Arg Glu Glu
            100                 105                 110

Val Glu Ser Lys Val Gly Ser Leu Ala Val Leu Pro Ile Leu Leu Leu
        115                 120                 125

Ala Glu Ile Phe His Pro Asp Asp Leu Pro Asp Ile Tyr Ala Ala Ile
130                 135                 140

Gly Ala Tyr Trp Phe Ser Arg Arg Ser Ser Thr Met Ser Asp Ser Gly
145                 150                 155                 160

Ser Ser Ser Ser Ser Thr Ser Ser Ser Val Ser Ser Ala
                165                 170

<210> SEQ ID NO 24
<211> LENGTH: 173
<212> TYPE: PRT
<213> ORGANISM: Nannochloropsis oculata
<220> FEATURE:
<221> NAME/KEY: misc_feature
<223> OTHER INFORMATION: Strain CCMP525
<220> FEATURE:
<221> NAME/KEY: misc_feature
<223> OTHER INFORMATION: PAS3 domain of ZnCys-2845 ortholog

<400> SEQUENCE: 24

Asn Leu Trp Thr Lys Thr Ser Ser Val Leu Ala Ser Gly Val Asp Met
 1               5                  10                  15

Thr Phe Gly Ile Cys Glu Gln Leu Gln Glu Val Val Gly Pro Ala Pro
             20                  25                  30

Thr Gly Thr Gly Pro Ile Ala Cys Ser Pro Ala Thr Arg Ser Lys Ser
         35                  40                  45

Gln Ala Val Gln Gln Ala Gln Leu Leu Thr His Pro Gly Ser Lys Glu
     50                  55                  60

Gly Met Gly Pro Trp Asn Leu Pro Asp Asp Leu Arg Lys Met Asp Asp
 65                  70                  75                  80

Gly Val Ser Met Leu Cys Gly Phe Met Phe Ile Gln Asp Glu Leu Phe
                 85                  90                  95

Val Tyr Thr Asp Glu Arg Phe Ala Ala Thr Phe Met Thr Arg Glu Glu
            100                 105                 110

Val Glu Gly Lys Val Glu Ser Phe Ala Val Leu Pro Ile Leu Leu Leu
        115                 120                 125

Ala Glu Ile Phe His Pro Asp Asp Leu Pro Asp Val Tyr Ala Ala Ile
130                 135                 140

Gly Ala His Trp Phe Arg Arg Arg Pro Ser Ser Gly Gly Gly Val Gly
145                 150                 155                 160

Gly Ser Asn Gly Ser Ile Ser Ser Met Thr Ser Asn Gly
                165                 170

<210> SEQ ID NO 25
<211> LENGTH: 173
<212> TYPE: PRT
<213> ORGANISM: Nannochloropsis granulata
<220> FEATURE:
<221> NAME/KEY: misc_feature
<223> OTHER INFORMATION: Strain CCMP529
<220> FEATURE:
<221> NAME/KEY: misc_feature
<223> OTHER INFORMATION: PAS3 domain of ZnCys-2845 ortholog
```

<400> SEQUENCE: 25

Asn Leu Trp Thr Lys Thr Ser Ser Val Leu Ala Ser Gly Val Asp Met
1               5                   10                  15

Thr Phe Gly Ile Cys Asp Gln Leu Gln Glu Val Val Gly Pro Ala Pro
                20                  25                  30

Thr Gly Ser Gly Pro Ile Ala Cys Ser Pro Ala Thr Arg Ser Lys Ser
            35                  40                  45

Gln Ala Ala Gln Gln Ala Gln Leu Leu Ser His Pro Gly Ser Lys Glu
        50                  55                  60

Gly Met Gly Pro Trp Asn Leu Pro Asp Asp Leu Arg Lys Met Asp Asp
65                  70                  75                  80

Gly Val Ser Met Leu Cys Gly Phe Met Phe Ile Gln Asp Glu Leu Phe
                85                  90                  95

Val Tyr Thr Asp Glu Arg Phe Ala Ala Thr Phe Met Thr Arg Glu Glu
                100                 105                 110

Val Glu Gly Lys Val Glu Ser Phe Ala Val Leu Pro Ile Leu Leu Leu
                115                 120                 125

Ala Glu Ile Phe His Pro Asp Asp Leu Pro Asp Val Tyr Ala Ala Ile
                130                 135                 140

Gly Ala His Trp Phe Arg Arg Arg Pro Ser Ser Gly Val Gly Val Gly
145                 150                 155                 160

Gly Ser Asn Gly Ser Ile Ser Ser Met Asn Ser Ser Ser
                165                 170

<210> SEQ ID NO 26
<211> LENGTH: 11263
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: vector pSGE-6206

<400> SEQUENCE: 26

```
gcggccgccg tatggtcgac ggttgctcgg atggggggg cggggagcga tggagggagg      60
aagatcaggt aaggtctcga cagactagag aagcacgagt gcaggtataa gaaacagcaa     120
aaaaaagtaa tgggcccagg cctggagagg gtatttgtct tgttttctt tggccaggaa      180
cttgttctcc tttcttcgtt tctaggaccc cgatccccgc tcgcatttct ctcttcctca     240
gccgaagcgc agcggtaaag catccatttt atcccaccga aagggcgctc ccagccttcg     300
tcgagcggaa ccgggggttac agtgcctcaa ccctcccaga cgtagccaga gggaagcaac    360
tccctgatgc caaccgctgt gggctgccca tcggaatctt tgacaattgc cttgatcccc     420
gggtgcaagt caagcagcac ctgccgacat cgcccgcacg agacagaat gccgcggttt      480
tcgttcccga tggccactat gcacgtcaga tttccggcag cagccgcagc ggccgttccg     540
aggaccacga gctccgcgca tggccctccg gtgaaatgat atacattcac gccggtaaag    600
atccgaccgt cggacgagag ggctgcactg gccaccgagt agtcctcgct aataggtatg    660
ctgttgatgg tcgcagttgc acgttcgatc agcgtggatt cctcttggga taaaggcttg    720
gccatcgagc tcggtacccg gggatccatg attgttgtat tatgtaccta tgtttgtgat    780
gagacaataa atatgagaag agaacgttgc ggccactttt ttctccttcc ttcgcgtgct    840
catgttggtg gtttgggagg cagaagatgc atggagcgcc acacattcgg taggacgaaa    900
```

```
cagcctcccc cacaaaggga ccatgggtag ctaggatgac gcacaagcga gttcccgctc      960
tcgaagggaa acccaggcat ttccttcctc ttttcaagcc acttgttcac gtgtcaacac     1020
aattttggac taaaatgccc ctcggaactc ggcaggcctc cctctgctcc gttgtcctgg     1080
tcgccgagaa cgcgagaccg tgccgcatgc catcgatctg ctcgtctgta ctactaatcg     1140
tgtgcgtgtt cgtgcttgtt tcgcacgaaa ttgtcctcgt tcggccctca caacggtgga     1200
aatcggtgct agaataaagt gaggtggctt atttcaatgg cggccgtcat catgcgggat     1260
caactgaagt acggcgggtt ctcgagattt catcgtgctc gtccagagca ggtgttttgc     1320
ctgcagctct tcatgtttag gggtcatgat ttcatctgat atgccgtaag aaaaccaata     1380
ttcacttctc aattttccat ggaaaggtga aggcctaggt tgtgtgcgag caacgactg      1440 gggagggatc gcaacattct tgctaacctc ccctctatct tggccgctgt gaatcggcat     1500
atttaccggg ctgaattgag aaagtgtttt gagggaatta aaaggtggct gtcttgcaag     1560
cttggcttca gtgcctgctt aattcgaacc gatccagctt gtgatgaggc cttcctaagc     1620
ctggtagtca gaagcgacat ggcgctataa atttcgtctc agttggagag tagaaaagca     1680
tgattcgaac acggttttca actgccaaag atatctccat tgtttccttc aatctgtaca     1740
cctgcacggt gcaccagttg gtacggcata ttatggttta ataagcatac atcatatgaa     1800
tacaattcag cttaaattta tcatacaaag atgtaagtgc agcgtgggtc tgtaacgatc     1860
gggcgtaatt taagataatg cgagggaccg gggagggttt tggaacggaa tgaggaatgg     1920
gtcatggccc ataataataa tatgggtttg gtcgcctcgc acagcaaccg tacgtgcgaa     1980
aaaggaacag atccatttaa taagttgaac gttattcttt cctatgcaat gcgtgtatcg     2040
gaggcgagag caagtcatag gtggctgcgc acaataattg agtctcagct gagcgccgtc     2100
cgcgggtggt gtgagtggtc atcctcctcc cggcctatcg ctcacatcgc ctctcaatgg     2160
tggtggtggg gcctgatatg acctcaatgc cgacccatat taaaacccag taaagcattc     2220
accaacgaac gaggggctct tttgtgtgtg ttttgagtat gattttacac ctctttgtgc     2280
atctctctgg tcttccttgg ttcccgtagt ttgggcatca tcactcacgc ttccctcgac     2340
cttcgttctt cctttacaac cccgacacag gtcagagttg gagtaatcaa aaaagggtg      2400 cacgaatgag atacattaga ttttgacaga tatcctttta ctggagaggg ttcaagggat     2460
caaatgaaca gcgggcgttg gcaatctagg gagggatcgg aggttggcag cgagcgaaag     2520
cgtgtccatc cttttggctg tcacacctca cgaaccaact gttagcaggc cagcacagat     2580
gacatacgag aatctttatt atatcgtaga ccttatgtgg atgaccttg gtgctgtgtg      2640 tctggcaatg aacctgaagg cttgataggg aggtggctcc cgtaaaccct tgtcctttc      2700 cacgctgagt ctcccccgca ctgtccttta tacaaattgt tacagtcatc tgcaggcggt     2760
ttttctttgg caggcaaaga tgcccaagaa aaagcggaag gtcggcgact acaaggatga     2820
cgatgacaag ttgagcctg gagagaagcc ctacaaatgc cctgagtgcg gaaagagctt      2880
cagccaatct ggagccttga cccggcatca acgaacgcat acacgagaca gaagtactc      2940 catcgggctg gacatcggga cgaactccgt gggatgggcc gtgatcacag acgaatacaa     3000
ggtgccttcc aagaagttca ggtgctggg gaacacggac agacactcca tcaagaagaa      3060
cctcatcggg gccttgctct tcgactccgg agaaaccgcc gaagcaacgc gattgaaaag     3120
aaccgccaga agacgataca cacgacggaa gaaccgcatc tgctacctcc aggagatctt     3180
cagcaacgag atgccaaagg tggacgactc gttctttcat cgcctggagg agagcttcct     3240
ggtggaggaa gacaagaaac atgagcgcca cccgatcttc gggaacatcg tggacgaagt     3300
```

```
ggcctaccac gagaaatacc ccacgatcta ccacttgcgc aagaaactcg tggactccac    3360
ggacaaagcg gacttgcggt tgatctactt ggccttggcc cacatgatca aatttcgggg    3420
ccacttcctg atcgagggcg acttgaatcc cgacaattcc gacgtggaca agctcttcat    3480
ccagctggtg cagacctaca accagctctt cgaggagaac cccatcaatg cctccggagt    3540
ggacgccaaa gccatcttgt ccgcccgatt gtccaaatcc agacgcttgg agaacttgat    3600
cgcacaactt cctggcgaga agaagaacgg cctcttcggc aacttgatcg cgctgtcgct    3660
gggattgacg cctaacttca agtccaactt cgacttggcc gaggacgcca agttgcaact    3720
gtccaaggac acctacgacg acgacctcga caacctgctg gcccaaattg gcgaccaata    3780
cgcggacttg ttttttggcgg ccaagaactt gagcgacgcc atcttgttga gcgacatctt    3840
gcgcgtgaat acggagatca ccaaagcccc tttgtccgcc tctatgatca agcggtacga    3900
cgagcaccac caagacttga ccctgttgaa agccctcgtg cggcaacaat gcccgagaa     3960 gtacaaggag atcttcttcg accagtccaa gaacgggtac gccggctaca tcgacggagg    4020
agcctcccaa gaagagttct acaagttcat caagcccatc ctggagaaga tggacggcac    4080
cgaggagttg ctcgtgaagc tgaaccgcga agacttgttg cgaaaacagc ggacgttcga    4140
caatggcagc atcccccacc aaatccattt gggagagttg cacgccatct gccgacggca    4200
agaggacttc tacccgttcc tgaaggacaa ccgcgagaaa atcgagaaga tcctgacgtt    4260
cagaatcccc tactacgtgg gaccctggc ccgaggcaat tcccggtttg catgatgac     4320 gcgcaaaagc gaagagacga tcaccccctg gaacttcgaa gaagtggtcg acaaaggagc    4380
atccgcacag agcttcatcg agcgaatgac gaacttcgac aagaacctgc ccaacgagaa    4440
ggtgttgccc aagcattcgc tgctgtacga gtacttcacg gtgtacaacg agctgaccaa    4500
ggtgaagtac gtgaccgagg gcatgcgcaa acccgcgttc ctgtcgggag agcaaaagaa    4560
ggccattgtg gacctgctgt tcaagaccaa ccggaaggtg accgtgaaac agctgaaaga    4620
ggactacttc aagaagatcg agtgcttcga ctccgtggag atctccggcg tggaggaccg    4680
attcaatgcc tccttgggaa cctaccatga cctcctgaag atcatcaagg acaaggactt    4740
cctggacaac gaggagaacg aggacatcct ggaggacatc gtgctgaccc tgaccctgtt    4800
cgaggaccga gagatgatcg aggaacggtt gaaaacgtac gcccacttgt tcgacgacaa    4860
ggtgatgaag cagctgaaac gccgccgcta caccggatgg ggacgattga ccgcaaact    4920 gattaatgga attcgcgaca agcaatccgg aaagaccatc ctggacttcc tgaagtccga    4980
cgggttcgcc aaccgcaact tcatgcagct catccacgac gactccttga ccttcaagga    5040
ggacatccag aaggcccaag tgtccggaca aggagactcc ttgcacgagc acatcgccaa    5100
tttggccgga tccccgcaa tcaaaaaagg catcttgcaa accgtgaaag tggtcgacga    5160
actggtgaag gtgatgggac ggcacaagcc cgagaacatc gtgatcgaaa tggcccgcga    5220
gaaccaaacc acccaaaaag acagaagaa ctcccgagag cgcatgaagc ggatcgaaga    5280
gggcatcaag gagttgggct cccagatcct gaaggagcat cccgtggaga taccccaatt    5340
gcaaaacgag aagctctacc tctactacct ccagaacggg cgggacatgt acgtcgacca    5400
agagctggac atcaaccgcc tctccgacta cgatgtggat catattgtgc cccagagctt    5460
cctcaaggac gacagcatcg acaacaaggt cctgacgcgc agcgacaaga accggggcaa    5520
gtctgacaat gtgccttccg aagaagtcgt gaagaagatg aagaactact ggcggcagct    5580
gctcaacgcc aagctcatca cccaacggaa gttcgacaac ctgaccaagg ccgagagagg    5640
```

```
aggattgtcc gagttggaca aagccggctt cattaaacgc caactcgtgg agacccgcca    5700
gatcacgaag cacgtggccc aaatcttgga ctcccggatg aacacgaaat acgacgagaa    5760
tgacaagctg atccgcgagg tgaaggtgat cacgctgaag tccaagctgg tgagcgactt    5820
ccggaaggac ttccagttct acaaggtgcg ggagatcaac aactaccatc acgcccatga    5880
cgcctacctg aacgccgtgg tcggaaccgc cctgatcaag aaatacccca agctggagtc    5940
cgaattcgtg tacggagatt acaaggtcta cgacgtgcgg aagatgatcg cgaagtccga    6000
gcaggagatc ggcaaagcca ccgccaagta cttcttttac tccaacatca tgaacttctt    6060
caagaccgag atcacgctcg ccaacggcga gatccgcaag cgccccctga tcgagaccaa    6120
cggcgagacg ggagagattg tgtgggacaa aggaagagat tttgccacag tgcgcaaggt    6180
gctgtccatg cctcaggtga acatcgtgaa gaagaccgag gtgcaaacag agggttttc    6240 caaagagtcc attttgccta agaggaattc cgacaagctc atcgcccgca agaaggactg    6300
ggaccccaag aagtacgggg gcttcgactc ccccacggtg gcctactccg tgttggtggt    6360
ggccaaagtg gagaaaggga agagcaagaa gctgaaatcc gtgaaggagt tgctcggaat    6420
cacgatcatg gaacgatcgt cgttcgagaa aaaccccatc gacttcctcg aagccaaagg    6480
gtacaaagag gtgaagaagg acctgatcat caagctgccc aagtactccc tgttcgagct    6540
ggagaacggc cgcaagcgga tgctggcctc cgccggggaa ctgcagaaag gaacgaatt    6600 ggccttgccc tccaaatacg tgaacttcct ctacttggcc tcccattacg aaaagctcaa    6660
aggatcccct gaggacaatg agcagaagca actcttcgtg gaacaacaca agcactacct    6720
ggacgagatc atcgagcaga tcagcgagtt ctccaagcgc gtgatcctcg ccgacgccaa    6780
cctggacaag gtgctctccg cctacaacaa gcaccgcgac aagcctatcc gcgagcaagc    6840
cgagaatatc attcacctgt ttaccctgac gaatttggga gcccctgccg cctttaaata    6900
ctttgacacc accatcgacc gcaaaagata cacctccacc aaggaagtct ggacgccac    6960 cctcatccac cagtccatca cgggcctcta cgagacgcgc atcgacctct cccaattggg    7020
cggcgactaa agtgatgcgg cctttaggaa acaccacaaa agtaattgac aatctcagga    7080
acgatctgcg tgtttacagc ttcccaaata acaattatac cacgtaccaa aaggggttta    7140
atgtatctca caaattcttc taataggtac agcttctcaa attgggtgta tgatgtgaca    7200
cttcgtctca cacgtcac gataattcag cgtatggctt cccttcatca cattcacgca    7260
aacttctaca caaccctggg catatttctt gtgttggcaa cactcccgaa atcgattctg    7320
cacacaatgg ttcattcaat gattcaagta cgttttagac ggactaggca gtttaattaa    7380
aaacatctat cctccagatc accagggcca gtgaggccgg cataaaggac ggcaaggaaa    7440
gaaaagaaag aaagaaaagg acacttatag catagtttga agttataagt agtcgcaatc    7500
tgtgtgcagc cgacagatgc tttttttttc cgtttggcag gaggtgtagg gatgtcgaag    7560
accagtccag ctagtatcta tcctacaagt caatcatgct gcgacaaaaa tttctcgcac    7620
gaggcctctc gataaacaaa actttaaaag cacacttcat tgtcatgcag agtaataact    7680
cttccgcgtc gatcaattta tcaatctcta tcatttccgc cccttttcctt gcatagagca    7740 agaaaagcga cccggatgag gataaacatgt cctgcgccag tagtgtggca ttgcctgtct    7800
ctcatttaca cgtactgaaa gcataatgca cgcgcatacc aatatttttc gtgtacggag    7860
atgaagagac gcgacacgta agatcacgag aaggcgagca cggttgccaa tggcagacgc    7920
gctagtctcc attatcgcgt tgttcggtag cttgctgcat gtcttcagtg gcactatatc    7980
cactctgcct cgtcttctac acgagggcca catcggtgca agttcgaaaa atcatatctc    8040
```

```
aatcttcaga tcctttccag aaacggtgct caggcgggaa agtgaaggtt ttctactcta    8100
gtggctaccc caattctctc cgactgtcgc agacggtcct tcgttgcgca cgcaccgcgc    8160
actacctctg aaattcgaca accgaagttc aattttacat ctaacttctt tcccattctc    8220
tcaccaaaag cctagcttac atgttggaga gcgacgagag cggcctgccc gccatggaga    8280
tcgagtgccg catcaccggc accctgaacg gcgtggagtt cgagctggtg ggcggcggag    8340
agggcacccc cgagcagggc cgcatgacca acaagatgaa gagcaccaaa ggcgccctga    8400
ccttcagccc ctacctgctg agccacgtga tgggctacgg cttctaccac ttcggcacct    8460
accccagcgc ctacgagaac cccttcctgc acgccatcaa caacggcggc tacaccaaca    8520
cccgcatcga gaagtacgag gacggcggcg tgctgcacgt gagcttcagc taccgctacg    8580
aggccggccg cgtgatcggc gacttcaagg tgatgggcac cggcttcccc gaggacagcg    8640
tgatcttcac cgacaagatc atccgcagca acgccaccgt ggagcacctg cacccatgg     8700
gcgataacga tctggatggc agcttcaccc gcaccttcag cctgcgcgac ggcggctact    8760
acagctccgt ggtggacagc cacatgcact tcaagagcgc catccacccc agcatcctgc    8820
agaacggggg ccccatgttc gccttccgcc gcgtggagga ggatcacagc aacaccgagc    8880
tgggcatcgt ggagtaccag cacgccttca agaccccgga tgcagatgcc ggtgaagaat    8940
aagggtggga aggagtcggg gagggtcctg gcagagcggc gtcctcatga tgtgttggag    9000
acctggagag tcgagagctt cctcgtcacc tgattgtcat gtgtgtatag gttaaggggg    9060
cccactcaaa gccataaaga cgaacacaaa cactaatctc aacaaagtct actagcatgc    9120
cgtctgtcca tctttatttc ctggcgcgcc tatgcttgta aaccgttttg tgaaaaaatt    9180
tttaaaataa aaaaggggac ctctagggtc cccaattaat tagtaatata atctattaaa    9240
ggtcattcaa aaggtcatcc agacgaaagg gcctcgtgat acgcctattt ttataggtta    9300
atgtcatgat aataatggtt cttagacgt caggtggcac ttttcgggga aatgtgcgcg     9360
gaaccctat ttgtttattt ttctaaatac attcaaatat gtatccgctc atgagacaat     9420
aaccctgata aatgcttcaa taatattgaa aaaggaagag tatgagtatt caacatttcc    9480
gtgtcgccct tattcccttt tttgcggcat tttgccttcc tgttttgct cacccagaaa     9540
cgctggtgaa agtaaaagat gctgaagatc agttgggtgc acgagtggg tacatcgaac      9600
tggatctcaa cagcggtaag atccttgaga gttttcgccc cgaagaacgt tttccaatga    9660
tgagcacttt taaagttctg ctatgtggcg cggtattatc ccgtattgac gccgggcaag    9720
agcaactcgg tcgccgcata cactattctc agaatgactt ggttgagtac tcaccagtca    9780
cagaaaagca tcttacggat ggcatgacag taagagaatt atgcagtgct gccataacca    9840
tgagtgataa cactgcggcc aacttacttc tgacaacgat cggaggaccg aaggagctaa    9900
ccgcttttt gcacaacatg gggatcatg taactcgcct tgatcgttgg aaccggagc       9960
tgaatgaagc cataccaaac gacgagcgtg acaccacgat gcctgtagca atggcaacaa    10020
cgttgcgcaa actattaact ggcgaactac ttactctagc ttcccggcaa caattaatag    10080
actggatgga ggcggataaa gttgcaggac cacttctgcg ctcggccctt ccggctggct    10140
ggtttattgc tgataaatct ggagccggtg agcgtgggtc tcgcggtatc attgcagcac    10200
tggggccaga tggtaagccc tcccgtatcg tagttatcta cacgacgggg agtcaggcaa    10260
ctatggatga acgaaataga cagatcgctg agataggtgc ctcactgatt aagcattggt    10320
aactgtcaga ccaagtttac tcatatatac tttagattga tttaaaactt catttttaat    10380
```

| | |
|---|---|
| ttaaaaggat ctaggtgaag atcctttttg ataatctcat gaccaaaatc ccttaacgtg | 10440 |
| agttttcgtt ccactgagcg tcagaccccg tagaaaagat caaaggatct tcttgagatc | 10500 |
| ctttttttct gcgcgtaatc tgctgcttgc aaacaaaaaa accaccgcta ccagcggtgg | 10560 |
| tttgtttgcc ggatcaagag ctaccaactc tttttccgaa ggtaactggc ttcagcagag | 10620 |
| cgcagatacc aaatactgtc cttctagtgt agccgtagtt aggccaccac ttcaagaact | 10680 |
| ctgtagcacc gcctacatac ctcgctctgc taatcctgtt accagtggct gctgccagtg | 10740 |
| gcgataagtc gtgtcttacc gggttggact caagacgata gttaccggat aaggcgcagc | 10800 |
| ggtcgggctg aacggggggt tcgtgcacac agcccagctt ggagcgaacg acctacaccg | 10860 |
| aactgagata cctacagcgt gagctatgag aaagcgccac gcttcccgaa gggagaaagg | 10920 |
| cggacaggta tccggtaagc ggcagggtcg aacaggaga cgcacgagg gagcttccag | 10980 |
| ggggaaacgc ctggtatctt tatagtcctg tcgggtttcg ccacctctga cttgagcgtc | 11040 |
| gatttttgtg atgctcgtca ggggggcgga gcctatggaa aaacgccagc aacgcggcct | 11100 |
| ttttacggtt cctggccttt tgctggcctt ttgctcacat gttctttcct gcgttatccc | 11160 |
| ctgattctgt ggataaccgt attaccgcct ttgagtgagc tgataccgct cgccgcagcc | 11220 |
| gaacgaccga gcgcagcgag tcagtgagcg aggaagcgga aga | 11263 |

<210> SEQ ID NO 27
<211> LENGTH: 4101
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Cas9 from S. pyogenes codon optimized for
      Nannochloropsis

<400> SEQUENCE: 27

| | |
|---|---|
| gacaagaagt actccatcgg gctggacatc gggacgaact ccgtgggatg ggccgtgatc | 60 |
| acagacgaat acaaggtgcc ttccaagaag ttcaaggtgc tggggaacac ggacagacac | 120 |
| tccatcaaga gaaccctcat cggggccttg ctcttcgact ccggagaaac cgccgaagca | 180 |
| acgcgattga aagaaccgc cagaagacga tacacacgac ggaagaaccg catctgctac | 240 |
| ctccaggaga tcttcagcaa cgagatggcc aaggtggacg actcgttctt tcatcgcctg | 300 |
| gaggagagct tcctggtgga ggaagacaag aaacatgagc gccacccgat cttcgggaac | 360 |
| atcgtggacg aagtggccta ccacgagaaa taccccacga tctaccactt cgcaagaaa | 420 |
| ctcgtggact ccacggacaa agcggacttg cggttgatct acttggcctt ggcccacatg | 480 |
| atcaaatttc ggggccactt cctgatcgag ggcgacttga atcccgacaa ttccgacgtg | 540 |
| gacaagctct tcatccagct ggtgcagacc tacaaccagc tcttcgagga acccccatc | 600 |
| aatgcctccg gagtggacgc caaagccatc ttgtccgccc gattgtccaa atccagacgc | 660 |
| ttggagaact tgatcgcaca acttcctggc gagaagaaga acggcctctt cggcaacttg | 720 |
| atcgcgctgt cgctgggatt gacgcctaac ttcaagtcca acttcgactt ggccgaggac | 780 |
| gccaagttgc aactgtccaa ggacacctac gacgacgacc tcgacaacct gctggcccaa | 840 |
| attggcgacc aatacgcgga cttgttttg gcggccaaga acttgagcga cgccatcttg | 900 |
| ttgagcgaca tcttcgcgt gaatacggag atcaccaaag ccccttttgtc cgcctctatg | 960 |
| atcaagcggt acgacgagca ccaccaagac ttgaccctgt tgaaagccct cgtgcggcaa | 1020 |
| caattgcccg agaagtacaa ggagatcttc ttcgaccagt ccaagaacgg gtacgccggc | 1080 |

```
tacatcgacg gaggagcctc ccaagaagag ttctacaagt tcatcaagcc catcctggag    1140
aagatggacg gcaccgagga gttgctcgtg aagctgaacc gcgaagactt gttgcgaaaa    1200
cagcggacgt tcgacaatgg cagcatcccc caccaaatcc atttgggaga gttgcacgcc    1260
atcttgcgac ggcaagagga cttctacccg ttcctgaagg acaaccgcga gaaaatcgag    1320
aagatcctga cgttcagaat cccctactac gtgggaccct tggcccgagg caattcccgg    1380
tttgcatgga tgacgcgcaa aagcgaagag acgatcaccc cctggaactt cgaagaagtg    1440
gtcgacaaag gagcatccgc acagagcttc atcgagcgaa tgacgaactt cgacaagaac    1500
ctgcccaacg agaaggtgtt gcccaagcat tcgctgctgt acgagtactt cacggtgtac    1560
aacgagctga ccaaggtgaa gtacgtgacc gagggcatgc gcaaaccgc gttcctgtcg    1620 ggagagcaaa agaaggccat tgtggacctg ctgttcaaga ccaaccggaa ggtgaccgtg    1680
aaacagctga agaggactc cttcaagaag atcgagtgct tcgactccgt ggagatctcc    1740
ggcgtggagg accgattcaa tgcctccttg ggaacctacc atgacctcct gaagatcatc    1800
aaggacaagg acttcctgga caacgaggag aacgaggaca tcctggagga catcgtgctg    1860
accctgaccc tgttcgagga ccgagagatg atcgaggaac ggttgaaaac gtacgcccac    1920
ttgttcgacg acaaggtgat gaagcagctg aaacgccgcc gctacaccgg atggggacga    1980
ttgagccgca aactgattaa tggaattcgc gacaagcaat ccggaaagac catcctggac    2040
ttcctgaagt ccgacgggtt cgccaaccgc aacttcatgc agctcatcca cgacgactcc    2100
ttgaccttca aggaggacat ccagaaggcc caagtgtccg acaaggaga ctccttgcac    2160 gagcacatcg ccaatttggc cggatccccc gcaatcaaaa aaggcatctt gcaaaccgtg    2220
aaagtggtcg acgaactggt gaaggtgatg ggacggcaca gcccgagaa catcgtgatc    2280 gaaatggccc gcgagaacca aaccacccaa aaaggacaga agaactcccg agagcgcatg    2340
aagcggatcg aagagggcat caaggagttg ggctcccaga tcctgaagga gcatcccgtg    2400
gagaataccc aattgcaaaa cgagaagctc tacctctact acctccagaa cgggcgggac    2460
atgtacgtcg accaagagct ggacatcaac cgcctctccg actacgatgt ggatcatatt    2520
gtgccccaga gcttcctcaa ggacgacagc atcgacaaca aggtcctgac gcgcagcgac    2580
aagaaccggg gcaagtctga caatgtgcct tccgaagaag tcgtgaagaa gatgaagaac    2640
tactggcggc agctgctcaa cgccaagctc atcacccaac ggaagttcga caacctgacc    2700
aaggccgaga gaggaggatt gtccgagttg acaaagccg gcttcattaa cgccaactc    2760 gtggagaccc gccagatcac gaagcacgtg gcccaaatct tggactcccg gatgaacacg    2820
aaatacgacg agaatgacaa gctgatccgc gaggtgaagg tgatcacgct gaagtccaag    2880
ctggtgagcg acttccggaa ggacttccag ttctacaagg tgcgggagat caacaactac    2940
catcacgccc atgacgccta cctgaacgcc gtggtcggaa ccgccctgat caagaaatac    3000
cccaagctga gtccgaattc gtgtacgga gattacaagg tctacgacgt gcggaagatg    3060
atcgcgaagt ccgagcagga gatcggcaaa gccaccgcca agtacttctt ttactccaac    3120
atcatgaact tcttcaagac cgagatcacg ctcgccaacg gcgagatccg caagcgcccc    3180
ctgatcgaga ccaacggcga gacgggagag attgtgtggg acaaaggaag agattttgcc    3240
acagtgcgca aggtgctgtc catgcctcag gtgaacatcg tgaagaagac cgaggtgcaa    3300
acaggagggt tttccaaaga gtccattttg cctaaggaga ttccgacaa gctcatcgcc    3360 cgcaagaagg actgggaccc caagaagtac ggggcttcg actcccccac ggtggcctac    3420
```

```
tccgtgttgg tggtggccaa agtggagaaa gggaagagca agaagctgaa atccgtgaag    3480
gagttgctcg gaatcacgat catggaacga tcgtcgttcg agaaaaaccc catcgacttc    3540
ctcgaagcca aagggtacaa agaggtgaag aaggacctga tcatcaagct gcccaagtac    3600
tccctgttcg agctggagaa cggccgcaag cggatgctgg cctccgccgg ggaactgcag    3660
aaagggaacg aattggcctt gccctccaaa tacgtgaact tcctctactt ggcctcccat    3720
tacgaaaagc tcaaaggatc ccctgaggac aatgagcaga agcaactctt cgtgaacaa    3780 cacaagcact acctggacga gatcatcgag cagatcagcg agttctccaa gcgcgtgatc    3840
ctcgccgacg ccaacctgga caaggtgctc tccgcctaca caagcaccg cgacaagcct    3900 atccgcgagc aagccgagaa tatcattcac ctgtttaccc tgacgaattt gggagcccct    3960
gccgccttta aatactttga caccaccatc gaccgcaaaa gatacacctc caccaaggaa    4020
gtcttggacg ccaccctcat ccaccagtcc atcacgggcc tctacgagac gcgcatcgac    4080
ctctcccaat gggcggcga c                                               4101

<210> SEQ ID NO 28
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes FLAG tag

<400> SEQUENCE: 28
gactacaagg atgacgatga caag                                             24

<210> SEQ ID NO 29
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes NLS

<400> SEQUENCE: 29
cccaagaaaa agcggaaggt cggc                                             24

<210> SEQ ID NO 30
<211> LENGTH: 147
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes peptide linker

<400> SEQUENCE: 30
atgcccaaga aaagcggaa ggtcggcgac tacaaggatg acgatgacaa gttggagcct      60
ggagagaagc cctacaaatg ccctgagtgc ggaaagagct cagccaatc tggagccttg     120 acccggcatc aacgaacgca tacacga                                         147

<210> SEQ ID NO 31
<211> LENGTH: 1000
<212> TYPE: DNA
<213> ORGANISM: Nannochloropsis gaditana
<220> FEATURE:
```

<221> NAME/KEY: misc_feature
<223> OTHER INFORMATION: RPL24 promoter

<400> SEQUENCE: 31

```
aataagcata catcatatga atacaattca gcttaaattt atcatacaaa gatgtaagtg      60
cagcgtgggt ctgtaacgat cgggcgtaat ttaagataat gcgagggacc gggggaggtt     120
ttggaacgga atgaggaatg ggtcatggcc cataataata atatgggttt ggtcgcctcg     180
cacagcaacc gtacgtgcga aaaggaaca gatccattta ataagttgaa cgttattctt      240
tcctatgcaa tgcgtgtatc ggaggcgaga gcaagtcata ggtggctgcg cacaataatt     300
gagtctcagc tgagcgccgt ccgcgggtgg tgtgagtggt catcctcctc ccggcctatc     360
gctcacatcg cctctcaatg gtggtggtgg ggcctgatat gacctcaatg ccgacccata    420
ttaaaaccca gtaaagcatt caccaacgaa cgaggggctc ttttgtgtgt gttttgagta    480
tgattttaca cctctttgtg catctctctg gtcttccttg gttcccgtag tttgggcatc    540
atcactcacg cttccctcga ccttcgttct tcctttacaa ccccgacaca ggtcagagtt    600
ggagtaatca aaaaggggt gcacgaatga gatacattag attttgacag atatccttt     660
actggagagg gttcaaggga tcaaatgaac agcgggcgtt ggcaatctag ggagggatcg    720
gaggttggca gcgagcgaaa gcgtgtccat ccttttggct gtcacacctc acgaaccaac    780
tgttagcagg ccagcacaga tgacatacga gaatctttat tatatcgtag accttatgtg    840
gatgaccttt ggtgctgtgt gtctggcaat gaacctgaag gcttgatagg gaggtggctc    900
ccgtaaaccc tttgtccttt ccacgctgag tctcccccgc actgtccttt atacaaattg    960
ttacagtcat ctgcaggcgg tttttctttg gcaggcaaag                          1000
```

<210> SEQ ID NO 32
<211> LENGTH: 317
<212> TYPE: DNA
<213> ORGANISM: Nannochloropsis gaditana
<220> FEATURE:
<221> NAME/KEY: misc_feature
<223> OTHER INFORMATION: bidirectional terminator 2

<400> SEQUENCE: 32

```
agtgatgcgg cctttaggaa acaccacaaa agtaattgac aatctcagga acgatctgcg     60
tgtttacagc ttcccaaata acaattatac cacgtaccaa aagggttta atgtatctca    120
caaattcttc taataggtac agcttctcaa attgggtgta tgatgtgaca cttcgtctca    180
cacacgtcac gataattcag cgtatggctt cccttcatca cattcacgca aacttctaca    240
caaccctggg catatttctt gtgttggcaa cactcccgaa atcgattctg cacacaatgg    300
ttcattcaat gattcaa                                                   317
```

<210> SEQ ID NO 33
<211> LENGTH: 399
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: blast gene from Aspergillus terreus codon
      optimized for N. gaditana

<400> SEQUENCE: 33

```
atggccaagc ctttatccca agaggaatcc acgctgatcg aacgtgcaac tgcgaccatc     60
aacagcatac ctattagcga ggactactcg gtggccagtg cagccctctc gtccgacggt    120
```

| | |
|---|---:|
| cggatcttta ccggcgtgaa tgtatatcat ttcaccggag ggccatgcgc ggagctcgtg | 180 |
| gtcctcggaa cggccgctgc ggctgctgcc ggaaatctga cgtgcatagt ggccatcggg | 240 |
| aacgaaaacc gcggcattct gtctccgtgc gggcgatgtc ggcaggtgct gcttgacttg | 300 |
| cacccgggga tcaaggcaat tgtcaaagat tccgatgggc agcccacagc ggttggcatc | 360 |
| agggagttgc ttccctctgg ctacgtctgg gagggttga | 399 |

<210> SEQ ID NO 34
<211> LENGTH: 999
<212> TYPE: DNA
<213> ORGANISM: Nannochloropsis gaditana
<220> FEATURE:
<221> NAME/KEY: misc_feature
<223> OTHER INFORMATION: TCTP promoter

<400> SEQUENCE: 34

| | |
|---|---:|
| cgtgcaggtg tacagattga aggaaacaat ggagatatct ttggcagttg aaaaccgtgt | 60 |
| tcgaatcatg cttttctact ctccaactga gacgaaattt atagcgccat gtcgcttctg | 120 |
| actaccaggc ttaggaaggc ctcatcacaa gctggatcgg ttcgaattaa gcaggcactg | 180 |
| aagccaagct tgcaagacag ccaccttta attccctcaa aacactttct caattcagcc | 240 |
| cggtaaatat gccgattcac agcggccaag atagagggga ggttagcaag aatgttgcga | 300 |
| tccctcccca gtcgttgcct cgcacacaac ctaggcettc accttccat ggaaaattga | 360 |
| gaagtgaata ttggttttct tacggcatat cagatgaaat catgacccct aaacatgaag | 420 |
| agctgcaggc aaaacacctg ctctggacga gcacgatgaa atctcgagaa cccgccgtac | 480 |
| ttcagttgat cccgcatgat gacggccgcc attgaaataa gccacctcac tttattctag | 540 |
| caccgatttc caccgttgtg agggccgaac gaggacaatt tcgtgcgaaa caagcacgaa | 600 |
| cacgcacacg attagtagta cagacgagca gatcgatggc atgcggcacg gtctcgcgtt | 660 |
| ctcggcgacc aggacaacgg agcagaggga ggcctgccga gttccgaggg gcattttagt | 720 |
| ccaaaattgt gttgacacgt gaacaagtgg cttgaaaaga ggaaggaaat gcctgggttt | 780 |
| cccttcgaga gcgggaactc gcttgtgcgt catcctagct acccatggtc cctttgtggg | 840 |
| ggaggctgtt tcgtcctacc gaatgtgtgg cgctccatgc atcttctgcc tcccaaacca | 900 |
| ccaacatgag cacgcgaagg aaggagaaaa aagtggccgc aacgttctct tctcatattt | 960 |
| attgtctcat cacaaacata ggtacataat acaacaatc | 999 |

<210> SEQ ID NO 35
<211> LENGTH: 318
<212> TYPE: DNA
<213> ORGANISM: Nannochloropsis gaditana
<220> FEATURE:
<221> NAME/KEY: misc_feature
<223> OTHER INFORMATION: EIF3 terminator

<400> SEQUENCE: 35

| | |
|---|---:|
| ggcactgtaa ccccggttcc gctcgacgaa ggctgggagc gcccttcgg tgggataaaa | 60 |
| tggatgcttt accgctgcgc ttcggctgag gaagagagaa atgcgagcgg ggatcggggt | 120 |
| cctagaaacg aagaaaggag aacaagttcc tggccaaaga aaaacaagac aaataccctc | 180 |
| tccaggcctg ggcccattac ttttttttgc tgtttcttat acctgcactc gtgcttctct | 240 |
| agtctgtcga gaccttacct gatcttcctc cctccatcgc tccccgcccc cccatccga | 300 |
| gcaaccgtcg accatacg | 318 |

<210> SEQ ID NO 36
<211> LENGTH: 702
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: TurboGFP gene codon optimized for
      Nannochloropsis gaditana

<400> SEQUENCE: 36

```
atgttggaga gcgacgagag cggcctgccc gccatggaga tcgagtgccg catcaccggc      60
accctgaacg gcgtggagtt cgagctggtg ggcggcggag agggcacccc cgagcagggc     120
cgcatgacca acaagatgaa gagcaccaaa ggcgccctga ccttcagccc ctacctgctg     180
agccacgtga tgggctacgg cttctaccac ttcggcacct accccagcgg ctacgagaac     240
cccttcctgc acgccatcaa caacggcggc tacaccaaca cccgcatcga gaagtacgag     300
gacggcggcg tgctgcacgt gagcttcagc taccgctacg aggccggccg cgtgatcggc     360
gacttcaagg tgatgggcac cggcttcccc gaggacagcg tgatcttcac cgacaagatc     420
atccgcagca acgccaccgt ggagcacctg cacccccatgg gcgataacga tctggatggc     480
agcttcaccc gcaccttcag cctgcgcgac ggcggctact acagctccgt ggtggacagc     540
cacatgcact tcaagagcgc catccacccc agcatcctgc agaacggggg ccccatgttc     600
gccttccgcc gcgtggagga ggatcacagc aacaccgagc tgggcatcgt ggagtaccag     660
cacgccttca gaccccggga tgcagatgcc ggtgaagaat aa                        702
```

<210> SEQ ID NO 37
<211> LENGTH: 822
<212> TYPE: DNA
<213> ORGANISM: Nannochloropsis gaditana
<220> FEATURE:
<221> NAME/KEY: misc_feature
<223> OTHER INFORMATION: 4A-III promoter

<400> SEQUENCE: 37

```
ggcataaagg acggcaagga aagaaaagaa agaaagaaaa ggacacttat agcatagttt      60
gaagttataa gtagtcgcaa tctgtgtgca gccgacagat gctttttttt tccgtttggc     120
aggaggtgta gggatgtcga agaccagtcc agctagtatc tatcctacaa gtcaatcatg     180
ctgcgacaaa aatttctcgc acgaggcctc tcgataaaca aaactttaaa agcacacttc     240
attgtcatgc agagtaataa ctcttccgcg tcgatcaatt tatcaatctc tatcatttcc     300
gccccttttcc ttgcatagag caagaaaagc gacccggatg aggataacat gtcctgcgcc     360
agtagtgtgg cattgcctgt ctctcattta cacgtactga agcataatg cacgcgcata     420
ccaatatttt tcgtgtacgg agatgaagag acgcgacacg taagatcacg agaaggcgag     480
cacggttgcc aatggcagac gcgctagtct ccattatcgc gttgttcggt agcttgctgc     540
atgtcttcag tggcactata tccactctgc ctcgtcttct acacgagggc cacatcggtg     600
caagttcgaa aaatcatatc tcaatcttca gatcctttcc agaaacggtg ctcaggcggg     660
aaagtgaagg ttttctactc tagtggctac cccaattctc tccgactgtc gcagacggtc     720
cttcgttgcg cacgcaccgc gcactacctc tgaaattcga caaccgaagt tcaattttac     780
atctaacttc tttcccattc tctcaccaaa agcctagctt ac                        822
```

<210> SEQ ID NO 38

```
<211> LENGTH: 200
<212> TYPE: DNA
<213> ORGANISM: Nannochloropsis gaditana
<220> FEATURE:
<221> NAME/KEY: misc_feature
<223> OTHER INFORMATION: bidirectional terminator 5

<400> SEQUENCE: 38
gggtgggaag gagtcgggga gggtcctggc agagcggcgt cctcatgatg tgttggagac    60
ctggagagtc gagagcttcc tcgtcacctg attgtcatgt gtgtataggt taaggggcc   120 cactcaaagc cataaagacg aacacaaaca ctaatctcaa caaagtctac tagcatgccg   180
tctgtccatc tttatttcct                                               200

<210> SEQ ID NO 39
<211> LENGTH: 18
<212> TYPE: DNA
<213> ORGANISM: Nannochloropsis gaditana
<220> FEATURE:
<221> NAME/KEY: misc_feature
<223> OTHER INFORMATION: 18 bp sequence homologous to a sequence within
      the ZnCys-2845 gene and upstream of a cas9 PAM sequence

<400> SEQUENCE: 39
agtaggccat tcccggag                                                  18

<210> SEQ ID NO 40
<211> LENGTH: 120
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Chimeric guide targeting ZnCys-2845 (knockout),
      first strand

<400> SEQUENCE: 40
taatacgact cactatagga gtaggccatt cccggaggtt ttagagctag aaatagcaag    60
ttaaaataag gctagtccgt tatcaacttg aaaaagtggc accgagtcgg tgcttttttt   120

<210> SEQ ID NO 41
<211> LENGTH: 120
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Chimeric guide targeting ZnCys-2845 (knockout),
      opposite strand

<400> SEQUENCE: 41
aaaaaaagca ccgactcggt gccactttt caagttgata acggactagc cttattttaa    60
cttgctattt ctagctctaa aacctccggg aatggcctac tcctatagtg agtcgtatta   120

<210> SEQ ID NO 42
<211> LENGTH: 120
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Generic first strand for construct to produce
      chimeric guide by in vitro transcription
<220> FEATURE:
```

```
<221> NAME/KEY: misc_feature
<222> LOCATION: (20)..(37)
<223> OTHER INFORMATION: n is a, c, g, or t

<400> SEQUENCE: 42
taatacgact cactataggn nnnnnnnnnn nnnnnnngtt ttagagctag aaatagcaag      60
ttaaaataag gctagtccgt tatcaacttg aaaaagtggc accgagtcgg tgcttttttt    120

<210> SEQ ID NO 43
<211> LENGTH: 120
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Generic opposite strand for construct to
      produce chimeric guide by in vitro transcription
<220> FEATURE:
<221> NAME/KEY: misc_feature
<222> LOCATION: (84)..(101)
<223> OTHER INFORMATION: n is a, c, g, or t

<400> SEQUENCE: 43
aaaaaaagca ccgactcggt gccactttttt caagttgata acggactagc cttattttaa    60
cttgctattt ctagctctaa acnnnnnnnn nnnnnnnnnn nnctatagtg agtcgtatta   120

<210> SEQ ID NO 44
<211> LENGTH: 2400
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Donor Fragment with HygR cassette

<400> SEQUENCE: 44
tccacagccc gaacccatga gagagaatca taatcaaaga tgagccagcc acgaagctac     60
cggagaattc tgtaagaaaa atgtttaaag ttgaaaatgc taacagtgaa gtgatatcct   120 ttttttaatgg agtgttgagg tgaagtctag catcgtaggg gaaaacagga ttctgtgtct   180
tccattctac tccttgataa agcgaagaaa tccgacaaaa ccaaagagat tgttcaagtt   240
taagatttgt aagcgtacaa ctatgaactt cttctctttg taggcctgag tggtcgtatg   300
catacgattc atgaagtgaa tcagtatcgc tggattttgc ttaggagtaa agcacaacta   360
agaaaatatg ctgcctggca ggcatcctga gacatgaggc aagcgacgta gcaattgaat   420
cctaatttaa gccagggcat ctgtatgact ctgttagtta attgatgaac caatgagctt   480
taaaaaaaaa tcgttgcgcg taatgtagtt ttaattctcc gccttgaggt gcggggccat   540
ttcggacaag gttctttgga cggagatggc agcatgtgtc ccttctccaa attggtccgt   600
gtggtagttg agatgctgcc ttaaaattct gctcggtcat cctgccttcg cattcactcc   660
tttcgagctg tcgggttcct cacgaggcct ccgggagcgg attgcgcaga aaggcgaccc   720
ggagacacag agaccataca ccgactaaat tgcactggac gatacggcat ggcgacgacg   780
atggccaagc attgctacgt gattattcgc cttgtcattc agggagaaat gatgacatgt   840
gtgggacggt ctttacatgg aagagggca tgaaaataac atggcctggc gggatggagc   900
gtcacacctg tgtatgcgtt cgatccacaa gcaactcacc atttgcgtcg ggcctgtct   960 ccaatctgct ttaggctact tttctctaat ttagcctatt ctatacagac agagacacac  1020
```

```
agggatcatg gggaagaaac cggaactgac cgctacgtcc gtggagaaat tccttattga   1080
gaagttcgac tctgtctccg acttgatgca actgagcgag ggagaggaga gtagggcgtt   1140
ctcgtttgac gtagggggtc ggggatacgt gttgagggtt aatagttgtg cggacgggtt   1200
ctacaaggat cggtatgtct accgtcattt cgcctccgcc gctctcccca taccagaggt   1260
actggacatt ggggagttta gcgaatctct cacgtactgc atctcgcgcc gagcccaggg   1320
agtgacgttg caagatctgc ccgaaactga attgcctgcc gttttgcaac ccgtggccga   1380
ggccatggac gcgatcgctg ccgcagatct gtctcagacg tccggctttg gaccttttgg   1440
gccccagggc atcgggcagt acacgacctg gcgagacttc atctgcgcca ttgccgatcc   1500
tcacgtctat cattggcaga cagtcatgga tgacaccgtg tctgcatccg tggcccaagc   1560
actggacgaa ctcatgttgt gggccgagga ttgccctgag gtcaggcacc tggtgcacgc   1620
ggatttcggc agcaataacg tacttacaga caatggtcgg attactgctg tcatcgactg   1680
gtccgaagcg atgtttggtg atagccaata cgaagtggcg aacatattct tctggcgtcc   1740
ctggttggcg tgcatggagc agcagacacg ctactttgaa cggaggcacc cggagctggc   1800
cggctcccca cgactccgcg cctatatgtt gcgtatcgga ctcgatcagc tttaccagtc   1860
tctcgtcgac ggcaacttcg acgacgccgc gtgggcgcag ggccgctgcg acgcgatagt   1920
ccgcagcggg gctgggacgg tgggtcggac ccaaatcgca cgccggtcgg ctgcggtgtg   1980
gacagacggc tgtgttgagg tgcttgcgga ctcgggcaac gtaggccga gcacccgacc   2040 gcgtgcaaag gagtgattga atcattgaat gaaccattgt gtgcagaatc gatttcggga   2100
gtgttgccaa cacaagaaat atgcccaggg ttgtgtagaa gtttgcgtga atgtgatgaa   2160
gggaagccat acgctgaatt atcgtgacgt gtgtgagacg aagtgtcaca tcatacaccc   2220
aatttgagaa gctgtaccta ttagaagaat ttgtgagata cattaaaccc cttttgtac   2280 gtggtataat tgttatttgg gaagctgtaa acacgcagat cgttcctgag attgtcaatt   2340
acttttgtgg tgtttcctaa aggccgcatc actgcccgaa tcgagttgat ggcccgcaaa   2400
```

<210> SEQ ID NO 45
<211> LENGTH: 1029
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Hygromycin resistance gene

<400> SEQUENCE: 45

```
atggggaaga aaccggaact gaccgctacg tccgtggaga aattccttat tgagaagttc    60
gactctgtct ccgacttgat gcaactgagc gaggagagg agagtagggc gttctcgttt   120
gacgtagggg tcggggata cgtgttgagg gttaatagtt gtgcggacgg gttctacaag   180
gatcggtatg tctaccgtca tttcgcctcc gccgctctcc ccataccaga ggtactggac   240
attggggagt ttagcgaatc tctcacgtac tgcatctcgc gccgagccca gggagtgacg   300
ttgcaagatc tgcccgaaac tgaattgcct gccgttttgc aacccgtggc cgaggccatg   360
gacgcgatcg ctgccgcaga tctgtctcag acgtccggct ttggaccttt tgggcccag   420 ggcatcgggc agtacacgac ctggcgagac ttcatctgcg ccattgccga tcctcacgtc   480
tatcattggc agacagtcat ggatgacacc gtgtctgcat ccgtggccca agcactggac   540
gaactcatgt tgtgggccga ggattgccct gaggtcaggc acctggtgca cgcggatttc   600
```

```
ggcagcaata acgtacttac agacaatggt cggattactg ctgtcatcga ctggtccgaa    660
gcgatgtttg gtgatagcca atacgaagtg gcgaacatat tcttctggcg tccctggttg    720
gcgtgcatgg agcagcagac acgctacttt gaacggaggc acccggagct ggccggctcc    780
ccacgactcc gcgcctatat gttgcgtatc ggactcgatc agctttacca gtctctcgtc    840
gacggcaact tcgacgacgc cgcgtgggcg cagggccgct gcgacgcgat agtccgcagc    900
ggggctggga cggtgggtcg gacccaaatc gcacgccggt cggctgcggt gtggacagac    960
ggctgtgttg aggtgcttgc ggactcgggc aaccgtaggc cgagcacccg accgcgtgca   1020
aaggagtga                                                           1029

<210> SEQ ID NO 46
<211> LENGTH: 1000
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: EIF3 promoter

<400> SEQUENCE: 46
tcataatcaa agatgagcca gccacgaagc taccggagaa ttctgtaaga aaaatgttta     60
aagttgaaaa tgctaacagt gaagtgatat ccttttttaa tggagtgttg aggtgaagtc    120
tagcatcgta ggggaaaaca ggattctgtg tcttccattc tactccttga taaagcgaag    180
aaatccgaca aaaccaaaga gattgttcaa gtttaagatt tgtaagcgta caactatgaa    240
cttcttctct ttgtaggcct gagtggtcgt atgcatacga ttcatgaagt gaatcagtat    300
cgctggattt tgcttaggag taaagcacaa ctaagaaaat atgctgcctg gcaggcatcc    360
tgagacatga ggcaagcgac gtagcaattg aatcctaatt taagccaggg catctgtatg    420
actctgttag ttaattgatg aaccaatgag ctttaaaaaa aaatcgttgc gcgtaatgta    480
gttttaattc tccgccttga ggtgcggggc catttcggac aaggttcttt ggacggagat    540
ggcagcatgt gtcccttctc caaattggtc cgtgtggtag ttgagatgct gccttaaaat    600
tctgctcggt catcctgcct tcgcattcac tcctttcgag ctgtcgggtt cctcacgagg    660
cctccgggag cggattgcgc agaaaggcga cccggagaca cagagaccat acaccgacta    720
aattgcactg gacgatacgg catggcgacg acgatggcca agcattgcta cgtgattatt    780
cgccttgtca ttcagggaga aatgatgaca tgtgtgggac ggtctttaca tgggaagagg    840
gcatgaaaat aacatggcct ggcgggatgg agcgtcacac ctgtgtatgc gttcgatcca    900
caagcaactc accatttgcg tcggggcctg tctccaatct gctttaggct acttttctct    960
aatttagcct attctataca gacagagaca cacagggatc                        1000

<210> SEQ ID NO 47
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5'ID sequence

<400> SEQUENCE: 47
tccacagccc gaacccatga gagagaa                                        27
```

```
<210> SEQ ID NO 48
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3'ID sequence

<400> SEQUENCE: 48
gcccgaatcg agttgatggc ccgcaaa                                          27

<210> SEQ ID NO 49
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: MA-ZnCys-FP

<400> SEQUENCE: 49
acctccttgt cactgagcag                                                  20

<210> SEQ ID NO 50
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: MA-ZnCys-RP

<400> SEQUENCE: 50
gatcccaaag gtcatatccg t                                                21

<210> SEQ ID NO 51
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bash-(-1) CRISPR target sequence

<400> SEQUENCE: 51
ctgtcaaatc aacaaaac                                                    18

<210> SEQ ID NO 52
<211> LENGTH: 18
<212> TYPE: DNA
<213> ORGANISM: Artificial Sequence
<220> FEATURE:
<223> OTHER INFORMATION: Synthetic

<400> SEQUENCE: 52
agctcagata tcttccag                                                    18

<210> SEQ ID NO 53
<211> LENGTH: 18
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<223> OTHER INFORMATION: Bash-2 CRISPR target sequence

<400> SEQUENCE: 53
atcttccagt ggtgggcg                                                    18

<210> SEQ ID NO 54
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bash-3 CRISPR target sequence

<400> SEQUENCE: 54
gggactgtcc cattgtgc                                                    18

<210> SEQ ID NO 55
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bash-4 CRISPR target sequence

<400> SEQUENCE: 55
tctgtctaaa tcagcaca                                                    18

<210> SEQ ID NO 56
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bash-6 CRISPR target sequence

<400> SEQUENCE: 56
gccaagtgca tcatgctc                                                    18

<210> SEQ ID NO 57
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bash-7 CRISPR target sequence

<400> SEQUENCE: 57
gctcaggtac gcatctca                                                    18

<210> SEQ ID NO 58
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bash-8 CRISPR target sequence

<400> SEQUENCE: 58
```

-continued attggaatca attttgaa                                                18

<210> SEQ ID NO 59
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bash-9 CRISPR target sequence

<400> SEQUENCE: 59
gctgttcatc acaaagag                                                18

<210> SEQ ID NO 60
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bash-10 CRISPR target sequence

<400> SEQUENCE: 60
ctctttgtga tgaacagc                                                18

<210> SEQ ID NO 61
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bash-11 CRISPR target sequence

<400> SEQUENCE: 61
cgtcggttca cgccaatc                                                18

<210> SEQ ID NO 62
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bash-12 CRISPR target sequence

<400> SEQUENCE: 62
aactcgctcg tcgatcac                                                18

<210> SEQ ID NO 63
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer MA-5'Bash-ZnCys-FP

<400> SEQUENCE: 63
tagcagagca ggctcatcac                                              20

```
<210> SEQ ID NO 64
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer MA-5'Bash-ZnCys-RP

<400> SEQUENCE: 64
gaatatgtgg tctagctcgt                                          20

<210> SEQ ID NO 65
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer MA-3'Bash-ZnCys-FP

<400> SEQUENCE: 65
atggctccac cctctgtaag                                          20

<210> SEQ ID NO 66
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer MA-3'Bash-ZnCys-RP

<400> SEQUENCE: 66
ctgactacag ctagcacgat                                          20

<210> SEQ ID NO 67
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer ZnCys-2845: Forward primer

<400> SEQUENCE: 67
atacaggaag cgtggttaca g                                        21

<210> SEQ ID NO 68
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer ZnCys-2845 Reverse primer

<400> SEQUENCE: 68
gaagtattaa gggactggcc g                                        21

<210> SEQ ID NO 69
<211> LENGTH: 849
<212> TYPE: DNA
<213> ORGANISM: Nannochloropsis gaditana
```

```
<220> FEATURE:
<221> NAME/KEY: misc_feature
<223> OTHER INFORMATION: 1T5001704 Housekeeping gene

<400> SEQUENCE: 69
atgtcacggt cgcggtcctg ttccgaagct tctgcggcct cttcgtcatc ggcagcagca      60
gcgtcttcga ctcacgcccc ttcttcgcgc ggagcttcgg tggccgacgg tgctgcaagg     120
gagcgagaag ataatggcaa acgcctgagg tcaccgagcc ctgccggtgg tgaagcttct     180
ggttccgagg aagcggaaga ggatgatgag cccgccaaat tgcatgtttc tggtctaaca     240
agaaacgtga cagaggagca tctcaacgag atattcgcca catttgggaa gctgtcgcgt     300
gtggaactgg tacttgaccg acgagtgggc ttatcgcggg gcttcgccta tgttgagtac     360
gatcatcgga aggacgctga ggaagcccag ctgtacatgg acggtggtca gcttgacggc     420
gcacctttga aagtgaactt tgtgcttttg ggcggagccg cagccgatct cctgtatccc     480
gtggcggtgg tcgagaaagg gacctttacg atcgcaatgg cggtccgccg gagaggaggg     540 gcggggagc tcaatgggag gggcggcggg gccggtctcg ttctccgcct cggggggtc      600 gacacgaccg aggtcggttg ccgccagggc ggtttactcg aggagagcgc ggacgcagcc     660 cccctaccg tcgccagcca gaccctcgcg gctggtcgcc gccacggcgc gggccgggtg      720
ggcgggcatc tccgcctcgg gccgcggtcg cagccggagc agccgctcct cacgcagccg     780
ttcctagatg gagggggcgg cgccaacagg gaaggcaagc aggagtctca cccgccgctt     840
gaggcttga                                                            849

<210> SEQ ID NO 70
<211> LENGTH: 408
<212> TYPE: DNA
<213> ORGANISM: Nannochloropsis gaditana
<220> FEATURE:
<221> NAME/KEY: misc_feature
<223> OTHER INFORMATION: Region of ZnCys-2845 gene

<400> SEQUENCE: 70
gtttaaacga tcagccacga cggctctcgc atgcacaacg atggcatgga ttggcgcgcg      60
aaggatgagg actgctcgta ccacaccgcc gtggacgcca gctgccacat cgacagtagc     120
taccaccatg ttgatgcctc aggccactcc atggtcgacg cctcgggtca cagcacgata     180
gacgcgtcgg gccacgactc cctcatcgac tcaagcggcc attacgacga ctatctggcg     240
cacaaggggg acgcccgcta catggagcac agttgtgaag cctgcaagcg ctcgaagaaa     300
cgatgcaacc gccgcaaccc ctgccagatc tgcacctcca ggggcatcaa gtgtgtgccg     360
caaatccggg gtcctgggcg cccccggggc agtaaaagca gtcggggc                 408

<210> SEQ ID NO 71
<211> LENGTH: 163
<212> TYPE: DNA
<213> ORGANISM: Nannochloropsis gaditana
<220> FEATURE:
<221> NAME/KEY: misc_feature
<223> OTHER INFORMATION: Terminator 9

<400> SEQUENCE: 71
gagtcaaggg ggaaggtgca tagtgtgcaa caacagcatt aacgtcaaag aaaactgcac      60
gttcaagccc gcgtgaacct gccggtcttc tgatcgccta catatagcag atactagttg     120
tacttttttt tccaaaggga acattcatgt atcaatttga aat                      163
```

```
<210> SEQ ID NO 72
<211> LENGTH: 2091
<212> TYPE: DNA
<213> ORGANISM: Phaeodactylum tricornutum
<220> FEATURE:
<221> NAME/KEY: misc_feature
<223> OTHER INFORMATION: Encodes ZnCys polypeptide of SEQ ID NO:5

<400> SEQUENCE: 72
```

| | | | | | |
|---|---|---|---|---|---|
| atgaacgaag | acagtaccga | agacccggat | gatggcagtg | tggcgctctg | tgcatcatgc | 60 |
| gatcgttgcc | gctcgcgaaa | gaccaagtgt | gacggccagc | gccctgtgg | aaactgcttg | 120 |
| gccaagtaca | tgaagaagaa | taaactcagt | agcgcggatg | gaatcgattt | taccgagtgt | 180 |
| gagtgtgtct | attcacccgc | taagcgtcgt | ggccctattc | cgggtcgtac | cgctggccaa | 240 |
| gctcggaagg | ccaccgagct | gcaacatcac | caacagcagc | agccgaatga | ttggcctcaa | 300 |
| aattatcaca | caaccccttc | gactggggtg | aacttgaacg | ggacaggatt | ggacgcccaa | 360 |
| atgactgctg | ctttattttc | cggccaaacc | gaacaggcgt | cgttgcagca | aaaactgaac | 420 |
| tttttgcagt | cactgcaaaa | tcaagacgaa | gatcatctca | tgatgcaaca | gcagcagcag | 480 |
| cagcatcaga | tggacgagcc | tgccaatcga | cgagtgaaac | gtgaagatgc | tggacagaat | 540 |
| accagcacga | acgggattcc | tcgcactatc | accacccaca | cgcaccttt | ggaacgctcc | 600 |
| aatccagatg | gagcccgtct | tcgtgcgtac | taccagctat | cgatcgacga | actctatcgt | 660 |
| ttgcctccga | taccgacgga | cgaagaatac | tgtgcccgcc | ttaacgttcc | ggggatgacg | 720 |
| cctcaaatga | tcccaggtcc | acatctggcc | gccctgagtg | ccgcacgctt | tgctgagatc | 780 |
| gcgctcggcg | cacttgttca | aacgaagtg | tcgttagcga | tggaattgtg | taatgcagtt | 840 |
| gttcactgct | tgcgggaatc | cgtacaggaa | cccgtgcaga | caccagtgat | gttcgaagtt | 900 |
| gccaaggcgt | acttttgct | cggcgttttc | cgtgcctgtc | gcggagacat | ggaacggtat | 960 |
| ttcaaatatc | gccgggtctg | tatgacgtat | ttggcgaagc | tggagaacga | tgataaaacg | 1020 |
| gcggtgctcc | ttgccgcagt | ggcctacttg | gactcttggg | ctccgtacgc | tactcagact | 1080 |
| gagctcaagt | atgatgtcaa | gttggatgct | ggtgccattg | ctagcgatcc | aagaatcaa | 1140 |
| aactggattc | aaggtgctcc | gccggtgtac | ctgaataatg | aggccccgtt | gcatgcacgg | 1200 |
| gctttggatg | ctttggcttg | tgccgttcgc | acttgttgcg | atcaagccaa | cagccgtttc | 1260 |
| gctcttatta | gcaaggaggc | taatatcgaa | ggtctggaca | cgattccttc | gaatccatt | 1320 |
| tcttctgcaa | cgtacaatgc | agttctatcg | cacgagaatg | agctctgcag | tcgcaatatt | 1380 |
| gttctttcag | cgtacactct | gatgcaacag | cacgaatcta | ctgacagttc | tcgacacaaa | 1440 |
| aacgagggac | agcacatggt | catttctgcg | atggacgcgt | ttctggaaaa | tagtgacgaa | 1500 |
| gatggcaatg | gtggattcac | cgacagtcag | attcagagtt | tgctttctgt | ttgtaacact | 1560 |
| gcgattgaga | atccgttcct | cttgcaccat | gctggtccaa | catatcacat | ggtgtccaac | 1620 |
| gcggccgtac | tattgtgtca | tttattaaac | ggccttcata | tggccaagat | gaacggtcaa | 1680 |
| gatttcggtc | ggatggaaca | gtccatgttt | gaagaagtct | tgacgctttt | tatatcgatt | 1740 |
| cgcaaactct | tgacgattca | tcgacgtaaa | ctaccggtca | aactgcgttg | ccatgctatt | 1800 |
| ccgagaccaa | gcatgacgg | tttaaaggaa | gggcagccgt | taattgattt | gggggaaaca | 1860 |
| attctttgtg | cgtgccgtgg | atgccagggt | tttgtcctta | tggcttgcag | tccctgtgta | 1920 |
| gcggcggagc | gtgccaggc | ggcgcaacat | gatttgtcag | tcgaagcggc | gaaggaagcc | 1980 |
| gaagcgattg | aaatgggcga | gctcgacaac | gaattggaca | acttgggagc | ggaatttgat | 2040 |
| atggacgacg | atatgttgtt | gggaatgatt | agcaatctca | tttcaagttg | a | 2091 |

```
<210> SEQ ID NO 73
<211> LENGTH: 744
<212> TYPE: DNA
<213> ORGANISM: Navicula sp.
<220> FEATURE:
<221> NAME/KEY: misc_feature
<223> OTHER INFORMATION: Encodes ZnCys polypeptide of SEQ ID NO:6

<400> SEQUENCE: 73
atggcttgca cggcgtgtca tcttgccaaa cgaaaatgcg acaagaaatc gccatgctcg      60
cgctgtatca gcaaatcgct cgaatgcatt cctcacattt cccgtcaagg aaaaagaag     120
gtccggcggg tcgaagagaa gaaagatgac ggtcttgatc gtttgcttct cgagcagttg    180
acggggaccg aaccagtgca aggtcataca caccatttcg gattgaagta tttggttcgg    240
tcttggattt cgtttgcgtt caaacggcgg agctttttcc tgatgcaacg aggatgtgca    300
ctggcaataa agttggcttt tcgatggat gagatattct gcgaacaatc taattctcgc     360
gaaatggatt ttctcaaaaa tattatttta gtacccaagg aagcgcagca tttgtatgtc    420
ccgacaccac ttcagtggac ggaaattccc gaacgccttc tcaggaacac ggatacaata    480
ggctcgtctg gaaacagaga gggtcggtgg atatggatgc gggagatgat caagggagaa    540
tctcggtatc ttgtatcgga agcatttgaa cgagacgttg caccctggag ctcactgcac    600
aaggcgtggg aagacaaccg gggggctgtg attgacctat cgtcattga agaagataag     660
cacaagcaca ccaagtcatt cgcacatcaa atttcgctct acaagaaca gccgtcaac     720
ggggaaggaa accgcttgac tcgt                                            744

<210> SEQ ID NO 74
<211> LENGTH: 1002
<212> TYPE: DNA
<213> ORGANISM: Navicula sp.
<220> FEATURE:
<221> NAME/KEY: misc_feature
<223> OTHER INFORMATION: Encodes ZnCys polypeptide of SEQ ID NO:7

<400> SEQUENCE: 74
atggtttgta ttggttgtca cgaatcgaaa cgcaagtgtg ataagcaaac tccgtgttcg      60
cgttgcctga aactaggaat tccttgcatc cctcaccttt cgcagcaagg caaacgcaag    120
agaggttcgc ccgacgagac accagaagat gtgacgattt gcgccaagt ttccttgccg     180
aaagatcact atggtttgtg ccatttgatt cgttcgtgga tatcgattgc ctttgtacga    240
cggagctttc ctttgcttaa caaagccacg acaatggcca atcaattggg cgtcacgatg    300
gacgaaatca tgagtcgttc gatgacccag cagggcatgc attggctggg tccggtcgta    360
gcgaccccgc aatccgaaca aatggcgggt ggtccacgct gcaatggaa cgaactgccc     420
gagggtctct tggtggcgac acgcacgctt catagtgttg actgcgaagc acggtggatt    480
tggattcgcg aattgagtca agggcgttct cgttatttgg tgacgcaagc ctttgaacga    540
gatatcgcta catgggcact ggtgcaaagc acgtggaatg agaaccgcat tcggtcgtc     600
gatctctttt tggacggtgc ggctcgtgaa aaacacgcca aatcagtggc gcatcagtat    660
tcgctgcatg cgaagcctcc gacgccgcac agtgcgcgct gcagtcgcca acgcagtcag    720
gtaaaactgc gcaacggaga catgatttca gtggaagaaa tttcctgcat ggatttcgtc    780
catatggatt tgtcgtacca tttttgtggaa tacgtcccgg tgtgtataca accgattcgc    840
tcccaagctt gtatccagaa caagtccag agcacgcagt cgttatttca agaaatgtcc    900
```
aaggtcatgt gggatgatta tcctctcatg gtgaatgtcg atgatattcc ggcggaagga    960
aacgagctgg atcagattct gcaattgtta aatggaggtt aa                      1002

<210> SEQ ID NO 75
<211> LENGTH: 512
<212> TYPE: DNA
<213> ORGANISM: Navicula sp.
<220> FEATURE:
<221> NAME/KEY: misc_feature
<223> OTHER INFORMATION: Encodes ZnCys polypeptide of SEQ ID NO:8

<400> SEQUENCE: 75
atggaagact tcaacaacaa caacacgcaa caagccgatg atgaaaagtt gtgtgcaagt     60
tgcgatcgct gccgatcgcg taaaacgaaa tgcgatggga acgtccctg tggaaactgt    120 gtggcaaagt acatgaagaa gtacaaagtc atgagtgtcg aaggcgtacc cgaatctgcc   180
tttgagtgcg tctattcacc ggccaagcgt cgcggccccg tccctggacg tacgccttcg   240
caagctcgtt ccttgaacga tgtaacgggt ggcaacatga atgtgaacat gacgggtggg   300
aataactttg attggaacat ggatctcatg tcgcaacaac aacagcagca gcaccaccaa   360
caacaacaac aaccaatgat gtcatcgtta attggtggat tggatgggaa caacattttg   420
aatcagttca atttgatgcg acaaatgcaa cttcagcagc aattgccgct ccagccacaa   480
caaatggcaa tgcagcagca catgatggac ac                                 512

<210> SEQ ID NO 76
<211> LENGTH: 2172
<212> TYPE: DNA
<213> ORGANISM: Cyclotella sp.
<220> FEATURE:
<221> NAME/KEY: misc_feature
<223> OTHER INFORMATION: Encodes ZnCys polypeptide of SEQ ID NO:9
<220> FEATURE:
<221> NAME/KEY: misc_feature
<222> LOCATION: (447)..(447)
<223> OTHER INFORMATION: n is a, c, g, or t

<400> SEQUENCE: 76
atggacgaca ccgtcgccgc agaggaagca aaagaagcaa ccgacctaca gtcatccgac     60
tccaaaccca cttcccccatc atcgacaccc ctcaatcgcg attccaccag cctctgctcc   120
tcctgtgatc cctgccgcgc tcgtaagacg aaatgcgatg gtcttcgccc ctgccgcgcg   180
tgcatcagca agcatgtcaa gaaacataag ctgtcgtctt acgagggat taccgccgaa   240 gattgcggat gcacctattc cgtagccaaa cggaggggtc cggtgcctgg ctttaagaat   300
gcgaaggacg aaaagggcga tgggaattta tcgacatcga agaagagagg tcccacgcaa   360
gacgggacgt tgcattctta ccctcccaaa agaagaaag agaagagaag tgttgatgtt   420
ctagcacgat ttcctcactc ggctgcncag gatgcgatgg ctgccgcttc ggacagcgcg   480
aggcaacaac ttgggttcat tgaacggctg cagcaacaac agcaggagtt tcagcgtcaa   540
cagcagcagc agatgcaaat gcaacagatg gcacaagcac aaaatgctca ggccatgcct   600
ttcatgtctc gggacggtga caacagcgct atttcgcgcc aaatgaataa taattataat   660
gagcaggtct ctgggcataa gccgtcgcag cagttttcgt ccactgaaca acatctgca   720 gtgggttgcg agaaaaccac ggtgcgcgaa ctgcttcacg tcctcgaccc aaaagatccg   780
ctgggatcac gattccgcgc atgctacggc atctcctttg gatcaatatt tggacttcct   840
ccaattctta cctatgacga atactgtcgt cagttcactc caacgattgc ttcaacttca   900
atgccaaaat acgacgtagc ggcacttcaa gcggcacaat ttgcagagct tgccttgggt   960

```
gccctcgctg atggagaccg ttgcatgatg ttcgccttaa ttaatgctag catattttgt    1020
cttcaggata cggtgaagga acctgttcat cgtagctgcc aattcgagct cgcaaaggct    1080
ttcttcttcc attccttaat tagatgtcac aatggggata tggagcggta tttcaagtat    1140
cgacgtgcag ctatgcacac tttggctcac ttggatgggt atcccaatgt tgaaacactg    1200
atggctgccg ttggatttca agacgcactg gcattcatgc tctacaatgg atgtgatgat    1260
gatgtaccgg acattgatag tgactatcct caagtgttag atcgattcga taccaaggaa    1320
tcgagcagcg tatccttcac accctcgaaa ctcgcatcag atcccacgaa taagacctgg    1380
atcactggcc ccccgatgtt ttcctcggag agttccgccc cacttaaaag tcgtattcta    1440
gatattctgg cctgtgcaac tcgatcgttt gttgaagagt ctcagttcaa gaaggagatc    1500
aaaagcgttg aaacgagcac tcgcaaacgt aggaatttca taactgcaga agacaagagg    1560
attaagtata aaatttgtct cggtcatcta acgaggctg aagactgct ggctgtagca    1620 aattgcaagt catcctccag ttccatttac gatgtgtacc atgtactggt tatggctttt    1680
cgtgtgatga ttcatgaaga tacttcggag ccggaagaat cacaagtcca aaatgcattt    1740
catgttttga agctatcat cagacaacca agcctattga atattggccc cattaatata    1800
tttgtccaca aatgcgtaat ttttgtagca cgccttatca acaagtcgca taggcagga    1860 ctcgaggatc aatcggcaag ggacctcttt gaagaatcaa ttgatttgta ccatgcctcc    1920
agaactattc tcaatataca aatagtaaa ctccccgacc aacttcgatg ccacgaaatt    1980
ccgaggccga aatccatcac tgcgaaagaa tgtgacacaa tcattacgtt aggcgacgag    2040
tcgatgatgc cccacaggat ggccagtgtg aaggaggaaa ccagcgcttc cacatctgac    2100
actgaaaagg aatgccacat caacgataaa gcctttttgg tgttttgag tggtctatat    2160 cttgcgcgtt aa                                                       2172
```

<210> SEQ ID NO 77
<211> LENGTH: 4548
<212> TYPE: DNA
<213> ORGANISM: Cyclotella sp.
<220> FEATURE:
<221> NAME/KEY: misc_feature
<223> OTHER INFORMATION: Encodes ZnCys polypeptide of SEQ ID NO:10

<400> SEQUENCE: 77

```
atgcatttct ctgcgcagcc gccccagggg aacggggaca tggcccagct cgacggcgta     60
tccacagcct ccaaaaagac tcgcgcctgc acggaatgcc acagagccaa gagcaaatgt    120 gtctttccg aagagggcca agaaaagtgt gatcgatgct tcaggttgaa caaggattgc    180
gtgcctcatt tatcgaggca gggccagagg aagaagaaaa gcgagaaagg tatgatgaaa    240
tcctccgtgg ccacctcgtt ggcggaggtc tcgaaaggga gcaacgtcgc cagtaaagcc    300
ccgatgtctg gcgaaagcaa aagtacaagc ccctttttcc cagacaacgc agtggaaggc    360 aaccggcct tttcattcca cgccgctagt caggatacgt cattgaacag gcttgctgca    420
acggcaactg gaggtccgtc aatgagccaa atggctcctc tagcaaaatt cattcctcaa    480
aagcacatgt tctcatccaa tcaccccact tttcataata ctggcccatg cggtctctac    540
gaagcccggc tcaggaggac tcaagccggc actgccttac cggtggatca acaaacata    600 actgtcacag agcaacggca agccgcaatg tcaatgtttt ctaatagtga tagaaccata    660
acggactcga cccatcaagg cgtcacattt cgtgaggact tgtcgtcgtc caggtcattg    720
ccactgagag agtggatgaa atgtgcactc aattcgaaca aaatccgtga cagcagcggg    780
```

```
agcagtccta tttcttccaa gtatattgca tcttgcctca aaatcgcact ctcgttggct    840
aaacaaatca gtgatgcaga ggttacttct tcgcgagaga tacttcaatg gctgcctcgc    900
gacagtatag attggccaca gtatattaca gtgaaattga caggaaatga aactcaagtt    960
cctccccatg atgctcggac tggatcttta gaccattcat ccgtggcgga tgatgagttg   1020
gacatgctcg aagcactttt ggactcaatc tgcgaagaaa atgaagtgga tacaacagat   1080
gttttcgata tttattcggc tgcaattctg ctggattata gcaaaaatag cgatgatggg   1140
gttgatcctc tttcgtttcc cgggcaagaa tatcgaatcc atgcccttgg actggtgttt   1200
tgcgaactgt tttcaggtgg acgagtcccg tccactgaac tagtgtcgga tggcctttgt   1260
caggacgatg tagtcacccc agcgatttct gaaaggttgg agtttacagg tatgctgaag   1320
ctcgagccaa acgagaacga catttacaag gacacaagct gcaaatatgt aggcacaaga   1380
aaaaaaacac gtgagcttga cgaatcgttg cactcgtcca ttgagtcact caggcggctt   1440
ggcatttcct gcccactgtg tgacttgatc ttcaacatac tagattccat caacggagac   1500
ttgggcagag atgactcgta ccgaaaaatg tcagacgtag ctatcgattt gcaaaacatg   1560
gtagacaaac caaaaacatt cctcaatgat ctcgatgtta ttactttatc gtcgacgggc   1620
ttgcaattga cggacaactt attcatgcga gatgaggagg tcgccttgct gcaacacgct   1680
tattatcgtt ccacattggg gtcgtctgag tttgctgtca tcactggcgg gtcggggaca   1740
gggaagtcac atttagcctt tcgtctaggc agtcacataa catctcatgg tggtatattc   1800
ctctccgtaa agttcaatca aatgaaacag gccgaccctt actcagcttt agtttcagcg   1860
ttcaatgagt atttcaacaa tttcacgatg acgaagcagt tagactcgat gaaacggatc   1920
gctagcaagc tgcgagatga actgggacaa gacgcacttc ttttagcgaa agtcattccc   1980
aatttagcag aggttcttga ttttgctgcg gttgatacag cctttgatgg agactgtgta   2040
aatgggcacg agaagatgca ttatatatta gtgtgttttg tcgaagtcat gtctgcttgt   2100
tcacacgtga cattgaccct gtttcttgac gatcttcaat gggcagatgc cttctcattg   2160
tcagtactcc aacagataat gattatgcct gatgagcaca aacaattctt ctttgtagga   2220
tgctatcgag acgaccagat ggaagatgac catccgttca agaaaatgat cagcagatgc   2280
ggtgattttg gtgtcaggct gacgatggtt tatttagaat gcatggacaa ggacggaatg   2340
aacacaatga tttcagaatt gctttgccta ccccctcggc tggtcaagag tctatctgag   2400
ttggtttact caaagacgaa aggaaaccca ttgttcttat cgcggttgtt gatatcgttg   2460
aataaggatg ggctgctcaa tctgagtctg ggccgccgcc gttgggtatg ggacgaaaaa   2520
cagattcaat cgaaagagtt gcctgatgat gtagcatcat tcttttctag cagggtgggc   2580
aagctatcac cagaggttca ggcagcgctt caggttttat catgttttgg ctctgttaac   2640
acgtacgaat tatcaatact cgagtcaggc cttagcctga atgtagtcaa accacttgaa   2700
agagccgtaa atgaaggatt cgtctccaag aatggcaatg attaccgttt ttctcatgac   2760
aagattcacg aagcggtcta tggtatggtt gagttagaag agcgtcgctt ccagcatcta   2820
aactacgcga ttagtttggt caagttcgca ttgggacaag atgatagcat cattttttacc   2880
gctattggcc aagctaatct cgctggccca tcgattacta ctgatgcact tcagtctgct   2940
gaatttgcga ggtgcaatat ggtagcgggg aaaaaagcaa tgagtctgtc agatttctcg   3000
tgtgcagcga tttgcttcag caagggctta tcatttctgg acgaaaatcg ttggagtgat   3060
tactataacc ttagccttga actgtttgag ttggcagcca aatgtgcgct ggtgctcgga   3120
```

```
gactttgcca gtcttgccac gatgtctgaa caggttgaaa acatagccg ttgtttcgaa    3180 gacaaactcg aggtgtcttt cttggttatg tgttcattgg catatgcatc taaaatctcg    3240
gattctgtcc atattggttt atcaattctt tcccaacttg gtcatgaatt acccacaaat    3300
tttactcgag cggagatcat cttttcacatc gaacaaacta aaacagttct tcactccatt    3360
tctgataaag acctaatgtt ctacaagaaa atgactgacc ctaaacacat catggcaatg    3420
aggtgtttgg ctaagttgga acttattgtg ctacagatca atccagattt gcaacctatc    3480
ataactttga aaatggtcaa catgaccatg gatctcgggg tgtcacacat gtcttcagtt    3540
ggaatggcct actttgctgg acttgttgct aaactagatg aaatccaaga cggcattcga    3600
tttgcaagac ttgcaaaaat gttgcttgac aaaagtgggt ccaaagagat cacaggagat    3660
gtcatcttta caacatcaga agttctctgc tttcatgagc cattacagag tgtcaacgag    3720
tatcgttttt acggacaaac tactgcattg gcagcaggtg acatgtactt tgcatgtgtg    3780
ctcaagatgt cgaattgtgg gacgatgctc tggatgggat caaatctcct gagtgtgaaa    3840
gatgcctttg ttcaggttgc tcgctactta aaagcgaaga accacttgtc aacgtacaat    3900
ctcttgctac tctcaaagcg tagtattttg atgctcatgg ggctagcaga tgaagatgaa    3960
cccctcactg ttgatcaact gaccaatccc taccaactga agtattttta ttttcaaaaa    4020
atgtttcaat ccttcgtatt taatcgaaat gatgatatga aacaatacac tgagaaattc    4080
ttgcaattca agatgccctc gtggttattg ctctcagtcc atgcgagaca tgagttttac    4140
gtaggcctta tttcatttca gatttaccgt gagtctggta tctctttgtg gtttgagagg    4200
ggccaacagt gcaagtcaaa agtgcaacta tggaaagagc aaggatcagt gtggaattt    4260 gaacataaac tctatttgtt acaggccgaa gaatattatt gcaacgatga cttcgagagg    4320
gctggagaat ctttcaagaa ttcgataaca tctgctaagt cacacaaatt cttaaatgat    4380
gaagctctgg cttgtgagct tgctgcaaac ttctatcttg gcaccggtga tttaacatct    4440
tcgatgaaat attttcgcct cgcccatgat aagtacaatg aatgggggtgc tcttggtaag    4500 gctgcacaac tggttacatt catgacagaa aagtttgcca gctgttga                 4548
```

<210> SEQ ID NO 78
<211> LENGTH: 2622
<212> TYPE: DNA
<213> ORGANISM: Cyclotella sp.
<220> FEATURE:
<221> NAME/KEY: misc_feature
<223> OTHER INFORMATION: Encodes ZnCys polypeptide of SEQ ID NO:11

<400> SEQUENCE: 78

```
atgacaaacc atttcgacaa caaccaatgg tccagcccct cacccccat gatggaagcc      60 cacgacgaca atcagcatca gcaacacgaa ggaggcgttc tcctctgcgc ctcgtgcgat     120
cgctgtcgtg cacgtaagac gaagtgcgat ggaatgagac cttgtgggaa ttgtaaaacc     180
aagtacatga gtctaagaa gctggacagc gtggaaggaa tcgaccttgc cgaattcgac     240
tgcatctact ctcccgccaa acgccgcggt cccgtccctg gcaaaagcgc tacgcgcaag     300
gcctccgaaa tgatgtctta cagcaaccca gatgtcatgc actttggagc cggggagga     360 ggcacccaag gaggggata tcattctcaa gtgggattcg acggaaccat gaatactgga     420
gggggattca atccgcagca gcagcagcag cttcagcaat tcaacaacaa ttcaagtgct     480
caattttcgg cggaagaatt gaaacagatg cttcttcttc agcaacagtt gttgttgcag     540
caacaagaga tgcagatgca gcagcagcaa cagcatcagc agggtttgtt gcagcagttg     600
```

```
actaatgtgg cgggaggggg gaacatcaat attgctaaca ctctaaggcg ggcgagcatg    660
aatgggggga ttactgcaaa tggcgagaca atgggagcaa tgaacaacga tgttggttcc    720
gtggacaggt caggcatggg aggaaacaat gggcacgtgg atgagcagtc actccaactc    780
attcagcaat atcagaatca gttgaatatc gggtcaaatc atggcatgac atcaggcaat    840
gcgtctatca ttggctctgt tgtcggagga ttgccagtgc agccatctcc tatgccttct    900
caacagtatg ttcaagagca gcagccagct aagcgtgctc accgtattga ttctgccatg    960
tctagcaata acgatggcac tcttccaaag tctgtgatta gccatctccc tctcctcgac   1020
cgtcatgacg gagacggcaa tgtccttcga gcctactacg acctcagtgt gaatgatatc   1080
ctcaacctcc cccccatccc ctcagatgaa gaatactgca gtcgtcttgc ccgcaataat   1140
tatcactgcc tacccagtaa tcttcccacc tatgatcact cagcgttaca agccgcacga   1200
tttgcggaac tagccttggg agcactcgcg aacaatcaga ttcccttggc gctagagttg   1260
agcaacgcct ctgtcatgtg catgaggaat tgtgcagagg aaccaagtga tgagagttgt   1320
atgtatgagg ttgcgcgggc gtatttgctg catggaattt ttaggagttt caggggagac   1380
ttcgtcaggt atttcaaata tcgacgagtt tgcatgacgc atgttgggca gttggcgaac   1440
acaccacatg tggaggcact ccttgccgcg gtgtctttcc acgatgcact cgcgtatatg   1500
atgcataacg ccaaggaaga atctcttccg gatattgatc aggtcttgcc gcgtctaaat   1560
cccggcaact gtgattttga cgacagtgat gaagttgagg ctaaatatgg catctcgact   1620
aatgccaaat cggtcgcttc agaccctaac aatcaaatgt ggattcaagg tgcgcctcct   1680
gtgtttctga ataacgaagc aaatctagcc aatcggtcat ggacggact  ggcatgcgca   1740 atccgttctt gttgtgatca tgcaaattca caattcgaag aaatggcaaa agctgtcggg   1800
gctgactttg ttggcggatc tggttcttgc ggaatgtccg ctacaactaa ggctgttacg   1860
gcaaatgaaa atgagctctg tagtcgaaat attgtgttgt cggctcgtac tctcctcgac   1920
cagtataatg gggtcagtca cgaaaaagcc aaaaaacatg ggctccaaat gttagcgtta   1980
gcgatggaag cattcttgga aaactctggg gaaagtgatg gtgttggagg gttcactgac   2040
aagcagatca agaacttgct tactgtgtgt gatactattg ttaagaatcc attacttctg   2100
catgctcctg gtcccgtata tcacatgatg acgaattcgg ctatcatgct ttgtcatctt   2160
ttgaatggca tgcatgcgaa ttgtggagaa ggatcaaact cgtcgggcaa atcaggcatc   2220
gaagaagttc tgtttgatga agtcctcgat tcattcatgg caacgaggaa gatattgaac   2280
gcccatcgaa aatccctacc agtaaaaactc cgttgccatg gcatcccacg accaaatgtc   2340
ggacccttca aaaagtctga ccccgaagct ccatttgtag accttggcga acattgctc   2400 tgtgcttgca gaggatgtca aggattcgta ttgatgggat gcagtccttg cgttgctgct   2460
gagagatcgg ctgcagcggc caaagcacaa catgcacatt cgtcttctac aaatggcaat   2520
tacaatgaag atgagtttga gagagaatta caagacatgg gagcttttga tatggacgat   2580
gatgccctgt tgaatgtcct ttctcggttt gtacagaact ag                      2622
```

<210> SEQ ID NO 79
<211> LENGTH: 1137
<212> TYPE: DNA
<213> ORGANISM: Thalassiosira pseudonana
<220> FEATURE:
<221> NAME/KEY: misc_feature
<223> OTHER INFORMATION: Encodes ZnCys polypeptide of SEQ ID NO:12

<400> SEQUENCE: 79

| | | |
|---|---|---|
| atggcaacaa ctactgaagt acaaaaacat gcagtctctg ctcctctccc cgcatcagca | 60 | |
| gcaacaacta caacaggagg aggaaataat gaatccaccg tcctttgcgc atcatgtgat | 120 | |
| cgctgtcgtg ctcgtaaaac gaagtgcaac ggcgctcatc cttgctcggg atgtgtttca | 180 | |
| aagtacatga agaagcacaa gttggaaagc tttgatggga ttgatcatgc attggttgaa | 240 | |
| tgtcactata gtgttgcgag aaaaagaggg cctcaacctg gttccagtaa gagcccaact | 300 | |
| gcgcccagag gatcaattcc ggcggatggg acgacgatct accaacagcc tgccaagaag | 360 | |
| aagccaaaga aagcgaagca ggcagctcca atgatgcacg atttggctgc catggcaagt | 420 | |
| gcatttggag gaggaaacct tgggcagatg cctcttcctc ttgaccctgc tgccgcggct | 480 | |
| ttgcaacagc agattctttc cagtctagga gctatcggtc tggggctcta tgcgaacttt | 540 | |
| accgctggtg gtggcagtgc gatgactgca gcttcgaata cgcaaggca gcagttggca | 600 | |
| gctgtggaat cgttgttgtc aaacaacaag tccgatgtgg acagtgtcac gaatccatta | 660 | |
| tccagcgaag aagaggctca tttccgtgca tgttacactc tctccgttgg cagtctcttt | 720 | |
| ggtcttcctg atgttcttaa gaaggaagac tacttcccga agtacgacgt ggctgtcttg | 780 | |
| caagctgctc gctttgcaga attggcaatc ggagcgttgg tcgacggaaa tggttccaag | 840 | |
| atgaccaagt tggccaatgc aactgttttg tgtctgaagg aagccgcgca agagcctgtc | 900 | |
| cacccgagct gcaagtttga tgttgcaagg gcatacttct tcctcgctat ttgtgagctc | 960 | |
| aacattggtg acgtggaagg gtacttgaag tacagaaggg agagtatgag acgtctgtcc | 1020 | |
| gagatgaatg atgcctctgg agccgatact cttttggcag caatgtccct tcaggactcg | 1080 | |
| ttcgtgtaca ttctttacaa gggcttggat gataccttc taacatcga ttctgca | 1137 | |

<210> SEQ ID NO 80
<211> LENGTH: 2691
<212> TYPE: DNA
<213> ORGANISM: Thalassiosira pseudonana
<220> FEATURE:
<221> NAME/KEY: misc_feature
<223> OTHER INFORMATION: Encodes ZnCys polypeptide of SEQ ID NO:13

<400> SEQUENCE: 80

| | | |
|---|---|---|
| atgagcaccg acgacaacaa catcatgcca gaagactggc agaataatcc acctcccctg | 60 | |
| ccacaggaca attggcagaa taatgagcag acaagcaact acgacaacgg caacagcaat | 120 | |
| ggagggcagt acagcacgca tcatcaacaa caaccaccgc aggagcaggt gaaccgtgct | 180 | |
| caatcgtcgt acaacaatca atacagcacc tcccaataca actccaacca acaacaagaa | 240 | |
| caacactacc aacagcagca gcaacaacag cagcttcaac tatgcgcctc gtgcgatcga | 300 | |
| tgccgcgctc gaaaaacgaa atgcgatgga gaacgaccgt gtgggaactg tgtcaataag | 360 | |
| ctcaagaaga agttgaagct tgacaacgtg acggaatcg acattgccga attcgactgt | 420 | |
| gtttactccc ccgccaaacg acgtggcccc atccccggta agacggggca gtctcgtaaa | 480 | |
| tcgagtgaaa tgatgtatca gcagccgcag cagaggggag gaggatatct cggtagtggg | 540 | |
| ggggagggag gatacccca gcagcagcat ggtctgcaag ggggagggta taattttggg | 600 | |
| ggaggacagc agcagcaaca acaacaacag tggatcaaca gcaacaacaa ccaaggaagt | 660 | |
| caattctcct ccgaagaatt gaaacaaatg ctatcactcc aacagcagct tctcattcaa | 720 | |
| cagcagcaaa tgcagcaaca gcaacaacag caggggatgc ttcaacagtt ggctactgtg | 780 | |
| acgagtggtg ttggaagtag tggtattgga ggggcaggtg gtattggagg aatggggaac | 840 | |
| accaacaatg tccaggtgga aaatggagca ttgcagcttc ttcagcagta tcaacagcag | 900 | |

```
ttgaacagtg gaaacaacac gctgggtagt agtggaagca tcaacatggg actgggatct        960
caaccctctc ccatgccgtc atcctcctac aatcaagaac aacaacagca acctaccaaa       1020
cgtgcccatc gccttgagcc tgtactatcc aacgccaact ccaccaatct ccccaactcg       1080
gtcgcctcac acctccccct cctctccctc acaaccccg acggcaacgt cctccgctcc        1140
tactaccaac tcagcgtcaa cgatctcctc aacctccccc ccatcccag cgacgaagac        1200
tactgcacca tcctctctca aaataactac aactgcctcc cgagcaatct tcccacctac       1260
gaccaatcgg cattgcaagc ggcgcggttt gcagagttgg cattgggagc gttggcgaac       1320
aatcaggttc cgttggcttt ggagttgagt aatgcttcgg taatgtgtat gagaaattgt       1380
gtggaggagc cgagtcacaa gagttgtatc tatgatgtgg cgagggcgta tttgttgcat       1440
gggatattta ggagttttag gggagactt tgtgaggtatt tcaagtatcg cagggtatgc       1500
atgagtcatc tttcgcagtt gaataacgaa cccaacgtgg aagctctcct cgctgccatt       1560
tcctatcacg atgccctcgc atacatgatg acaacgcaa gtgaagatgc cctccccgac        1620
attgacgaag tattgcctcg tctcaacgac tgcggtaaga acgattctgg ctgtgacatt       1680
gaggccaagt acggcatttc caccaatgct tcgtccgttg taacaaacgc caacaaccaa       1740
atgtggatgc agggtgctcc tcccgtcttc ttgaacaatg aagccagtct cgtcaatcgt       1800
tcgttagatg ccttggcttg cgctgtccgt tcgtgctgtg atcaagccaa ttccagcttt       1860
gaggagatgg cgaaggaagc aggagttgat ttgcctgcag ggggaggatc ttgtggaacg       1920
agtgctacca cgcaagctgt gatggcgaat gaaaacgagt tgtgcagtcg caacattgtg       1980
ctttcggctc agactcttct cagtcagcat gcgggcacga gtcacgagaa gagtaagaag       2040
catgggcttg tcatggtagc tacggcaatg aagccttttt tggagaatgg gggaggagat       2100
gaggaaggaa tgggagtttt caccgacaag cagattaaga acttgttggc tgtgtgtaat       2160
acgattgtca agaatccgtt gctactcttt gcgcctggac cgacgtatca tatggttagc       2220
aacgtggcga ttttgttgtg ccatctgttg aatggaatac atgccaactg tggagggtct       2280
tctggcaatg ccaaatctgg gatggaagaa gttctatttg atgaggtact tgatgctttc       2340
atggcaataa ggaagctatt gaacctccac cgaaagaatc ttccagtcaa actccgctgt       2400
catggcattc ctcgccccaa attgggacct ttcaaaaagt cggatcccga cacccctt         2460
attgatttgg gcgatacttt aatgtgtgtt tgtcggggtt gtcagggctt tgtgctcatg       2520
ggatgctcgc cttgtgtggc tgcagagaga tcggcatcct cggcaaggat gcatgccaat       2580
caaagtgaag atgacgacga tgagtttgaa cgggaacttg acaattgga cgatttcaac         2640
ctggacgacg atgctttgtt gagtctgctt tctcgcatcg ttcagaattg a                2691
```

<210> SEQ ID NO 81
<211> LENGTH: 2070
<212> TYPE: DNA
<213> ORGANISM: Thalassiosira pseudonana
<220> FEATURE:
<221> NAME/KEY: misc_feature
<223> OTHER INFORMATION: Encodes ZnCys polypeptide of SEQ ID NO:14

<400> SEQUENCE: 81

```
atgtcccaaa caagcaacac cgaacccaaa ggcgccaaac gcaaaaccca agcatgcacc         60
gaatgccaca gtccaaatc caaatgcacc tatcccgatc ccaccacaac cgccgccggc        120
ggcaccgcta aactgtgttg caatcgttgc atacggctgg gacgagactg cattcctcac       180
atctcacagc agggcaagag gaacaaaaag accgaggagg agacgatgaa gaatgagaag       240
```

```
agagtgaacg aagatgatat gcaagatggc ttatgcaagt cgaccatgtg tgctgccgcg    300
attggtaatc aagataagat tttgaaggag aataatctga gcttggaatt gcccagacat    360
attaccaatt caatggctgg tcagtttcct gctggtggag gtggaggtat gatgggtggt    420
cagtttgccg ggagaagtgg tgcgggtata cttcaccctg cggatattct atcgggtggg    480
atgaattcga gtcagttgag tctaatgttg aatcatttca gtggtactag tggaggtcag    540
agcgatacaa tgtcgacact gaataatatc atgtcttcat ctgcaatggg agctacggga    600
cctccacctt cggtagatgc attgctcatg ttggcttctc gtagtactag tattgggagc    660
aacagtggag tgaacttggg ggggacagca tcagcagcac ccgctttgcc ggggacaagt    720
cagcatctca ttcaacaatg gcaacatcag caaaaccaac ttcgttatgc tgtcatgggg    780
ggtatgcaga ctgcgactat gatgggcatg actcaggcat ctggagatgg cagtgctact    840
ggaaatcagt tggatagtgc cattattacg aaaaaggaac gcacttcatc atttggcagc    900
gagaatgatc agccgaagaa taagaagcaa aaggcgatcc aggaggcgaa ggagtggtgt    960
gctggtggag gtggcgacga tcagaaacaa tcagtgctgg aagcattggc tgctgctacg   1020
aaaaatgaaa cgacgccaaa gttcgtgcca cctcacattc attaccctcc cgtatccctc   1080
cttgccgaga ccaccaccac tgctatcaac gacaacgctt cttcttctgc agcagcagca   1140
gcagataaca ctacagacac tcaagaaagc caactccgac gttcgtccta caacgctcaa   1200
ttcgtcacac ccgaagatgc aatcggcaat cacataactg gtcaaaagct cccatgtctc   1260
caaaatcact atgggcttca atgtcaaatc cgtgaatgga tctcaatggc tttagtacga   1320
cgaagctttg cattgttaag caaggcgtcg tcttggcga atcgatgtgg tattagtatg   1380
gataggatat tttgtggggt tgtagaggaa gtggagaaga agggtggcgc tgaaaagaaa   1440 acgaagggg gttgcaagat gaacgttggt gggaagatga actatctgct ttctgtcttt   1500
ctggagccaa ggactgcaca ggttgttccc atggaacagc cttttgagcg aaacttattg   1560
tgttggcgtc acatctctca aatctttgag gacaacctgg cagatggctt ctctttgatg   1620
tttgcaaaag aggactttcg tagatttttg gcttgttatg ctcatcagat ttcatcgcaa   1680
ccgagcgcag agagtcctat tcgtccagta tatgcaccga agattactgt tcgtttgttg   1740
agcagggatt ggggccagac ggaagctgtg acggaggaaa tgatcgaggg tgtgggtaag   1800
aacgaagcgg agactactga aatggacgct ctctttgtcg tcgttccaac aatgacaag    1860 gttacatact acttggagct gtttcatccc aaccttgagt cggatgcgaa ggattgcgag   1920
gccgatgata atgacgaggg aactgaaact cccgagtcca accctcccgc cttggatacc   1980
gtcatggagg gcgaagattg gcaaggaatc gatgagattt tggccagtgg tgatgacatg   2040
gatgctttga tgaaggcatt gttggattaa                                   2070
```

<210> SEQ ID NO 82
<211> LENGTH: 1233
<212> TYPE: DNA
<213> ORGANISM: Fragilariopsis cylindrus
<220> FEATURE:
<221> NAME/KEY: misc_feature
<223> OTHER INFORMATION: Encodes ZnCys polypeptide of SEQ ID NO:15

<400> SEQUENCE: 82

```
atggggacgt ctgctaatag agcctgtact gaatgccata aggctaaggt caagtgtgtc     60
agggatgatg atggaaacat aatatgcaaa cgatgtgaaa gaattggact gaaatgcgtc    120
gaacatatct ctagacaagg acaaggtaca agacgccgaa aaaaggtaaa gaaggaaaca    180
```

```
acgacggcga cgggagcggc aaataaaaac aatgaagata agacggtaga tgaagctcta    240
gcgatcacga tagcactatc ttctccaagt cccatgccct cgtgtccagt atctggtgga    300
tcaaacatcg tgttcagcgg taatggtaac gttaacggcg ttccatcgtc cgcatgcaat    360
gcacttacgg ctatgaatgg acaagctatg accaacaaca aagagggact atgtaatggt    420
atggcttcgt tacaagttga agatagtatt atctgtaaga gtattactaa tggattaggt    480
aaagaacatt atgggattca tcatctaatc cgtatgtggg ttgcattatc atttacacgt    540
cgaagttttt cattacttgc ccgtgcgtca tttattgcat ccagaatggg gatttcgatg    600
gacgaaatta tatcgaatca atcgaatttt gctatcgatt ctggttcaca accgatgtac    660
ttcttgggga gagatatatt ggtaccgaag agtcaaagaa agacgatcgg tcttccactt    720
aatatcgaag aaattccctg ggatcttctc gaagctgttc agatcgatcc ggtacgtcct    780
gatgagacct tccgtaatcg atggtgtgct attcgaatga cagtacaggg cacttcccga    840
ttcttgacat cccctctttt ttctagagac ttttcttctg ttgacgaaat caataaggtt    900
tgggacgaaa acaaaccaaa taagaagtt gttgatctat ggatgccaaa gtctgaaaag    960
gggaatatta ataatgataa taataataat aataattcct cggaccgtaa tagtcaatat   1020
ggaggaacaa catcaagtgc caagaaacgc gacattattg atgtagcagg aggcacatca   1080
aataatgaaa ttgaaagcga tgtttgcgat cccatcatgc atgatgatgg tatcgaattt   1140
actgatttgg ttgttacaga agaaatgcag gaattttttc aattacttgc tggtgatcaa   1200
agagtgcaag cagatctgaa tagtctattc tag                                1233

<210> SEQ ID NO 83
<211> LENGTH: 2418
<212> TYPE: DNA
<213> ORGANISM: Fragilariopsis cylindrus
<220> FEATURE:
<221> NAME/KEY: misc_feature
<223> OTHER INFORMATION: Encodes ZnCys polypeptide of SEQ ID NO:16

<400> SEQUENCE: 83
atgactacta gtactagatt aagaggcaaa aggggggaaaa aagattcgag aaatgatgcc    60
gtcgccacca gcgacaacgg cgtagctatg acaacggcga atgctgtagt agtggtcaac   120
gatgagaaga ataagcaaga taattataac aacgaaggcg atccagttga atttaaagtt   180
agagtagaat tagaagtaga agctcccatc aatgaacaaa aagctgtcga taataatgag   240
aagaagaaga gcagtgccga gactactaag gctgaggctg ctgttgtgaa ttcagatgag   300
gatgtaaatg atgatgtaaa tgatgatgta aatgatggaa aggacgatgc agtcgttgta   360
gtaaagaaca gtaaagaaaa caatgacgat gacaatgata gtgataccaa aaagatgcag   420
gacgcaacga agaagaagat ggcgcctcat caagatgatg cttgtgtagt tgaagttgtt   480
caagtttctg acagaccatc atttcttggt gggactgtat taaaacgtga tactgttgga   540
ttaggattac gatataaaac agaaaaagaa aaagagaaag tacatgaaaa tgatattcta   600
ttttcaagtg ttgatcttgg tttacaatca ggatcaggag gatcatcttc tagtcaattt   660
ttgaatcata cagatcatag tggtaataag aaattacaat ctataatcaa ggcaagaaaa   720
tcaaattatt ttgtgaatga tgttactaat attgattcat gtagtattgc agtaaatgaa   780
gaagaacgta ctaaaattgc aaaagaaatc tttcatgaaa taacaacaac aacaacaaca   840
actggtaaag atgtaggtat tggtgttggt cgattttttaa attttaaatc aatgactaaa   900
gcaaagtatg agaatttagg ttgtgatttt gtatgggaaa ttatgatga aataacatca   960
```

| | |
|---|---|
| ataataaaaa tatgtcaaac tatgaattat atctttatgt ccgatcaaga acgtactgaa | 1020 |
| cgtagtcttg caatagaaac acagcaaaaa caacaacaaa atgactatcg gaatgaacga | 1080 |
| caacaaaaga atgggaagac tttatcatca tctgataaaa agtcgaaaac gaaaaagtca | 1140 |
| acaaaacaaa ataaaattct tttacaacaa cgtcaacaag aacaagaaca acgtgaaaac | 1200 |
| gctcagatac aagaacaaca gcttcaacaa caacaacaac aacaacaaca atgtcaacaa | 1260 |
| gttcagatgc gaatatacca attacagcaa cagttacagc agcagcaagt gtattaccct | 1320 |
| ccaacaccgc ttattcaaca gtatccgacg gcaatgccaa tgccaatgcc attatcaagt | 1380 |
| ccttcaccac tactaccaaa agacggtaag aagaagaaga cgaagggaga aagagaaag | 1440 |
| gcaccagttc cagcagcaat ggcaagtgaa agaagtggta ttattgaagg ccgtgttatt | 1500 |
| gttgatacta ttgttggtgg tgatagtgat gaacacattg ggaatgaaaa tttagttaaa | 1560 |
| ttaattgtca agaaaaaatc agaatatgat tatattgaag ttaaggatat aaaaaagtta | 1620 |
| ggtatagcaa gagtacgtca aaatgtatca ttgaatatag tcaaatctat tgttaaagaa | 1680 |
| aatggtggcc gattcttatt ccgtagaaag aaagacgttg atgatgattt gttagagact | 1740 |
| cctacagtag aggcgacgat cgctgtaatt aaagatggag aagatgctat agcaagagca | 1800 |
| gaagcagcat tacgaggaga aaaaacacca acgaagacgt cgaacgatat tgaggatgag | 1860 |
| gatgaggatg ataacatcaa aaatgaagat tctggtcctg ttgtttggga ggaattgaaa | 1920 |
| gatgaaagta tgatacaagc gattgtatgg agatgtatga aagatatata tgaattagct | 1980 |
| gacgaaaata agacagagat attagaaaag agaaggaag caaaaaagga aagaaaacgt | 2040 |
| ttacatgaat atgatcatga tgatgaatca gcaggcccag cagcagcagc aaccgcacgg | 2100 |
| aaaaaacaag cagtagagga agatccatct ggtcgtaaga ataaaagttg tgattttttgt | 2160 |
| cgtgataaaa aactgaaatg caatcgtaca agcccttgtg aaaactgtac tacaaagtac | 2220 |
| atgaaggatc acaatttgac tagtgaggaa gtcgaagaat ccaaaattgc caatagtatt | 2280 |
| aatgcggtag cggtggtcgc aaaagttgaa gaagcaaaga aactggaatc aatgccagaa | 2340 |
| acgaagcgtc ctcgtacgag aagtatattc cattttttag tattttaat actagaatgt | 2400 |
| tccgtgccga tggagtaa | 2418 |

<210> SEQ ID NO 84
<211> LENGTH: 3120
<212> TYPE: DNA
<213> ORGANISM: Nannochloropsis oceanica
<220> FEATURE:
<221> NAME/KEY: misc_feature
<223> OTHER INFORMATION: Encodes ZnCys polypeptide of SEQ ID NO:17

<400> SEQUENCE: 84

| | |
|---|---|
| atgacgaccc tccttggaca gccccctcc tcgttggggg cgatggggag tgcattttac | 60 |
| gatgaggacg ctcagagcgt cgtggccctc ggccaacacg ctgcaggcag tggcacggag | 120 |
| gacgagatga atacagacca tttcgatgag ttggaccgca tcatcttcga catgccgtac | 180 |
| gtgtcagagc aggatcccctt gagcagctgt agcgtcggag ggcagtcgca agggcaaacc | 240 |
| aacgggcagg gccatgggca ccaagagcgg ggggcgtcac agcacggggg cgcgggtctc | 300 |
| ttgatgccta accccacaa tggccacatc acggtgatgg gggtcaccca cataaatcac | 360 |
| aacaaccatg gaagcgtccg agggggaggg atggactggc acgcgaagga ggaggacgcc | 420 |
| tcatatcata ctgcggtgga ctccagctgt cacactgacc ggagctacca tcgtgtggat | 480 |
| gcctcggggc attccatgat cgacgcctcc agccatagca tgatggatgc atcggggcac | 540 |

-continued

```
gagtccctga ttgattcgag tgggcattac gacgacttcg ccgcgcacaa gggcgacccc      600
agatatatgg agcacagctg cgaggcctgc aagcgatcca agaaacgctg taaccgtcgc      660 aaccectgcc aaatatgcac ctcccgaggc atcaagtgcg tgccccaaat ccgcggaccc      720
ggtcgtcctc caggcagtaa gagcagcaga ggctcctcct cctcttcctc cctcactctg      780
ggcagttccc gccatggtgg ctcccgggga gatgtgcgct cttccctcaa cagcacccag      840
catagcacca acagcagtgc caccacctcc gccgcatctt ccactgcctc ctccctctct      900
cgctctttgt ctggtaacgg gttgttacag caagagcagg acttggtggt agtggctgct      960
gctgcttcta cgagacaatc ccctccaagg gaccettggc actgtcgatt cttcttcgag     1020
gcggcgcggc attgcaagga ggcgtttctg aaggcctggc atgacaatga gttggatacg     1080
tccaagtgta ttatgctcag gaacctctgg accaagacgt cctccatcct cgcctcaggg     1140
gtcgacatga ccttcggtat ctgtgaccag ctccaagaag tggttgggcc cgccccaacg     1200
ggctcgggcc cgattgcctg tagtcctgcg acgagaagca agagccaggc ggcgcaacaa     1260
gcccagctct tgtcgcaccc ggggtcgaag gagggaatgg gtccttggaa tctgcccgat     1320
gatttgagga agatgatga tggagtgtcg atgttgtgtg ggttcatgtt tatccaggac     1380
gagttgttcg tgtttacaga cgagaggttc gccgctacat tcatgacacg cgaggaggtg     1440
gaggggaagg tggagagctt cgcagtgttg ccgatactgt tgttggcgga gatattccac     1500
cctgacgacc tacctgatgt ttatgcagca attggcgcgc attggtttag gcggcggccg     1560
agctctggtg tagggggtggg gggaagtaat gggagtatca gcagcatgaa cagcagtagc     1620
ggtagtacga gcagtaggga ctcggcaagc ccggggccag tgtctcggga ggtacctgag     1680
gcggcttgga tttgcaaatg cattgataag cggaatacgg agataacggc cttggtgcgg     1740
tttcggtcat ttgcggcacc gacggagggt tacgcgggtg cggctatgtt atcgatcttg     1800
ccgttgacaa gaagcaagta tattgcggat ccggatgtac agacgaacat gaggtcgggg     1860
gtgtcgtcga ggcaccactt gagggataca tttgggcat tgcctactgc tttgccggag      1920
cacgatgacg aagacgatga cgacgagcat caccatctgg tgttagaaag gagaggggaa     1980
agagtggggg cgtcggggca tggccaggat ttgttaaatg aggaggagga cgatgaaatt     2040
tttttggatg cacacggtga cgacgctatg ttccggccct tgcggcgggg gatgacggtg     2100
ttgtcggctg agacgagcgg tcctcaaccg gtgcctcttt ccaagcatgc ctctgacccct    2160 ctacctcatc acaacgagca ccacttccac agccagcccc agcacacctc ttctcatttg     2220
tctagtttga gtagcatggc gtcgcatcag acaggcgtgt cgtgggggg tggaaggatt      2280 tctgaatgcc tggggaacca aaaccgcagc gcctcgcaat tctacaacac agtgcagcat     2340
caagagcggc ctaagcggga gcaagaggag ccgcaccagc agcaccgtga agaacaacag     2400
caacatcgcc ttccaggcaa caatagcttg gacgggagca gcagccacgg aggcgccatg     2460
gaccaagacc tccctactgt tcagctgacc caggcgcagc tcttcctctt gcaggggggc     2520
actggcagtg gcatcggttt atttaaagat atacagcagg agcagcagca catgtgcaac     2580
cagatttcgc cagacggcgt gacagcagcg gaggagagcg cagagagagt cgctactgag     2640
ctgtacggtt cgagtcccag tccggagccg cacctccttg gccattcccg tcacagccca     2700
acgcaacgtg cacagcagca gcagcagcag cagaaaaggc aacaagaacg ccagcaagaa     2760
gatcagcaac aagaacaagg acatcaacag cagcaacagc agcaacagca gcagggggatg    2820 gtgctgcccc tgccacacct gcctgggatg gtgccgtcgc ttgtccgcac cgtgagcagc     2880
agcgccatgt tgggtgcccg ccccacaacc atatcccaag gaaaggacga agggggacgt     2940
```

```
ggagggggcgt tgagtcacag caatagcagc accgacctgg atatgtcttg tcatggcccg    3000
gcggatccga atgggtatgg tggattgcat tggacgccgg cgccattggc ttctttttttg   3060 ggggtttcct cttggggatc aaggcgtggc tcaaggaagg aggagagatc taaagattag    3120

<210> SEQ ID NO 85
<211> LENGTH: 8315
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Knockdown construct

<400> SEQUENCE: 85
gcggccgccg tatggtcgac ggttgctcgg atgggggggg cggggagcga tggagggagg      60
aagatcaggt aaggtctcga cagactagag aagcacgagt gcaggtataa gaaacagcaa     120
aaaaaagtaa tgggcccagg cctggagagg gtatttgtct tgttttttctt tggccaggaa    180 cttgttctcc tttcttcgtt tctaggaccc cgatccccgc tcgcatttct ctcttcctca     240
gccgaagcgc agcggtaaag catccatttt atcccaccga aagggcgctc ccagccttcg     300
tcgagcggaa ccggggttac agtgcctcac tcctttgcac gcggtcgggt gctcggccta     360
cggttgcccg agtccgcaag cacctcaaca cagccgtctg tccacaccgc agccgaccgg     420
cgtgcgattt gggtccgacc caccgtccca gccccgctgc ggactatcgc gtcgcagcgg     480
ccctgcgccc acgcggcgtc gtcgaagttg ccgtcgacga gagactggta aagctgatcg     540
agtccgatac gcaacatata ggcgcggagt cgtgggagc cggccagctc cgggtgcctc      600
cgttcaaagt agcgtgtctg ctgctccatg cacgccaacc agggacgcca gaagaatatg     660
ttcgccactt cgtattggct atcaccaaac atcgcttcgg accagtcgat gacagcagta     720
atccgaccat tgtctgtaag tacgttattg ctgccgaaat ccgcgtgcac caggtgcctg     780
acctcagggc aatcctcggc ccacaacatg agttcgtcca gtgcttgggc cacggatgca     840
gacacggtgt catccatgac tgtctgccaa tgatagacgt gaggatcggc aatggcgcag     900
atgaagtctc gccaggtcgt gtactgcccg atgccctggg gcccaaaagg tccaaagccg     960
gacgtctgag acagatctgc ggcagcgatc gcgtccatgg cctcggccac gggttgcaaa    1020
acggcaggca attcagtttc gggcagatct tgcaacgtca ctccctgggc tcggcgcgag    1080
atgcagtacg tgagagattc gctaaactcc ccaatgtcca gtacctctgg tatggggaga    1140
gcggcggagg cgaaatgacg gtagacatac cgatccttgt agaacccgtc cgcacaacta    1200
ttaaccctca acacgtatcc ccgacccccct acgtcaaacg agaacgccct actctcctct    1260
ccctcgctca gttgcatcaa gtcggagaca gagtcgaact tctcaataag gaatttctcc    1320
acggacgtag cggtcagttc cggtttcttc cccatcgagc tcggtacccg gggatccatg    1380
attgttgtat tatgtaccta tgtttgtgat gagacaataa atatgagaag agaacgttgc    1440
ggccactttt ttctccttcc ttcgcgtgct catgttggtg gtttgggagg cagaagatgc    1500
atggagcgcc acacattcgg taggacgaaa cagcctcccc cacaaaggga ccatgggtag    1560
ctaggatgac gcacaagcga gttcccgctc tcgaagggaa acccaggcat ttccttcctc    1620
ttttcaagcc acttgttcac gtgtcaacac aattttggac taaaatgccc ctcggaactc    1680
ggcaggcctc cctctgctcc gttgtcctgg tcgccgagaa cgcgagaccg tgccgcatgc    1740
catcgatctg ctcgtctgta ctactaatcg tgtgcgtgtt cgtgcttgtt tcgcacgaaa    1800
```

```
ttgtcctcgt tcggccctca caacggtgga atcggtgct agaataaagt gaggtggctt    1860
atttcaatgg cggccgtcat catgcgggat caactgaagt acggcgggtt ctcgagattt    1920
catcgtgctc gtccagagca ggtgttttgc ctgcagctct tcatgtttag gggtcatgat    1980
ttcatctgat atgccgtaag aaaaccaata ttcacttctc aattttccat ggaaaggtga    2040
aggcctaggt tgtgtgcgag gcaacgactg gggagggatc gcaacattct tgctaacctc    2100
ccctctatct tggccgctgt gaatcggcat atttaccggg ctgaattgag aaagtgtttt    2160
gagggaatta aaaggtggct gtcttgcaag cttggcttca gtgcctgctt aattcgaacc    2220
gatccagctt gtgatgaggc cttcctaagc ctggtagtca gaagcgacat ggcgctataa    2280
atttcgtctc agttggagag tagaaaagca tgattcgaac acggttttca actgccaaag    2340
atatctccat tgtttccttc aatctgtaca cctgcacggt gcaccagttg gtacggcata    2400
ttatggttta aagttgaaaa tgctaacagt gaagtgatat cctttttta tggagtgttg    2460 aggtgaagtc tagcatcgta ggggaaaaca ggattctgtg tcttccattc tactccttga    2520
taaagcgaag aaatccgaca aaaccaaaga gattgttcaa gtttaagatt tgtaagcgta    2580
caactatgaa cttcttctct ttgtaggcct gagtggtcgt atgcatacga ttcatgaagt    2640
gaatcagtat cgctggattt tgcttaggag taaagcacaa ctaagaaaat atgctgcctg    2700
gcaggcatcc tgagacatga ggcaagcgac gtagcaattg aatcctaatt taagccaggg    2760
catctgtatg actctgttag ttaattgatg aaccaatgag ctttaaaaaa aaatcgttgc    2820
gcgtaatgta gtttaattc tccgccttga ggtgcgggc catttcggac aaggttcttt    2880
ggacggagat ggcagcatgt gtcccttctc caaattggtc cgtgtggtag ttgagatgct    2940
gccttaaaat tctgctcggt catcctgcct tcgcattcac tcctttcgag ctgtcgggtt    3000
cctcacgagg cctccgggag cggattgcgc agaaaggcga cccggagaca cagagaccat    3060
acaccgacta aattgcactg gacgatacgc catggcgacg acgatggcca agcattgcta    3120
cgtgattatt cgccttgtca ttcagggaga aatgatgaca tgtgtgggac ggtctttata    3180
tgggaagagg gcatgaaaat aacatggcct ggcgggatgg agcgtcacac ctgtgtatgc    3240
gttcgatcca caagcaactc accatttgcg tcggggcctg tctccaatct gctttaggct    3300
acttttctct aatttagcct attctataca gacagagaca cacgggatc gtttaaacga    3360 tcagccacga cggctctcgc atgcacaacg atggcatgga ttggcgcgcg aaggatgagg    3420
actgctcgta ccacaccgcc gtggacgcca gctgccacat cgacagtagc taccaccatg    3480
ttgatgcctc aggccactcc atggtcgacg cctcgggtca cagcacgata gacgcgtcgg    3540
gccacgactc cctcatcgac tcaagcggcc attacgacga ctatctggcg cacaaggggg    3600
acgcccgcta catggagcac agttgtgaag cctgcaagcg ctcgaagaaa cgatgcaacc    3660
gccgcaaccc ctgccagatc tgcacctcca ggggcatcaa gtgtgtgccg caaatccggg    3720
gtcctgggcg cccccggg agtaaaagca gtcgggctg cacctccttg tcactgagca    3780
gctcacggca tggaagctcc aggggtgaca tacgcgccgc gaacggaagc gggcagagcc    3840
acaacagcag tgccacgaac cgccccgact gcttttactg cccgggggc gcccaggacc    3900 ccggatttgc ggcacacact tgatgcccct ggaggtgcag atctggcagg ggttgcggcg    3960
gttgcatcgt ttcttcgagc gcttgcaggc ttcacaactg tgctccatgt agcgggcgtc    4020 cccttgtgc gccagatagt cgtcgtaatg gccgcttgag tcgatgaggg agtcgtggcc    4080
cgacgcgtct atcgtgctgt gacccgaggc gtcgaccatg gagtggcctg aggcatcaac    4140
```

```
atggtggtag ctactgtcga tgtggcagct ggcgtccacg gcggtgtggt acgagcagtc   4200
ctcatccttc gcgcgccaat ccatgccatc gttgtgcatg cgagagccgt cgtggctgat   4260
cgtttaaacg agtcaagggg gaaggtgcat agtgtgcaac aacagcatta acgtcaaaga   4320
aaactgcacg ttcaagcccg cgtgaacctg ccggtcttct gatcgcctac atatagcaga   4380
tactagttgt acttttttttt ccaaagggaa cattcatgta tcaatttgaa ataaacatct   4440
atcctccaga tcaccagggc cagtgaggcc ggcataaagg acggcaagga agaaaaagaa   4500
agaaagaaaa ggacacttat agcatagttt gaagttataa gtagtcgcaa tctgtgtgca   4560
gccgacagat gcttttttttt tccgtttggc aggaggtgta gggatgtcga agaccagtcc   4620
agctagtatc tatcctacaa gtcaatcatg ctgcgacaaa aatttctcgc acgaggcctc   4680
tcgataaaca aaactttaaa agcacacttc attgtcatgc agagtaataa ctcttccgcg   4740
tcgatcaatt tatcaatctc tatcatttcc gccccttttcc ttgcatagag caagaaaagc   4800
gacccggatg aggataacat gtcctgcgcc agtagtgtgg cattgcctgt ctctcattta   4860
cacgtactga aagcataatg cacgcgcata ccaatatttt tcgtgtacgg agatgaagag   4920
acgcgacacg taagatcacg agaaggcgag cacggttgcc aatggcagac gcgctagtct   4980
ccattatcgc gttgttcggt agcttgctgc atgtcttcag tggcactata tccactctgc   5040
ctcgtcttct acacgagggc cacatcggtg caagttcgaa aaatcatatc tcaatcttca   5100
gatccttttcc agaaacggtg ctcaggcggg aaagtgaagg ttttctactc tagtggctac   5160
cccaattctc tccgactgtc gcagacggtc cttcgttgcg cacgcaccgc gcactacctc   5220
tgaaattcga caaccgaagt tcaatttttac atctaacttc tttcccattc tctcaccaaa   5280
agcctagctt acatgttgga gagcgacgag agcggcctgc ccgccatgga gatcgagtgc   5340
cgcatcaccg gcaccctgaa cggcgtggag ttcgagctgg tgggcggcgg agagggcacc   5400
cccgagcagg gccgcatgac caacaagatg aagagcacca aaggcgccct gaccttcagc   5460
ccctacctgc tgagccacgt gatgggctac ggcttctacc acttcggcac ctaccccagc   5520
ggctacgaga accccttcct gcacgccatc aacaacggcg gctacaccaa cacccgcatc   5580
gagaagtacg aggacggcgg cgtgctgcac gtgagcttca gctaccgcta cgaggccggc   5640
cgcgtgatcg cgacttcaa ggtgatgggc accggcttcc ccgaggacag cgtgatcttc   5700
accgacaaga tcatccgcag caacgccacc gtggagcacc tgcacccccat gggcgataac   5760
gatctggatg gcagcttcac ccgcaccttc agcctgcgcg acggcggcta ctacagctcc   5820
gtggtggaca gccacatgca cttcaagagc gccatccacc ccagcatcct gcagaacggg   5880
ggccccatgt tcgccttccg ccgcgtggag gaggatcaca gcaacaccga gctgggcatc   5940
gtggagtacc agcacgcctt caagaccccg gatgcagatg ccggtgaaga ataagggtgg   6000
gaaggagtcg gggagggtcc tggcagagcg gcgtcctcat gatgtgttgg agacctggag   6060
agtcgagagc ttcctcgtca cctgattgtc atgtgtgtat aggttaaggg ggcccactca   6120
aagccataaa gacgaacaca aacactaatc tcaacaaagt ctactagcat gccgtctgtc   6180
catctttatt tcctggcgcg cctatgcttg taaaccgttt tgtgaaaaaa ttttttaaaat   6240
aaaaaagggg acctctaggg tccccaatta attagtaata taatctatta aaggtcattc   6300
aaaaggtcat ccagacgaaa gggcctcgtg atacgcctat ttttataggt taatgtcatg   6360
ataataatgg tttcttagac gtcaggtggc acttttcggg gaaatgtgcg cggaaccccct   6420
atttgtttat ttttctaaat acattcaaat atgtatccgc tcatgagaca ataaccctga   6480
taaatgcttc aataatattg aaaaaggaag agtatgagta ttcaacattt ccgtgtcgcc   6540
```

```
cttattccct tttttgcggc attttgcctt cctgttttg ctcacccaga aacgctggtg    6600
aaagtaaaag atgctgaaga tcagttgggt gcacgagtgg gttacatcga actggatctc    6660
aacagcggta agatccttga gagttttcgc cccgaagaac gttttccaat gatgagcact    6720
tttaaagttc tgctatgtgg cgcggtatta tcccgtattg acgccgggca agagcaactc    6780
ggtcgccgca tacactattc tcagaatgac ttggttgagt actcaccagt cacagaaaag    6840
catcttacgg atggcatgac agtaagaaa ttatgcagtg ctgccataac catgagtgat    6900
aacactgcgg ccaacttact tctgacaacg atcggaggac cgaaggagct aaccgcttt    6960 ttgcacaaca tggggatca tgtaactcgc cttgatcgtt gggaaccgga gctgaatgaa    7020
gccataccaa acgacgagcg tgacaccacg atgcctgtag caatggcaac aacgttgcgc    7080
aaactattaa ctggcgaact acttactcta gcttcccggc aacaattaat agactggatg    7140
gaggcggata agttgcagg accacttctg cgctcggccc ttccggctgg ctggtttatt    7200
gctgataaat ctggagccgg tgagcgtggg tctcgcggta tcattgcagc actggggcca    7260
gatggtaagc cctcccgtat cgtagttatc tacacgacgg ggagtcaggc aactatggat    7320
gaacgaaata gacagatcgc tgagataggt gcctcactga ttaagcattg gtaactgtca    7380
gaccaagttt actcatatat actttagatt gatttaaaac ttcatttta atttaaaagg    7440 atctaggtga agatccttt tgataatctc atgaccaaaa tcccttaacg tgagttttcg    7500
ttccactgag cgtcagaccc cgtagaaaag atcaaaggat cttcttgaga tcctttttt    7560 ctgcgcgtaa tctgctgctt gcaaacaaaa aaaccaccgc taccagcggt ggtttgtttg    7620
ccggatcaag agctaccaac tctttttccg aaggtaactg gcttcagcag agcgcagata    7680
ccaaatactg tccttctagt gtagccgtag ttaggccacc acttcaagaa ctctgtagca    7740
ccgcctacat acctcgctct gctaatcctg ttaccagtgg ctgctgccag tggcgataag    7800
tcgtgtctta ccgggttgga ctcaagacga tagttaccgg ataaggcgca gcggtcgggc    7860
tgaacggggg gttcgtgcac acagcccagc ttggagcgaa cgacctacac cgaactgaga    7920
tacctacagc gtgagctatg agaaagcgcc acgcttcccg aagggagaaa ggcggacagg    7980
tatccggtaa gcggcagggt cggaacagga gagcgcacga gggagcttcc agggggaaac    8040
gcctggtatc tttatagtcc tgtcgggttt cgccacctct gacttgagcg tcgatttttg    8100
tgatgctcgt caggggggcg gagcctatgg aaaaacgcca gcaacgcggc ctttttacgg    8160
ttcctggcct tttgctggcc ttttgctcac atgttctttc ctgcgttatc ccctgattct    8220
gtggataacc gtattaccgc ctttgagtga gctgataccg ctcgccgcag ccgaacgacc    8280
gagcgcagcg agtcagtgag cgaggaagcg gaaga                              8315
```

<210> SEQ ID NO 86
<211> LENGTH: 111
<212> TYPE: DNA
<213> ORGANISM: Nannochloropsis gaditana
<220> FEATURE:
<221> NAME/KEY: misc_feature
<223> OTHER INFORMATION: SNARE terminator (inverted orientation)

<400> SEQUENCE: 86

```
tatgcttgta aaccgttttg tgaaaaaatt tttaaaataa aaagggggac ctctagggtc    60
cccaattaat tagtaatata atctattaaa ggtcattcaa aaggtcatcc a            111
```

<210> SEQ ID NO 87
<211> LENGTH: 17

-continued

```
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding CCT domain-containing protein

<400> SEQUENCE: 87
ttccgaagta ctggttc                                                  17

<210> SEQ ID NO 88
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Target sequence for guide RNA targeting gene
      encoding Zn(2)-C6 fungal-type DNA-binding domain protein (ZnCys-
      2845)

<400> SEQUENCE: 88
agtaggccat tcccggag                                                 18

<210> SEQ ID NO 89
<211> LENGTH: 18
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Zinc finger, TAZ-type protein

<400> SEQUENCE: 89
tgtggcagac gccgacgg                                                 18

<210> SEQ ID NO 90
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding RpoD family RNA polymerase sigma factor SigA protein

<400> SEQUENCE: 90
gtactgcctg acaaactagg                                               20

<210> SEQ ID NO 91
<211> LENGTH: 17
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Fungal Zn(2)-Cys(6) binuclear cluster domain-containing
      protein

<400> SEQUENCE: 91
tgagcagtcg tacgaaa                                                  17

<210> SEQ ID NO 92
<211> LENGTH: 18
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
``` encoding Zinc finger, CCCH-type-containing protein

<400> SEQUENCE: 92
cgaagtcaac catggggc                                                18

<210> SEQ ID NO 93
<211> LENGTH: 18
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Winged helix-turn-helix transcription repressor DNA-
      binding protein

<400> SEQUENCE: 93
tcctgtgact tgacggtg                                                18

<210> SEQ ID NO 94
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding SANT/Myb domain protein

<400> SEQUENCE: 94
ggcaatacaa gcagtggaag                                              20

<210> SEQ ID NO 95
<211> LENGTH: 18
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding CCT motif family protein

<400> SEQUENCE: 95
ctgatctcga gatggctg                                                18

<210> SEQ ID NO 96
<211> LENGTH: 18
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Fungal specific transcription factor domain-containing
      protein

<400> SEQUENCE: 96
gtgaagattg gtcccact                                                18

<210> SEQ ID NO 97
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Myb-like DNA-binding shaqkyf class family protein

<400> SEQUENCE: 97
ggacgctacg accgtgcggg                                              20

```
<210> SEQ ID NO 98
<211> LENGTH: 18
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Nucleic acid-binding protein

<400> SEQUENCE: 98
ctgcaccaga cacaaatt                                                 18

<210> SEQ ID NO 99
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Activating transcription factor 6

<400> SEQUENCE: 99
gggaaatatt aagactggag                                               20

<210> SEQ ID NO 100
<211> LENGTH: 18
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Fungal Zn(2)-Cys(6) binuclear cluster domain-containing
      protein

<400> SEQUENCE: 100
tcacgggaga tgtcctgt                                                 18

<210> SEQ ID NO 101
<211> LENGTH: 18
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Zn(2)-C6 fungal-type transcription factor

<400> SEQUENCE: 101
aggactctcc tcagctga                                                 18

<210> SEQ ID NO 102
<211> LENGTH: 18
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Winged helix-turn-helix transcription repressor

<400> SEQUENCE: 102
tcttcatctg cgacaacg                                                 18

<210> SEQ ID NO 103
<211> LENGTH: 18
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Fungal Zn(2)-Cys(6) binuclear cluster domain-containing
``` protein

<400> SEQUENCE: 103
acgtccgaat ataccgaa                                                18

<210> SEQ ID NO 104
<211> LENGTH: 19
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Myb-like dna-binding domain-containing protein

<400> SEQUENCE: 104
gtagaacaag cgttagacc                                               19

<210> SEQ ID NO 105
<211> LENGTH: 19
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Fungal Zn(2)-Cys(6) binuclear cluster domain-containing
      protein

<400> SEQUENCE: 105
cgccaccctc gcacgtgtc                                               19

<210> SEQ ID NO 106
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA targeting gene
      encoding Aureochrome1-like protein

<400> SEQUENCE: 106
ggcaccatcc ccaccggttt                                              20

<210> SEQ ID NO 107
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Sense Primer from gene encoding CCT domain-
      containing protein

<400> SEQUENCE: 107
aagtgcgcaa gacgctccag                                              20

<210> SEQ ID NO 108
<211> LENGTH: 21
<212> TYPE: DNA
<213> ORGANISM: Nannochloropsis gaditana
<220> FEATURE:
<221> NAME/KEY: misc_feature
<223> OTHER INFORMATION: Antisense Primer from gene encoding CCT domain-
      containing protein

<400> SEQUENCE: 108
gatcccaaag gtcatatccg t                                            21

<210> SEQ ID NO 109

```
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 109
acctccttgt cactgagcag                                                 20

<210> SEQ ID NO 110
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 110
gatcccaaag gtcatatccg t                                               21

<210> SEQ ID NO 111
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 111
actctgtgct accaattgct g                                               21

<210> SEQ ID NO 112
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 112
cgtcagcaaa tcttgcacca                                                 20

<210> SEQ ID NO 113
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 113
gagatgctgt ccgagacacg                                                 20

<210> SEQ ID NO 114
<211> LENGTH: 20
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<223> OTHER INFORMATION: Primer

<400> SEQUENCE: 114
gtatctcgga cagggcactg                                                     20

<210> SEQ ID NO 115
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 115
atccatgtaa agacgatgtg c                                                   21

<210> SEQ ID NO 116
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 116
tgatatcaca tgctcaaggt c                                                   21

<210> SEQ ID NO 117
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 117
agatgaggat caagcaccga gcca                                                24

<210> SEQ ID NO 118
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 118
ggaagaaata gtagttgcgt g                                                   21

<210> SEQ ID NO 119
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer
```

```
<400> SEQUENCE: 119
aggcgctctg attgctgtgg c                                          21

<210> SEQ ID NO 120
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 120
tcttccacgt cggatggcca g                                          21

<210> SEQ ID NO 121
<211> LENGTH: 23
<212> TYPE: DNA
<213> ORGANISM: Artificial Sequence
<220> FEATURE:
<223> OTHER INFORMATION: Synthetic

<400> SEQUENCE: 121
attgtggagg gtaacaaact acg                                        23

<210> SEQ ID NO 122
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 122
tgagtcccgt ggagaggagt cg                                         22

<210> SEQ ID NO 123
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 123
aggttccaat ggaggccgca                                            20

<210> SEQ ID NO 124
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 124
cactttcctt cgtacgctca gc                                         22

<210> SEQ ID NO 125
```

```
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 125
ctcgaggtag gtggtgaaag                                          20

<210> SEQ ID NO 126
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 126
gtgattcgca tggacgaac                                           19

<210> SEQ ID NO 127
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 127
atgggtacgg acttgttcg                                           19

<210> SEQ ID NO 128
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 128
acagcgatac ggacagtgac                                          20

<210> SEQ ID NO 129
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 129
gacgttgcat gagaaaggag                                          20

<210> SEQ ID NO 130
<211> LENGTH: 20
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<223> OTHER INFORMATION: Primer

<400> SEQUENCE: 130
gatgcacagg tgcttgttag                                              20

<210> SEQ ID NO 131
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 131
tgcaaagcct atttccgacg                                              20

<210> SEQ ID NO 132
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 132
ctcattcgtg aggtgaccat                                              20

<210> SEQ ID NO 133
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 133
gagcaaactg acattgatac                                              20

<210> SEQ ID NO 134
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 134
gtaccacaca tacacatg                                                18

<210> SEQ ID NO 135
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer
```

<400> SEQUENCE: 135
cacatccacc atcattccac                                              20

<210> SEQ ID NO 136
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 136
gagtgttccc agtgagccag                                              20

<210> SEQ ID NO 137
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 137
ctgacaagaa gatggacatg                                              20

<210> SEQ ID NO 138
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 138
ctttagttat acgtctgaag                                              20

<210> SEQ ID NO 139
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 139
gagaggatag ttctcagag                                               19

<210> SEQ ID NO 140
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 140
gtcccacaat ctattgtg                                                18

```
<210> SEQ ID NO 141
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 141
atgagtactt gcgcgctttg                                               20

<210> SEQ ID NO 142
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 142
gcatgcctcc gtcacagagt                                               20

<210> SEQ ID NO 143
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 143
atccattgag catgccgacg                                               20

<210> SEQ ID NO 144
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 144
gcaacatgtt aatgcatcgt                                               20

<210> SEQ ID NO 145
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 145
tcgtcctcga actcttcctc                                               20

<210> SEQ ID NO 146
<211> LENGTH: 20
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 146
cgggaacaac caaggtgtaa                                              20

<210> SEQ ID NO 147
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 147
tagcagagca ggctcatcac                                              20

<210> SEQ ID NO 148
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 148
gaatatgtgg tctagctcgt                                              20

<210> SEQ ID NO 149
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 149
atggctccac cctctgtaag                                              20

<210> SEQ ID NO 150
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Primer

<400> SEQUENCE: 150
ctgactacag ctagcacgat                                              20

<210> SEQ ID NO 151
<211> LENGTH: 25
<212> TYPE: DNA
<213> ORGANISM: Nannochloropsis gaditana
<220> FEATURE:
<221> NAME/KEY: misc_feature
<223> OTHER INFORMATION: Primer
```

```
<400> SEQUENCE: 151
aagactttgg aggatgtctg agtgg                                          25

<210> SEQ ID NO 152
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 152
acgaagctac atccagtgca agg                                            23

<210> SEQ ID NO 153
<211> LENGTH: 21
<212> TYPE: DNA
<213> ORGANISM: Nannochloropsis gaditana
<220> FEATURE:
<221> NAME/KEY: misc_feature
<223> OTHER INFORMATION: NAR1 gene, sense Primer

<400> SEQUENCE: 153
gccaacctgc cagtaaaatt c                                              21

<210> SEQ ID NO 154
<211> LENGTH: 20
<212> TYPE: DNA
<213> ORGANISM: Nannochloropsis gaditana
<220> FEATURE:
<221> NAME/KEY: misc_feature
<223> OTHER INFORMATION: NAR1 gene, antisense Primer

<400> SEQUENCE: 154
agagcgggat tctgttcttg                                                20

<210> SEQ ID NO 155
<211> LENGTH: 21
<212> TYPE: DNA
<213> ORGANISM: Nannochloropsis gaditana
<220> FEATURE:
<221> NAME/KEY: misc_feature
<223> OTHER INFORMATION: Amt2 gene, sense Primer

<400> SEQUENCE: 155
agaacgtggg taagatgcaa c                                              21

<210> SEQ ID NO 156
<211> LENGTH: 19
<212> TYPE: DNA
<213> ORGANISM: Nannochloropsis gaditana
<220> FEATURE:
<221> NAME/KEY: misc_feature
<223> OTHER INFORMATION: Amt2 gene, antisense Primer

<400> SEQUENCE: 156
accagccaaa ccagagaag                                                 19

<210> SEQ ID NO 157
<211> LENGTH: 22
<212> TYPE: DNA
<213> ORGANISM: Nannochloropsis gaditana
<220> FEATURE:
<221> NAME/KEY: misc_feature
<223> OTHER INFORMATION: GS2 gene, sense Primer
```

```
<400> SEQUENCE: 157 ggcatacccta ttcatccgct ag                                          22

<210> SEQ ID NO 158
<211> LENGTH: 21
<212> TYPE: DNA
<213> ORGANISM: Nannochloropsis gaditana
<220> FEATURE:
<221> NAME/KEY: misc_feature
<223> OTHER INFORMATION: GS2 gene, antisense Primer

<400> SEQUENCE: 158
caaatgacca agcaccaact c                                            21

<210> SEQ ID NO 159
<211> LENGTH: 20
<212> TYPE: DNA
<213> ORGANISM: Nannochloropsis gaditana
<220> FEATURE:
<221> NAME/KEY: misc_feature
<223> OTHER INFORMATION: NAR2 gene, sense Primer

<400> SEQUENCE: 159
gcgaggcatc ttgtgaattg                                              20

<210> SEQ ID NO 160
<211> LENGTH: 20
<212> TYPE: DNA
<213> ORGANISM: Nannochloropsis gaditana
<220> FEATURE:
<221> NAME/KEY: misc_feature
<223> OTHER INFORMATION: NAR2 gene, antisense Primer

<400> SEQUENCE: 160
acggagtgtt caaatcccag                                              20

<210> SEQ ID NO 161
<211> LENGTH: 21
<212> TYPE: DNA
<213> ORGANISM: Nannochloropsis gaditana
<220> FEATURE:
<221> NAME/KEY: misc_feature
<223> OTHER INFORMATION: GS1 gene, sense Primer

<400> SEQUENCE: 161
catggactca ttctcctacg g                                            21

<210> SEQ ID NO 162
<211> LENGTH: 20
<212> TYPE: DNA
<213> ORGANISM: Nannochloropsis gaditana
<220> FEATURE:
<221> NAME/KEY: misc_feature
<223> OTHER INFORMATION: GS1 gene, antisense Primer

<400> SEQUENCE: 162
atcctcgaaa tatccgcacc                                              20

<210> SEQ ID NO 163
<211> LENGTH: 21
<212> TYPE: DNA
<213> ORGANISM: Nannochloropsis gaditana
<220> FEATURE:
<221> NAME/KEY: misc_feature
<223> OTHER INFORMATION: GOGAT1 gene, sense primer
```

<400> SEQUENCE: 163
tggatgcaaa cgagatgcta g    21

<210> SEQ ID NO 164
<211> LENGTH: 20
<212> TYPE: DNA
<213> ORGANISM: Nannochloropsis gaditana
<220> FEATURE:
<221> NAME/KEY: misc_feature
<223> OTHER INFORMATION: GOGAT1 gene, antisense primer

<400> SEQUENCE: 164
aggaaagcgg gaatagtgtg    20

<210> SEQ ID NO 165
<211> LENGTH: 20
<212> TYPE: DNA
<213> ORGANISM: Nannochloropsis gaditana
<220> FEATURE:
<221> NAME/KEY: misc_feature
<223> OTHER INFORMATION: GDH gene, sense primer

<400> SEQUENCE: 165
gggactcgtt ggaaggtaag    20

<210> SEQ ID NO 166
<211> LENGTH: 21
<212> TYPE: DNA
<213> ORGANISM: Nannochloropsis gaditana
<220> FEATURE:
<221> NAME/KEY: misc_feature
<223> OTHER INFORMATION: GDH gene, antisense primer

<400> SEQUENCE: 166
catttccaca agtttctccg c    21

<210> SEQ ID NO 167
<211> LENGTH: 20
<212> TYPE: DNA
<213> ORGANISM: Nannochloropsis gaditana
<220> FEATURE:
<221> NAME/KEY: misc_feature
<223> OTHER INFORMATION: GOGAT2 gene, sense primer

<400> SEQUENCE: 167
aagggaatgt cttggaaccg    20

<210> SEQ ID NO 168
<211> LENGTH: 20
<212> TYPE: DNA
<213> ORGANISM: Nannochloropsis gaditana
<220> FEATURE:
<221> NAME/KEY: misc_feature
<223> OTHER INFORMATION: GOGAT2 gene, antisense primer

<400> SEQUENCE: 168
agtgggtaga cagtggagag    20

<210> SEQ ID NO 169
<211> LENGTH: 20
<212> TYPE: DNA
<213> ORGANISM: Nannochloropsis gaditana
<220> FEATURE:
<221> NAME/KEY: misc_feature
<223> OTHER INFORMATION: NRT2 gene, sense primer

<400> SEQUENCE: 169
agtgctatgg agttttgcgg                                           20

<210> SEQ ID NO 170
<211> LENGTH: 20
<212> TYPE: DNA
<213> ORGANISM: Nannochloropsis gaditana
<220> FEATURE:
<221> NAME/KEY: misc_feature
<223> OTHER INFORMATION: NRT2 gene, antisense primer

<400> SEQUENCE: 170
agtgggtaga cagtggagag                                           20

<210> SEQ ID NO 171
<211> LENGTH: 20
<212> TYPE: DNA
<213> ORGANISM: Nannochloropsis gaditana
<220> FEATURE:
<221> NAME/KEY: misc_feature
<223> OTHER INFORMATION: NiR gene, sense primer

<400> SEQUENCE: 171
gccgatcctt tcttgcaaac                                           20

<210> SEQ ID NO 172
<211> LENGTH: 20
<212> TYPE: DNA
<213> ORGANISM: Nannochloropsis gaditana
<220> FEATURE:
<221> NAME/KEY: misc_feature
<223> OTHER INFORMATION: NiR gene, antisense primer

<400> SEQUENCE: 172
agcgttcaat caggtccaag                                           20

<210> SEQ ID NO 173
<211> LENGTH: 21
<212> TYPE: DNA
<213> ORGANISM: Nannochloropsis gaditana
<220> FEATURE:
<221> NAME/KEY: misc_feature
<223> OTHER INFORMATION: NR gene, sense primer

<400> SEQUENCE: 173
gctatattgg agaatccggc g                                         21

<210> SEQ ID NO 174
<211> LENGTH: 22
<212> TYPE: DNA
<213> ORGANISM: Nannochloropsis gaditana
<220> FEATURE:
<221> NAME/KEY: misc_feature
<223> OTHER INFORMATION: NR gene, antisense primer

<400> SEQUENCE: 174
gggaacgtca acagtgatag tg                                        22

<210> SEQ ID NO 175
<211> LENGTH: 19
<212> TYPE: DNA
<213> ORGANISM: Nannochloropsis gaditana
<220> FEATURE:
<221> NAME/KEY: misc_feature
<223> OTHER INFORMATION: Amt1 gene, sense primer

<400> SEQUENCE: 175

```
ccttcggtgc ctatttcgg                                                    19

<210> SEQ ID NO 176
<211> LENGTH: 21
<212> TYPE: DNA
<213> ORGANISM: Nannochloropsis gaditana
<220> FEATURE:
<221> NAME/KEY: misc_feature
<223> OTHER INFORMATION: Amt1 gene, antisense primer

<400> SEQUENCE: 176
catgtcgctg gtataggatg c                                                 21

<210> SEQ ID NO 177
<211> LENGTH: 20
<212> TYPE: DNA
<213> ORGANISM: Nannochloropsis gaditana
<220> FEATURE:
<221> NAME/KEY: misc_feature
<223> OTHER INFORMATION: UreT gene, sense primer

<400> SEQUENCE: 177
atggcagtag aaatggaccc                                                   20

<210> SEQ ID NO 178
<211> LENGTH: 21
<212> TYPE: DNA
<213> ORGANISM: Nannochloropsis gaditana
<220> FEATURE:
<221> NAME/KEY: misc_feature
<223> OTHER INFORMATION: UreT gene, sense primer

<400> SEQUENCE: 178
agtaagagaa cgaaaagggc g                                                 21

<210> SEQ ID NO 179
<211> LENGTH: 21
<212> TYPE: DNA
<213> ORGANISM: Nannochloropsis gaditana
<220> FEATURE:
<221> NAME/KEY: misc_feature
<223> OTHER INFORMATION: Sense primer, gene of unkown function

<400> SEQUENCE: 179
ctctcctatt gctttccctc g                                                 21

<210> SEQ ID NO 180
<211> LENGTH: 22
<212> TYPE: DNA
<213> ORGANISM: Nannochloropsis gaditana
<220> FEATURE:
<221> NAME/KEY: misc_feature
<223> OTHER INFORMATION: Antisense primer, gene of unkown function

<400> SEQUENCE: 180
ctaccaacac ctctacactt cc                                                22

<210> SEQ ID NO 181
<211> LENGTH: 14
<212> TYPE: PRT
<213> ORGANISM: Nannochloropsis gaditana
<220> FEATURE:
<221> NAME/KEY: misc_feature
<223> OTHER INFORMATION: Acetyl-CoA Carboxylase peptide 1

<400> SEQUENCE: 181

Phe Lys Phe Ala Asp Thr Pro Asp Glu Glu Ser Pro Leu Arg
```

```
<210> SEQ ID NO 182
<211> LENGTH: 14
<212> TYPE: PRT
<213> ORGANISM: Nannochloropsis gaditana
<220> FEATURE:
<221> NAME/KEY: misc_feature
<223> OTHER INFORMATION: Acetyl-CoA Carboxylase peptide 2

<400> SEQUENCE: 182

Ala Glu Asn Phe Lys Glu Asp Pro Leu Arg Arg Asp Met Arg
1               5                   10

<210> SEQ ID NO 183
<211> LENGTH: 14
<212> TYPE: PRT
<213> ORGANISM: Nannochloropsis gaditana
<220> FEATURE:
<221> NAME/KEY: misc_feature
<223> OTHER INFORMATION: 3-Hydroxyacyl ACP Dehydrase peptide 1

<400> SEQUENCE: 183

Thr Ala Asn Glu Pro Gln Phe Thr Gly His Phe Pro Glu Arg
1               5                   10

<210> SEQ ID NO 184
<211> LENGTH: 13
<212> TYPE: PRT
<213> ORGANISM: Nannochloropsis gaditana
<220> FEATURE:
<221> NAME/KEY: misc_feature
<223> OTHER INFORMATION: 3-Hydroxyacyl ACP Dehydrase peptide 2

<400> SEQUENCE: 184

Ile Asp Gly Val Phe Arg Lys Pro Val Val Pro Gly Asp
1               5                   10

<210> SEQ ID NO 185
<211> LENGTH: 14
<212> TYPE: PRT
<213> ORGANISM: Nannochloropsis gaditana
<220> FEATURE:
<221> NAME/KEY: misc_feature
<223> OTHER INFORMATION: Enoyl-ACP Reductase peptide 1

<400> SEQUENCE: 185

Pro Glu Asp Val Pro Glu Ala Val Lys Thr Asn Lys Arg Tyr
1               5                   10

<210> SEQ ID NO 186
<211> LENGTH: 14
<212> TYPE: PRT
<213> ORGANISM: Nannochloropsis gaditana
<220> FEATURE:
<221> NAME/KEY: misc_feature
<223> OTHER INFORMATION: Enoyl-ACP Reductase peptide 2

<400> SEQUENCE: 186

Ala Ile Gly Gly Gly Glu Lys Gly Lys Lys Thr Phe Ile Glu
1               5                   10

<210> SEQ ID NO 187
<211> LENGTH: 14
<212> TYPE: PRT
<213> ORGANISM: Nannochloropsis gaditana
<220> FEATURE:
<221> NAME/KEY: misc_feature
```

<223> OTHER INFORMATION: Beta-Ketoacyl-ACP Reductase peptide 1

<400> SEQUENCE: 187

Val Ala Ile Lys Ala Asp Met Ser Lys Pro Glu Glu Val Glu
1               5                   10

<210> SEQ ID NO 188
<211> LENGTH: 14
<212> TYPE: PRT
<213> ORGANISM: Nannochloropsis gaditana
<220> FEATURE:
<221> NAME/KEY: misc_feature
<223> OTHER INFORMATION: Beta-Ketoacyl-ACP Reductase peptide 2

<400> SEQUENCE: 188

Ser Asp Met Thr Glu Lys Leu Asp Leu Asp Gly Ile Lys Lys
1               5                   10

<210> SEQ ID NO 189
<211> LENGTH: 14
<212> TYPE: PRT
<213> ORGANISM: Nannochloropsis gaditana
<220> FEATURE:
<221> NAME/KEY: misc_feature
<223> OTHER INFORMATION: Beta-Ketoacyl-ACP Synthase 1 peptide 1

<400> SEQUENCE: 189

Tyr Met Arg Gly Ser Lys Gly Gln Ile Tyr Met Lys Glu Lys
1               5                   10

<210> SEQ ID NO 190
<211> LENGTH: 14
<212> TYPE: PRT
<213> ORGANISM: Nannochloropsis gaditana
<220> FEATURE:
<221> NAME/KEY: misc_feature
<223> OTHER INFORMATION: Beta-Ketoacyl-ACP Synthase 1 peptide 2

<400> SEQUENCE: 190

Asp Ala Lys Pro Tyr Phe Lys Asp Arg Lys Ser Ala Val Arg
1               5                   10

<210> SEQ ID NO 191
<211> LENGTH: 14
<212> TYPE: PRT
<213> ORGANISM: Nannochloropsis gaditana
<220> FEATURE:
<221> NAME/KEY: misc_feature
<223> OTHER INFORMATION: Beta-Ketoacyl-ACP Synthase 3 peptide 1

<400> SEQUENCE: 191

Met Gly Lys Arg Ser Thr Ala Ser Ser Thr Gly Leu Ala Tyr
1               5                   10

<210> SEQ ID NO 192
<211> LENGTH: 14
<212> TYPE: PRT
<213> ORGANISM: Nannochloropsis gaditana
<220> FEATURE:
<221> NAME/KEY: misc_feature
<223> OTHER INFORMATION: Beta-Ketoacyl-ACP Synthase 3 peptide 2

<400> SEQUENCE: 192

Pro Pro Ser Ile Arg Glu Val Thr Pro Tyr Lys Gly Lys Tyr
1               5                   10

<210> SEQ ID NO 193

```
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for guide RNA, nitrate
      reductase gene

<400> SEQUENCE: 193
gggttggatg gaaaaaggca                                               20
```